(12) United States Patent
Kokhanenko et al.

(10) Patent No.: US 12,337,101 B2
(45) Date of Patent: Jun. 24, 2025

(54) DIRECTED GAS FLOW SURGICAL CANNULA FOR PROVIDING GASES TO A PATIENT

(71) Applicant: FISHER & PAYKEL HEALTHCARE LIMITED, Auckland (NZ)

(72) Inventors: Pavlo Kokhanenko, Auckland (NZ); Benjamin Elliot Hardinge Pegman, Auckland (NZ); Charlotte Grace Laus, Auckland (NZ); Callum James Thomas Spence, Auckland (NZ); Abigail Sharmini Rajen Arulandu, Auckland (NZ); Zane Paul Gell, Auckland (NZ); Zach Jonathan Warner, Auckland (NZ); Vincent Verdoold, Auckland (NZ); Gabor Papotti, Auckland (NZ); German Klink, Auckland (NZ); Richard John Boyes, Auckland (NZ); Bernard Tsz Lun Ip, Auckland (NZ); Monika Baumann, Auckland (NZ); James Robert Jarmey Greenfield, Auckland (NZ); Katie-Ann Jane Buckels, Auckland (NZ); Donald Roy Kuriger, Auckland (NZ); Joshua Robert Lee, Auckland (NZ); Jesus Antonio Amador Noriega, Auckland (NZ); James Michael Gilbert, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1046 days.

(21) Appl. No.: 17/269,145

(22) PCT Filed: Aug. 16, 2019

(86) PCT No.: PCT/NZ2019/050100
§ 371 (c)(1),
(2) Date: Feb. 17, 2021

(87) PCT Pub. No.: WO2020/036498
PCT Pub. Date: Feb. 20, 2020

(65) Prior Publication Data
US 2021/0236749 A1    Aug. 5, 2021

Related U.S. Application Data

(60) Provisional application No. 62/719,550, filed on Aug. 17, 2018.

(51) Int. Cl.
| | | |
|---|---|---|
| A61B 17/34 | (2006.01) | |
| A61B 1/12 | (2006.01) | |
| A61M 13/00 | (2006.01) | |

(52) U.S. Cl.
CPC ........... A61M 13/003 (2013.01); A61B 1/127 (2013.01); A61B 17/3423 (2013.01);
(Continued)

(58) Field of Classification Search
CPC ............ A61B 17/3421; A61B 17/3474; A61B 17/3498; A61B 17/3462; A61B 2017/3464; A61B 1/015
See application file for complete search history.

(56) References Cited

U.S. PATENT DOCUMENTS

| | | | | |
|---|---|---|---|---|
| 2002/0128603 A1* | 9/2002 | Booth | ................ | A61B 17/3421 604/164.01 |
| 2004/0204671 A1* | 10/2004 | Stubbs | ............... | A61B 17/3423 604/164.01 |

(Continued)

FOREIGN PATENT DOCUMENTS

| | | |
|---|---|---|
| CN | 102264309 A | 11/2011 |
| CN | 105962997 A | 9/2016 |

(Continued)

OTHER PUBLICATIONS

International Search Report and Written Opinion for International Application No. PCT/NZ2019/050100 dated Dec. 24, 2019, 24 pages.

*Primary Examiner* — Eduardo C Robert
*Assistant Examiner* — Michelle C Green
(74) *Attorney, Agent, or Firm* — Knobbe Martens Olson & Bear LLP

(57) ABSTRACT

Disclosed herein is a surgical cannula configured as an instrument retaining or centering apparatus, configured for providing insufflation gases to a surgical cavity of a patient (such as the pneumoperitoneum) and allowing insertion of medical instruments into the surgical cavity through the (Continued)

cannula. The cannula can include features to direct gas flow in particular directions to prevent or reduce smoke, fog/condensation, or other unwanted media from contacting a portion of a medical instrument.

22 Claims, 119 Drawing Sheets

(52) U.S. Cl.
CPC ............. *A61M 2205/3334* (2013.01); *A61M 2205/3368* (2013.01); *A61M 2205/36* (2013.01); *A61M 2206/20* (2013.01)

(56) References Cited

U.S. PATENT DOCUMENTS

| | | | |
|---|---|---|---|
| 2005/0059934 A1* | 3/2005 | Wenchell | A61B 18/1445 604/167.01 |
| 2005/0203342 A1 | 9/2005 | Kucklick et al. | |
| 2006/0041186 A1 | 2/2006 | Vancaillie | |
| 2007/0191759 A1 | 8/2007 | Stoller et al. | |
| 2010/0241079 A1* | 9/2010 | Abrams | A61B 17/3498 604/167.01 |
| 2012/0197084 A1* | 8/2012 | Drach | A61B 1/00119 600/123 |
| 2012/0316512 A1* | 12/2012 | Ott | A61B 17/3421 604/256 |
| 2013/0131580 A1* | 5/2013 | Blackhurst | A61M 13/003 340/618 |
| 2014/0371763 A1* | 12/2014 | Poll | A61B 34/30 606/130 |
| 2016/0228671 A1 | 8/2016 | Jackson et al. | |
| 2017/0007295 A1* | 1/2017 | Geisz | A61B 17/3421 |
| 2018/0028768 A1* | 2/2018 | Boyes | A61M 13/003 |
| 2018/0055536 A1* | 3/2018 | Geisz | A61B 17/3417 |

FOREIGN PATENT DOCUMENTS

| | | |
|---|---|---|
| CN | 106456929 A | 2/2017 |
| CN | 106943657 A | 7/2017 |
| EP | 2060295 | 5/2009 |
| EP | 2329774 A1 | 8/2011 |
| EP | 2851020 | 3/2015 |
| JP | 2010502360 A | 1/2010 |
| JP | 2018086168 A | 6/2018 |
| WO | WO2009094644 A1 | 7/2009 |
| WO | WO 2012/122263 | 9/2012 |
| WO | WO2018013734 A1 | 1/2018 |
| WO | WO 2020/036498 | 2/2020 |

* cited by examiner

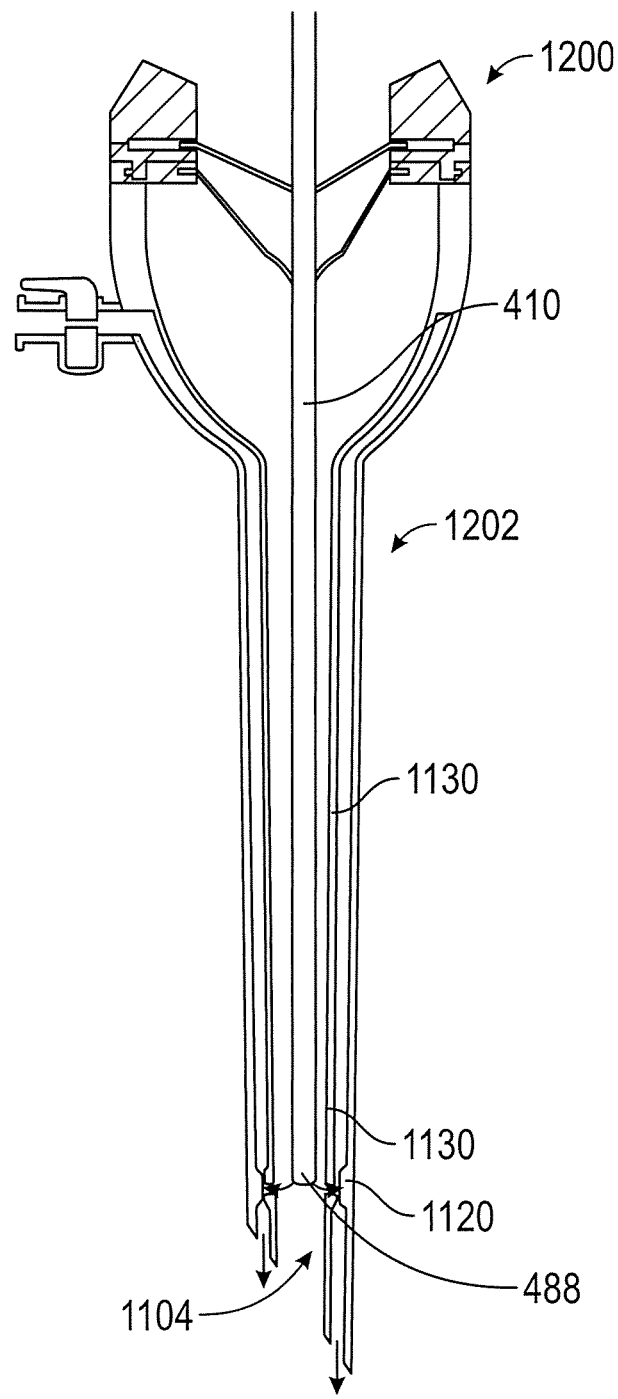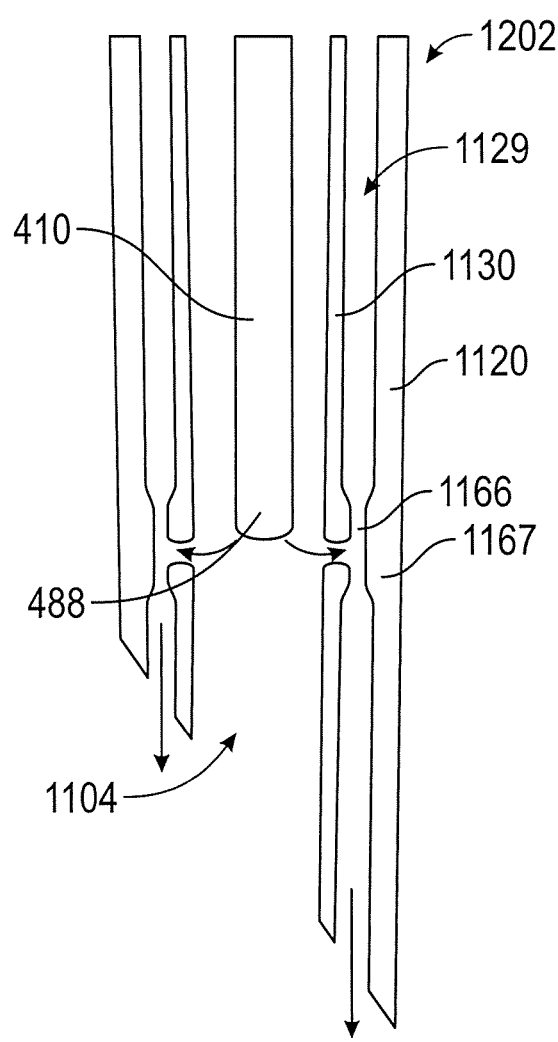
FIG. 12A
FIG. 12B

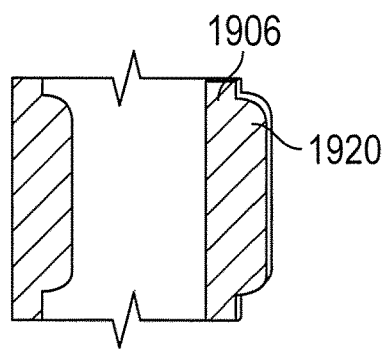
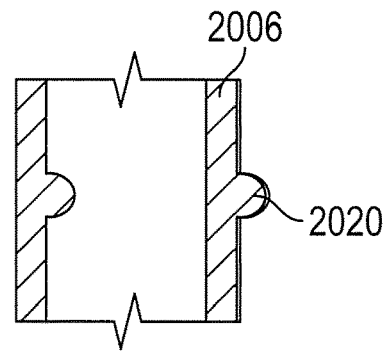
FIG. 19A    FIG. 20A
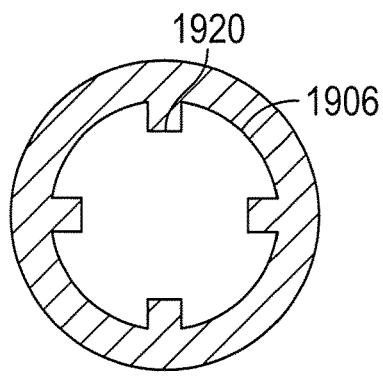
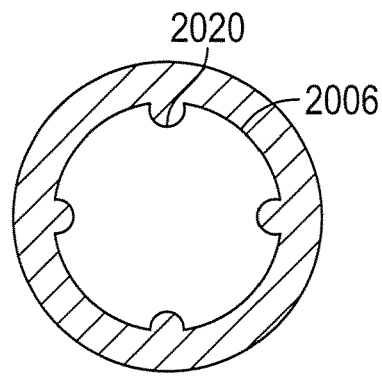
FIG. 19B    FIG. 20B
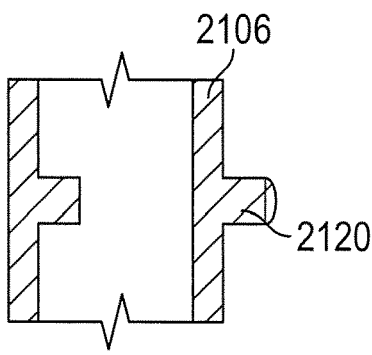
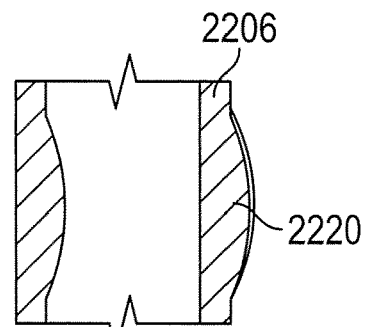
FIG. 21A    FIG. 22A
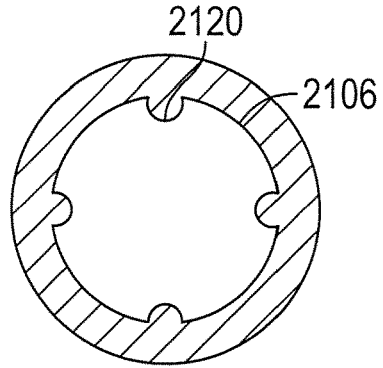
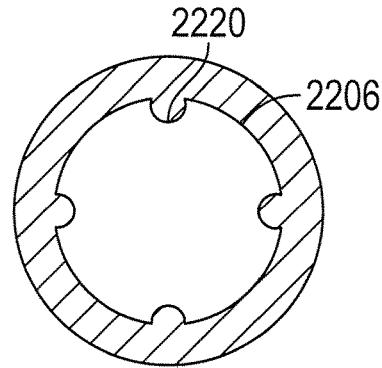
FIG. 21B    FIG. 22B

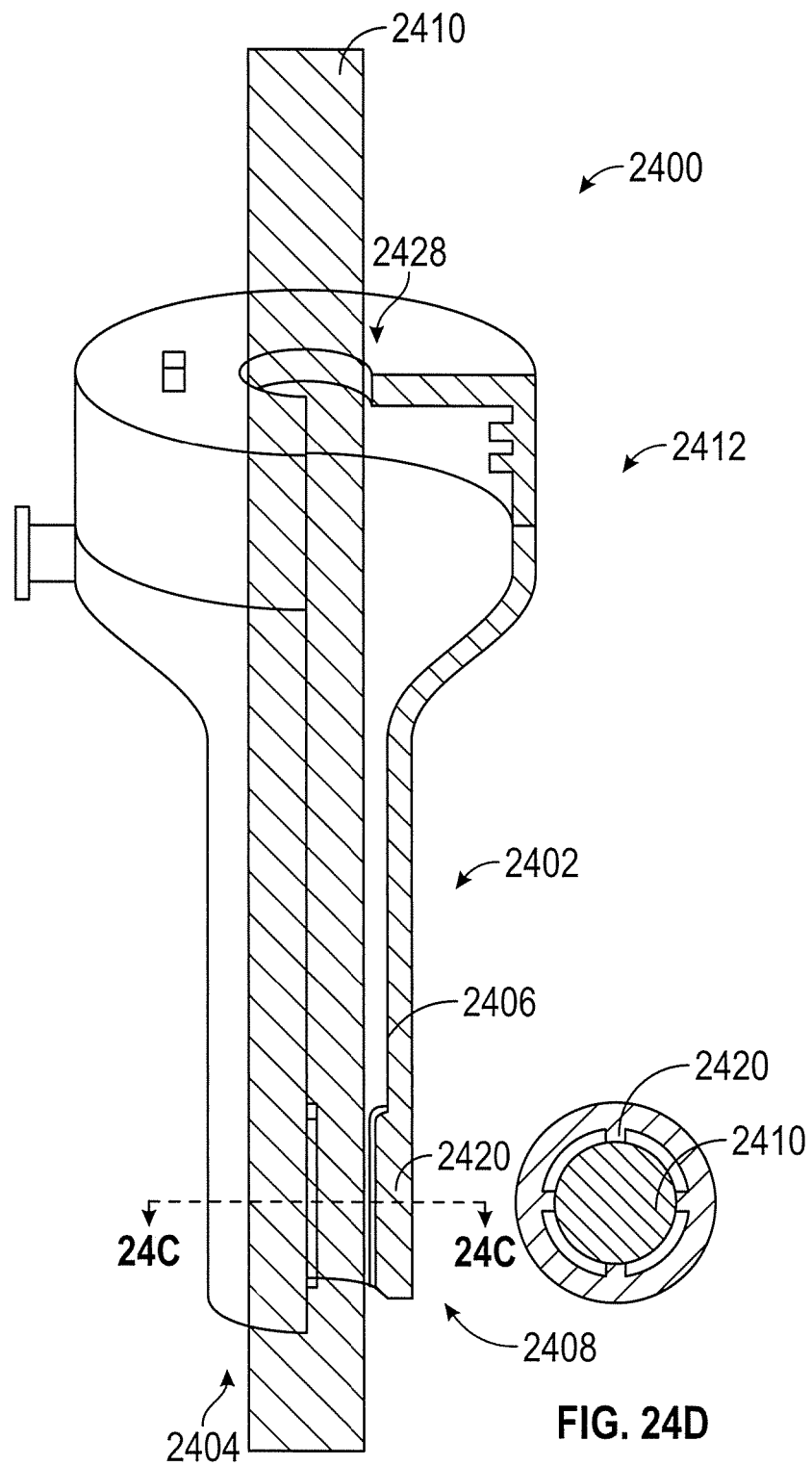

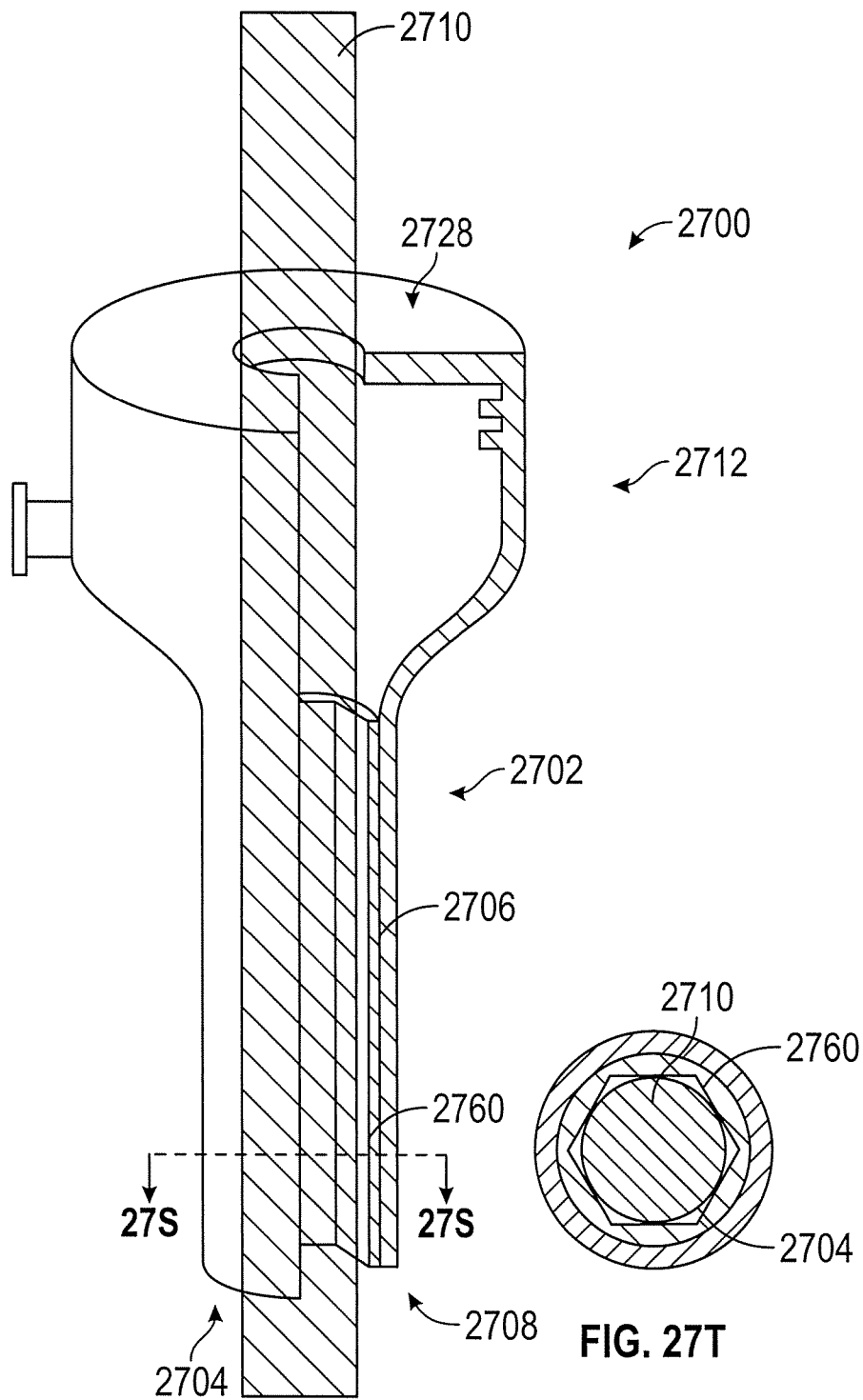

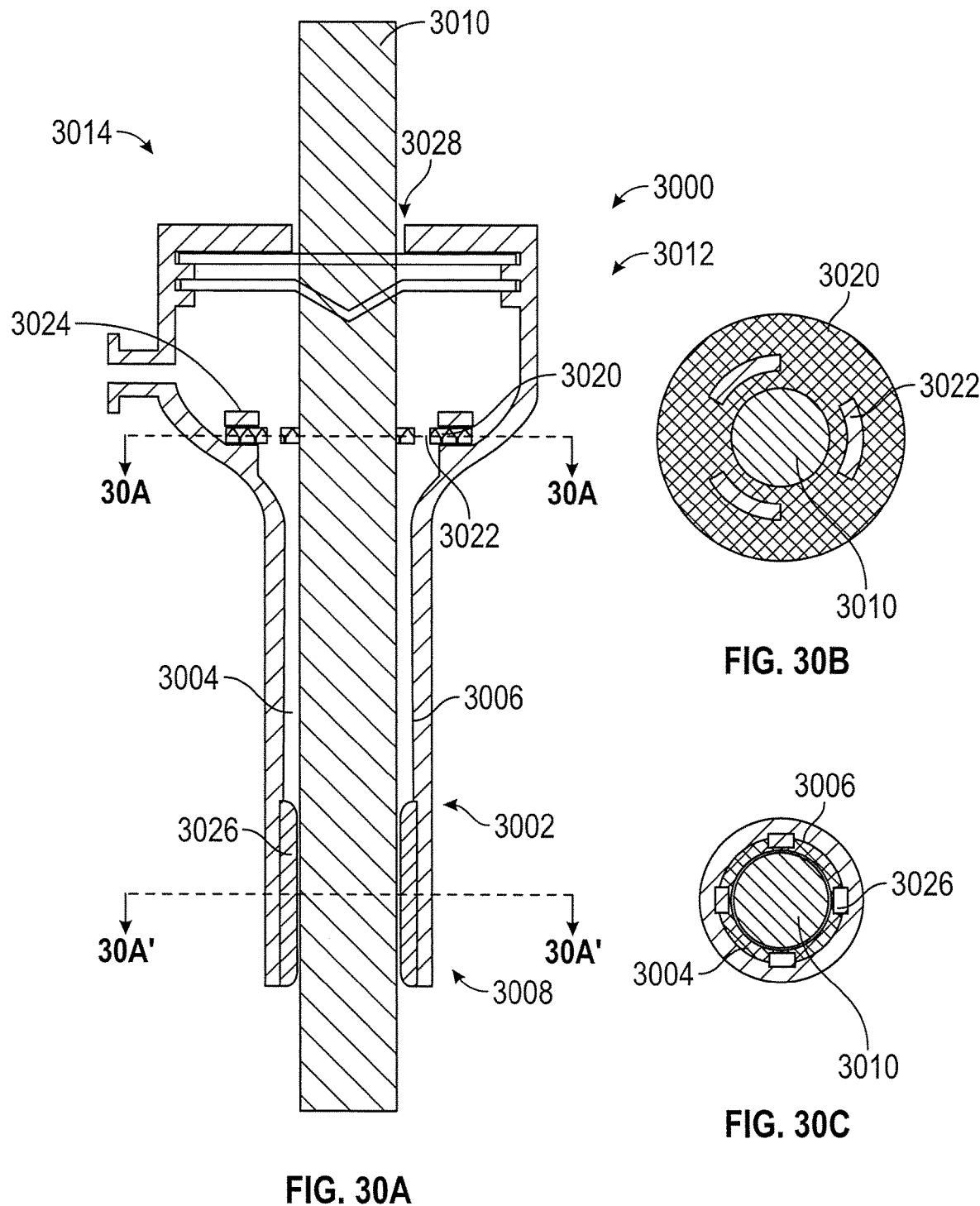

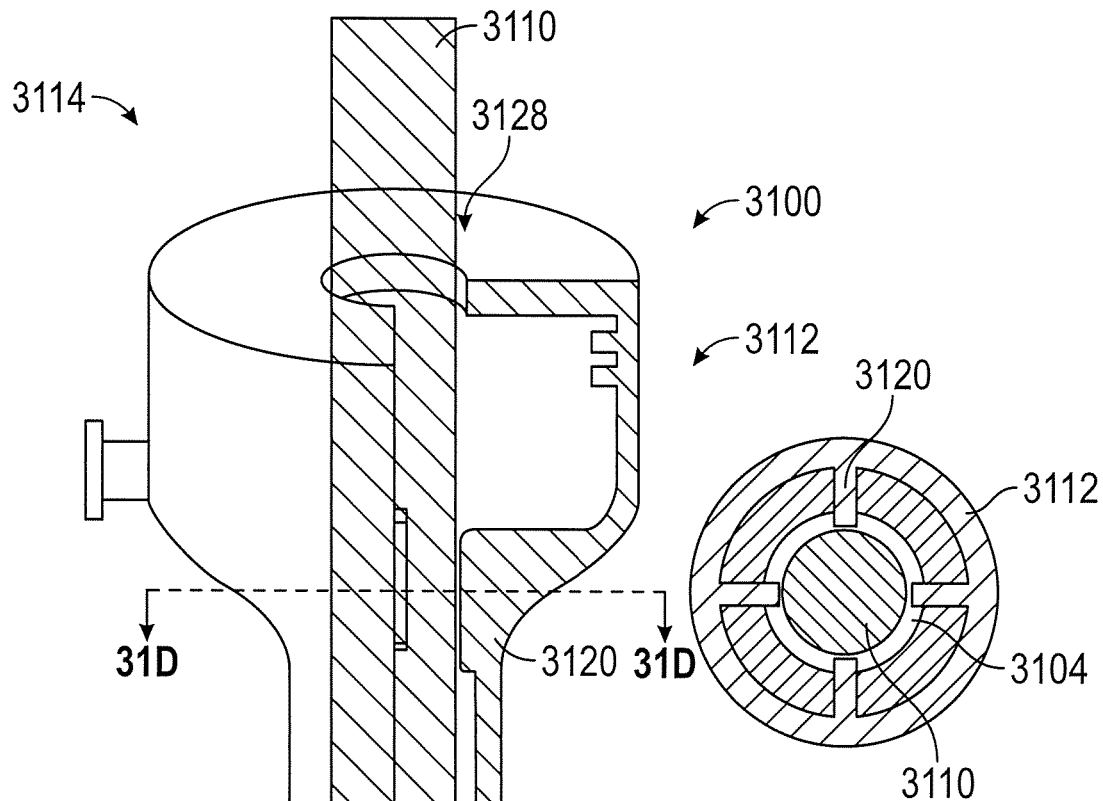
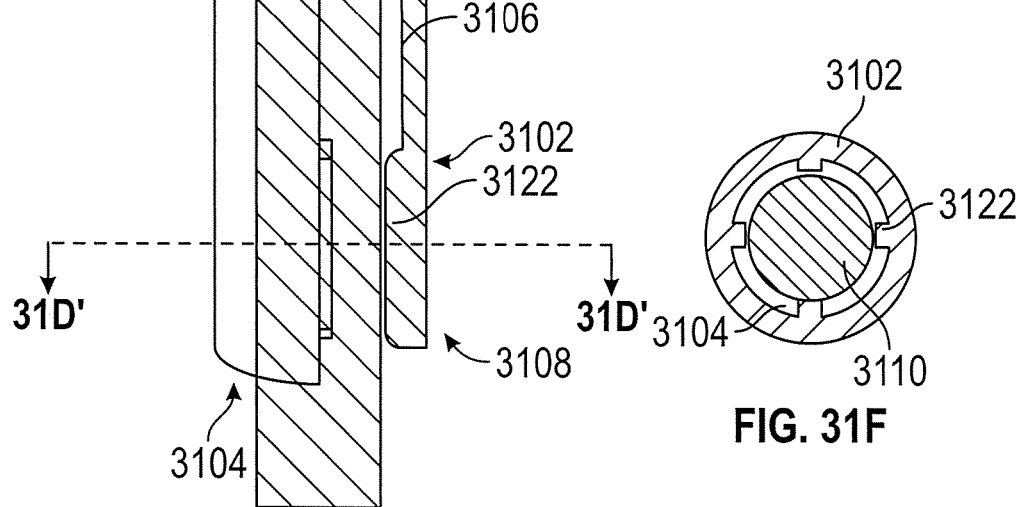
FIG. 31D
FIG. 31E
FIG. 31F

DIRECTED GAS FLOW SURGICAL CANNULA FOR PROVIDING GASES TO A PATIENT

FIELD OF THE DISCLOSURE

The present disclosure relates in some aspects to humidifier systems and components of humidifier systems configured to supply gases to a patient, in particular during a medical procedure.

BACKGROUND

Various medical procedures require the provision of gases, typically carbon dioxide, to a patient during the medical procedure. For example, two general categories of medical procedures often require providing gases to a patient. These include closed type medical procedures and open type medical procedures.

In closed type medical procedures, an insufflator is arranged to deliver gases to a body cavity of the patient to inflate the body cavity and/or to resist collapse of the body cavity during the medical procedure. Examples of such medical procedures include laparoscopy and endoscopy, although an insufflator may be used with any other type of medical procedure as required. Endoscopic procedures enable a medical practitioner to visualize a body cavity by inserting an endoscope or the like through one or more natural openings, small puncture(s), or incision(s) to generate an image of the body cavity. In laparoscopy procedures, a medical practitioner typically inserts a medical instrument through natural openings, small puncture(s), or incision(s) to perform a medical procedure in the body cavity. In some cases an initial endoscopic procedure may be carried out to assess the body cavity, and then a subsequent laparoscopy carried out to operate on the body cavity. Such procedures are widely used, for example, on the peritoneal cavity, or during a thoracoscopy, colonoscopy, gastroscopy or bronchoscopy.

In open type medical procedures, for example, open surgeries, gases are used to fill a surgical cavity, with excess gases spilling outward from the opening. The gases can also be used to provide a layer of gases over exposed body parts for example, including internal body parts where there is no discernible cavity. For these procedures, rather than serving to inflate a cavity, the gases can be used to prevent or reduce desiccation and infection by covering exposed internal body parts with a layer of heated, humidified, sterile gases.

An apparatus for delivering gases during these medical procedures can include an insufflator arranged to be connected to a remote source of pressurized gases, for example, a gases supply system in a hospital. The apparatus can be operative to control the pressure and/or flow of the gases from the gases source to a level suitable for delivery into the body cavity, usually via a cannula or needle connected to the apparatus and inserted into the body cavity, or via a diffuser arranged to diffuse gases over and into the wound or surgical cavity.

The internal body temperature of a human patient is typically around 37° C. It can be desirable to match the temperature of the gases delivered from the apparatus as closely as possible to the typical human body temperature. It can also be desirable to deliver gases above or below internal body temperature, such as, for example, 1° C., 2° C., 3° C., 4° C., 5° C., 6° C., 7° C., 8° C., 9° C., 10° C., or 15° C., or more or less above or below internal body temperature for example, or ranges including any two of the foregoing values. It can also be desirable to deliver gases of a desired fixed or variable humidity and/or a desired fixed or variable temperature. The gases at the desired gas temperature and/or humidity (which may be also referred to herein as standard) can be dry cold gas, dry hot gas, humidified cold gas, or humidified hot gas for example. Further, the gases delivered into the patient's body can be relatively dry, which can cause damage to the body cavity, such as for example cell desiccation, cell death or adhesions. In many cases, a humidifier is operatively coupled to the insufflator. A controller of the apparatus can energize a heater of the humidifier located in the gases flow path to deliver humidification fluid to the gases stream prior to entering the patient's body cavity. The humidification fluid may be water.

The humidified gas can be delivered to the patient via further tubing which may also be heated. The insufflator and humidifier can be located in separate housings that are connected together via suitable tubing and/or electrical connections, or located in a common housing arranged to be connected to a remote gas supply via suitable tubing.

SUMMARY

Condensation and/or fogging occurs when the temperature of a gas falls below the dew point temperature for the level of humidity the gas is carrying, and/or if there are surfaces significantly below the dew-point temperature. The human body is a warm and humid environment, having a temperature of about 37° C. When cold (for example, at or below typical room temperature and/or below a typical human body temperature) cameras, scopes, or other medical instruments are inserted into this environment, condensation can form as fog on the lens, and/or as droplets of water on the scope, which can drip down onto the lens area. Further condensation and/or fogging can also form on the internal wall of the cannula upper housing and drip down, such as, for example, onto the lens area. Further, although the humidification and heating of the insufflation gases can reduce damage to the patient's tissue in the surgical cavity, the humidification and heating of the gases can exacerbate the problem of condensation and/or fogging.

The fog and/or condensed droplets can impede vision, for example, vision of a surgeon or other medical personnel participating in the medical procedure (for example, surgery). When fogging and/or condensation occurs, it may be necessary to remove the camera and/or the other medical instruments and wipe it (or them) down to remove the fog and/or droplets. However, removing the medical instruments out of the surgical cavity can cause them to cool down again to below the patient's body temperature. As a result, the fogging and/or condensation problem can recur in the absence of any other interventions, for example, pre-warming of the medical instruments, and/or using the light at the end of the camera to warm up the lens. These interventions require additional products and/or costs.

The present disclosure provides examples of a cannula configured for directed gas flow that can remedy the aforementioned problems and/or other problems (including, for example, preventing or at least reducing condensation and/or fogging). The directed gases flow cannula examples disclosed herein can prevent or at least reduce condensation and/or fogging through directed gas flow causing the medical instruments to heat up more rapidly, and/or can prevent or at least reduce condensation and/or fogging once it has occurred through heat radiation and conduction causing fluid evaporation. Some configurations can also advantageously direct gases flow in order to control the environment around the scope/medical instrument. Smoke generated within the surgical cavity can potentially cause fogging, or can reduce visibility due to deposition of smoke on the instrument, e.g. onto the lens. The directed gases flow cannula can direct insufflation gases in a manner to move smoke, condensation, or other unwanted media away from the desired location of the instrument.

In some aspects, disclosed herein is a surgical cannula for providing insufflation gases to a surgical cavity and providing a passage for insertion of one or more medical instruments. The cannula can include any number of a cannula body including an inlet; an elongate shaft extending from the cannula body, the shaft defining a lumen defined by a sidewall, the lumen configured to provide the insufflation gases to the surgical cavity between a gases inlet and an outlet proximate a distal end of the elongate shaft, the lumen in fluid communication with the inlet and the outlet, the lumen also configured to receive a medical instrument therethrough; and a guiding element disposed on, within, or around at least a portion of the lumen, the guiding element configured to limit radial movement of the medical instrument within the lumen and prevent the medical instrument from contacting the sidewall of the lumen such that gases flowing into the lumen flow around the medical instrument and create an envelope of insufflation gases that extends distally beyond a distal end of the instrument.

In some aspects, disclosed herein is a surgical cannula for providing insufflation gases to a surgical cavity and providing a passage for insertion of one or more medical instruments. The cannula can include any number of: a cannula body including an inlet; an elongate shaft extending from the cannula body, the shaft defining a lumen defined by a sidewall, the lumen configured to provide the insufflation gases to the surgical cavity between a gases inlet and an outlet proximate a distal end of the elongate shaft, the lumen in fluid communication with the inlet and the outlet, the lumen also configured to receive a medical instrument therethrough; and/or a guide element disposed on, within, or around at least a portion of the lumen, the guide element configured to limit radial movement of the medical instrument within the lumen and prevent the medical instrument from contacting the sidewall of the lumen such that gases flowing into the lumen flow around the medical instrument and create an envelope of insufflation gases that extends along and distally beyond a distal end of the instrument. The structure and stability of the flow along the instrument is affected by the presence of the wall of the medical instrument.

In some configurations the guide element can be further configured to maintain the medical instrument substantially co-axially and/or concentrically within the lumen.

The guide element can also be configured such that the envelope maintains the temperature of a portion of the instrument above a dew point.

In some configurations, the envelope reduces or prevents fogging and/or condensation formation on the medical instrument.

In some configurations, the envelope reduces or prevents smoke from contacting the medical instrument.

In some configurations, the envelope reduces or prevents smoke from obstructing the field of view of the medical instrument.

In some configurations, the guide element is configured such that the envelope substantially surrounds the entire or a portion of the medical instrument (e.g., the distal end of the medical instrument).

In some configurations, the envelope extends beyond the outlet of the elongate shaft and surrounds the medical instrument distally beyond the outlet of the elongate shaft.

In some configurations, the medical instrument extends beyond the outlet of the elongate shaft and the envelope extends distally beyond the outlet of the elongate shaft and the medical instrument.

In some configurations, the envelope concentrically surrounds the medical instrument within the lumen and distally beyond the outside of the shaft.

In some configurations, the envelope concentrically surrounds the medical instrument within the lumen and beyond the outlet of the elongate shaft.

In some configurations, the envelope extends a predetermined distance distally beyond the outlet.

In some configurations, the envelope extends a predetermined distance beyond the outlet of the shaft.

In some configurations, the envelope maintains a temperature controlled environment about the elongate shaft and outlet of the elongate shaft, and the envelope maintains the temperature above the dew point.

In some configurations, the envelope is created by a Coanda effect of gases passing along the medical instrument.

In some configurations, the envelope is affected by the Coanda effect as gases pass beyond the distal end of the medical instrument.

In some configurations, the guiding element includes a plurality, e.g., 2 or more ribs extending radially inward from an inner sidewall of the lumen toward a center of the lumen.

In some configurations, the guide element includes a plurality, e.g., 2 or more ribs extending inward from an inner sidewall of the lumen toward a center of the lumen.

In some configurations the two or more ribs can be configured to contact the medical instrument to grasp the instrument concentrically within the lumen, and/or limit radial movement of the medical instrument to prevent the medical instrument from contacting the sidewall of the lumen.

In some configurations, the guide element can maintain the medical instrument between 0 to 30 degrees off axis with respect to the lumen.

In some configurations the guide element can include about or at least about 2, 3, 4, 5, 6, 7, 8, 9, 10 or more radially or axially spaced-apart ribs.

In some configurations, the guide element can comprise at least four spaced-apart ribs.

In some configurations, the ribs can be positioned at any location axially on the elongate shaft including but not limited to the distal end of the elongate shaft. The ribs can be molded or over-molded into the cannula.

In some configurations, the surgical cannula can further comprise a removable insert positioned within the lumen, wherein the plurality of ribs can be positioned on the removable insert.

In some configurations, the removable insert can comprise a top portion and a shaft portion extending distally from the top portion.

In some configurations, the guide element can be configured to prevent the scope from contacting a wall adjacent an outlet of the cannula. This prevents a flow non-uniformity from being created (which can also be referred to as a stagnation zone). The guide element can ensure that the scope is guided/held within the cannula such that gases surround the circumference of the scope at the distal end of the medical instrument.

In some configurations the plurality of ribs can include at least a first set of ribs, and a second set of ribs spaced axially apart by a gap between the first set of ribs and the second set of ribs.

The gap between the first set of ribs and the second set of ribs can be sized and configured to reduce flow velocity and/or reduce flow turbulence of the insufflation gases.

In some configurations the first set of ribs can include additional ribs, the same number of ribs, or less ribs than the second set of ribs.

In some configurations, the guide element can also include a vane.

In some configurations, the guide element can also include a disk.

In some configurations, the guiding element can also include a flange including an opening in communication with the cannula inlet, the opening configured to receive the medical instrument therethrough.

In some configurations, the guide element can also include a flange including an opening in fluid communication with the cannula inlet, the opening configured to receive the medical instrument therethrough.

The guide element can also be configured such that the opening is concentric with respect to the lumen.

In some configurations the disk or flange can be, for example, flexible, rigid, or semi-rigid, and include a plurality of apertures located around the opening.

In some configurations, the plurality of apertures can be configured to allow gas flow therethrough and direct insufflation gases concentrically around the medical instrument to form the envelope around the medical instrument.

In some configurations, the apertures can include an arcuate, polygonal, or other shape and be evenly disposed about the opening.

In some configurations, the lumen can include a vane or series of vanes connected to a sidewall of the lumen.

In some configurations, the vane or series of vanes can be configured to incompletely or partially block flow in the lumen such that the insufflation gases are diverted to an unblocked region of the lumen.

In some configurations, the vane can include a flexible wall, and be configured to block about or at least about 5% or more or less of the lumen.

In some configurations, the vane can be configured to remove at least one stagnant flow zone distal to the medical instrument to prevent fogging.

In some configurations, the vane can be configured to remove at least one stagnant flow zone at the distal end of the medical instrument to prevent condensation and/or fogging.

In some configurations, the guide element can comprise a plurality of pins extending inward from an inner sidewall of the lumen toward a center of the lumen.

In some configurations, the plurality of pins can be configured to contact the medical instrument to grasp the instrument concentrically within the lumen.

In some configurations, the plurality of pins can be configured to limit radial movement of the medical instrument to prevent the medical instrument from contacting the sidewall of the lumen.

In some configurations, the guide element can comprise at least four radially spaced-apart pins, wherein the pins are flexible or rigid.

In some configurations, the pins can be flexible and positioned on a ring positioned on an outer surface of the cannula body and the pins can be configured to extend through openings in the cannula.

In some configurations the guide element can comprise radially spaced-apart protrusions.

In some configurations, the guide element can comprise a plurality of fins extending inward and distally from the distal end of the elongate shaft.

In some configurations, the guide element can comprise a plurality of flexible fins extending extend radially inward into the cannula.

In some configurations, the guide element can comprise a bellows and a ring with pins, wherein the bellows can be attached to the distal end of the elongate shaft and the ring is attached to a distal end of the bellows.

In some configurations, the guide element can comprise a non-circular elongate shaft cross-section.

In some configurations, the guide element can comprise a plurality of rigid bumps.

In some configurations, the guide element can comprise a plurality of pivoting structures within the elongate shaft, wherein the pivoting structures can be configured to rotate as the medical instrument is insert or removed from the cannula.

In some configurations, the guide element can comprise a foam material.

In some configurations, the guide element can comprise adjustable structures, the adjustable structures are spring loaded and are configured to rotate to support the medical instrument in the lumen.

In some configurations, the guide element can comprise a seal at the inlet of the cannula body.

In some configurations, the guide element can comprise a tight fitting channel that aligns with the inlet of the cannula body.

In some configurations, the medical instrument could be, for example, a laparoscope, a camera, a video laparoscope, an electrocautery device, a hand instrument, a choledoscope, and/or any other suitable instrument.

In some configurations, disclosed is a cannula for providing insufflation gases to a surgical cavity and providing a passage for insertion of one or more medical instruments. The cannula can include one or more of the following: a cannula body including an inlet; an elongate shaft extending from the cannula body, the shaft including an inner wall and an outer wall, a first lumen defined by a sidewall of the inner wall, and a second lumen positioned between the inner wall and the outer wall.

In some configurations, the first lumen and the second lumen can be concentric or substantially concentric.

In some configurations, the first lumen can include a first lumen inlet and a first lumen outlet, and be configured to house a medical instrument therethrough.

In some configurations, the second lumen can be configured to provide the insufflation gases to the surgical cavity between a second lumen inlet and a second lumen outlet proximate a distal end of the elongate shaft, such that gases flowing out of the second lumen outlet flow around the medical instrument and create an envelope of insufflation gases that extends distally beyond the end of the instrument.

In some configurations, the second lumen can also be configured that the envelope maintains the temperature of the instrument above a dew point.

In some configurations, the envelope clears fog, reduces or prevents fogging and/or condensation formation on or around the medical instrument.

In some configurations, the envelope reduces or prevents smoke from contacting the medical instrument.

In some configurations, the envelope substantially surrounds the medical instrument.

In some configurations, the envelope extends beyond the outlet of the elongate shaft and surrounds the medical instrument beyond the outlet of the elongate shaft.

In some configurations, the envelope extends beyond the outlet of the elongate shaft and surrounds the medical instrument distally beyond the outlet of the elongate shaft.

In some configurations, the envelope concentrically surrounds the medical instrument within the hollow passage and distally beyond the outside of the shaft.

In some configurations, the envelope concentrically surrounds the medical instrument within the lumen and distally beyond the outlet of the elongate shaft.

In some configurations, the envelope extends a predetermined distance distally beyond the outlet of the elongate shaft.

In some configurations, the envelope maintains a temperature controlled environment about the elongate shaft and outlet of the elongate shaft.

In some configurations, the envelope maintains the temperature above the dew point.

In some configurations, the envelope is created by a Coanda effect of gases passing along the medical instrument.

In some configurations, the envelope is affected by the Coanda effect as gases pass beyond the distal end of the medical instrument.

In some configurations, the second lumen can have a diameter that is less than that of the first lumen.

In some configurations, the outlet of the elongate shaft can, for example include the outlet of the first lumen and the outlet of the second lumen.

In some configurations, the outlet of the first lumen and the outlet of the second lumen can be co-planar to each other.

In some configurations, the outlet of the second lumen can be angled radially inwardly with respect to a longitudinal axis of the elongate shaft such that insufflation gases exiting the second lumen outlet flow radially inward toward the medical instrument.

In some configurations, the medical instrument can be between 0 to 30 degrees off axis with respect to the first lumen.

In some configurations, a cannula may optionally include an additional lumen defined within the elongate shaft. The additional lumen can be a venting passageway.

In some configurations, the cannula may include a venting element. The venting element may comprise one or more filter elements that are arranged in a gases pathway, e.g., arranged within the venting pathway.

In some configurations, the cannula may include one or more heating elements disposed on or within the cannula.

In some configurations, the heating element can heat the pathway that delivers gases into the surgical cavity.

In some configurations, the heating element may also be in thermal communication with the venting pathway to heat vented gases or vented smoke in order to prevent condensation in the venting pathway.

In some configurations, the heating element may also be in thermal communication with the filter elements to prevent condensation in the filter.

In some configurations, disclosed herein is a surgical cannula for providing insufflation gases to a surgical cavity and providing a passage for insertion of one or more medical instruments, including one or more of the following: a cannula body including an inlet; and an elongate shaft extending from the cannula body, the shaft comprising a first lumen comprising a first lumen inlet and a first lumen outlet and configured to house a medical instrument therethrough, and a second lumen extending substantially parallel to the first lumen, the second lumen configured to provide the insufflation gases to the surgical cavity between a second lumen inlet and a second lumen outlet proximate a distal end of the elongate shaft.

In some configurations, the second lumen outlet can include a side-facing outlet such that gases flowing out of the second lumen outlet flow across a portion of the medical instrument to reduce or prevent fogging and/or condensation.

In some configurations, the second lumen outlet is oriented radially inwardly.

In some configurations, gases can flow across a distal end of the medical instrument once the medical instrument is partially removed from the first lumen.

In some configurations, gases can flow across a distal end of the medical instrument once the medical instrument is partially retracted from the outlet of the first lumen.

In some configurations, the second lumen can include an arcuate shape defined between a concentric inner wall and outer wall of the cannula.

In some configurations, the second lumen can, for example surround, and/or be concentric with the first lumen.

In some configurations, the second lumen outlet can be configured such that the insufflation gases exiting the second lumen outlet are directed across the portion of the medical instrument from all sides of the instrument, or directed across an end of the medical instrument.

In some configurations, the inner wall can include a plurality of apertures configured to allow the insufflation gases to enter the first lumen through the plurality of apertures.

In some configurations, the plurality of apertures can be sized and configured to allow the insufflation gases to flow radially inwardly with respect to the cannula.

In some configurations, the outer wall can include one or more apertures configured to allow the insufflation gases to exit into the surgical cavity.

In some configurations, the one or more medical instrument can be between 0 to 30 degrees off axis with respect to the first lumen.

In some configurations, disclosed herein is a surgical cannula for providing insufflation gases to a surgical cavity and providing a passage for insertion of one or more medical instruments, the cannula including one or more of the following: a cannula body including an inlet; and an elongate shaft extending from the cannula body, the shaft comprising a first lumen, a second lumen, and a third lumen. The first lumen can be configured to house a medical instrument therethrough. The second lumen can be configured to be connected to a source of dry gases. The third lumen can be configured to be connected to a source of humidified gases. The second lumen can include an outlet configured such that the dry gases flowing out of the second lumen outlet flow across a portion of the medical instrument when the medical instrument is inserted into the first lumen.

In some configurations, the second lumen can be positioned between the first lumen and the third lumen.

In some configurations, the third lumen can be isolated from the first lumen by the second lumen.

In some configurations, the second lumen can be configured to direct the dry gases about or across the medical instrument.

In some configurations, the second lumen can surround the first lumen such that the first lumen is nested within the second lumen.

In some configurations, the second lumen can be concentric with respect to the first lumen.

In some configurations, the second lumen can also be configured to direct the dry gases to form an envelope extending distally beyond an outlet of the first lumen and an outlet of the second lumen.

In some configurations, the envelope can be configured to maintain a controlled gases environment; and/or reduce fogging, clear fogging, and/or reduce smoke from contacting the medical instrument.

In some configurations, the envelope can be configured to reduce fogging, clear fogging, reduce condensation, reduce particulates, and/or reduce smoke from contacting the medical instrument.

In some configurations, the medical instrument can comprise a lens, wherein the envelope is configured to reduce fogging, clear fogging, reduce condensation, reduce particulates, and/or reduce smoke from entering a region near the lens.

In some configurations, the first lumen and the second lumen can be nested within the third lumen.

In some configurations, the first lumen, second lumen, and third lumen can be concentric with respect to each other.

In some configurations, the first lumen can have a smaller diameter than the second lumen.

In some configurations, the second lumen has a smaller diameter than the third lumen.

In some configurations, the second lumen can be configured to isolate humidified gases from the third lumen from the medical instrument.

In some configurations, the surgical cannula can also include a controller configured to deliver the dry gases as a continuous or substantially continuous and/or intermittent (e.g., cyclic) flow.

In some configurations, the medical instrument can be between 0 to 30 degrees off axis with respect to the first lumen.

Also disclosed herein is a method of directing a flow of gases onto a medical instrument within a body cavity. The method can include inserting a cannula into the body cavity; inserting a medical instrument through a first lumen of the cannula; flowing humidified insufflation gases through a second lumen of the cannula; and/or flowing dry gases through a third lumen of the cannula such that an envelope of dry gases is formed extending distally beyond an outlet of the first lumen and an outlet of the second lumen.

In some configurations, flowing dry gases through the third lumen occurs continuously or substantially continuously, or intermittently.

In some configurations, flowing dry gases can be sufficient to isolate humidified gases from the third lumen from the medical instrument, and/or reduce or clear fogging, and/or reduce smoke from contacting a distal end of the medical instrument.

In some configurations, the medical instrument can be between 0 to 30 degrees off axis with respect to the first lumen.

In some configurations, disclosed herein is a surgical cannula for providing insufflation gases to a surgical cavity and providing a passage for insertion of one or more medical instruments. The cannula can include a cannula body including an inlet; an elongate shaft extending from the cannula body, the shaft comprising a first wall and a second wall defining a first lumen therebetween, and a second lumen defined by an inner surface of the second wall.

In some configurations, the second wall can include a first diameter section and a distally spaced apart second diameter section.

In some configurations, the second diameter can be less than the first diameter.

In some configurations, the second diameter section can be configured to create a first flow restriction sufficient to create a Venturi effect sufficient to draw insufflation gases away from the second lumen.

In some configurations, the first lumen and second lumen are concentric with respect to each other.

In some configurations, the second lumen can be nested within the first lumen.

In some configurations, the first wall and the second wall can be continuous.

In some configurations, the surgical cannula can include a vent opening within the second wall adjacent the second diameter section.

In some configurations, the first wall can include a flow restriction configured to create another Venturi effect adjacent the flow restriction of the second wall.

In some configurations, the first flow restriction and the second flow restriction can have the same diameter and form a continuous flow restriction.

In some configurations, the one or more medical instruments can be between 0 to 30 degrees off axis with respect to the first lumen.

Also disclosed herein is a surgical cannula for providing insufflation gases to a surgical cavity and providing a passage for insertion of one or more medical instruments, the cannula including one or more of: a cannula body including a cavity; and an elongate shaft extending from the cannula body, the shaft defining a first wall defining a first lumen to receive insufflation gases to the surgical cavity, the lumen also configured to receive a medical instrument. The inner surface of the first wall can include one or more features causing turbulence within the insufflation gases flow, the turbulent flow reducing stagnation zones about the instrument.

Also disclosed herein is a surgical cannula for providing insufflation gases to a surgical cavity and providing a passage for insertion of one or more medical instruments, the cannula including one or more of: a cannula body including a cavity; and an elongate shaft extending from the cannula body, the shaft defining a first wall defining a first lumen to receive insufflation gases to the surgical cavity, the lumen also configured to receive a medical instrument. The inner surface of the first wall can include one or more features causing turbulence within the insufflation gases flow, the turbulent flow reducing flow non-uniformity about the instrument.

In some configurations, the features can include dimples.

In some configurations, the features can also include radially outward and/or inward extending surfaces configured to create the turbulent flow.

In some configurations, the shaft can also include a second wall, the first wall and the second wall concentric with respect to each other, and the first wall and the second wall defining a second lumen therebetween.

In some configurations, the second lumen can be an insufflation gases lumen helically wrapping around the second wall thereby creating a helical gases path.

In some configurations, the helical path can be configured to create a vortex flow out of the cannula.

In some configurations, the one or more medical instruments can be between 0 to 30 degrees off axis with respect to the first lumen.

Also disclosed herein is a surgical cannula for providing insufflation gases to a surgical cavity and providing a passage for insertion of one or more medical instruments, the cannula comprising one or more of: a cannula body including an inlet; an elongate shaft extending from the cannula body, the shaft comprising a lumen defined by a sidewall and configured to house the one or more medical instruments therethrough; and/or a vane comprising a continuous spirally-wound wall within the lumen, the vane extending substantially the entire axial length of the lumen and configured to direct gases in a vortex flow around the one or more medical instruments.

Also disclosed herein is a surgical cannula for providing insufflation gases to a surgical cavity and providing a passage for insertion of one or more medical instruments, the cannula comprising one or more of: a cannula body including an inlet; an elongate shaft extending from the cannula body, the shaft comprising a lumen defined by a sidewall and configured to house the one or more medical instruments therethrough; and/or a vane comprising a continuous spirally-wound wall within the lumen, the vane extending at least partially along an axial length of the lumen and configured to direct gases in a vortex flow around the one or more medical instruments.

In some configurations, the vane can be configured to restrict radial movement of the one or more medical instruments.

In some configurations, the vane can also be configured to direct gases in the vortex flow beyond an outlet of the lumen and create a zone of controlled temperature and humidity distal to a distal end of the cannula.

In some configurations, the vane can also be configured to direct gases in the vortex flow beyond an outlet of the lumen and create a zone of controlled temperature and humidity beyond a distal end of the cannula.

In some configurations, the one or more medical instruments can be between 0 to 30 degrees off axis with respect to the first lumen.

Also disclosed herein is a medical instrument retaining apparatus, including a body including a wall defining a lumen; and one or more ribs or fins extending from the wall. The medical instrument may be a surgical instrument. The body can include a tube that can be removably inserted into the lumen of a cannula. The retaining apparatus can include a first set of ribs and a second set of ribs. The first set of ribs can be spaced apart from the second set of ribs via a region of no ribs being located between the first and second set of ribs.

In some configurations, a cannula can include a heating element. The heating element can be integrated into a wall, positioned on an inner surface, or wrapped about the outside of the cannula.

In some configurations, the heating element could be, for example, heater wire, a conductive ink, discrete Positive Temperature Coefficient ("PTC") heaters, conductive plastic/polymer, or a flexible or rigid PCB. Optionally, the heating element can include an inductive heating element. Optionally, the heating element can include a chemical heating element, for example, including but not limited to silica beads. Optionally, the cannula can be pre-heated prior to insertion.

In some configurations, the heating element can extend a portion of the shaft of the cannula, such as the entire length of the cannula.

In some configurations, the heating element can be disposed in an upper region of the cannula adjacent the instrument inlet.

In some configurations, the heating element may be located within the cannula to heat the cannula lumen thereby increasing the dew point of the gases within the cannula.

In some configurations, a portion of the heating element or a second heating element may be positioned within the venting passage to prevent condensation in the venting passage. Furthermore, the heating element or another heating element may be arranged in contact with the filter to prevent condensation in the filter.

In some configurations, a cannula can also include one or more venting passageways defined within the cannula. For example, a cannula may include one, two, or more additional passageway/lumens that defines a venting passage to vent gases/smoke out of the surgical cavity.

In some configurations, the venting lumen could be, for example, concentric, offset, or sharing a common lumen with respect to a gas supply lumen and/or an instrument retaining lumen.

In some configurations, the cannula may optionally include a filter integrated into the cannula to filter gases delivered into the cannula.

In some configurations, the filter may also be arranged in fluid communication with the venting passage (if it is present) such that the vented gases/smoke is filtered.

In some configurations, the cannula can be configured to create a gases envelope or shroud created while the gases are delivered through the cannula while the instrument is retained concentrically. The gases envelope or shroud can form a protection zone and a region of controlled temperature and humidity, such as around and/or distal to the distal end of the cannula and/or distal end of the medical instrument.

Also disclosed herein is a surgical cannula including a body including an opening formed therein and a shaft extending from the body. The shaft including an outlet of the elongate shaft. The shaft defining a lumen therein. The lumen terminating at the outlet of the elongate shaft and the lumen positioned in fluid communication with the opening. The shaft and/or body comprising at least one guide element projecting from an inner surface or structure of the shaft and/or body. The at least one guide element can be configured to retain the instrument received within the lumen, such that the medical instrument does not come into physical contact with the inner surface of the shaft and/or body.

In some configurations, the body can comprise a first seal, wherein the first seal is configured to prevent insufflation gases from escaping when instrument is inserted or wherein the first seal is configured to prevent insufflation gases from escaping prior to inserting an instrument.

In some configurations, the body can comprise at least a first and second seal configured to prevent insufflation gases from escaping when instrument is inserted or configured to prevent insufflation gases from escaping prior to inserting an instrument.

In some configurations, the at least one guide element in the body can be proximal to the first seal.

In some configurations, the at least one guide element in the body can be distal to the second seal.

In some configurations, the at least one guide element in the body can be between the first and second seal.

In some configurations, the at least one guide element can be integrated with the first and/or second seal.

Also disclosed herein is a surgical cannula can comprise a body including an opening formed therein; and a shaft extending from the body, the shaft including an outlet of the elongate shaft, the shaft defining a lumen therein, the lumen terminating at the outlet, the lumen positioned in fluid communication with the opening. The body comprises a first sealing structure arranged to limit gas escape, and a second sealing structure to provide an instrument seal when a medical instrument is inserted into the lumen. The shaft and/or body can comprise at least one guide element projecting from an inner surface or structure of the shaft and/or body. The at least one guide element can be configured to retain the instrument received within the lumen, such that the medical instrument does not come into physical contact with the inner surface of the shaft.

In some configurations, the first sealing structure can be a seal configured to form a seal over the cannula when no medical instrument is present in the cannula.

In some configurations, the second sealing structure can be an instrument seal configured to form a seal around the medical instrument inserted through the cannula.

In some configurations, the at least one guide element in the body can be proximal to the first sealing structure.

In some configurations, the at least one guide element in the body can be distal to the second sealing structure.

In some configurations, the at least one guide element in the body can be between the first and second sealing structure.

In some configurations, the at least one guide element can be integrated with the first and/or second sealing structure.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure. In some cases, a "slice" has been shown for clarity purposes for some sectional and cross-sectional views of a three dimensional cannula. A person reasonably skilled in the art would be able to appreciate that these figures illustrate a slice of a three dimensional cannula. In some cases, the projection surfaces have not been shown for clarity. For example, projecting hole surfaces have not been shown in some views.

FIGS. 12A-12B illustrate longitudinal cross-sectional views of embodiments of a cannula configured to create a Venturi effect.

FIGS. 19A-B, 20A-B, 21A-B, and 22A-B illustrate a vertical cross-section of the cannula wall and a horizontal cross-section of the cannula shaft.

FIGS. 30A-30H illustrate views of embodiments of cannulas with flexible features at a proximal end and a distal end of the cannula to aid in concentricity of the medical instrument within the cannula.

FIGS. 31A-31H illustrate views of embodiments of cannulas with rigid features at a proximal end and a distal end of the cannula to aid in concentricity of the medical instrument within the cannula.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Example Medical Gases Delivery Systems

Fluids, for example, gases can be introduced to a surgical cavity, for example, the peritoneal cavity via a cannula inserted through an incision made in a patient's body (for example, the abdominal wall). The cannula can be coupled to an insufflator. The gases flow from the insufflator can be increased to inflate the surgical cavity (for example, to maintain a pneumoperitoneum, which is a cavity filled with gas within the abdomen). The introduced gases can inflate the surgical cavity. A medical instrument can be inserted through the cannula into the inflated surgical cavity. For example, an endoscope, another vision system, including but not limited to a scope, or a camera unit can be inserted into the cavity and visibility in the cavity can be assisted by insertion of fluid (gas or liquid), which can be air, carbon dioxide, saline, or any other suitable gas or liquid. In some cases, while the term gas or gases can be used to refer to the fluid that is inserted through the cannula and/or into the cavity as described herein, it is understood that any fluid, including any gas or liquid, can be used. After initial insufflation and insertion of the instrument (for example, a laparoscope) through the cannula, additional cannulas can be placed in the surgical cavity under laparoscopic observation. At the end of the operating procedure, all instruments and cannulas are removed from the surgical cavity, the gases are expelled, and each incision is closed. In some embodiments, the pressure within the surgical cavity is maintained to be substantially constant by the insufflator. The system can also include one or more vents to remove (e.g., vent out) smoke and gases from the cavity. The vent may in some cases include a tap that is manually activated by a medical professional. The insufflator may be controlled to compensate for reduction in pressure during venting, e.g., via controlling delivery of fresh insufflation gases into the cavity. For thoracoscopy, colonoscopy, sigmoidoscopy, gastroscopy, bronchoscopy, and/or others, the same or substantially similar procedure for introducing gases to a surgical cavity can be followed. The quantity and flow of gases can be controlled by the clinician performing the examination and/or automatically by the surgical system.

In some figures described herein, a slice of the cannula can be shown as opposed to a cross-section.

Figure 1:
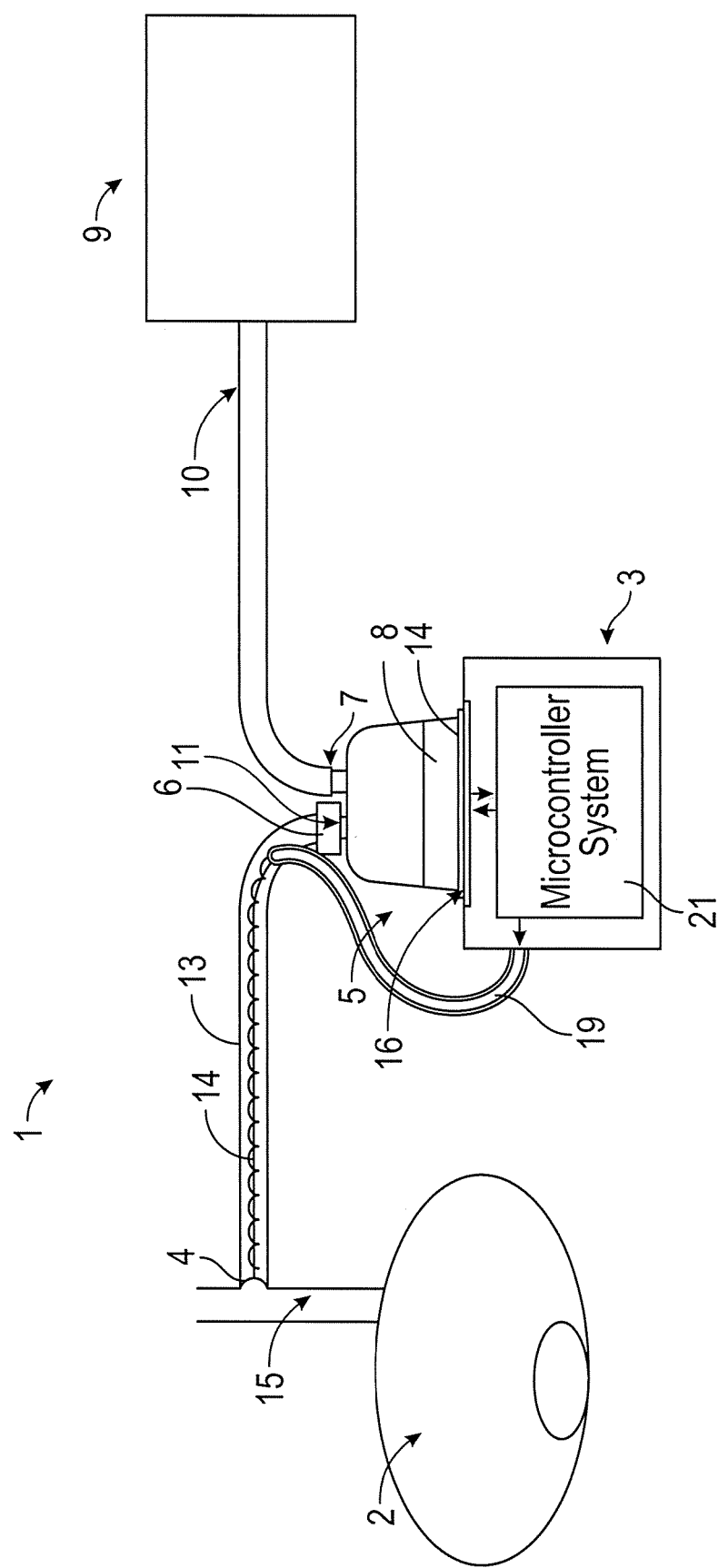
FIG. 1 illustrates schematically an example medical gases delivery apparatus in use in surgery.
Figure 2:
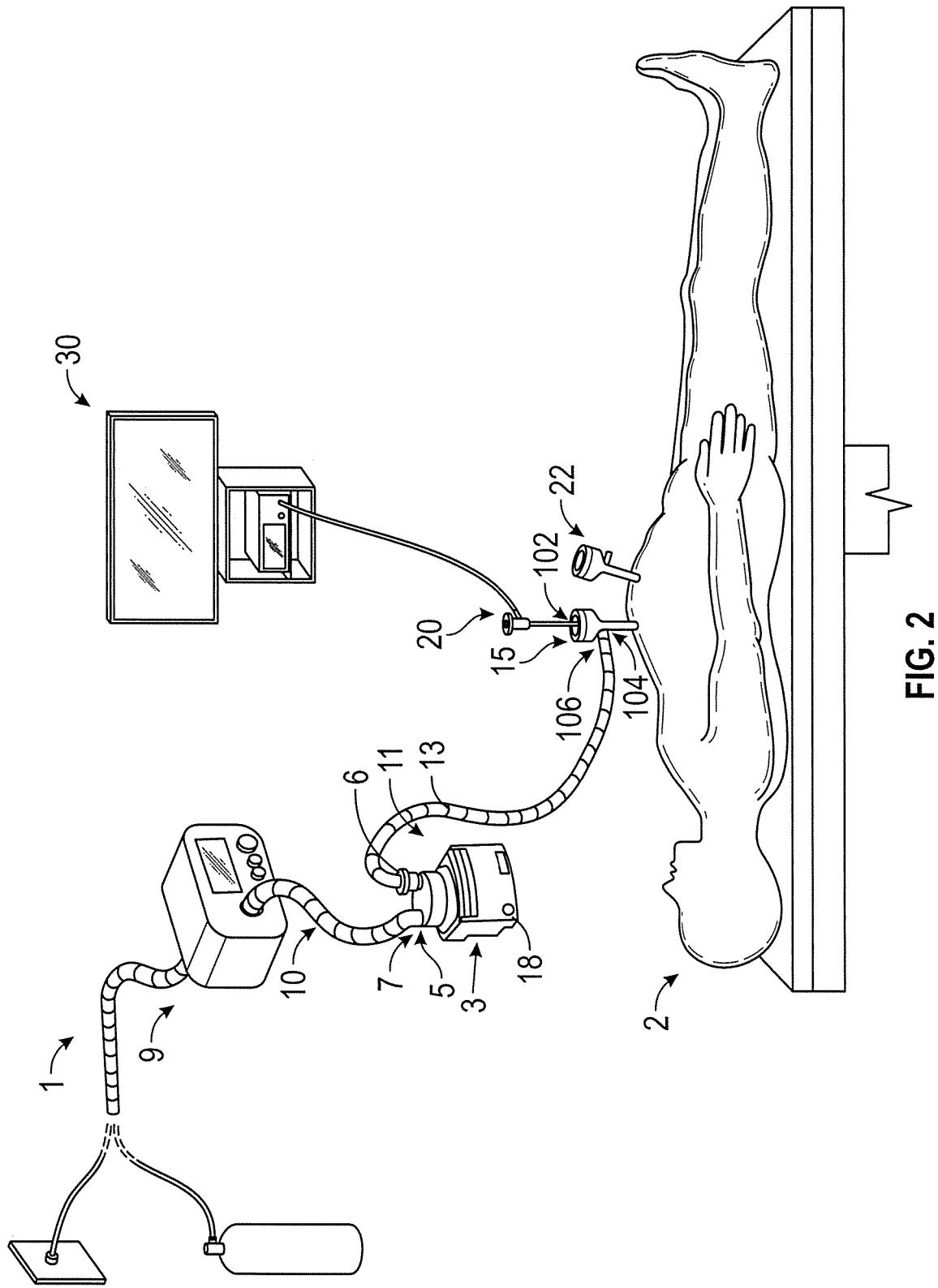
FIG. 2 illustrates schematically an example medical gases delivery apparatus.

FIGS. 1 and 2 illustrate schematically using an example surgical, for example, insufflation system 1 during a medical procedure. Features of FIGS. 1 and 2 can be incorporated into each other. The same features have the same reference numerals in FIGS. 1 and 2. As shown in FIG. 1, the patient 2 can have a cannula 15 inserted within a cavity of the patient 2 (for example, an abdomen of the patient 2 in the case of a laparoscopic surgery), as previously described.

As shown in FIGS. 1 and 2, the cannula 15 can be connected to a gases delivery conduit 13 (for example, via a Luer lock connector 4). The cannula 15 can be used to deliver gases into a surgical site, for example, within the cavity of the patient 2. The cannula 15 can include one or more passages to introduce gases and/or one or more medical instruments 20 into the surgical cavity. The medical instrument may be a surgical instrument. The medical instrument can be a scope, tool for electrocautery, electrosurgery, energy and laser cutting and/or cauterizing, among others, or any other instrument. The medical instrument 20 can be coupled to an imaging device 30, which can have a screen. The imaging device 30 can be part of a surgical system, which can include a plurality of surgical tools and/or apparatuses. While the application of fluids, for example gases, surrounding the medical instrument is described as important for visualization of the surgical area by a scope or other visualization device, the application of fluids as described herein can be used in applications such as electrocautery tools, graspers, and other instruments.

The system can also optionally include a venting cannula 22, which can have substantially the same features as the cannula 15. The venting cannula may include a valve that allows venting. The valve can be automatically controlled by a controller associated with the gases source (e.g., insufflator), humidifier, or other independent controller of the system. The valve can also be manually actuated (for example, by turning a tap by hand or by a foot pedal, or otherwise). The venting cannula 22 can be coupled to a filtration system to filter out smoke and the like. The venting cannula 22 can also alternatively be coupled to a recirculation system that is configured to recirculate the gases from the surgical cavity back to the insufflator for re-delivery into the surgical cavity. The gases can be filtered and/or dehumidified prior to being returned to the insufflator. Alternatively, the system may include a venting attachment configured to be removably coupled to a standard cannula. The venting attachment may include one or more passages that are in fluid communication with the surgical cavity. The venting attachment may include one or more filter elements to filter smoke and other gases from the surgical cavity prior to venting into atmosphere. The venting attachment may be coupled to the outer side of the cannula or inserted into the cannula or may surround a portion of the cannula.

The gases delivery conduit 13 can be made of a flexible plastic and can be connected to a humidifier chamber 5. The humidifier chamber 5 can optionally or preferably be in serial connection to a gases supply 9 via a further conduit 10. The gases supply or gases source can be an insufflator, bottled gases, or a wall gases source. The gases supply 9 can provide the gases without humidification and/or heating. A filter 6 can be connected downstream of the humidifier's outlet 11 or upstream of the humidifier inlet. The filter can also be located along the further conduit 10, or at an inlet of the cannula 15. The filter can be configured to filter out pathogens and particulate matter in order to reduce infection or contamination of the surgical site from the humidifier or gases source. The gases supply can provide a continuous or intermittent (e.g., cyclic) flow of gases. The further conduit 10 can also preferably be made of flexible plastic tubing.

The gases supply 9 can provide one or more insufflation fluids including liquids and/or gases, for example carbon dioxide, to the humidifier chamber 5. The gases can be humidified as they are passed through the humidifier chamber 5, which can contain a volume of humidification fluid 8, such as water. The gases can be dry cold gas, dry hot gas, humidified gas, or otherwise. Optionally, the gases supply 9 can include two gas sources.

Any type of humidifier can be configured to incorporate the humidifier chamber 5. The humidifier chamber 5 can include plastic formed chamber having a metal or otherwise conductive base 14 sealed thereto. The base can be in contact with the heater plate 16 during use. The volume of water 8 contained in the chamber 5 can be heated by a heater plate 16, which can be under the control of a controller or control means 21 of the humidifier. The volume of humidification fluid, for example, water 8 within the chamber 5 can be heated such that it evaporates, mixing water vapor or other humidification fluids with the gases flowing through the chamber 5 to heat and humidify the gases. The illustrated humidifier is a warm passover humidifier. The warm passover humidifier can be adapted to humidify gases by heating a humidification fluid (e.g. water) within a chamber and passing the gases over the heated humidification fluid. The gases become humidified as the gases pass over the heated humidification fluid.

The controller or control means 21 can be housed in a humidifier base unit 3, which can also house the heater plate 16. The heater plate 16 can have an electric heating element therein or in thermal contact therewith. One or more insulation layers can be located between in the heater plate 16 and the heater element. The heater element can be a base element (or a former) with a wire wound around the base element. The wire can be a nichrome wire (or a nickel-chrome wire). The heater element can also include a multilayer substrate with heating tracks electrodeposited thereon or etched therein. The controller or control means 21 can include electronic circuitry, which can include a microprocessor for controlling the supply of energy to the heating element. The humidifier base unit 3 and/or the heater plate 16 can be removably engageable with the humidifier chamber 5. The humidifier chamber 5 can also alternatively or additionally include an integral heater. Alternatively, the controller or control means 21 can be housed or partially housed external to the humidifier base unit 3.

The heater plate 16 can include a first temperature sensor, for example, a temperature transducer or otherwise, which can be in electrical connection with the controller 21. The heater plate temperature sensor can be located within the humidifier base unit 3. The controller 21 can monitor the temperature of the heater plate 16, which can approximate a temperature of the water 8.

In some embodiments, the system can optionally include a further, e.g., second temperature sensor located at the outlet 11 of the chamber 5. Further, additional sensors can also be present configured to monitor temperature and/or other parameters (e.g., humidity, flow, gas concentration, and other parameters), including a patient end sensor. The patient end sensor can be located adjacent the cannula, within the cannula, or within a connector of the cannula, for example. The patient end temperature sensor and the chamber outlet temperature sensor can be configured to be in electronic communication with the controller. The controller may be configured to control the heater plate and/or heater wire energization based on the sensor values.

The gases can exit out through the humidifier's outlet 11 and into the gases delivery conduit 13. The gases can move through the gases delivery conduit 13 into the surgical cavity of the patient 2 via the cannula 15, thereby inflating and maintaining the pressure within the cavity. The gases delivery conduit 13 can be made of plastic or other suitable materials. Preferably, the gases leaving the outlet 11 of the humidifier chamber 5 can have a relative humidity up to 100%, for example at around 100%, or a therapeutic effective level of humidity. As the gases travel along the gases delivery conduit 13, further condensation and/or fogging can occur so that water vapor can condense on a wall of the gases delivery conduit 13. Further condensation and/or fogging can have undesirable effects, for example, detrimentally reducing the water content of the gases delivered to the patient. In order to reduce and/or minimize the occurrence of condensation within the gases delivery conduit 13, a heater wire 14 can be provided within, throughout, or around the gases delivery conduit 13. The heater wire 14 can be electronically connected to the humidifier base unit 3, for example by an electrical cable 19 to power the heater wire.

Condensation can occur on various surfaces on a medical instrument. When condensation forms on a viewing surface of a medical instrument, this is observed as a fogging effect which manifests as an impairment of visibility through a lens or any other viewing surface of a medical instrument (such as, for example, a mirror or transparent or translucent window). When condensation forms on various surfaces of a medical instrument, the condensation can coalesce into water droplets. This can occur directly on the viewing surface or other surfaces which can then migrate to or be deposited on the viewing surface. Accordingly, as used herein condensation and/or fogging means condensation generally and in some instances, specifically with respect to condensation on a viewing surface (i.e. fogging).

The heater wire 14 can include an insulated copper alloy or nichrome resistance wire, other types of resistance wire, or other heater element, and/or be made of any other appropriate material. The heater wire can be a straight wire or a helically wound element. An electrical circuit including the heater wire 14 can be located within walls of the gases delivery tube 13. The gases delivery tube 13 can be a spiral wound tube. The heater wire 14 can be spirally wound around an insulating core of the gases delivery conduit 13. The insulating coating around the heater wire 14 can include a thermoplastics material which, when heated to a predetermined temperature, can enter a state in which its shape can be altered and the new shape can be substantially elastically retained upon cooling. The heater wire 14 can be wound in a single or double helix. Measurements by the temperature sensor and/or the additional sensor(s) at the patient end of the conduit 13 can provide feedback to the controller 21 so that the controller 21 can optionally energize the heater wire to increases and/or maintain the temperature of the gases within the gases delivery conduit 13 (for example, above or below internal body temperature of about 37° C., such as, for example, 1° C., 2° C., 3° C., 4° C., 5° C., 6° C., 7° C., 8° C., 9° C., 10° C., or 15° C. or more or less above or below internal body temperature for example, or ranges including any two of the foregoing values).

The controller or control means 21 can, for example, include the microprocessor or logic circuit with associated memory or storage means, which can hold a software program. When executed by the control means 21, the software can control the operation of the system 1 in accordance with instructions set in the software and/or in response to external inputs. For example, the controller or control means 21 can be provided with input from the heater plate 16 so that the controller or control means 21 can be provided with information on the temperature and/or power usage of the heater plate 16. The controller or control means 21 can be provided with inputs of temperature of the gases flow. For example, the temperature sensor can provide input to indicate the temperature of the humidified gases flow as the gases leave the outlet 11 of the humidifier chamber 5. A flow sensor can also be provided in the same position as or near the temperature sensor or at other appropriate location within the system 1. The controller 21 can control a flow regulator which regulates the flow rate of gases through the system 1. The regulator can include a flow inducer and/or inhibiter such as a motorized fan or pump. Valves and/or vents can additionally or alternatively be used to control the gases flow rate.

A patient input 18 located on the humidifier base unit 3 can allow a user (such as a surgeon or nurse) to set a desired gases temperature and/or gases humidity level to be delivered. Other functions can also optionally be controlled by the user input 18, such as control of the heating delivered by the heater wire 14. The controller 21 can control the system 1, and in particular to control the flow rate, temperature, and/or humidity of gas delivered to the patient, to be appropriate for the type of medical procedure for which the system 1 is being used.

The humidifier base unit 3 can also include a display for displaying to the user the characteristics of the gas flow being delivered to the patient 2.

Although not shown, the humidifier can also optionally be a passover humidifier, which can include the chamber with a volume of water, but may not include a heater plate for heating the water. The chamber can be in fluid communication with the gases supply such that the insufflation gases are humidified by water vapor wicked or evaporated from the volume of water as the insufflation gases pass over the volume of water.

When in use, the humidifiers described above can be located outside an "operating sterile zone" and/or adjacent the insufflator. As a result, the medical personnel would not be required to touch the humidifier when moving the cannula during the operation to maneuver the surgical instruments within the surgical cavity. The humidifier may not need to be sterilized to the same extent as the medical instruments. Furthermore, the humidifier being located outside the "operating sterile zone" can reduce obstructions to the medical personnel during the operating procedure that may restrict movements of the medical personnel and/or the medical instruments in the already crowded space. As described herein, a proximal direction with respect to a cannula generally can refer to the top end of the cannula body, while a distal direction with respect to a cannula generally can refer to the bottom end of the cannula shaft configured to be the first section of the cannula inserted into the surgical cavity. More detailed examples of the directed gases flow cannulas are described below. As described herein, a proximal direction with respect to a medical instrument generally can refer to the top end of the medical instrument body, while a distal direction with respect to a medical instrument generally can refer to the bottom end of the medical instrument body configured to be the first section of the medical instrument inserted into the cannula and/or surgical cavity. Reference numerals of the same or substantially the same features may share the same last two digits.

Examples of Directed Gases Flow Cannulas

Condensation and/or fogging occurs when the temperature of a gas falls below the dew point temperature for the level of humidity the gas is carrying, and/or if there are surfaces significantly below the dew-point temperature. In FIGS. 1 and 2, as the insufflation gases travel from the gas delivery conduit 13 into the cannula 15, the heated and humidified gases can cool down to be closer to the dew point within the cannula 15 if the cannula 15 is not heated. Further, one or more medical instruments, such as cameras and/or surgical scopes, which are at a temperature lower than the human body, can be inserted into the surgical cavity via the cannula 15. The humidified gases can thus condense as fog on the lens, and/or as droplets of water on the surgical scope, which can drip down onto the lens area. The fog and/or droplets can impede vision, such as vision of a surgeon or other medical personnel participating in the surgery. Removal of the medical instruments to wipe off the fog and/or droplets can slow down the surgical procedure and/or result in rain out recurring upon reinserting the medical instruments, which would have cooled down when removed from the surgical cavity.

The present disclosure provides examples of a cannula (e.g., a surgical cannula), which can be used as the cannula 15 disclosed herein, and which includes directed gases flow for reducing, preventing, and/or removing condensation and/or fogging of the medical instruments without requiring additional components or tools. The example directed gases flow cannulas disclosed herein can be implemented into existing surgical, for example, insufflation systems without requiring customized and/or more expensive systems. The example directed gases flow cannulas disclosed herein can therefore improve optical clarity of the lens and/or maintain a clear field of vision, which can aid in minimizing operation time and post-operation complications (for example, pain, adhesions, and/or others), and/or can make it easier for the medical personnel, such as the surgeon, in navigating the cannula during the medical procedure. Directed gas flow helps to prevent condensation from forming by affecting the zone around the scope lens, manipulating flows, temperatures, and/or humidity. This can advantageously have the effect of keeping the scope lens (or sensor, or other desired element) temperature above the dew point of the gas in the zone adjacent to the scope lens. A directed gases flow cannula can also help to prevent smoke particles, condensate, and/or other debris from depositing on the instrument, e.g., on the lens of a scope. The cannula can be single use (disposable) or reusable. Alternatively, parts of the cannula can be single use (disposable) or reusable. The cannula may be made of materials that are biocompatible and/or sterilizable. In the present disclosure, features of the different examples of heated cannulas can be incorporated into or combined with one another.

The example directed gases flow cannulas can have any of the features of the cannula 15. For example, the directed gases flow cannula can have a cannula body 102 connected to an elongate shaft 104. The elongate shaft 104 can optionally have a pointed end for easier insertion of the cannula 100 into the surgical cavity. In some cases, the elongate shaft 104 of the cannula can be utilized in combination with an obturator to function as a trocar. A trocar can include a cannula and an obturator. The cannula body 102 can have a guiding feature to aid insertion of the medical instruments into the cannula. As used herein, a guiding element, guiding feature, guide element, and/or guide feature can be used interchangeably herein to refer to a feature used to aid insertion or provide support for a medical instrument within a cannula.

As shown in FIG. 2, the cannula body 102 can have generally a funnel shape, with a cross-sectional dimension (for example, diameter) decreasing from a location further from the elongate shaft 104 to a location closer to the elongate shaft 104. A gases inlet 106 can be located on the cannula body 102. The cannula body 102 can include a cavity. The elongate shaft 104 can include a hollow passage. The cavity and the hollow passage can be in fluid communication. The directed gases flow cannula can optionally include a heating element releasably coupled to (for example, via a sleeve) or integrated into the directed gases flow cannula (for example, in at least a portion of the cannula body 102 and/or a portion of the elongate shaft 104). The heating element may be positioned in any desired location, e.g., inside the shaft, integrated in the wall, or wrapped around the outside of the shaft. The heating element can increase the temperature of the cannula, and therefore also increase the temperature of gases as the gases travels through the cannula. Heating the gases can reduce and/or prevent condensation since the cannula has an increased temperature and can maintain the temperature of the gases above the dew point. The directed gases flow cannula can also include a filter module that is removably coupled to or integrated with the cannula (for example, located proximally in the cannula body 102 or a sleeve attached (described below), or coupled to the cannula via a tube). The heating element can be arranged to be in contact with or extend through the filter module. Cannulas as disclosed herein could include, for example, angled (beveled) or square (flat) distal ends.

A surgical, for example, insufflation system for supplying insufflation gases to a surgical cavity, such as any surgical, for example, insufflation systems disclosed herein, can incorporate any of the example directed gases flow cannulas disclosed herein. As described above, the system can include a gases supply configured to provide the insufflation gases, a humidifier in fluid communication with the gases supply and configured to humidify the insufflation gases received from the gases supply, and a gases delivery tube extending between and in fluid communication with the humidifier and the cannula, respectively. The gases delivery tube can also be in electrical communication with the humidifier and the cannula, respectively. When the system is in use, the gases delivery tube can direct the insufflation gases into the surgical cannula and can also direct an electrical current from the humidifier to the heating element within the cannula. The heating element can be configured to transfer heat to the insufflation gases passing through the cannula, and/or a portion of the medical instrument inserted into and/or removed from the cannula, to raise the temperature of the gases and/or the instrument so as to reduce and/or prevent condensation. The temperature of the insufflation gases and/or the instrument can be increased above a dew point to prevent condensation of the gases and/or reduce and/or prevent condensation (and/or remove by evaporation condensation already formed) on the medical instrument. The temperature of the insufflation gases and/or the instrument (for example, on or near an optical elements such as a lens, or other area of the instrument) can also be measured, for example, with thermocouples and/or other sensors, and closed loop feedback can be provided to a controller to maintain the temperature proximate the instrument at or above a predetermined or calculated value, for example, the dew point. In some embodiments, the system may optionally include one or more humidity sensors. The humidity sensors can provide feedback information to a controller which in turn controls the heating element, e.g., the heater plate or heater wire in the tube to keep the humidity within desired parameters, e.g., a preset range.

During laparoscopic surgery, there will generally be some form of electrosurgery/electrocautery/ultrasonic or laser device surgery to cause cutting or coagulation within the insufflated cavity. This produces surgical smoke which can increase in concentration over time in the sealed and pressurized peritoneum or other cavity, especially when there are no significant gas leaks or suction/irrigation. A high concentration of smoke in the insufflated cavity, and in the field of vision can severely impede the optical clarity when viewing the space inside the peritoneum through a camera or lens inserted through a cannula. Without the use of venting or suction, surgeons generally have no option but to release all or a portion of the gas from inside the pneumoperitoneum through deflation, then re-insufflate. A smoke plume can be generated, for example, due to electrocautery. The smoke plume can move toward the scope/lens and reduce visibility for the surgeon.

Directed gas flow can advantageously mitigate the effect of concentrated smoke in the insufflated cavity by eliminating non-uniformity of gas flow around the scope. This helps to push the smoke away from the scope and direct line of sight which improves the surgeon's field of vision. The directed gases flow cannula can prevent the smoke plume contacting the medical instrument due to the smoke plume being pushed away.

Figure 3A:
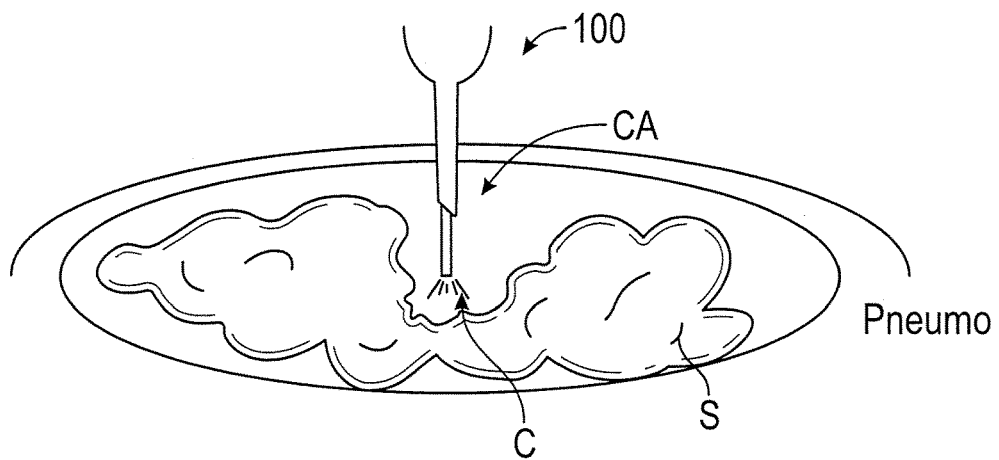
FIGS. 3A-3C illustrate schematic views of an embodiment of a cannula configured to direct flow of gases within a surgical cavity.
Figure 3B:
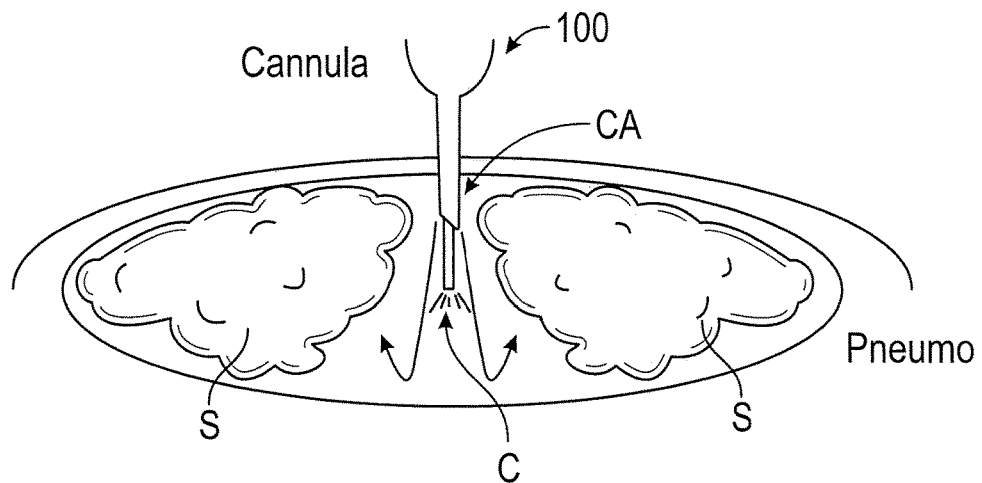
Figure 3C:
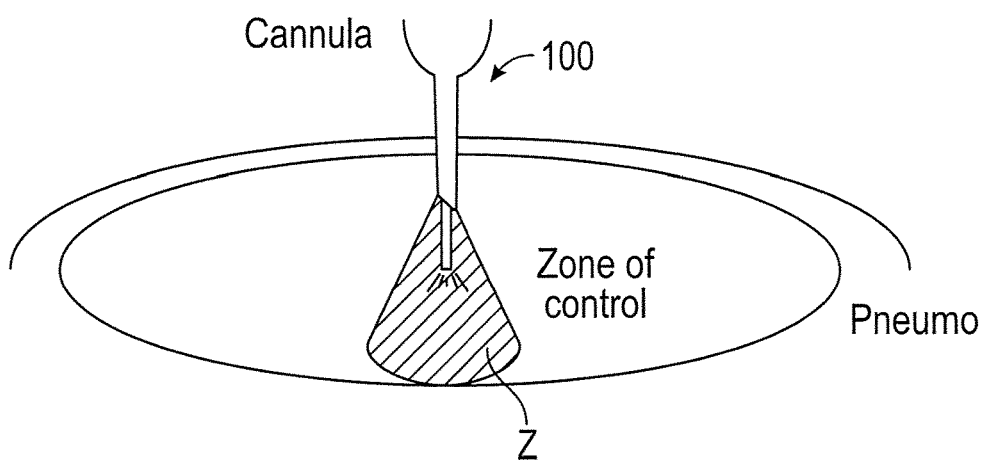
Figure 3D:
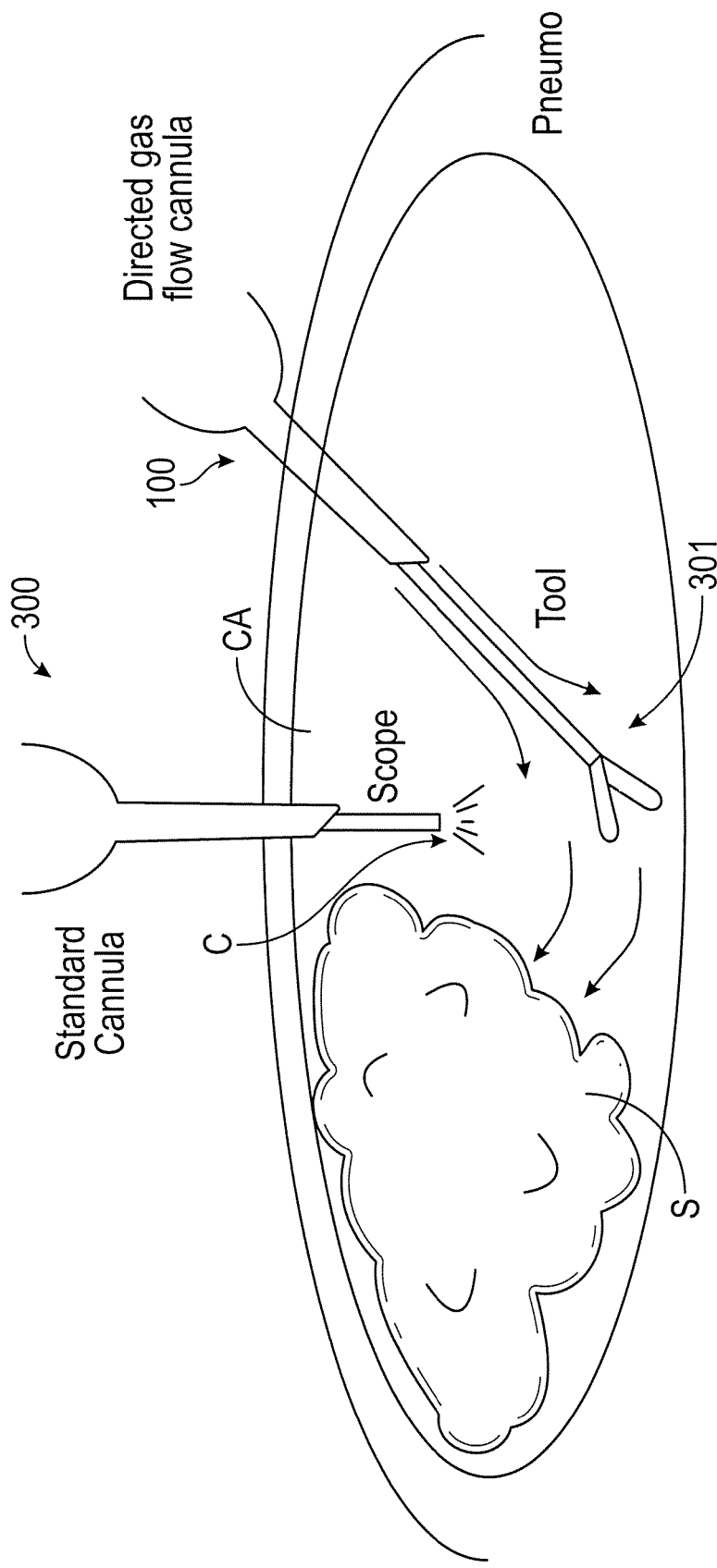

FIG. 3A schematically illustrates a surgical cavity with a cannula 100 inside an insufflated cavity CA within the pneumoperitoneum with a scope lens C on the distal end of the scope inserted through the cannula 100. Also shown is surgical smoke S surrounding the scope lens C. FIG. 3B schematically illustrates the surgical cavity scenario of FIG. 3A with directed gas flow as shown by arrows, moving the smoke S away from the scope lens C. As illustrated, the instrument can be held concentric and the gases are directed to be substantially concentric and coaxial with the instrument. The gases extend around the scope as they travel through the cannula 100 and along the scope. FIG. 3C illustrates schematically that the cannula can include one, two, or more features as described elsewhere herein to create a zone of control Z that can advantageously reduce or prevent smoke, condensation, or other unwanted media from contacting a target section of the medical instrument. In other words, in some cases a gas barrier or envelope, also referred to herein as a gases shroud, gases sheath, protection zone, or region of controlled temperature and humidity, can be created via the directed gases flow cannula, such that gases flow from an opening, through a lumen of the cannula, and through an outlet. FIG. 3D schematically illustrates the surgical cavity scenario similar to that of FIGS. 3A-3C. FIG. 3D illustrates a directed gases flow cannula 100 used in combination with a second cannula 300. In some cases, a first medical instrument can include a scope lens C and can be inserted through the second cannula 300 and the directed gases flow can be introduced through the directed gases flow cannula 100. As illustrated in FIG. 3D, the directed gases flow cannula 100 can provide directed gas flow, as shown by arrows, within the insufflated cavity CA and the directed gas flow can move the smoke S away from the scope lens C inserted through the second cannula 300. In some cases, the directed gases flow cannula 100 can also support a second medical instrument 301 that can be inserted through the directed gases flow cannula 100 as illustrated in FIG. 3D.

The directed gases flow cannula can be configured to create a gases envelope extending distally beyond the end of the medical instrument, and/or onto or past a portion of the medical instrument, such as an endoscope lens, sensor, or other element for example. The gases envelope formed could have any number of potential advantages, including but not limited to maintaining the temperature of the instrument above a dew point; preventing or reducing fogging and/or condensation forming on the instrument; reducing or preventing smoke, debris or other unwanted media from contacting the instrument or directing the smoke, debris or other unwanted media away from the instrument and/or an outlet of a lumen such that a gas envelop disperses the smoke plume; substantially surrounding a portion of the instrument (or substantially the entire instrument portion positioned within the surgical cavity and/or the cannula shaft); concentrically surrounding the instrument inside the shaft and/or distally beyond the outlet of the shaft; extending a predetermined or calculated distance in a desired direction beyond the outlet; and/or maintaining a temperature, humidity, and/or pressure controlled environment about the shaft (e.g., distal end of the shaft) and outlet of the elongate shaft, such as maintaining the temperature in the envelope above a dew point.

The flow separates and diverges from the scope surface at some distance from the outlet of the cannula. This distance and jet divergence angles do not necessarily depend significantly on scope insertion depth. The distance at which the flow separates and diverges from the scope surface decreases with increasing flow rate. In some embodiments, the gases envelope can be controlled to extend to about, no more than about, or at least about 10 mm, 25 mm, 50 mm, 75 mm, or 100 mm, or more or less past the distal end of a medical instrument and/or luminal outlet, or ranges including any two of the foregoing values. In some configurations, the gases envelope can extend beyond between about 10 mm and about 100 mm past the distal end of a medical instrument and/or luminal outlet. In some configurations, the gases envelope can extend no more than about 100 mm past the distal end of a medical instrument and/or luminal outlet. The distance the envelope extends can be based on the flow rate of gases delivered.

The surgical, for example, insufflation system can be configured to deliver intermittent (e.g., cyclic) and/or constant flow of gases. In some embodiments, a constant flow provides a more stable envelope, however intermittent/cyclic flow also allows for an envelope being formed to de-fog the scope. The flow rate of the gases delivered can be sufficient to maintain a pressurized surgical cavity. The flow rate can be, for example, at least about 2 liters per minute (1 pm). In one example the flow rate provided is at least about 6 1 pm. In one example the flow rate provided is at least about 7 1 pm. In another example the flow rate is at least about 10 1 pm or between about 10 1 pm and about 12 1 pm, or about, at least about, or no more than about 2, 4, 6, 8, 10, 12, 14, 16, 20, 30, 40, 50, 60, or more or less 1 pm, or ranges incorporating any two of the foregoing values. The flow rates can be any suitable flow rate. In one example the flow rate can be as high as between about 40 L/min to about 50 L/min, or more. Further the flow limit is based on the pressure in the surgical cavity. The pressure in the surgical cavity can be defined in regulatory standards, e.g. established clinical practice, and for example can be up to about 50 mmHg in some cases. The example flow rates listed above can be continuous flow rates. If an intermittent flow rate is delivered, the flow rate can vary between an upper and a lower value, including values listed for continuous flow rates. The concentric arrangement of the instrument can ensure that the insufflation gases are maintained in contact with the instrument, e.g. a lens of a scope. This contact also allows for defogging of the instrument. In general, increasing the flow rate of the insufflation gases can reduce the required defogging time. Cold dry gas provided to the cannula while the instrument is held concentric can also help to defog the lens. The defogging can be improved with warming of gases. This can be achieved using a humidifier such as the SH870 humidifier from Fisher & Paykel Healthcare (Auckland, NZ) which can further humidify the gases. Humidifying the gases has advantages of reducing cell/tissue damage. A larger flow rate provides an increased distance such that the envelope covers the scope as the scope is inserted beyond the cannula. The distance between the end of the shaft and the distal end of the scope can be referred to as the insertion depth. The insertion depth can be, for example, between about 20 mm and about 100 mm. The insertion depth can be, for example, up to about 80 mm. The defogging time may increase as the insertion depth extends beyond a threshold distance, such as for example 100 mm in some cases. The flow rate from the flow generator, e.g., insufflator, can be controlled to vary the length of the envelope. The flow may be controlled at the insufflator or there may be a flow control device positioned in the gases path or the humidifier may include a device or structures to control the flow rate delivered to the cannula.

Flow non-uniformity (which may also be referred to herein as stagnation zones) along the medical instrument can reduce the effectiveness of the protection envelope/protection zone. Flow non-uniformity can also prevent the envelope from forming. Features as disclosed herein, such as directed gas flow vanes among others can be particularly useful in a cannula with a pointed end. A cannula with a pointed end is particularly susceptible to a flow non-uniformity due to one portion or one side of the cannula end being elongated. Positioning a vane or series of vanes on the longer portion can help to reduce the flow non-uniformity or prevent the flow non-uniformity from being created. Flow non-uniformity can be created when the medical instrument, such as a scope, rests against a wall at the outlet of the cannula. The scope resting against the wall prevents flow surrounding the scope, which causes a flow non-uniformity beyond the outlet of the cannula.

More detailed examples of the directed gases flow cannula features are described below with reference to FIGS. 4A-16.

Examples of a Directed Gases Flow Cannula Shaft

Figures 4A, 4B:
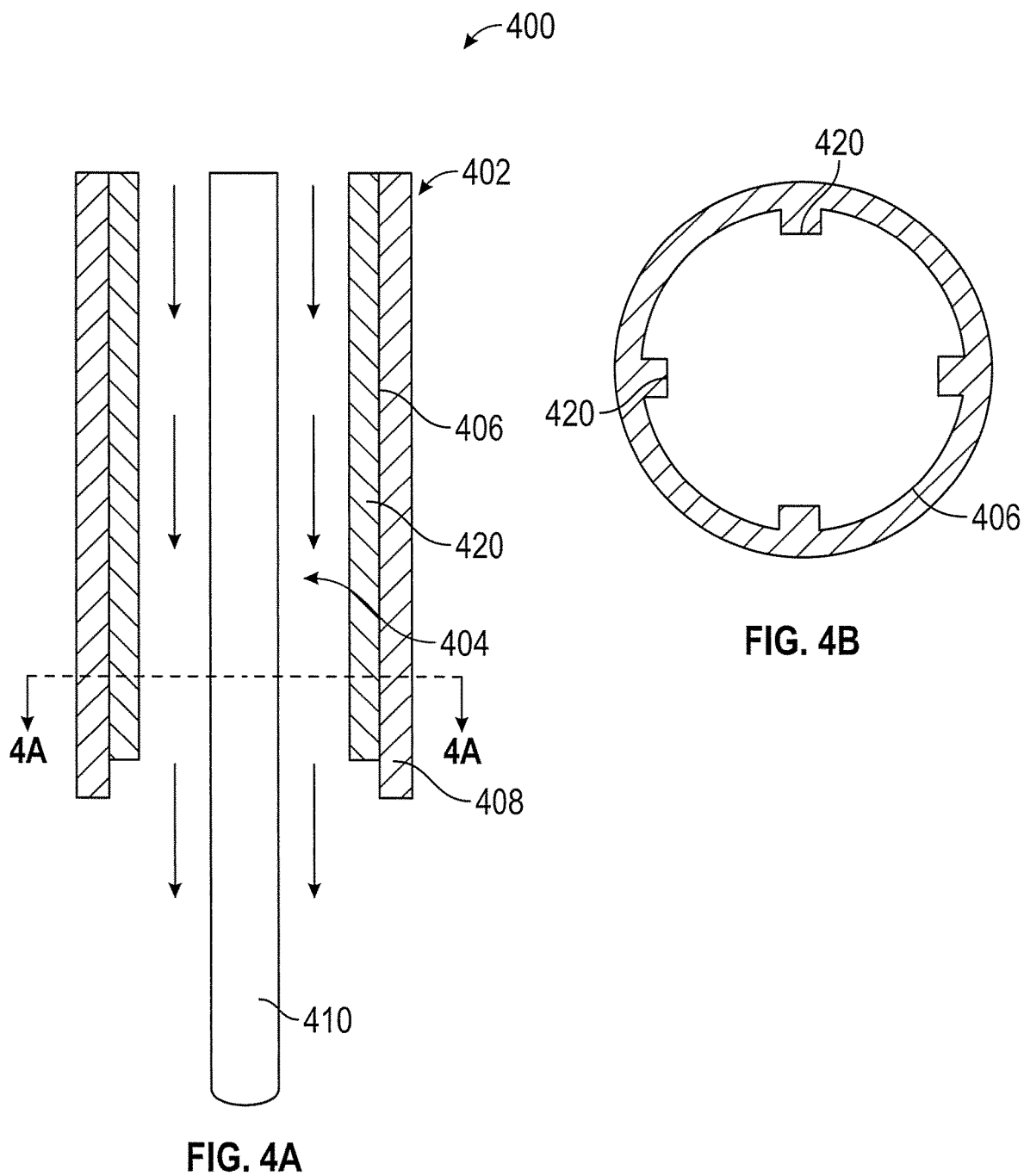
FIGS. 4A-4C illustrate various views of an embodiment of a cannula with a directed gas flow lumen and a medical instrument guide element.
Figure 4C:
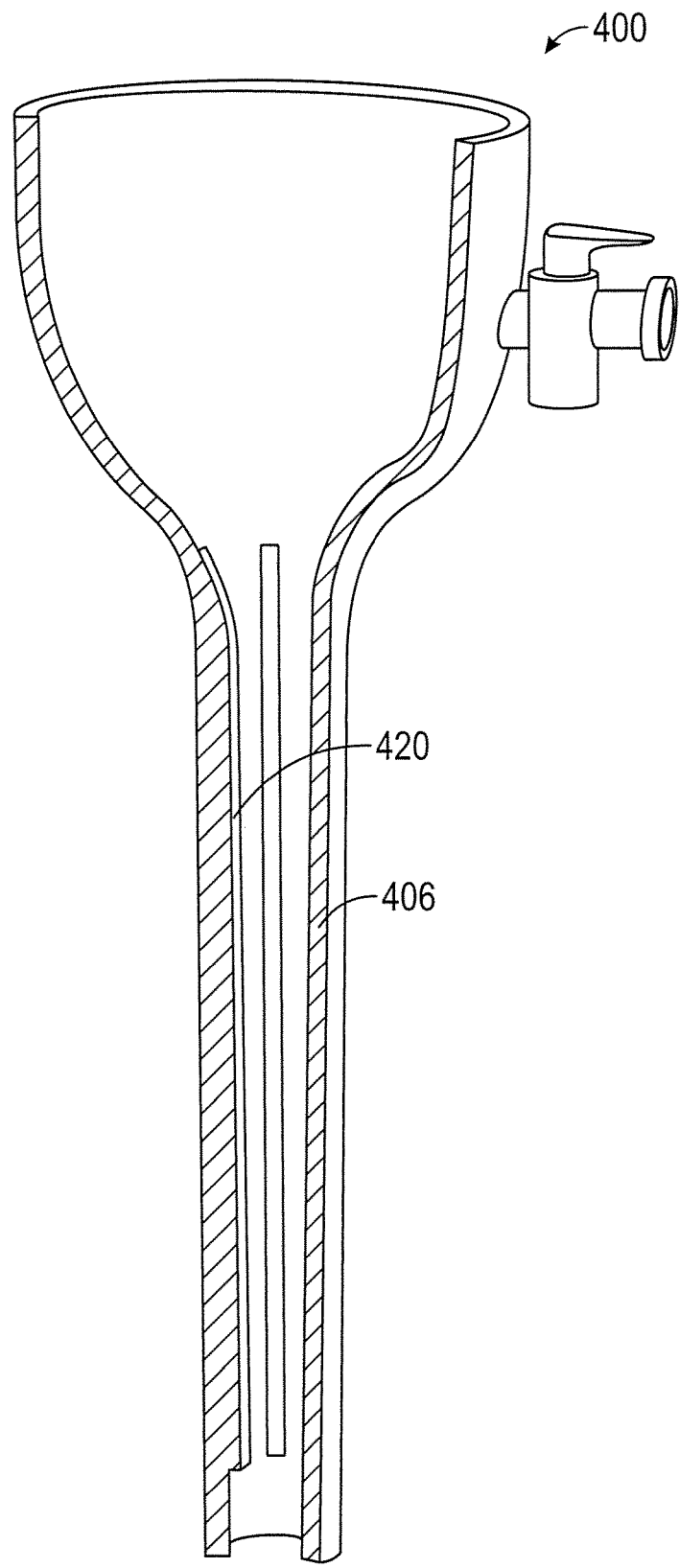

FIGS. 4A-16 illustrate examples of a cannula with one, two, or more lumens configured to direct gas flow within a cannula shaft and/or around or beyond the cannula. As shown in FIGS. 4A-4C, the cannula 400 can include a cannula body (not shown) with a distal end integrally formed or operably connected to a proximal end of a cannula elongate shaft 402. One, two, or more lumens can be present in both the cannula body and the cannula elongate shaft 402, e.g., central lumen 404. The one, two, or more lumens can extend from and be in fluid communication with an opening (not shown) to one, two, or more outlets (e.g., at or near distal end 408 of the cannula shaft 402). A lumen 404 can be defined by a sidewall, such as inner sidewall 406 of the cannula shaft 402 (as well as the cannula body). Also shown is a medical instrument 410, such as an endoscope or camera or other scope device, for example, including an elongate shaft of the medical instrument extending within the lumen 404 of the cannula shaft 402. A free end 408 at the outlet of the cannula elongate shaft 402 can optionally have a pointed (or otherwise sharp) end 408, or a square end or any other geometry. The cannula body or elongate shaft 402 can include a gases inlet port (not shown) coupled to a wall (e.g., outer wall) of the cannula 400. The gases inlet port can be connected to a gases delivery tube of a surgical, for example, insufflation system (such as any of the systems disclosed herein, for example).

FIG. 4B is a cross-section through line 4A-4A of FIG. 4A without the medical instrument 410 shown in the lumen. As shown in FIG. 4B, the interior sidewall 406 of the cannula shaft 402 can include a medical instrument guide element 420 configured to retain the medical instrument within the lumen and/or encourage concentricity of the medical instrument with the lumen 404 of the cannula shaft 402 to prevent the medical instrument from contacting the sidewall of the lumen.

In some embodiments, the medical instrument guide element can include radially spaced-apart ribs and/or fins 420 extending inward from the cannula shaft 402 into the lumen 404. The ribs and/or fins 420 can be oriented generally along the longitudinal axis of the cannula shaft 402 as shown in FIG. 4B, or angled in other embodiments. The fins 420, ribs, or other structures can extend generally along part of or the entire axial length of the cannula body 402. The fins 420 can be configured to contact the medical instrument to grasp the instrument substantially concentrically within the lumen 404. In some embodiments, the fins 420, ribs, or other structures need not necessarily contact the medical instrument while in use, but can act as radial limits or stops, such that the fins/ribs prevent the medical instrument from contacting the interior sidewall 406 of the cannula shaft 402, and in some cases promote centering of the medical instrument with respect to the center of the lumen 404. The fins/ribs 402 can provide a gases passageway for insufflation gases to travel around the periphery/circumference of the scope. Some embodiments could include about or at least about 2, 3, 4, 5, 6, 7, 8, 9, 10, or more fins 420, or ranges incorporating any of the aforementioned values, and could be spaced axially and/or longitudinally apart regularly or irregularly along the inner circumference of the cannula 400 and/or along the cannula shaft 402.

FIG. 4C is a sectioned perspective view of the cannula 400 shown in FIGS. 4A and 4B, illustrating fin 420 relative to medical instrument (not shown) and interior sidewall 406 of the cannula 400.

A gas barrier or envelope can be created, shielding at least a portion of the medical instrument 410, e.g., endoscope, from the warm humid environment of the pneumoperitoneum (insufflated cavity) to prevent or reduce condensation formation on the scope lens. Gases (flowing in the direction of arrows shown in FIG. 4A) can pass along gaps between the fins 420 and can be directed along the scope to remove fog/condensation, smoke, or other applications as described for example above.

Figure 4D:
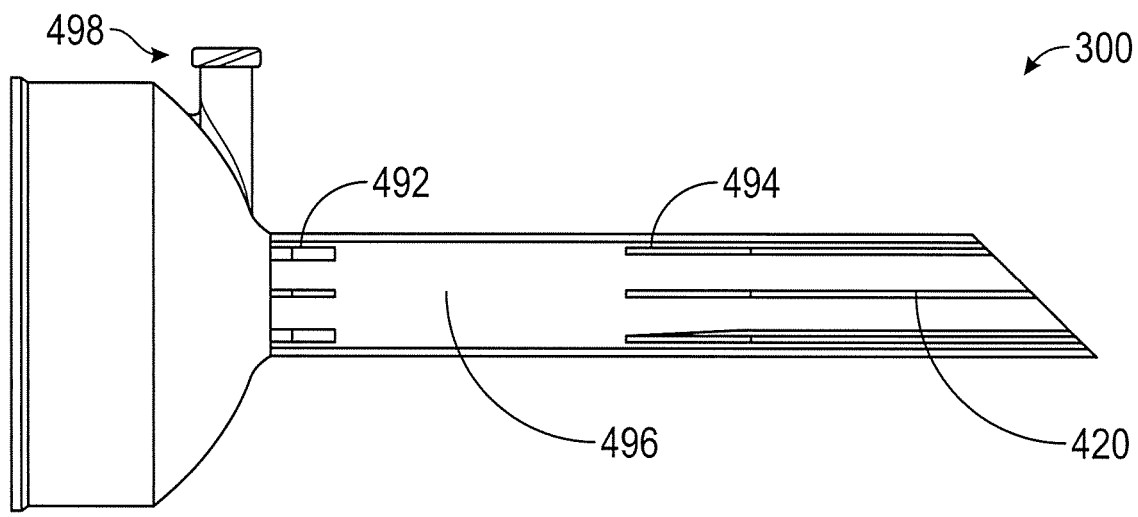
FIGS. 4D-4E illustrate views of another embodiment of a cannula with a directed gas flow lumen and a medical instrument guide element.
Figure 4E:
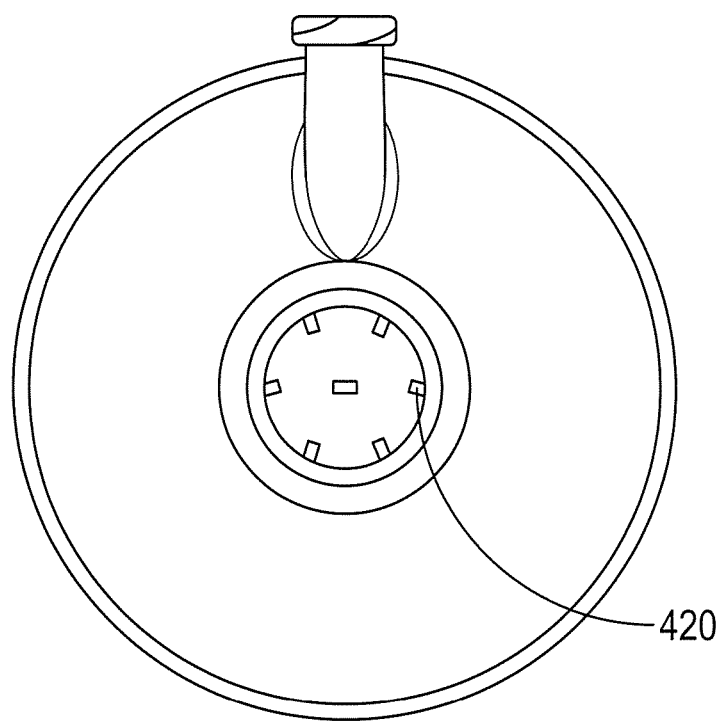

FIGS. 4D-4E illustrate views of additional embodiments of a cannula 490 including ribs/fins 420 that can include features similar to those shown in FIGS. 4A-4C above. FIG. 4D is a partial cross section of cannula as the elongate shaft is cross sectioned but the cannula body is not. The cannula can include 6 ribs disposed equally angularly spaced apart around the circumference of the cannula shaft, although other numbers of ribs can be utilized as previously noted. In some cases, the ribs or fins 420 are not equally angularly spaced apart around the circumference of the cannula shaft. The cannula can include a first set of ribs 492 and a second set of ribs 494 spaced axially apart from each other, as seen in FIG. 4D. In the illustrated configuration, the first set of ribs 492 and second set of ribs 494 include an equal number of ribs. Alternatively the first set of ribs 492 could include more or less ribs than the second set of ribs 494. Additional sets of ribs (e.g., a third, fourth, or more sets of ribs) are possible in other embodiments. A rib-free gap 496 can be present between sets of ribs 492, 494 as illustrated. The gap 496 between the sets of ribs 492, 494 can allow insufflation gases to mix and stabilize. The insufflation gases can enter the gases inlet 498 of the cannula 490 vertically as shown or at any other angle. The insufflation gases can enter as a turbulent flow and can bounce/redirect off a wall of the cannula 490. The gap 496 between the two sets of ribs 492, 494 allows for the insufflation gases to become more linear and mix, and thereby surround the scope when placed within the cannula 490.

As noted above, the ribs 420 help to stabilize the annular position of the instrument within the cannula 490, and can act as limits/stops that limit the annular movement and the limit the angle of the scope relative to the longitudinal axis of the shaft/lumen. The ribs 420 also act as a guide when inserting the instrument within the cannula 490. Alternatively, the ribs may act as a retainer and may grasp the instrument in a concentric arrangement within the cannula.

Figures 5A, 5B:
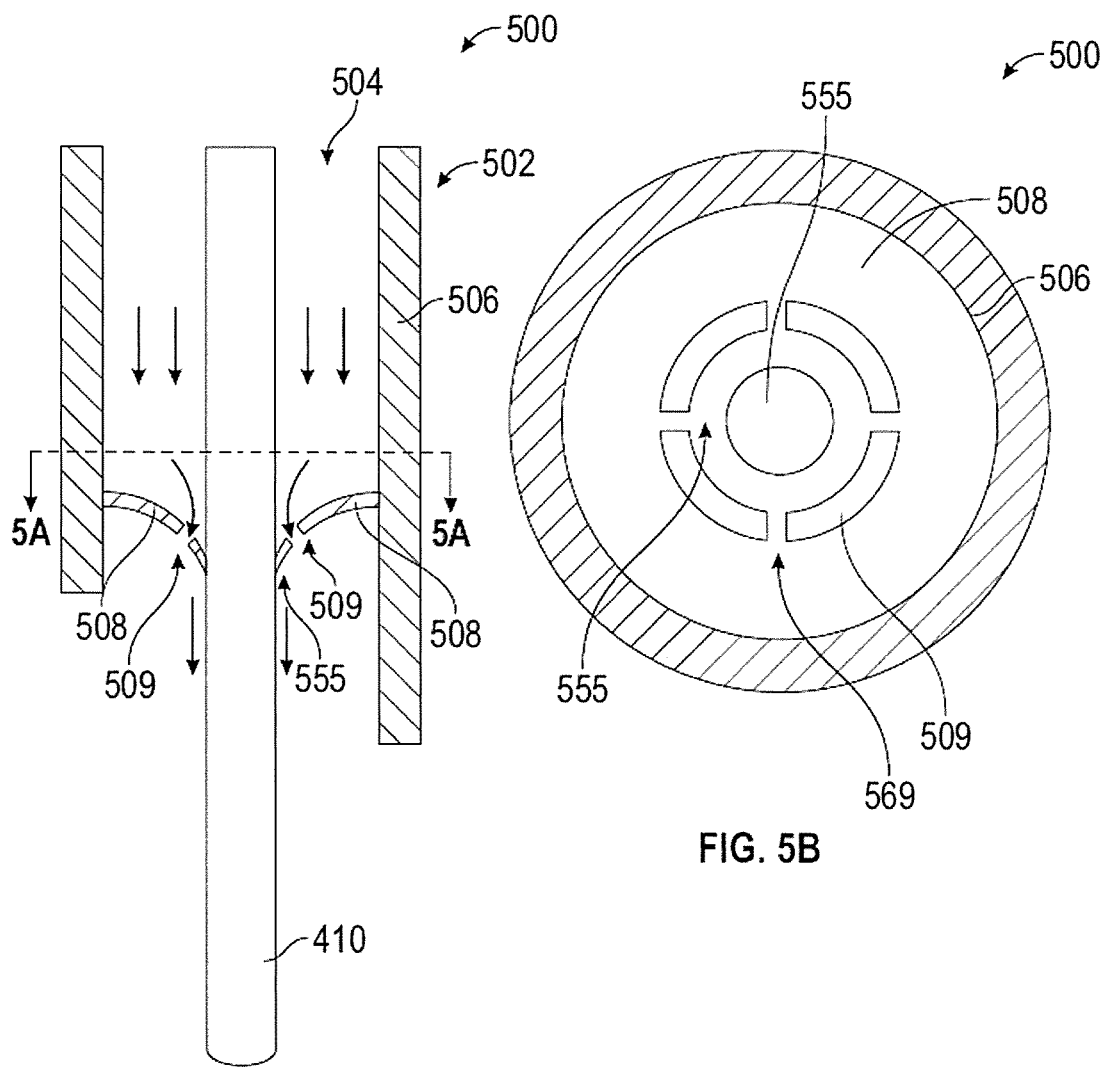
FIG. 5A illustrates a partial longitudinal cross-sectional view of an embodiment of a cannula having a plurality of seals configured to direct gas flows with respect to a medical instrument.
FIG. 5B illustrates a transverse cross-sectional view of the embodiment of a cannula as shown in FIG. 5A.
Figure 5C:
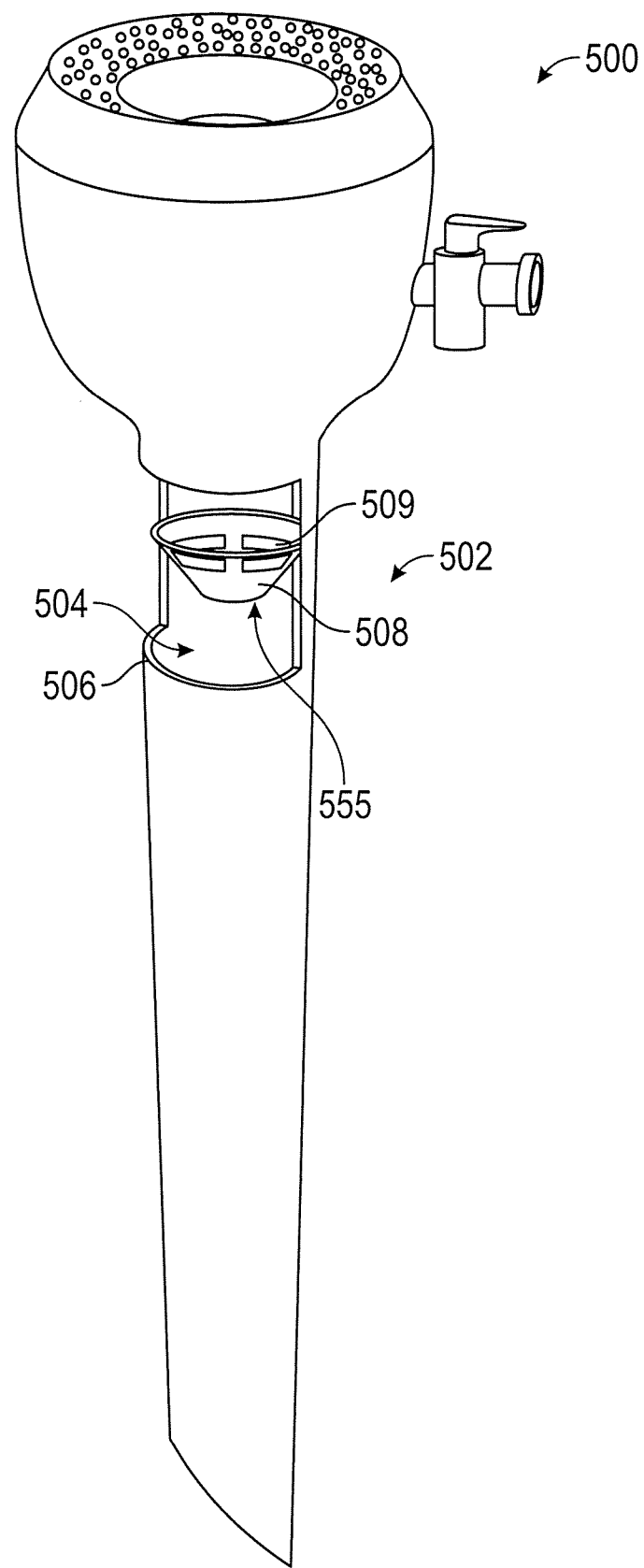
FIG. 5C illustrates a partial cut-away schematic view of the cannula of FIGS. 5A-5B.

FIG. 5A illustrates another example of a cannula 500 with cannula elongate shaft 502, and interior sidewall 506 defining a lumen 504 configured to house a medical instrument 410 therethrough. FIG. 5A is a partial longitudinal sectional view. The structures 508 can be operably connected, e.g., at an outer perimeter of the structures 508 from the interior sidewall 506 of the cannula elongate body 502, and include an instrument opening configured to contact a medical instrument 410. The structures 508 could be flexible or semi-rigid in some embodiments. Gases can pass through small openings or apertures, e.g., gaps 509 in the structures 508 and can be directed along the medical instrument 410 (e.g., scope) to remove fog, condensation, or other elements along the scope 410 that might obstruct the view of the scope. Each structure 508 can include only one gap 509 or a plurality of (e.g., 2, 3, 4, 5, 6, 7, 8, 9, 10, or more, or ranges including any of the aforementioned values) gaps 509 in other embodiments. The structures 508 or groups of structures 508 can be spaced apart along multiple longitudinal levels of the cannula elongate body in some embodiments. In some embodiments, the structures 508 can be mechanically or electronically actuated to reversibly open or close depending on the desired result. FIG. 5B is a cross-section through line 5A-5A of FIG. 5A without the medical instrument 410 shown in the lumen. FIG. 5B is a cross-section through the shaft of the cannula 500 of FIG. 5A above a structure 508, illustrating interior sidewall 506 defining a lumen. Also shown is the structure 508, which can take the form of a disk or flange in some cases, and including at least one instrument opening 555, that can be located centrally as shown, configured to receive and grasp an instrument 410. The structure 508 can be positioned within the lumen in a position such that the instrument opening 555 is concentric or substantially concentric with the lumen. The structure 508 can include a plurality of gas openings 509 located radially outward with respect to the instrument opening 555 configured to direct insufflation gases concentrically around the instrument to form a gases envelope to form a protection zone and region of controlled temperature and humidity around the instrument as previously described. In some embodiments, the gas openings 509 are arcuate or polygonal in shape and evenly, or irregularly disposed about the instrument opening 555. The structure 508 can be flexible, rigid, or semi-rigid as previously described. FIG. 5C is a schematic view of the cannula 500 of FIGS. 5A-5B with a selective cut-out view illustrating the structure 508 and related structures as previously described. With regard to the embodiments of FIGS. 4A-4B, 5A-5C, and others as described herein, gases can be delivered continuously or intermittently (e.g., cyclically) via the gases source.

Figures 6A, 6B:
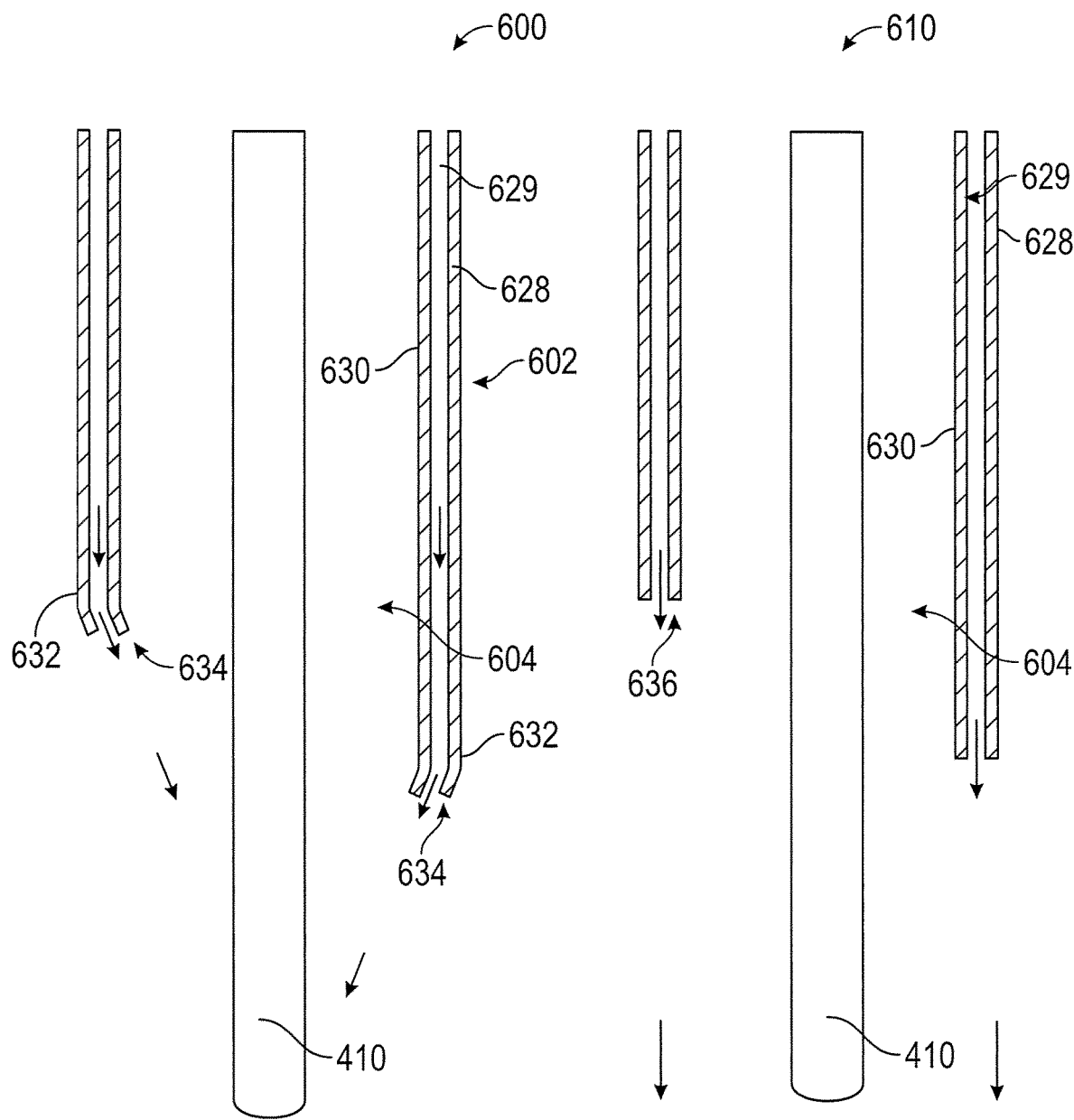
FIGS. 6A-6B illustrate partial longitudinal cross-sectional view of embodiments of cannulas with dual concentric lumens.

FIGS. 6A and 6B illustrate further examples of cannulas 600, 610 with a first lumen 604, as well as a second lumen 629 in between a first outer wall 628 and a second inner wall 630 of the cannula elongate body 602. The second lumen 629 can be offset from the center of the cannula elongate shaft 602, concentric with, and/or spaced radially outward of the first lumen 604 housing the medical instrument therethrough 410. The first lumen 604 can be defined by an inner surface of the second inner wall 630. The second lumen 629 could have a relatively straight proximal portions, and a bend 632 forming angled distal ends 634 (e.g., angled radially inwardly toward the medical instrument 310) as shown in FIG. 6A, or straight distal ends 636 as shown in FIG. 6B. In some embodiments with angled distal ends, the bend could form an angle of, for example, about 5, 10, 20, 30, 40, 50, 60, 70, 80, or 90 degrees, or ranges and in-between values of ranges, including any two of the foregoing values, or any other natural angle between any of the values disclosed. In some cases, the distal ends 634 can be a curved end or a stepped end. The gases flowing from the second lumen 629 can advantageously create a gas barrier or envelope along the medical instrument to prevent condensation/fogging or other conditions as described elsewhere herein. The second lumen 629 can be connected to a gases source (e.g., humidified insufflation gases), while no insufflation gases flow through the first lumen 604 in some embodiments.

Figures 7A, 7B:
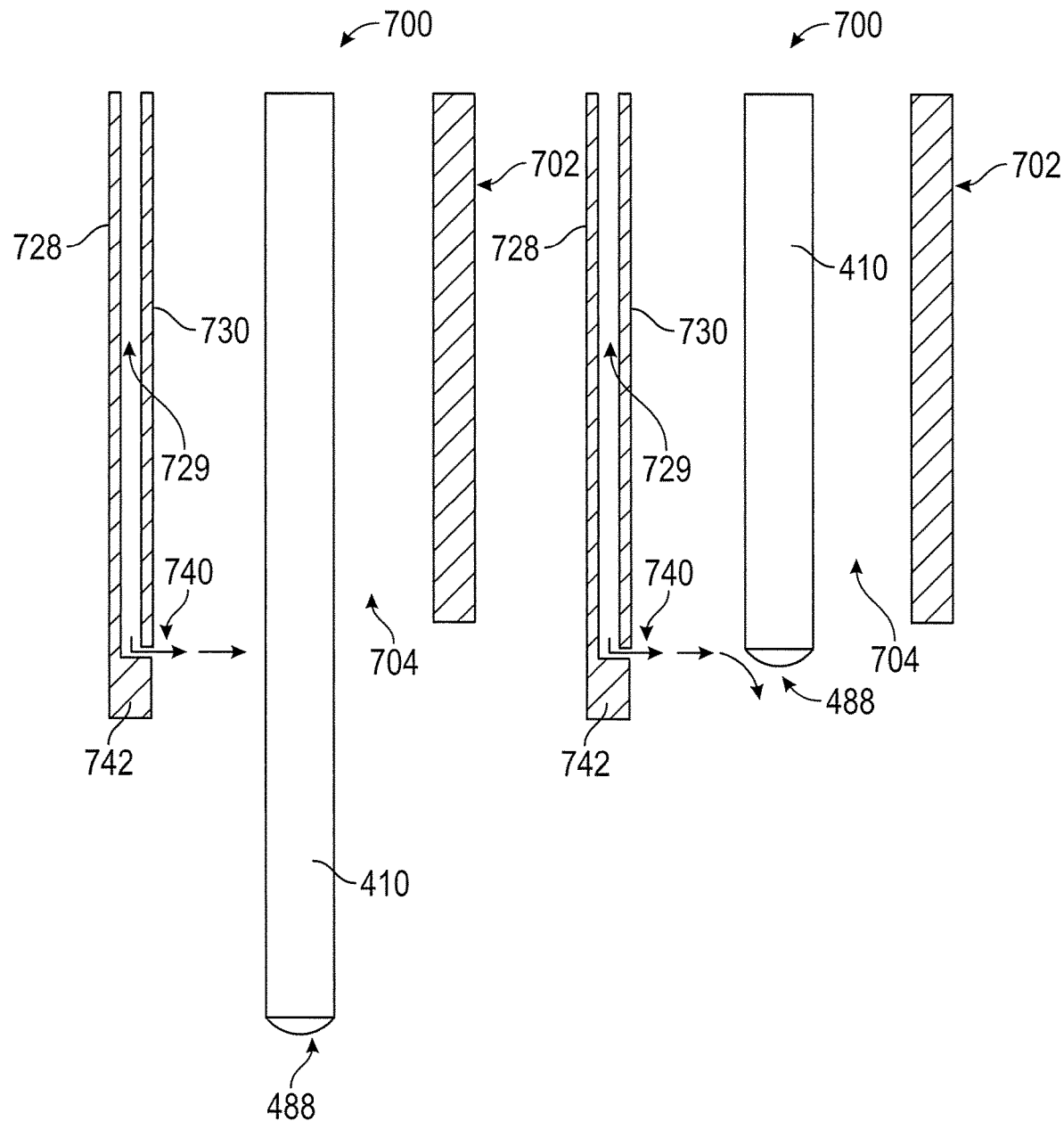
FIGS. 7A-7B illustrate partial longitudinal cross-sectional view of embodiments of cannulas with dual lumens.

FIGS. 7A and 7B illustrate further examples of cannulas 700 somewhat similar to that of FIGS. 6A to 6B. The second lumen 729 may be spaced in between a first outer wall 728 and a second inner wall 730 but need not necessarily be concentric around the first lumen 704. The second lumen 729 includes an inlet (not shown) and an exit port 740 oriented in a direction generally transverse to the longitudinal axis of the cannula elongate shaft (or at an oblique angle in other embodiments), functionally creating a gas blade. In some cases, the exit port can be positioned anywhere along the elongate shaft, not just at the distal end. In some embodiments, the exit port 740 of the second lumen 729 can be side-facing as shown, directed radially inward with respect to the elongate shaft of the cannula body 702, including a closed or plugged distal end 742, and/or being in fluid communication with the first lumen 704. Gases can be forced across a desired portion of the medical instrument 410, e.g., an endoscope or other scope lens, to remove or prevent accumulation of any condensation, smoke, or undesired media on the medical instrument 410. In some embodiments, gases can flow continuously or substantially continuously, and the endoscope lens 488 moved proximally to the transverse level of the gas blade (e.g., at exit port 740) to remove fogging and/or condensation. In some embodiments, the exit port 740 of the second lumen 729 can be marked with indicia (e.g., markings, a color, etc.) to better identify the gas blade to an operator.

Figures 8A, 8B:
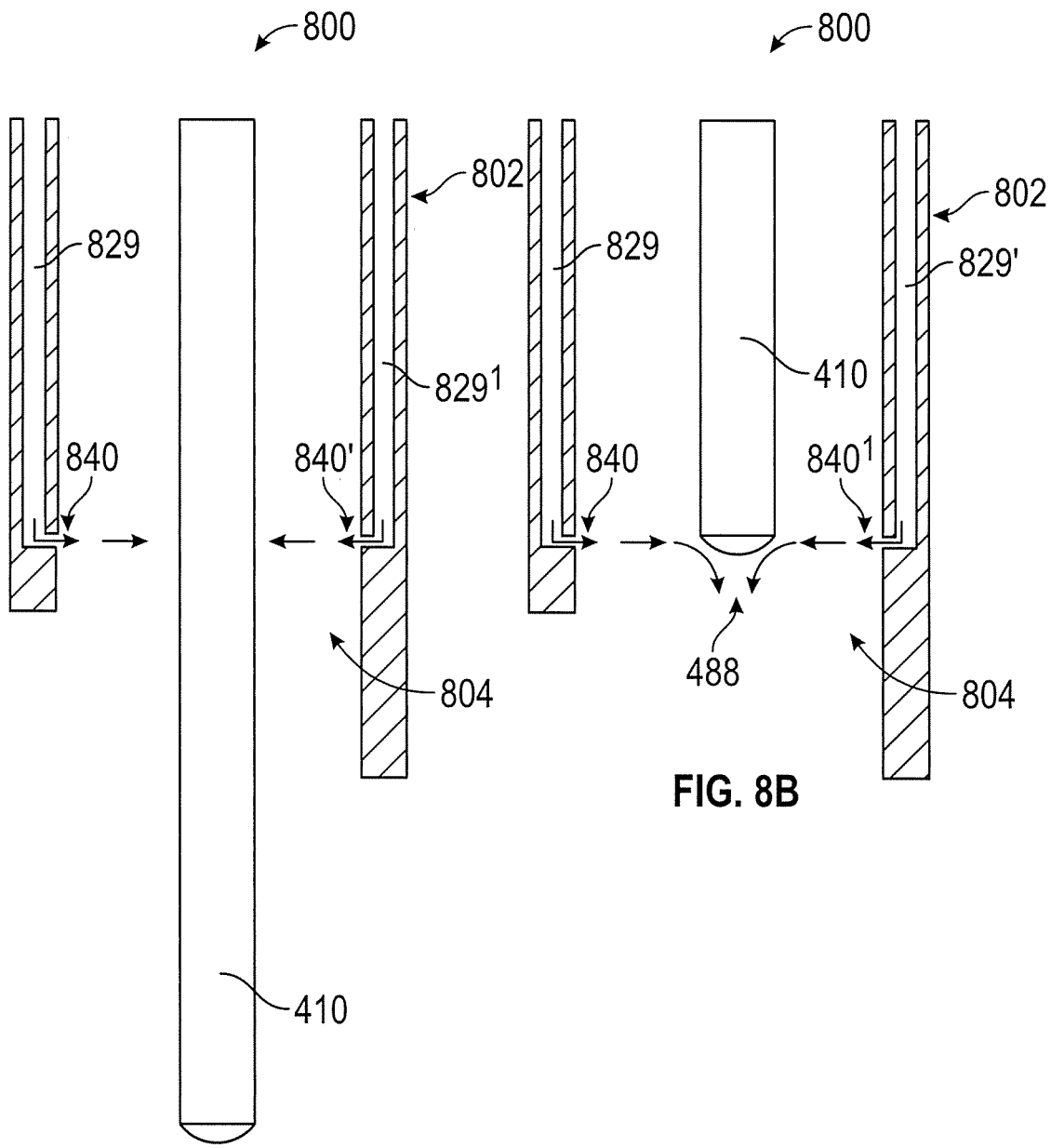
FIGS. 8A-8B illustrate partial longitudinal cross-sectional view of embodiments of cannulas with one or more lumens configured to function as a gas blade.

FIGS. 8A and 8B illustrate further examples of cannulas 800 similar to that of FIGS. 7A and 7B, except having a plurality of auxiliary lumens (e.g., lumens 829 and 829')(or alternatively a single concentric lumen with respect to the leading to dual gas blades (e.g., gas exits through exit ports 840, 840'). The gas blades can be spaced regularly or irregularly circumferentially apart along a transverse level of the cannula body 802, such as 180 degrees apart as shown (or 3 gas blades spaced 120 degrees apart, 4 gas blades spaced 90 degrees apart, etc.). As shown in FIG. 8B, the scope lens 488 at or near the distal end of the medical instrument 410 can be moved proximally to be level with the transverse level of the gas blade to remove fogging as described in connection with FIG. 7B.

Figures 9A, 9B:
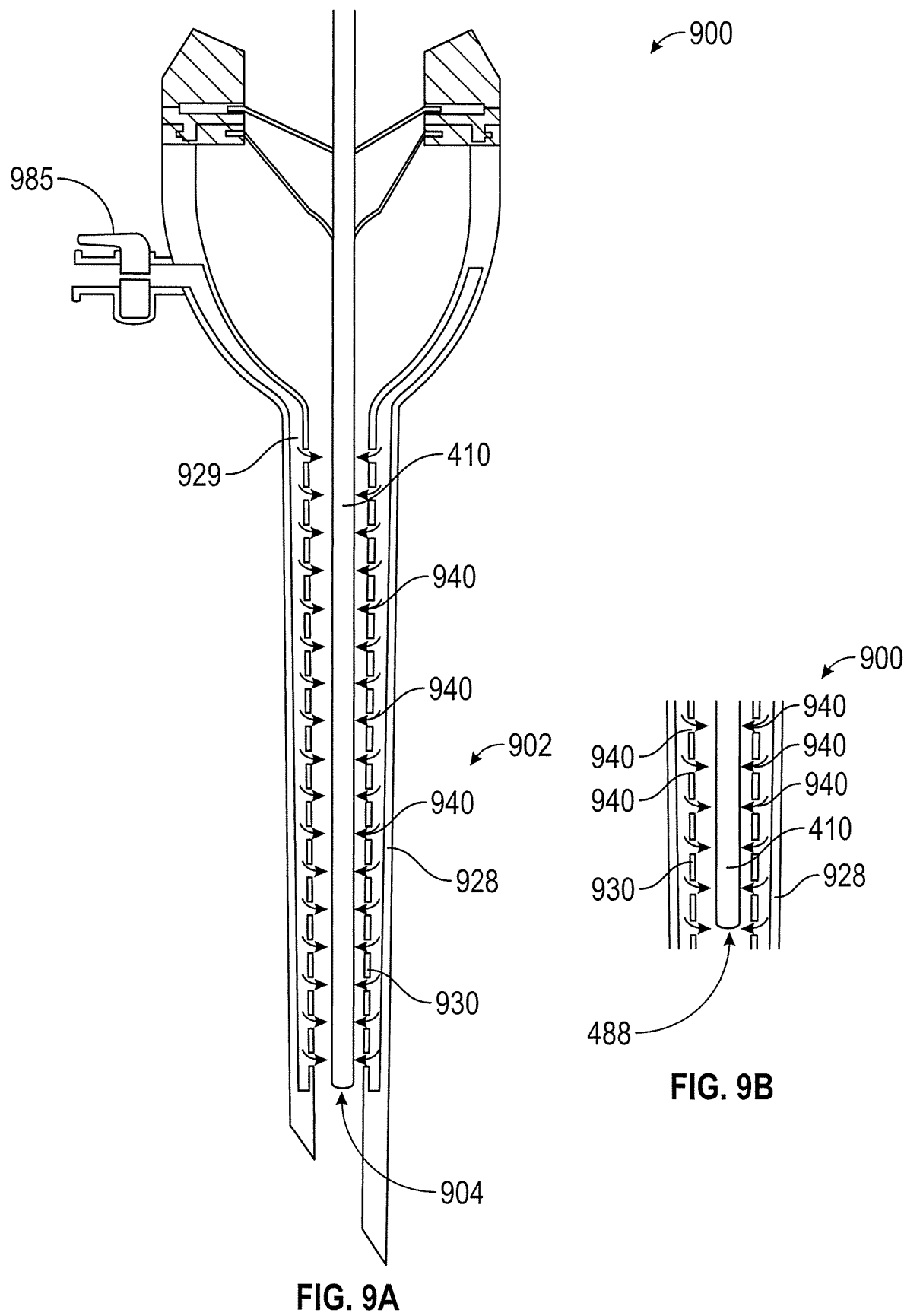
FIGS. 9A-9B illustrate longitudinal cross-sectional views of an embodiment of a cannula with an array of gas blades spaced axially apart.

FIGS. 9A and 9B illustrates cross-sectional views of another example of cannulas 900 similar to FIGS. 7A-7B and 8A-8B in some respects, with second lumen 929 present in between first outer wall 928 and second inner wall 930 and operably connectable proximally to inlet 985 except the gas blades extend from an array of sidewall ports 940 which are present at a plurality of regularly or irregularly axially spaced-apart transverse levels along the cannula elongate shaft 902 and discharging into the first lumen 904 defined by an inner surface of the second inner wall 930. In some cases, the array of sidewall ports 940 may be randomly spaced-apart or may be spaced-apart in a pattern. FIG. 9B is a close-up view of the shaft of the embodiment shown in FIG. 9A. As illustrated, the medical instrument 410 can be pulled in an appropriate direction (e.g., proximally) from the surgical site and back into the cannula shaft 902 such that the gas blades remove fog/condensation from the lens 488. In some embodiments, a subset of the array of gas blades can be actuatable (e.g., via valves) to control gas flow at different axial levels of the cannula 900.

Figure 10:
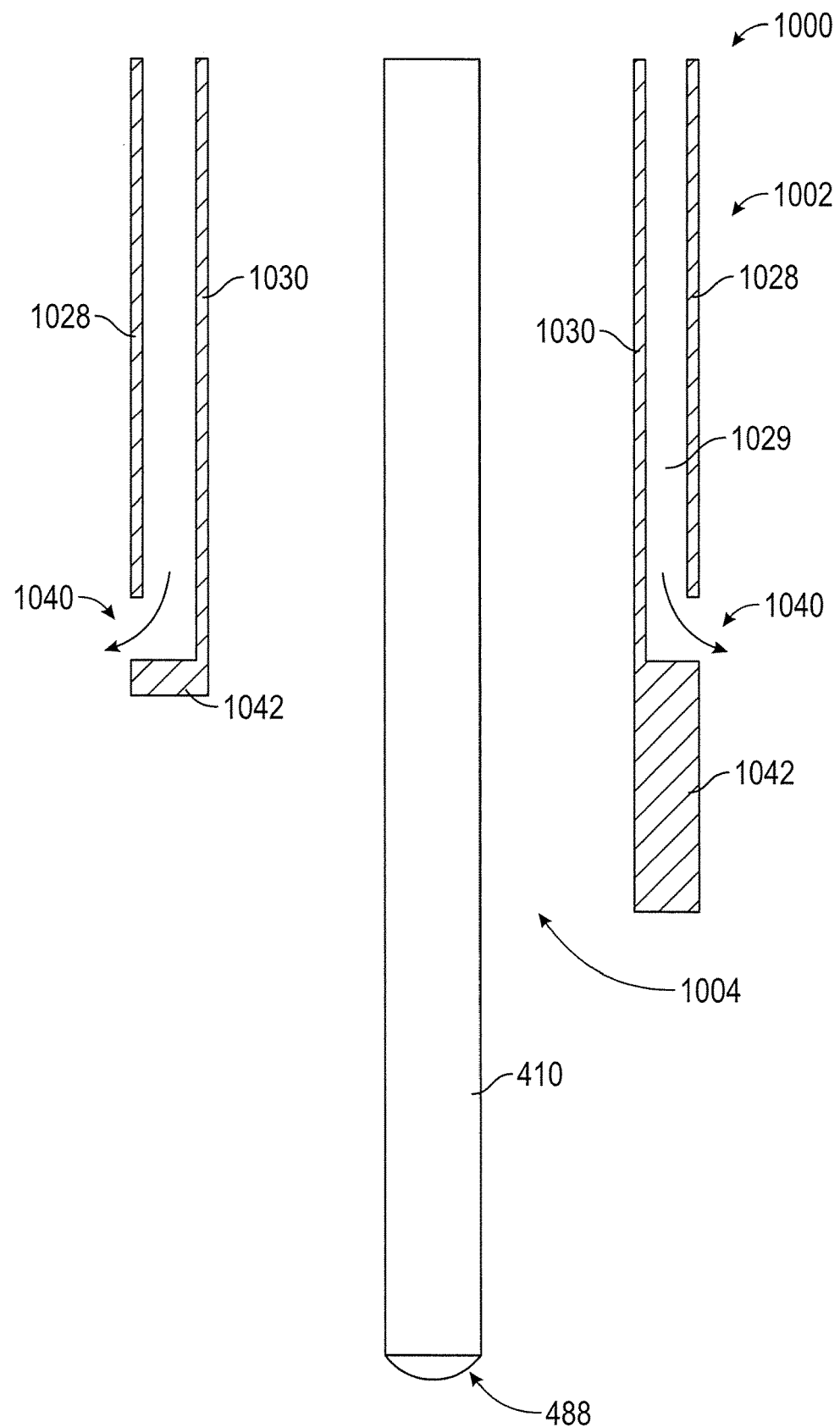
FIG. 10 illustrate a partial longitudinal cross-sectional view of embodiments of a cannula with a plurality of lumens.

FIG. 10 illustrates a partial longitudinal cross-sectional view of another embodiment of a cannula 1000 in which warm, humid gas is delivered directly to the pneumo/insufflated cavity through second lumen 1029 in between first outer wall 1028 and second inner wall 1030 and spaced radially outward of the first lumen 1004 for housing the medical instrument 410 therethrough, and bypassing the medical instrument 410 or a portion thereof (e.g., endoscope lens) 488. The exit ports 1040 can be angled radially outward of the cannula body 1002, and do not communicate with the interior sidewall of the first lumen 1030. In other words, the first lumen 1004 housing the medical instrument 410 therethrough may not in some cases be configured to be connected to a source of humidified gas, and humidified gas does not flow through the first lumen 1004. As such, the endoscope lens 488 or other desired part of the medical instrument 410 is advantageously not exposed to warm humid gas directly which reduces or prevents fogging.

Figure 11B:
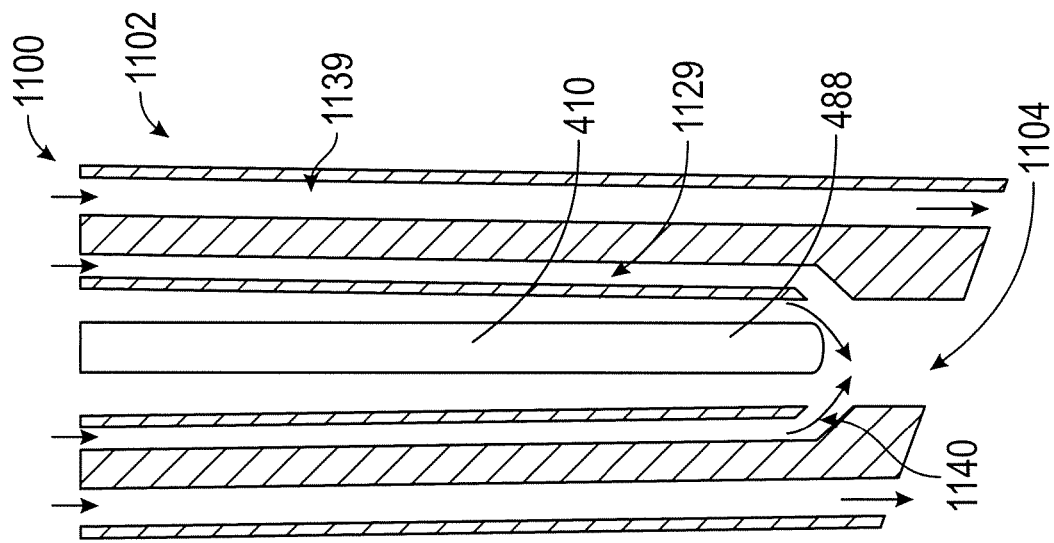
FIGS. 11A-11B illustrate partial longitudinal cross-sectional views of embodiments of a cannula with three lumens.
Figure 11A:
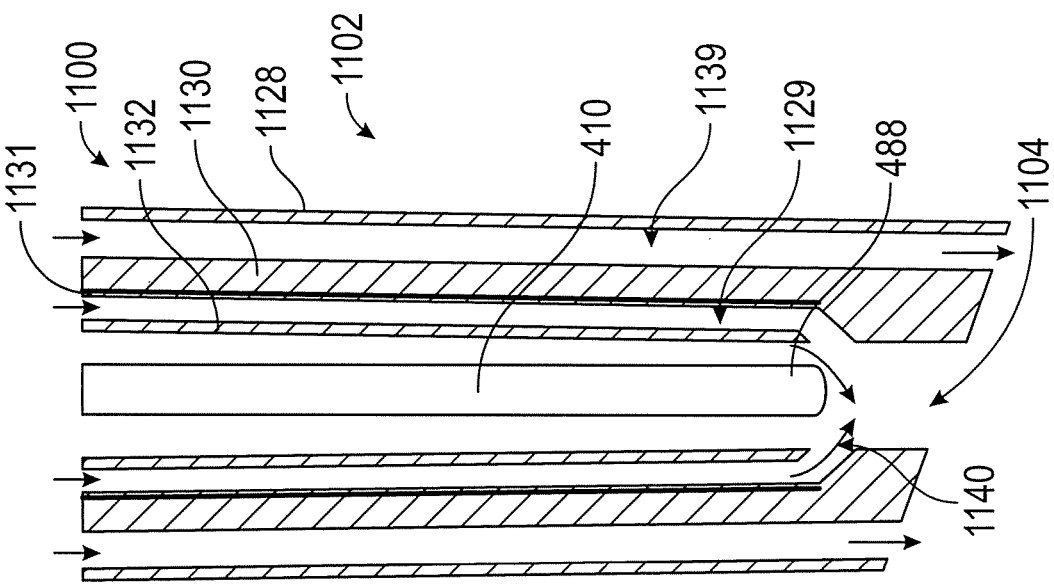

FIGS. 11A and 11B illustrate partial longitudinal cross-sectional views of embodiments of a cannula that can be similar in some respects to FIG. 10, with a first lumen 1104 to house the medical instrument 410 therethrough, the first lumen 1104 defined by an inner surface of an inner wall 1132, and a second lumen 1129 in between an inner wall 1132 and a mid-wall 1130 configured to be connected to a source of humidified gases to flow to the pneumoperitoneum/insufflated cavity. In some embodiments, the second lumen 1129 is insulated from a cannula heating element such that the gas is delivered at any desired therapy temperature and relative humidity, including parameters set forth elsewhere herein. In some embodiments, the second lumen 1129 is radially outward of the first lumen 1104. The cannula shaft 1102 can also include a third lumen 1139 in between the mid-wall 1130 and an outer wall 1128 that is configured to be connected proximally to a source of relatively dry gases (e.g., $CO_2$) to remove condensation/fogging from the medical instrument 410. The second lumen 1129 can be in direct fluid communication with the first lumen 1104, and can have exit ports 1140 into the first lumen 1104 as illustrated.

In some embodiments, the third lumen 1139 can be positioned in between the first lumen 1104 and the second lumen 1129. In some embodiments, the third lumen is the outermost lumen and gases traveling down the third lumen 1139 can be directed perpendicularly or at an angle from the outlet of the lumen 1104, similar to but not limited to the directing of the gases described with reference to FIG. 10, as opposed to directing the gases out of the end of the shaft. In some embodiments, the second lumen 1129 is isolated from the first lumen 1104 by the third lumen 1139. The second lumen 1129 can be shaped and configured to direct dry gases about and/or across the medical instrument 410. In some embodiments, the third lumen 1139 surrounds the first lumen 1104 such that the first lumen 1104 is nested within the third lumen 1139. In some embodiments, any two or more of the first lumen 1104, second lumen 1129, and/or third lumen (or other embodiments that include only two lumens, or four or more lumens) could be concentric or nested, or non-concentric and non-nested with respect to each other. In some embodiments, the first lumen 1104 has a diameter that is the same size, larger, or smaller than the diameter of the second lumen 1129. In some embodiments, the first lumen 1104 has a diameter that is the same size, larger, or smaller than the diameter of the third lumen 1139. In some embodiments, the second lumen 1129 has a diameter that is the same size, larger, or smaller than the diameter of the third lumen 1139. As illustrated in FIG. 11A, the mid-wall 1130 can include a heating element 1131 within the mid-wall 1130.

FIGS. 12A and 12B illustrate sectional views of an embodiment of a cannula 1200 with elongate shaft 1202 that includes features configured to create a Venturi effect to remove gas from around the medical instrument 410 or a portion thereof, e.g., endoscope lens 488. The Venturi effect is the reduction in fluid pressure that results when a fluid flows through a restriction section 1166 (or choke point) of a lumen with a reduced inner diameter, such as the second lumen 1129 as shown in FIG. 12B. The Venturi effect can create a partial vacuum, creating a pressure drop about the restriction section 1166, in the second outer lumen 1129, moving the lower pressure gas/moisture away from the scope lens positioned in the first inner lumen 1104 to remove condensation/fogging. In some embodiments, the reduction in inner diameter at the restriction section is about, at least about, or no more than about 10%, 20%, 30%, 40%, 50%, 60%, 70%, 80%, or 90% or more or less of the unrestricted diameter just proximal to the restriction section 1166, or ranges including any two of the foregoing values. The second lumen 1129 can increase in inner diameter distally of the constricted section as shown. FIG. 12B is a close-up view of the tip of the shaft shown in FIG. 12A, illustrating the restriction section 1166 of the second lumen 1129 can be created via an area of increased thickness, such as a lump or protrusion 1167 in the outer wall 1120.

Figure 13:
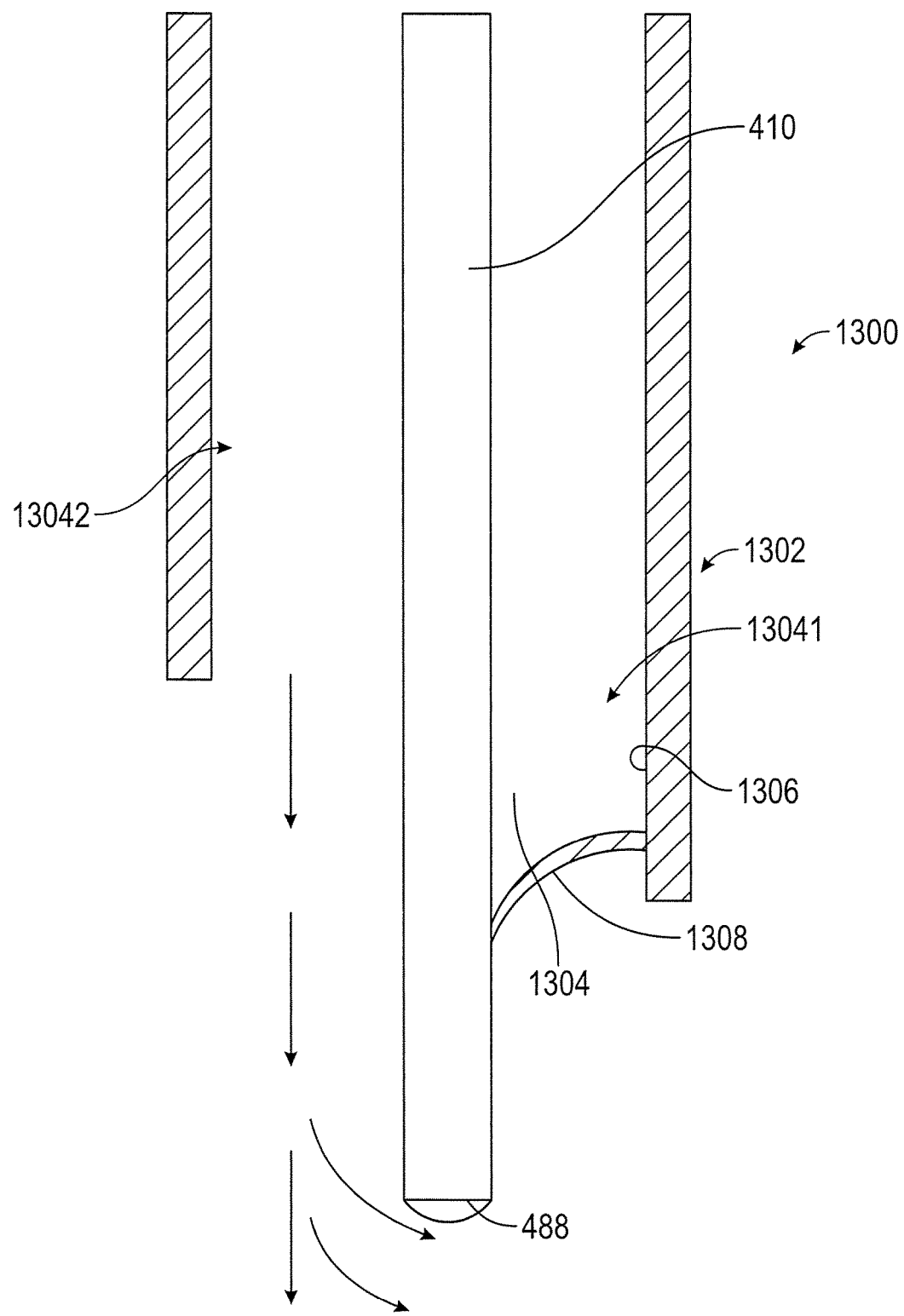
FIG. 13 illustrates a partial longitudinal cross-sectional view of an embodiment of a distal end of a cannula configured for blocking gas flow across a portion of a lumen.

FIG. 13 illustrates a partial longitudinal cross-sectional view of an embodiment of a distal end of an elongate shaft 1302 of a cannula 1300 and medical instrument 410 within a lumen 1304 formed by an inner sidewall 1306 of the cannula 1300, illustrating the cannula 1300 is configured to allow free gas flow through a first portion 13042 of the lumen 1304 of the cannula 1300, while configured to prevent gas flow through a second portion 13041 of the cannula 1300. Gas flow can be prevented, for example, on one or more halves, thirds, quarters, or other fractional portion of the lumen 1304 of the cannula 1300 such as via one, two, or more flexible or semi-rigid flaps 1308, or other elements. Such configurations can advantageously allow for directed gas flow to displace (e.g., in direction of arrows) a stagnant zone of unwanted gas (e.g., smoke, condensation/fog, etc.) away from the medical instrument 410, such as the distal tip 488 of an endoscope, for example.

Figures 14A, 14B:
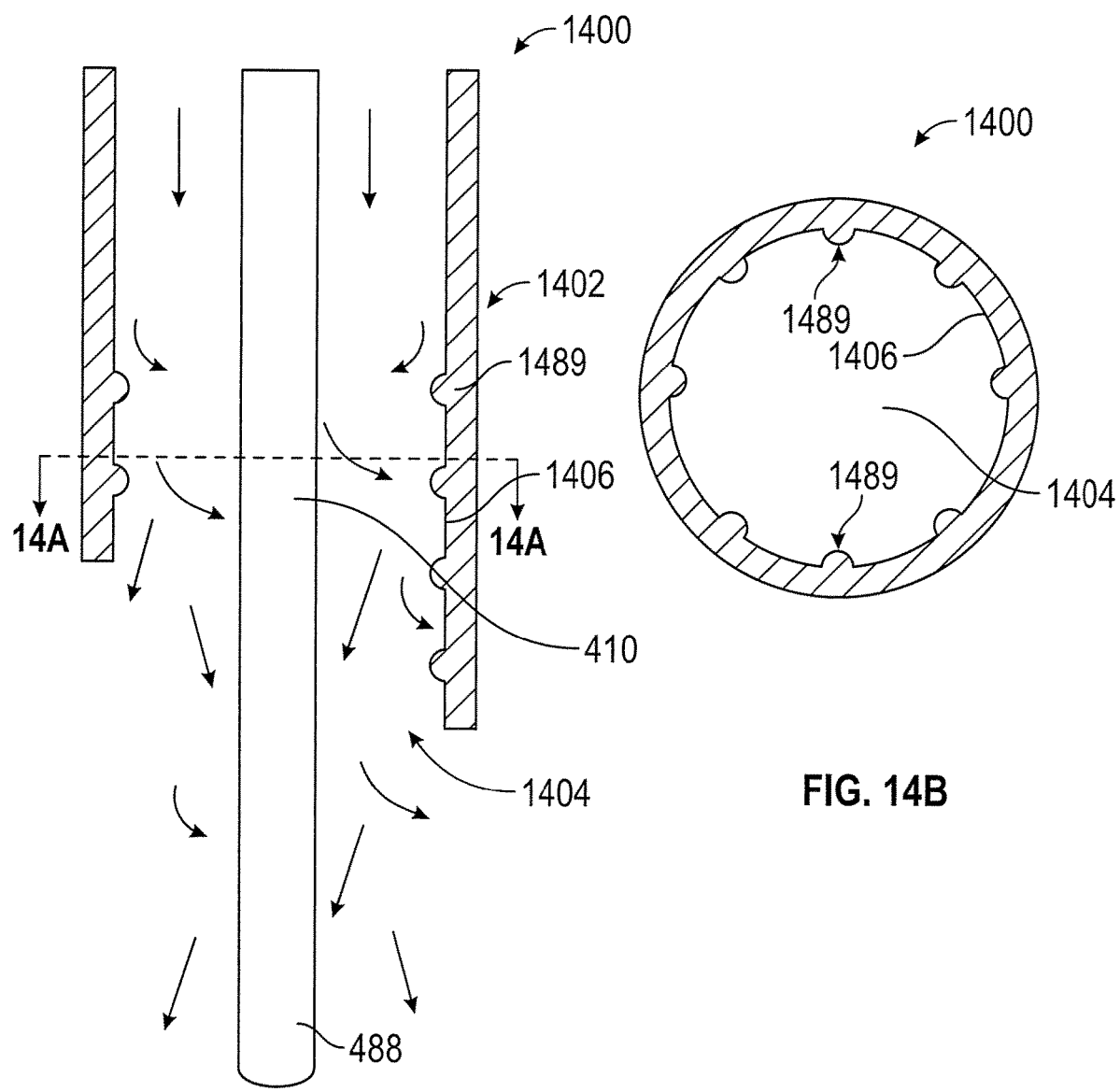
FIGS. 14A-14B illustrate views of an embodiment of a distal end of a cannula including irregularities configured to create turbulent flow.

FIGS. 14A-14B illustrate cross-sectional views of an embodiment of a distal end of an elongate shaft 1402 of a cannula 1400 and medical instrument 410 within a lumen 1404 of the cannula 1400. FIG. 14B is a cross-section through line 14A-14A of FIG. 14A without the medical instrument 410 shown in the lumen 1404. The inner sidewall 1406 of the lumen 1404 of the cannula 1400 can include irregularities 1489 such that the lumen 1404 is not perfectly arcuate (e.g., circular or oval for example). The irregularities 1489 could include dimples or other features extending radially inwardly into the lumen 1404, and spaced axially and/or longitudinally apart (at regular intervals, irregularly and/or randomly disposed along the lumen 1404) from each other causing turbulent gas flow (in the direction of arrows) within the lumen 1404 of the cannula 1400. Some embodiments can also, alternatively or in addition, include features such as grooves or slots extending radially outwardly from the lumen 1404 which can also cause turbulent gases flow. Such features can advantageously move a stagnant zone of unwanted gas (e.g., smoke, condensation/fog, etc.) away from the medical instrument 410, such as the distal tip 488 of an endoscope, for example.

Figures 15A, 15B:
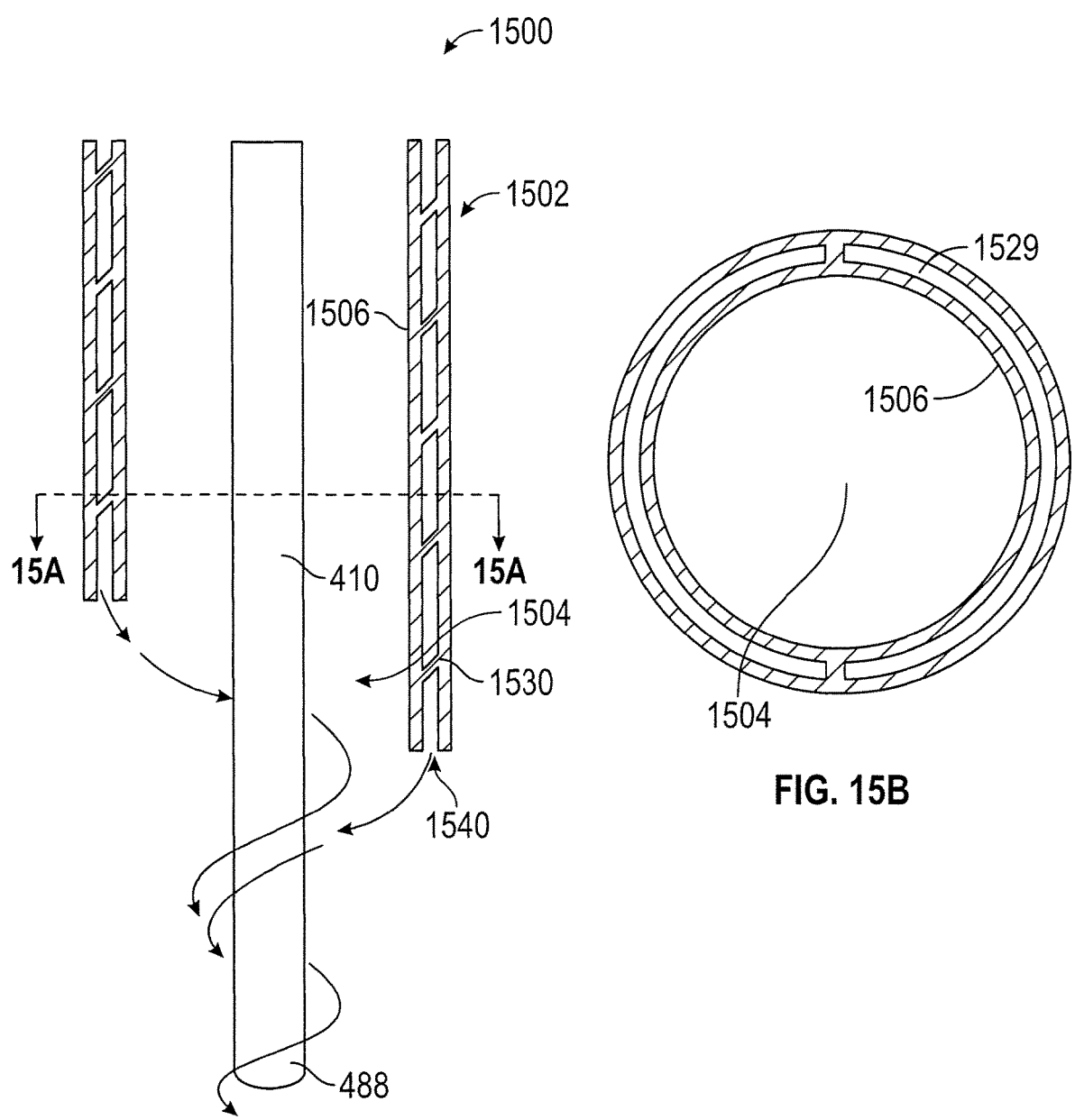
FIGS. 15A-15B illustrate views of an embodiment of a distal end of a cannula including a helical lumen configured to create a vortex luminal flow.

FIGS. 15A-15B illustrate cross-sectional views of embodiments of a distal end of an elongate shaft 1502 of a cannula 1500 with medical instrument 410 positioned within a first lumen 1504 of the cannula 1500, where the cannula elongate body 1502 can include one, two, or more helical shaped additional vanes 1530 which wind down the elongate shaft 1502. FIG. 15B is a cross-section through line 15A-15A of FIG. 15A without the medical instrument 410 shown in the lumen 1504. The spiral-shaped lumens 1529 can circumscribe the sidewall 1506 of the first lumen 1504, or be present within the first lumen 1504 in some cases, and be configured to be connected to a source of gases proximally. The spiral-shaped lumens 1529 can include distal exit ports 1540 such that exiting gases create a vortex flow pattern along a target location of the medical instrument 410 (e.g., distal end of the endoscope 488) to advantageously create a gas barrier, and remove flow non-uniformity to reduce or prevent fogging, condensation, or other debris on the medical instrument or a portion thereof (e.g., an endoscope lens).

Figure 16:
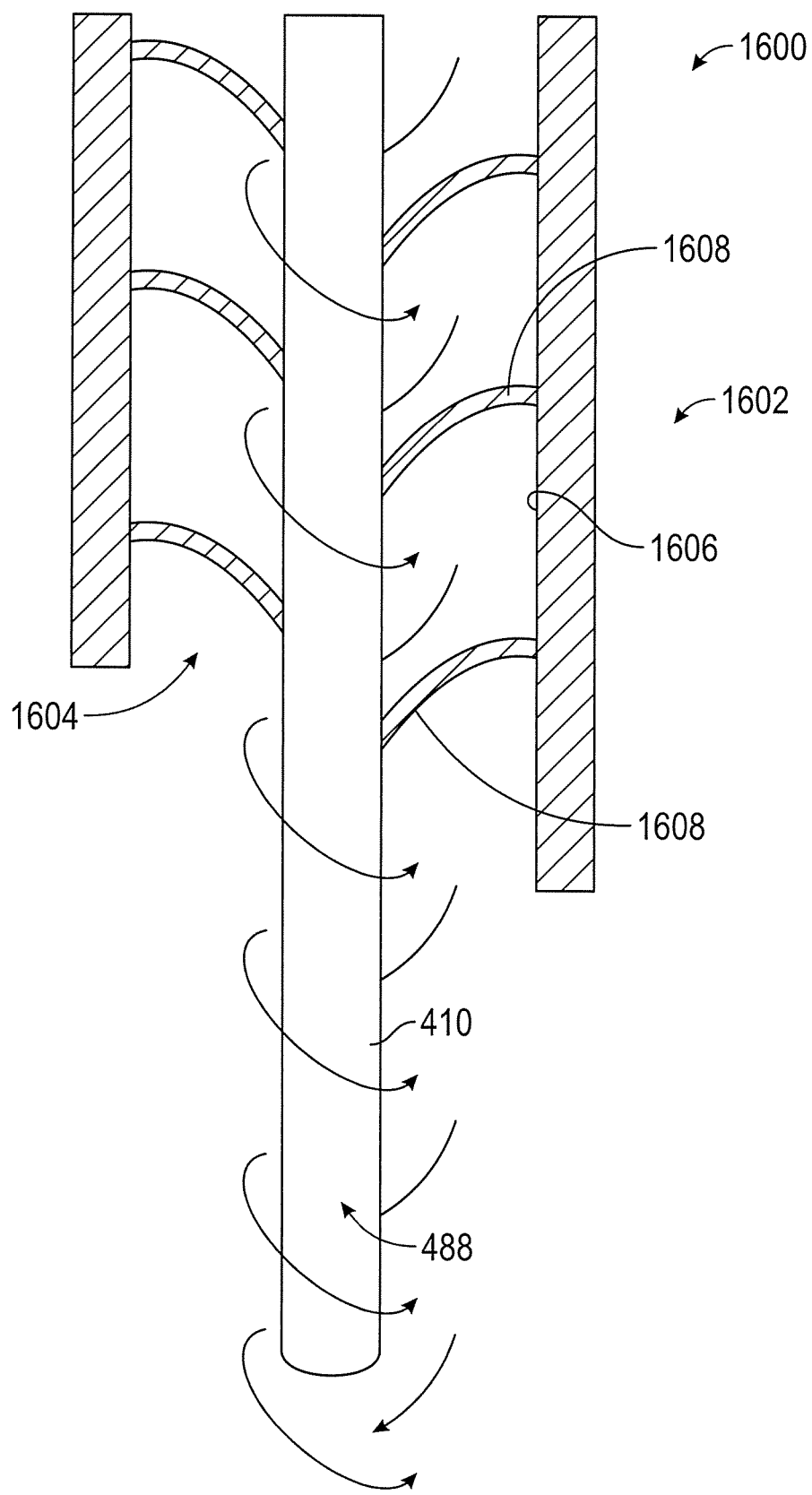
FIGS. 16-17 illustrate views of an embodiment of a cannula including a single continuous helical vane configured to create a vortex luminal flow.
Figure 17:
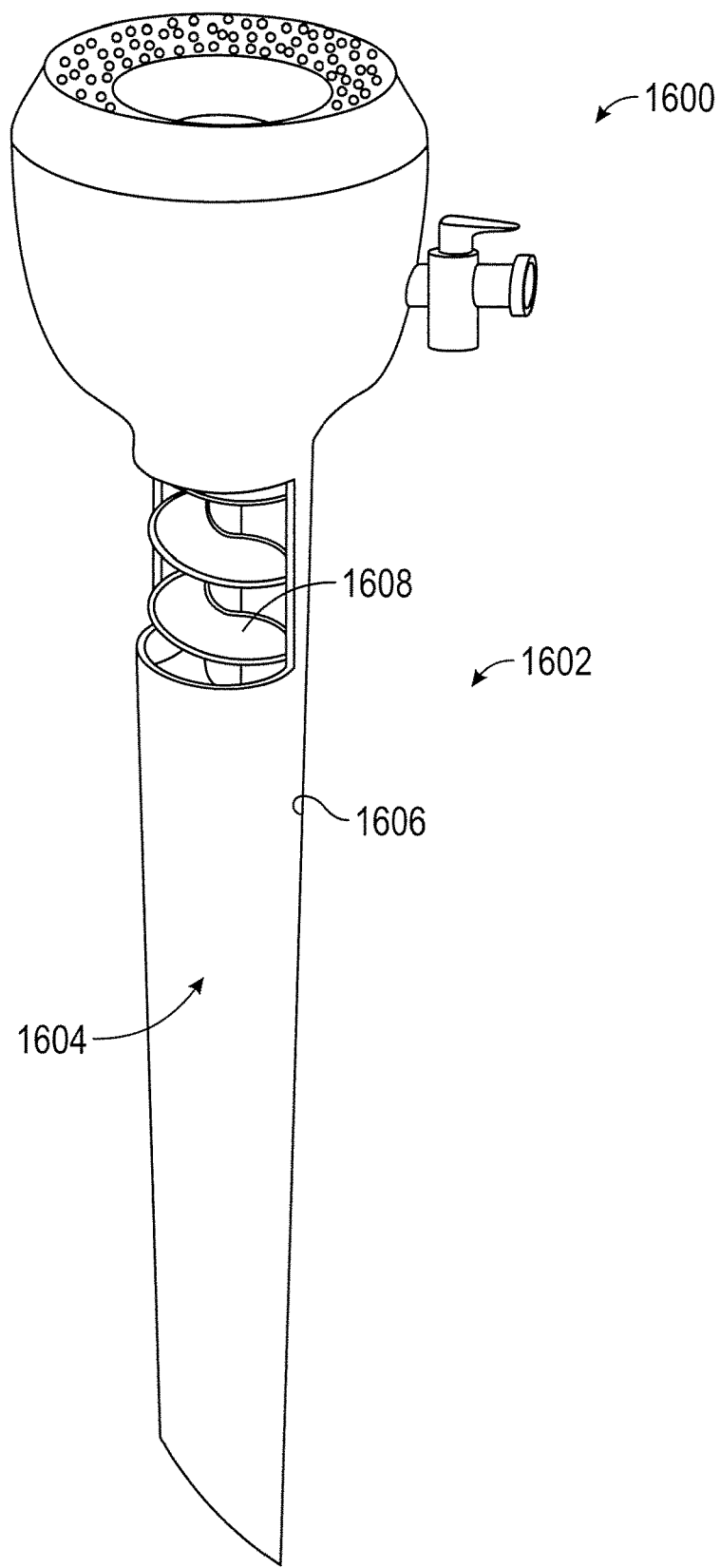

FIGS. 16-17 illustrates an embodiment of an elongate shaft 1602 of a cannula 1600 and endoscope lens 488 of medical instrument (e.g., a scope) 410 within a lumen 1604 (e.g., central lumen defined by an inner sidewall 1606 of the cannula 1600 as shown), including one or more helical vanes 1608 geometrically configured to create a vortex flow of gases (in direction of arrows) somewhat similar to that described in connection with FIGS. 15A-15B. FIG. 17 illustrates a partial cut-away schematic view of the cannula 1600. The helical vane 1608 can be in some cases a single spirally-wound wall that extends the entire or substantially the entire length of the lumen 1604. The helical vane 1608 can restrict radial movement of the scope. The vane 1608 may also grip and retain the scope 410 within the lumen 1604. The gases flow inside the lumen 1604 is directed around the scope 410 by the continuous vane 1608. The continuous vane 1608 acts as a guide wall that directs the insufflation gases in a vortex flow along the scope 410. The vortex flow extends beyond the outlet of the cannula and also creates a gases envelope as previously described. The envelope in such embodiments could be a vortex flow envelope due to the shape of the helical/spiral shaped vane 1608 that promotes a helical/vortex flow.

Figures 18A, 18B:
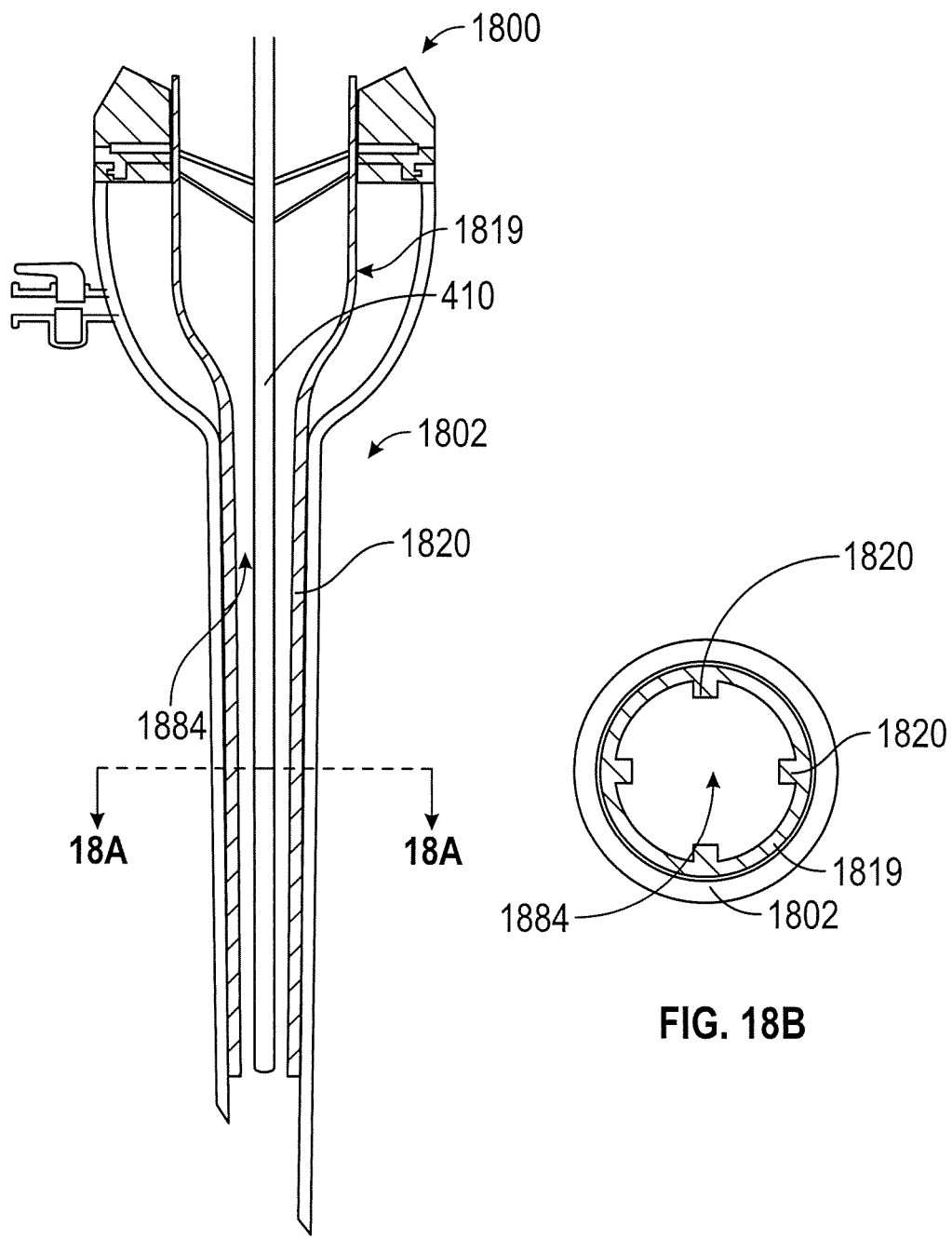
FIGS. 18A-18C illustrate views of a cannula insert configured to be positioned into a cannula.
Figure 18C:
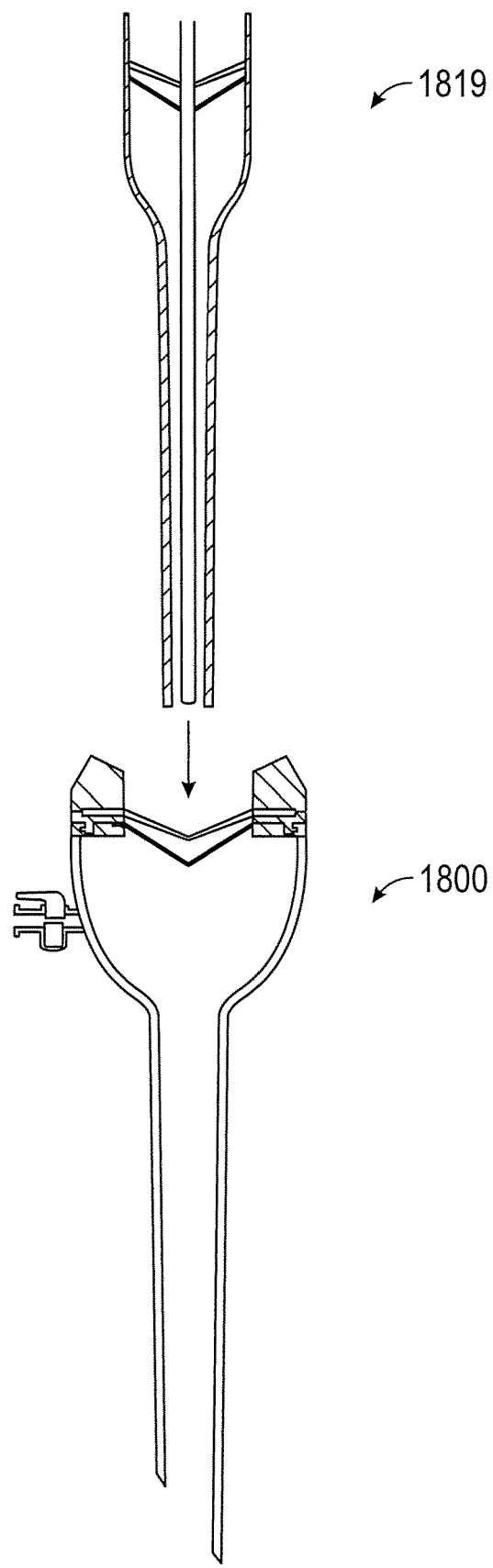

In some embodiments, any number of features for facilitating directed gas flow with respect to a medical instrument therethrough, including but not limited to guide elements (e.g., ribs or fins) configured to retain the medical instrument within the lumen and/or encourage concentricity of the medical instrument to prevent the medical instrument from contacting the sidewall of the lumen, gas blades, vanes, restrictions, and/or other features described in various embodiments herein need not necessarily be integrally formed with the cannula, but rather be formed as part of an insert that can be slid into a lumen of the cannula and secured via friction fit, adhesives, or other techniques. FIGS. 18A-18B illustrate an embodiment of a cannula 1800 including elongate cannula body 1802, with a directed gas flow insert 1819 positioned therethrough, including a plurality of ribs or fins 1820 described and illustrated, for example, in connection with FIGS. 4A-4C above. Also shown is medical instrument 410 within insert lumen 1884. FIG. 18B is a cross-section through line 18A-18A of FIG. 18A, better illustrating fins 1820. FIG. 18C schematically illustrates a method in which the insert 1819 (e.g., the distal end of the insert) can be positioned within the proximal end of a conventional cannula 1800 to form a directed gases flow cannula as illustrated in FIGS. 18A-18B.

The directed gases flow cannula described herein can provide optical clarity for the user and can allow a clear field of vision (for example, a field of view affected by lens fog, condensation, and smoke) to be maintained. The directed gases flow cannula can minimize and manage surgical smoke caused by electrosurgery/electrocautery and can maintain a stable operating space within pneumoperitoneum (stable in terms of insufflation). The directed gases flow cannula can minimize operation time and post-operation complications. In some cases, the directed gases flow cannula can be used for alternative applications (e.g. electrocautery tools, graspers etc.).

The directed gases flow cannula can provide optical clarity in the pneumo-peritoneum during surgery by removing fog, condensation, smoke, and/or other debris on the laparoscope lens. The optical clarity can be achieved by holding a medical instrument (such as a laparoscope) concentrically in a directed gases flow cannula with insufflation gas flowing through it. Holding the medical instrument concentrically allows the insufflation gas to flow down over the scope lens and prevent fog, condensation, smoke, and/or other debris forming on the medical instrument, for example the lens of a laparoscopic device. For example, the insufflation gas can form a micro-environment or envelope around the lens to isolate the lens from the pneumo-peritoneum gas. The insufflation gas humidity and temperature can be controlled which allows the micro-environment or envelope around the lens to be controlled to gas conditions favorable to preventing fog, condensation, smoke, and/or other debris forming. This fog, condensation, smoke, and/or other debris prevention can be a desirable outcome for the operating theatre staff who use the laparoscope to perform the surgery.

A medical instrument held concentrically in the cannula can prevent fog, condensation, smoke, and/or other debris forming on the medical instrument including a scope lens of a laparoscopic device. For example, condensation or fogging occurs on the scope lens when the temperature of the lens falls below the dew point temperature for the level of humidity the gas is carrying. Fogging therefore occurs when the scope is initially inserted or when it is removed and re-inserted during surgery as it is colder than the warm and humid environment of the pneumo-peritoneum. Fogging may also occur when the dew point temperature is raised through activities like electrosurgery.

The fogging or other optical obstructions impedes vision and when it occurs usually the only option is to remove the lens and wipe it down. This can cause the scope to cool down again and the problem can keep on repeating in the absence of any other interventions such as anti-fog solution, scope warming, or using the light at the end of the lens to warm up the lens.

As described herein the concentric cannula technology can allow for a small micro-environment or envelope to be controlled around the scope lens. This envelope can isolate the scope lens from the warm and humid environment of the pneumo-peritoneum. This gas can then isolate the scope lens from the surgical environment. If the delivered gas conditions are controlled, then the environment around the scope can be controlled.

The direct gases flow cannula can include the use of a concentric cannula that directs the gas to form a micro-environment or envelope around the scope lens. The concentric cannula can utilize a medical instrument that is surrounded by a cannula during use.

In some cases, the concentric cannula can have heating technology integrated into it to either maintain the gas temperature from the humidifier or to further heat the gas reducing the dew point of the gas which may help prevent fogging of the scope lens.

The concentric cannula can have venting capabilities added to it which would allow for a flow of gas to be delivered over a lens of the medical instrument without over inflating the patient. The venting technology can allow the patient to be retained at the same pressure. In some cases, the smoke filter technology can filter the vented gas.

In some cases, a flow rate more than the flow required to maintain pressure can also increase the optical clarity from a smoke management perspective.

The concentric cannula can deliver better fog, condensation, smoke, and/or other debris prevention performance if a certain flow algorithm is used which can be controlled by a gas supply, similar to gas supply described with reference to FIG. 2.

The concentric cannula may need a higher than usual flow rate which can be accomplished with a tube set which can deliver higher flow rates. The system incorporating the concentric cannula can include reduced restriction at gas connection, a tube set with less friction, a tube set with consistent diameter, and/or a tube set with multiple connections.

The concentric cannula can have an optimized humidity source. The concentric cannula technology can allow for a small environment or envelope around the scope to be controlled. The optimized humidity source can allow the micro-environment or envelope to be set to parameters that favor fog, condensation, smoke, and/or other debris prevention. In some cases, this envelope can be dynamic.

The concentric cannula can include concentric features such as ribs or guides which can be used to hold the laparoscope concentrically in the cannula shaft while still allowing the insufflation gas to pass down the main lumen. FIGS. 19A-B, 20A-B, 21A-B, and 22A-B illustrate examples of concentric feature guide elements that can be used. The concentric feature guide element, however, are not limited to the examples shown in FIGS. 19A-B, 20A-B, 21A-B, and 22A-B and variations of these features can be feasibly used to hold the scope concentrically in the cannula.

FIGS. 19A-B, 20A-B, 21A-B, and 22A-B show a vertical cross-section of the cannula shaft and a horizontal cross-section of the cannula shaft. Any of the cannula embodiments described herein can incorporate any of the features or guide elements described with reference to FIGS. 19A-B, 20A-B, 21A-B, and/or 22A-B and the features or guide elements described in FIGS. 19A-B, 20A-B, 21A-B, and/or 22A-B can be used interchangeable with each other or with any of the other guide elements described herein. FIG. 19A illustrates a vertical cross-section of the cannula wall 1906 with guide elements, such as a rib concentric feature 1920. FIG. 19B illustrates a horizontal cross-section of the cannula shaft with the rib concentric feature 1920 with squared edges. The rib concentric feature 1920 can have rounded top and bottom edges as shown in FIG. 19A. As shown in FIG. 19A, the rib concentric feature 1920 can be elongated and extend along the cannula shaft. FIG. 20A illustrates a vertical cross-section of the cannula wall 2006 with guide elements, such as a bump or dimple concentric feature 2020. FIG. 20B illustrates a horizontal cross-section of the cannula shaft with the bump or dimple concentric feature 2020. The bump or dimple concentric feature 2020 can be rounded or half sphere shape as shown in FIGS. 20A-20B. FIG. 21A illustrates a vertical cross-section of the cannula wall 2106 with guide elements, such as a pin concentric feature 2120. FIG. 21B illustrates a horizontal cross-section of the cannula shaft with the pin concentric feature 2120. The pin concentric feature 2120 can be rounded or have a rounded end or can be sharp as shown in FIGS. 21A-21B or, in some cases, the pin concentric feature 2120 can have pointed edges or ends. FIG. 22A illustrates a vertical cross-section of the cannula wall 2206 with guide elements, such as a rounded rib concentric feature 2220. FIG. 22B illustrates a horizontal cross-section of the cannula shaft with the rounded rib concentric feature 2220. In some cases, the rounded rib concentric feature 2220 can be elongated and extend along the longitudinal axis of the cannula shaft.

The concentric cannula can hold the medical instrument (such as a laparoscope) in the directed gases flow within the cannula. Various designs that can be used to hold the medical instrument concentrically in the cannula shaft while allowing the insufflation gas to pass down the main cannula lumen. The examples described herein include features that can be integrated into the cannula so that the concentric features and the cannula form one complete assembly. The examples of concentric features shown in FIGS. 19A-B, 20A-B, 21A-B, and 22A-B illustrate various features that can be used to accomplish scope concentricity in the cannula shaft, however, any structural features that can support the medical instrument concentrically within the cannula shaft can be used. In some cases, the guide elements can the maintain the medical instrument concentrically or substantially concentrically within the lumen. In some cases, the guide elements can maintain the medical instrument at 0 degrees or between 0 to 30 degrees with respect to the lumen.

Figures 23A, 23B:
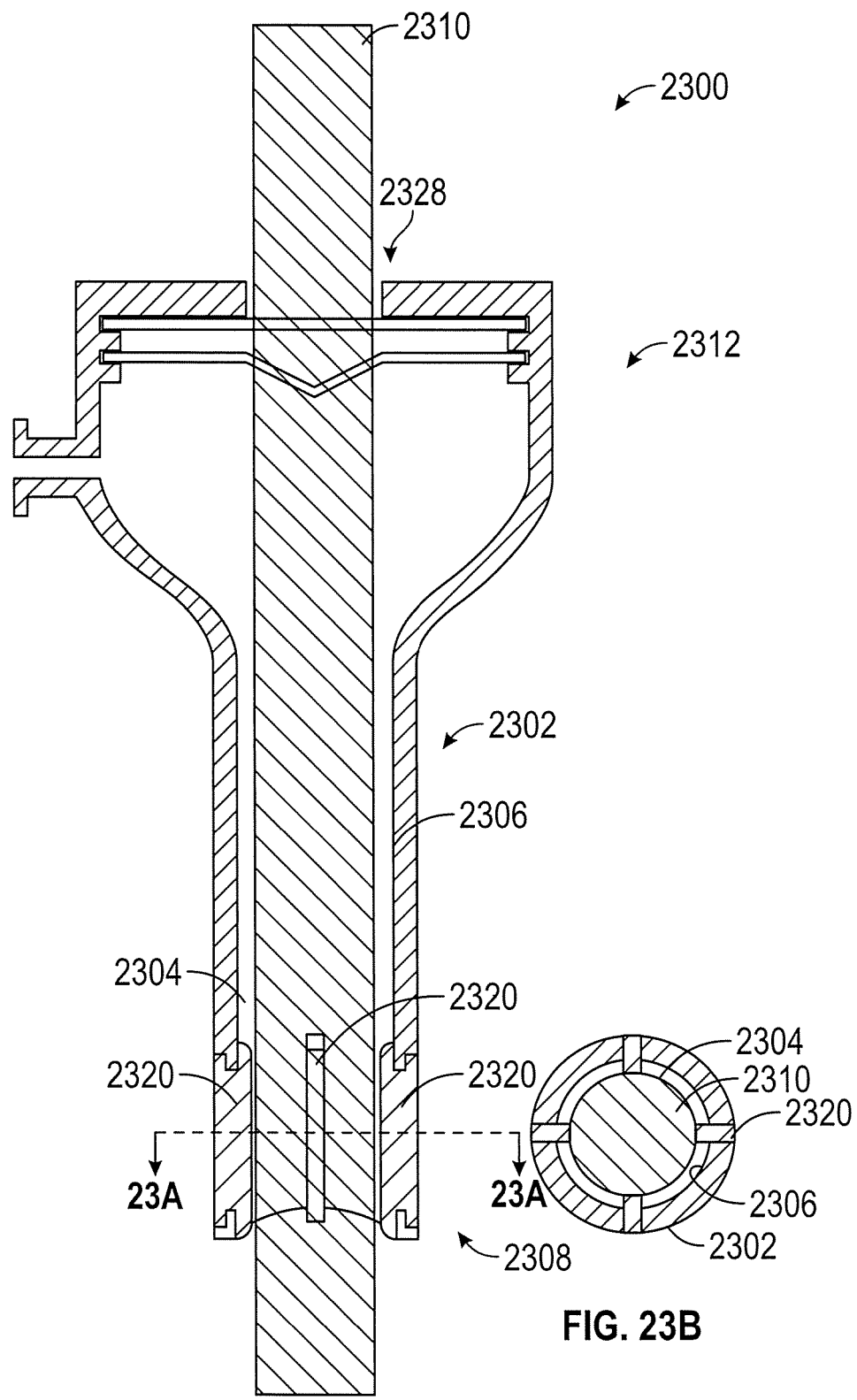
FIGS. 23A-23T illustrate views of embodiments of cannulas with flexible features at the distal end of the cannula to aid in concentricity of the medical instrument.
Figures 23C, 23D:
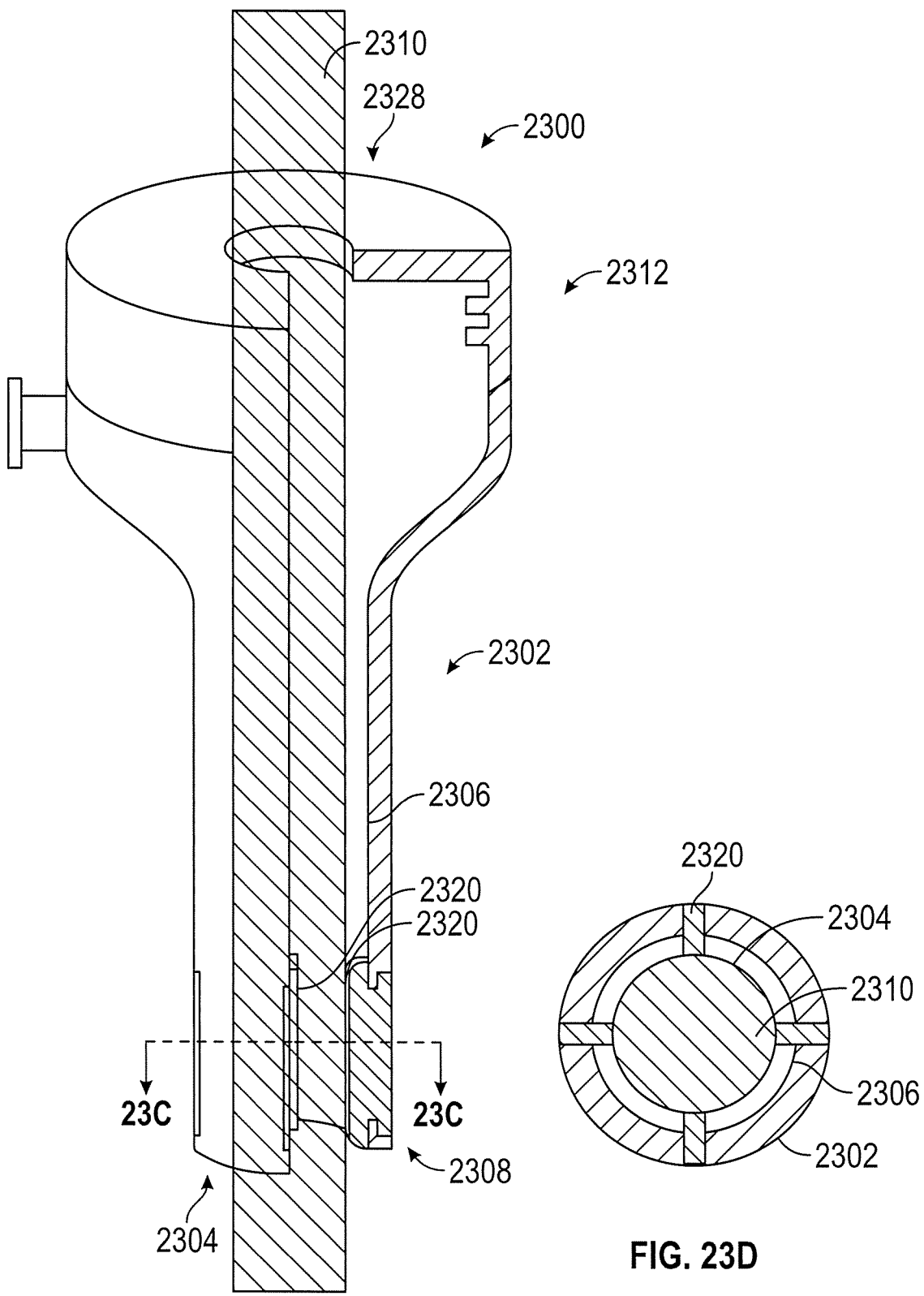
Figure 23E:
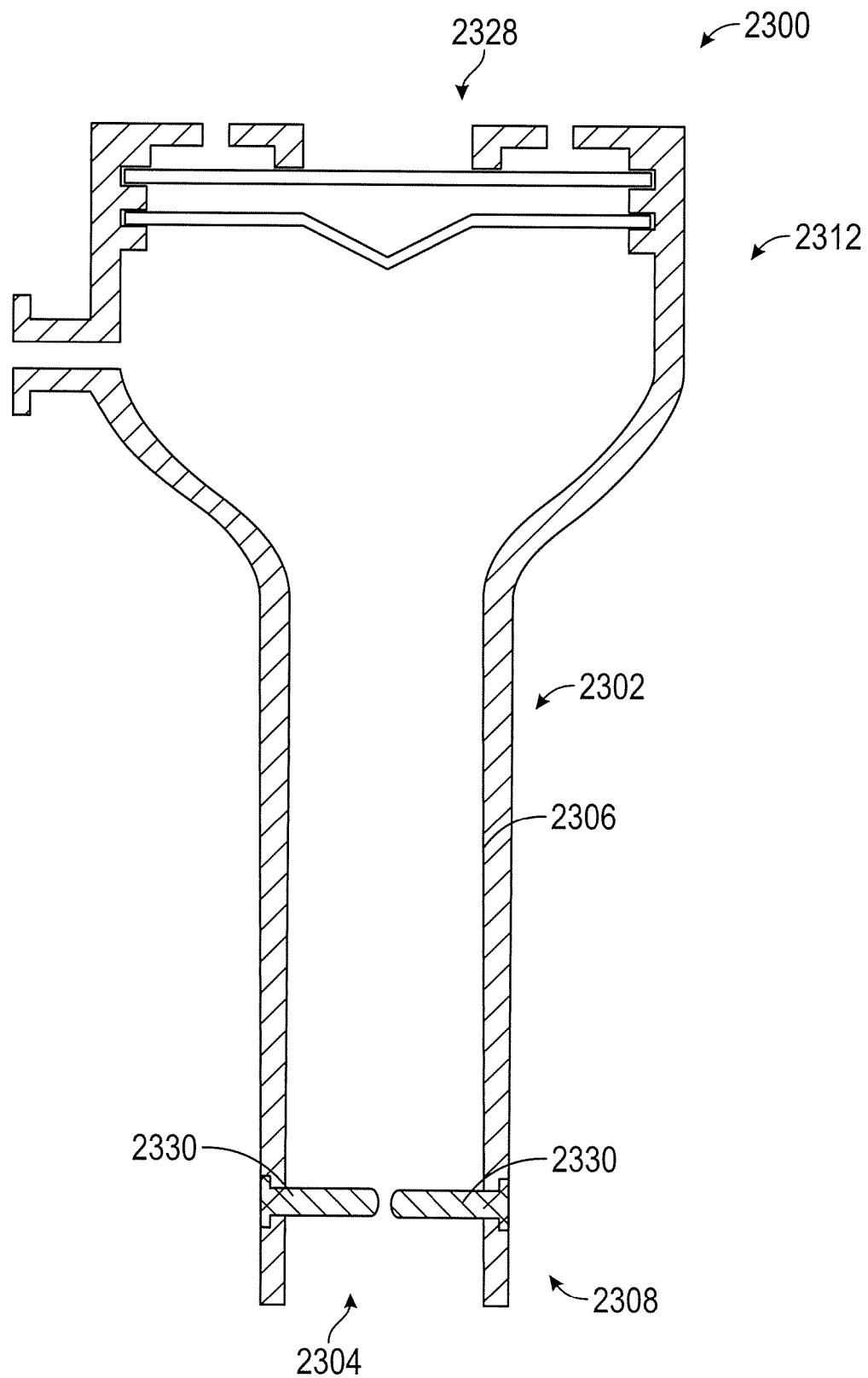
Figure 23F:
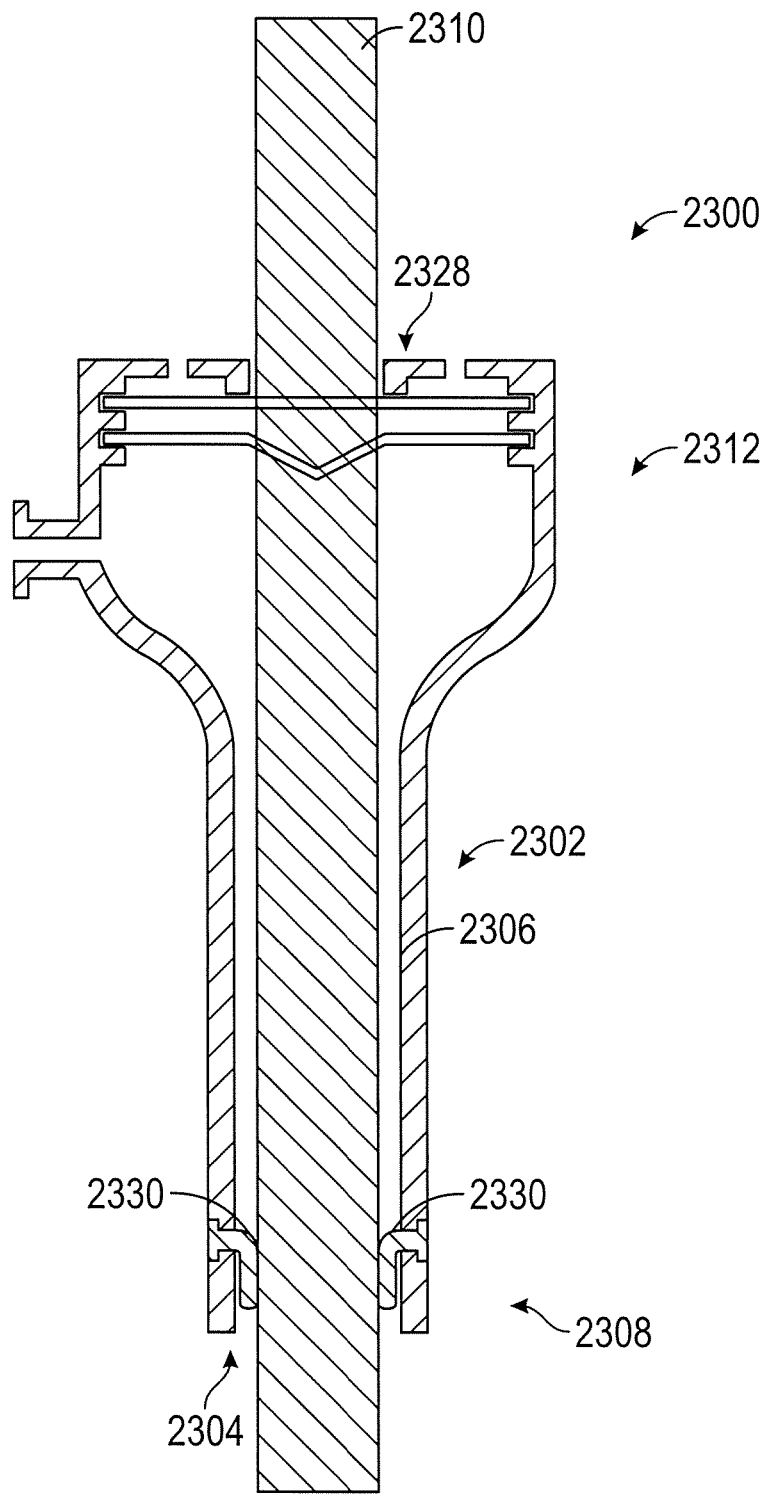
Figure 23G:
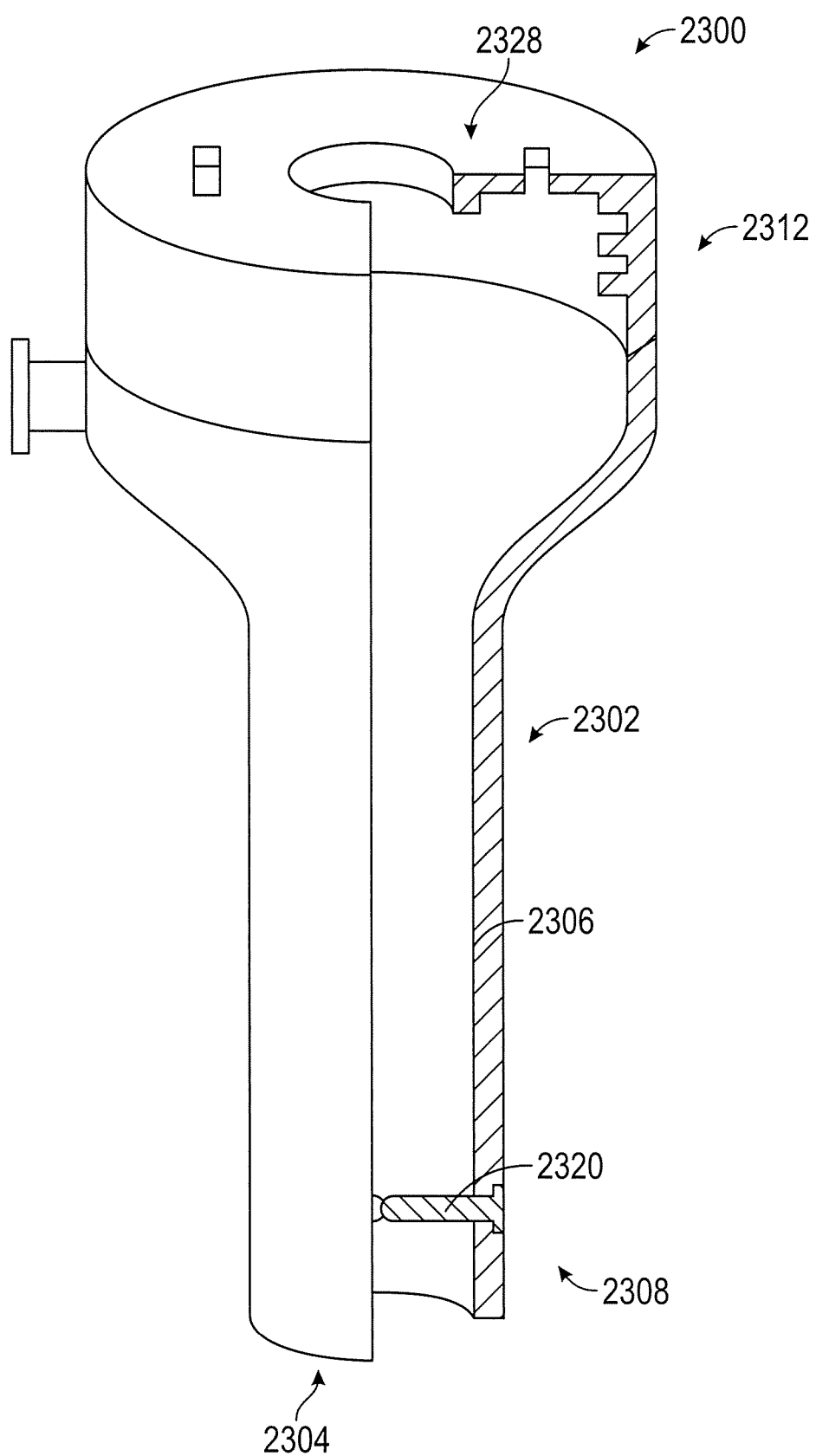
Figure 23H:
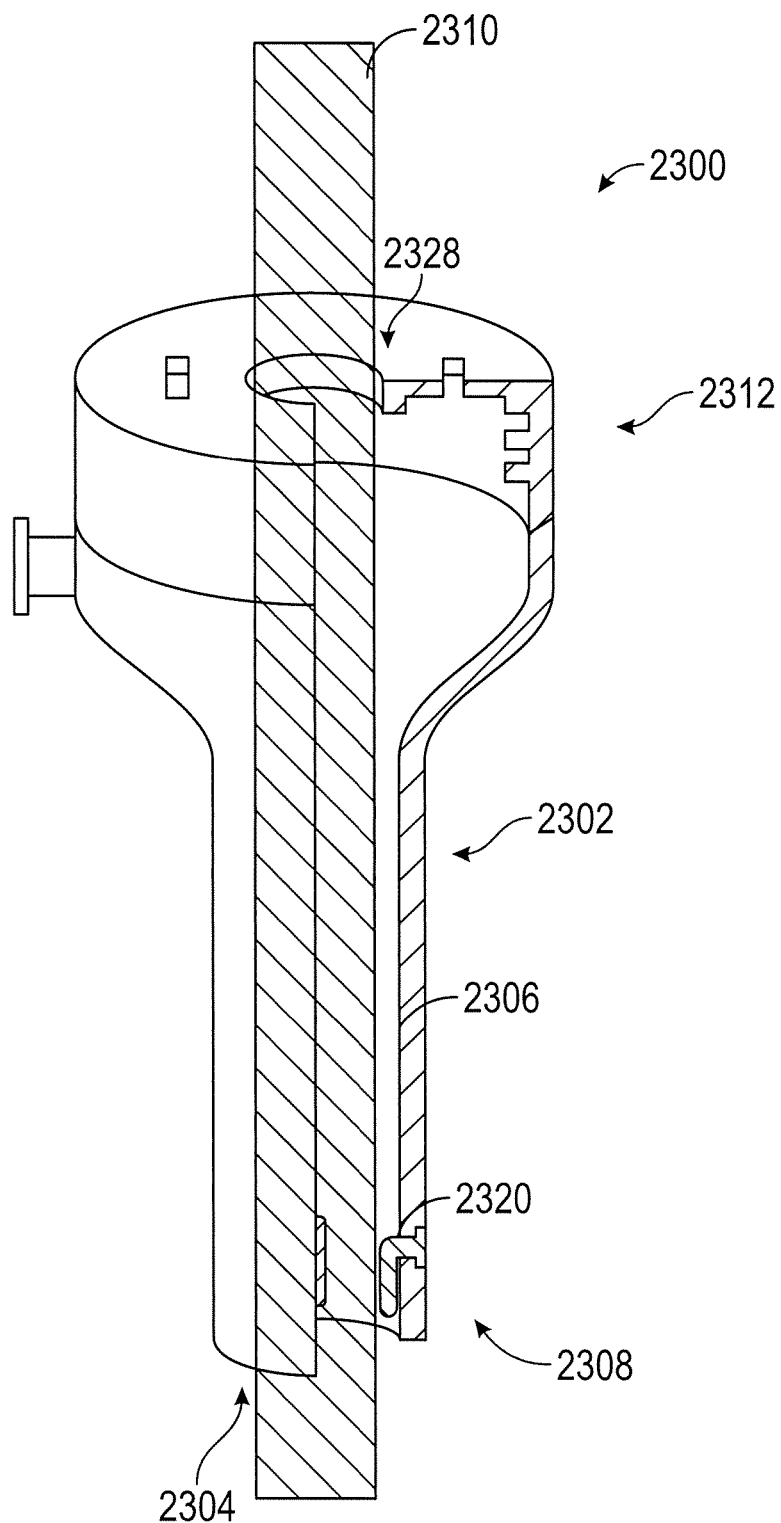
Figure 23I:
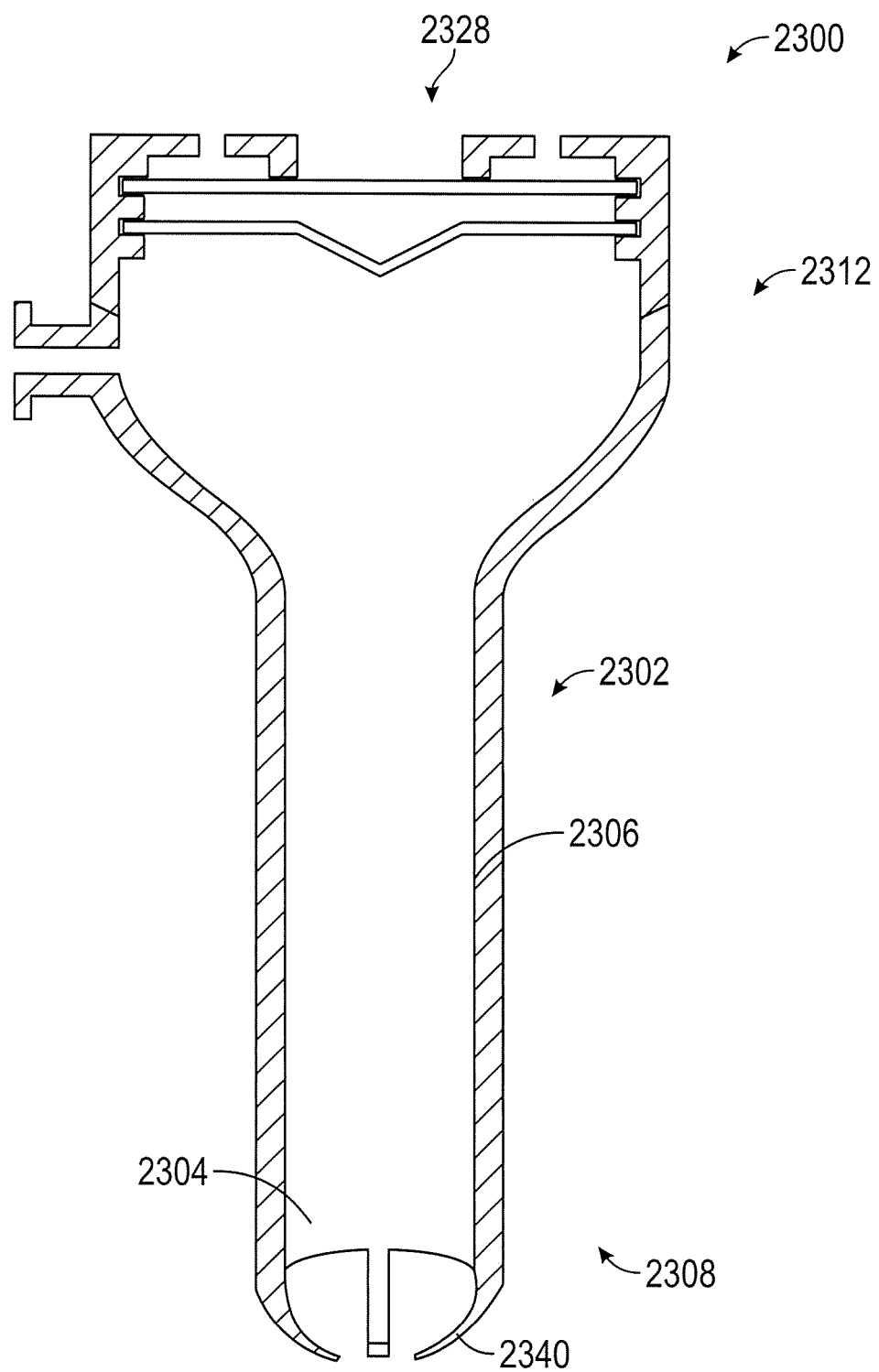
Figure 23J:
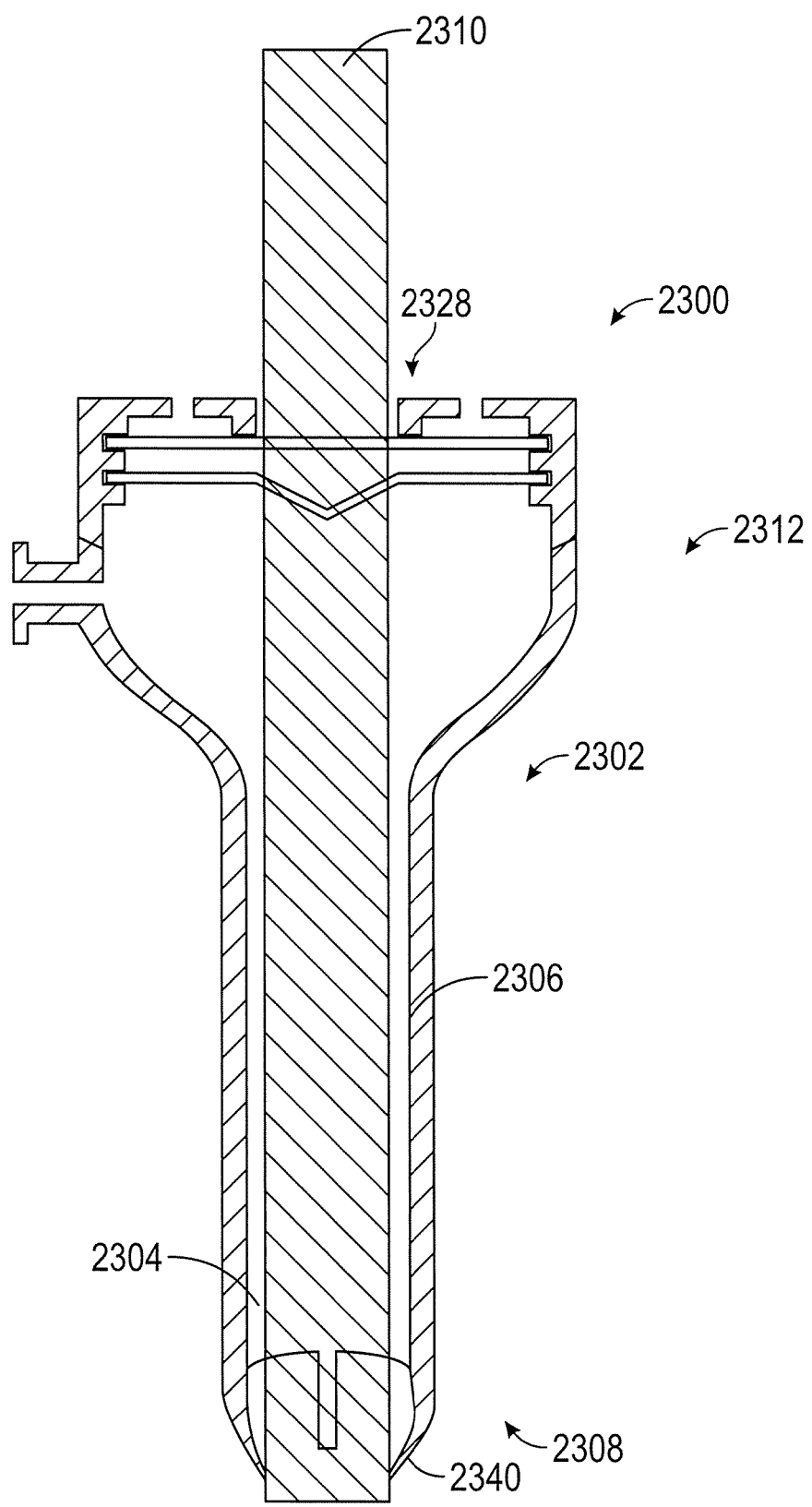
Figure 23K:
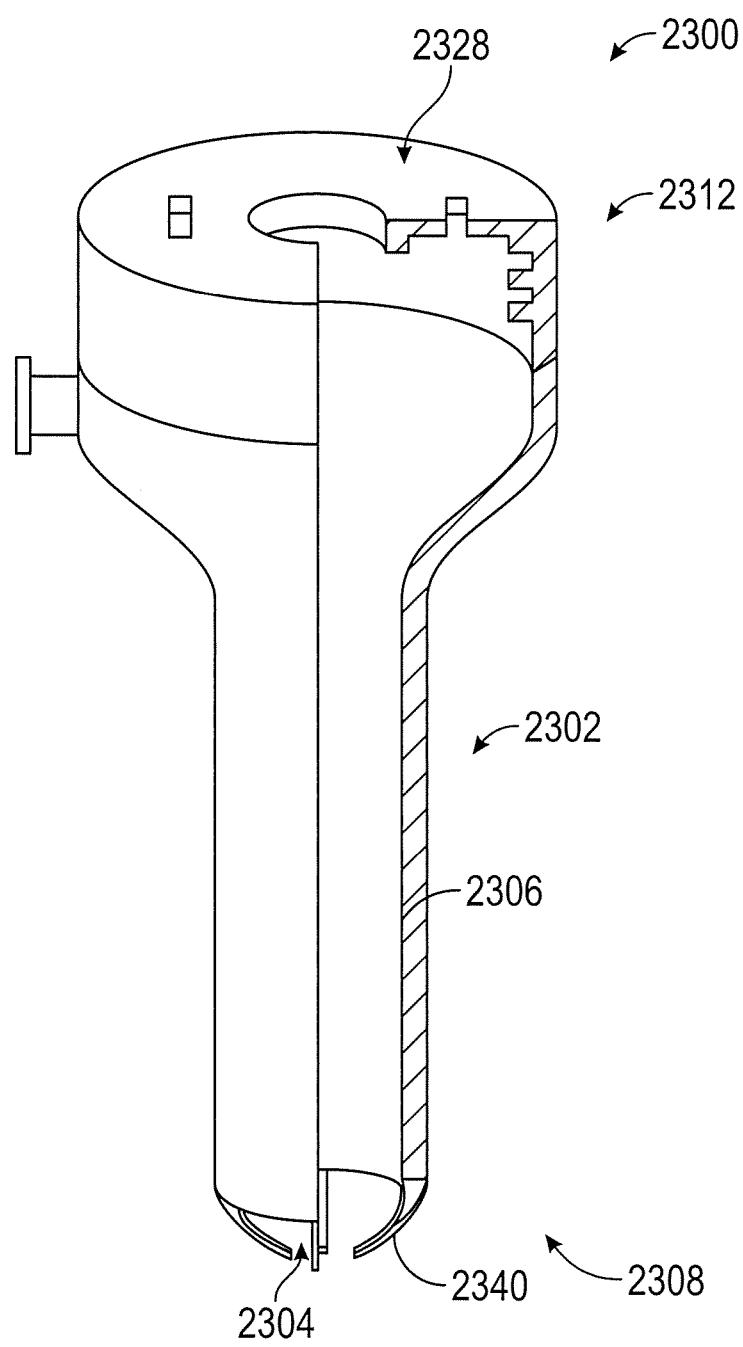
Figure 23L:
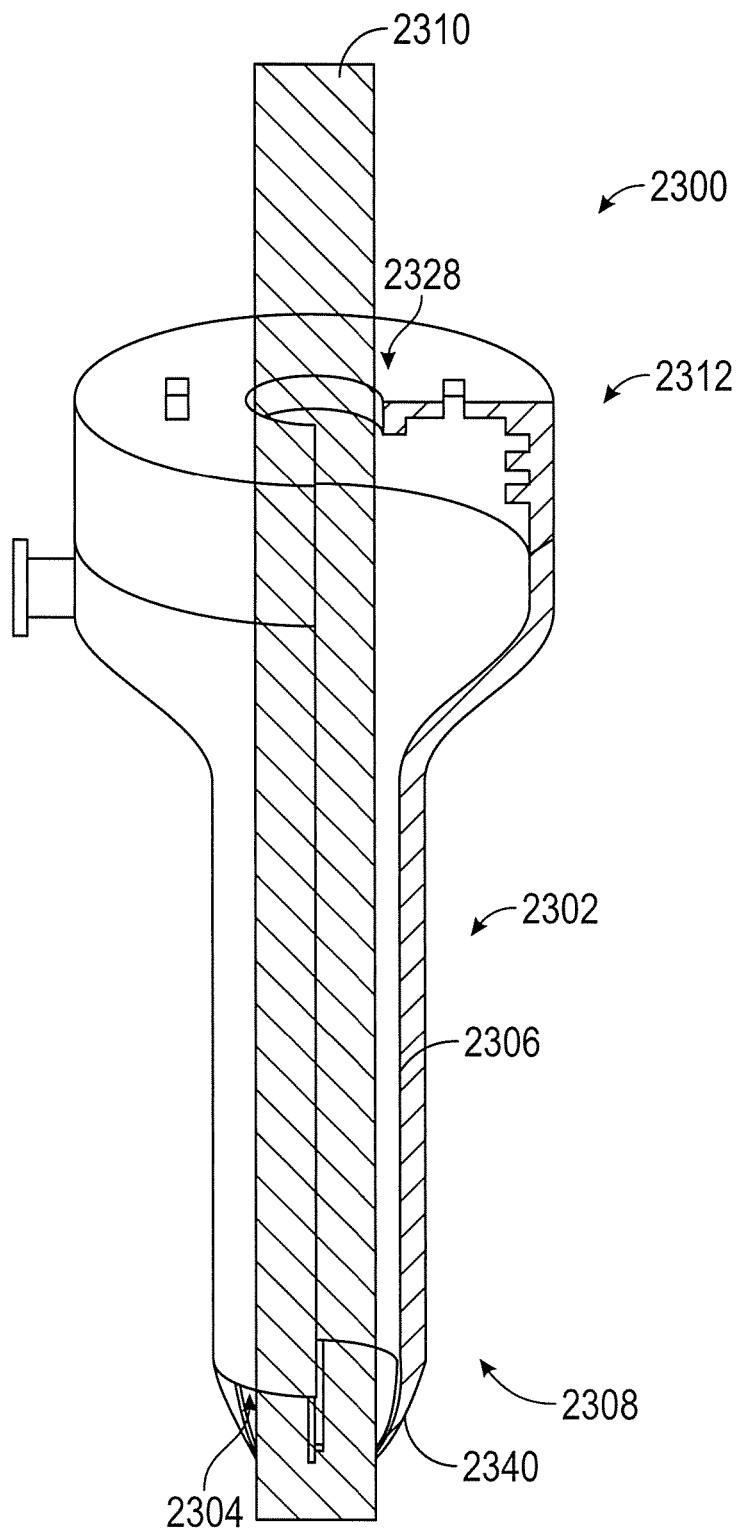
Figure 23M:
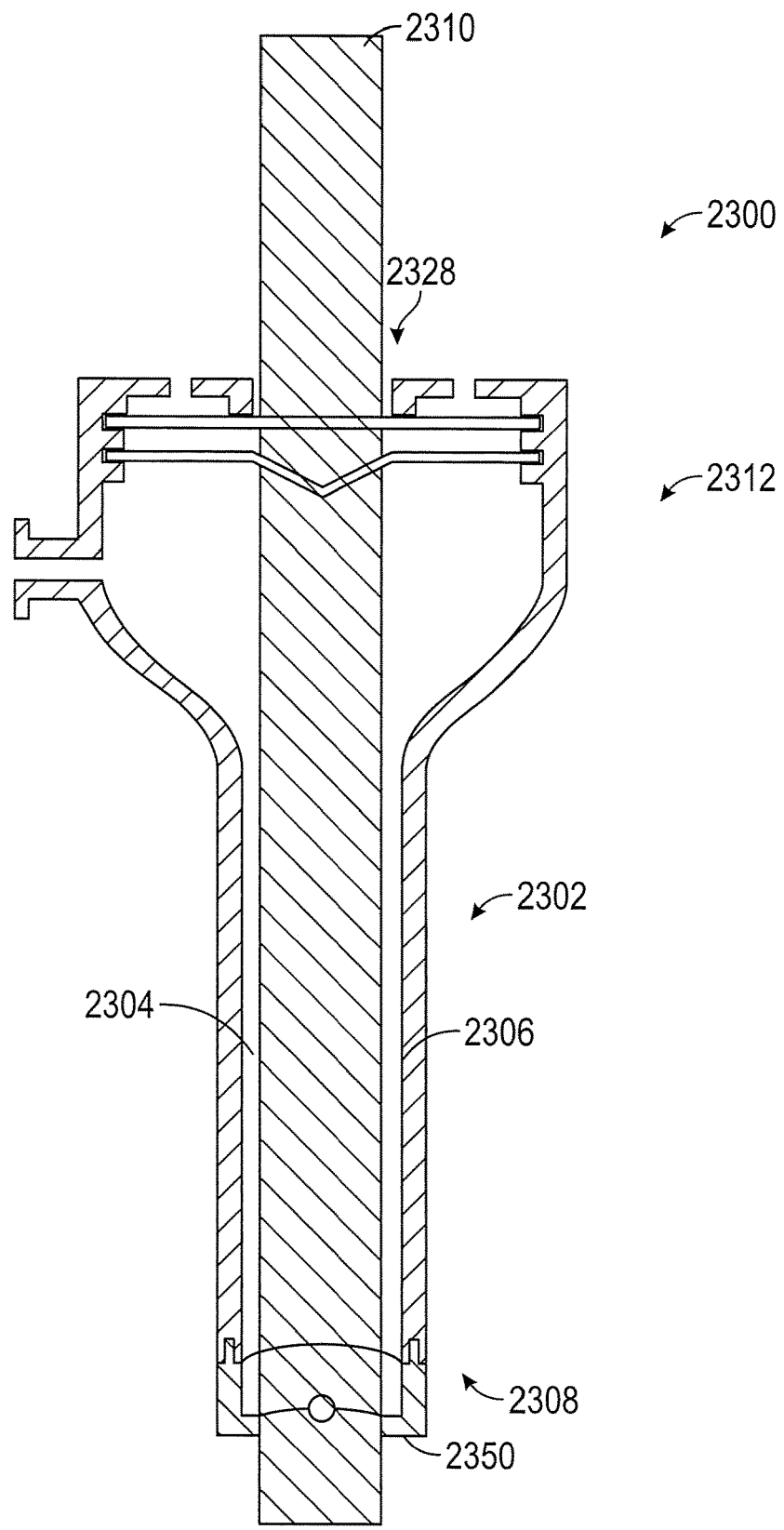
Figure 23N:
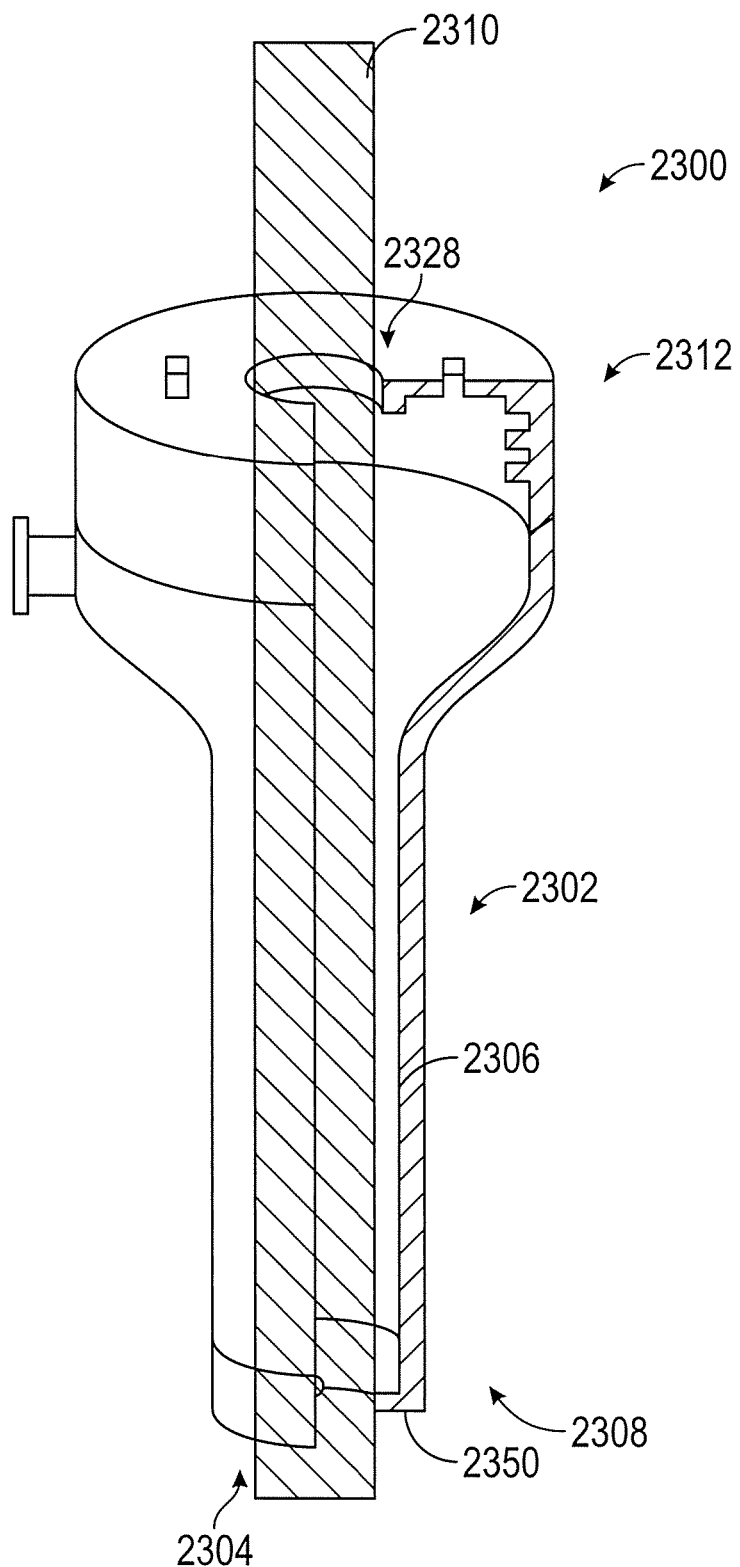
Figure 23O:
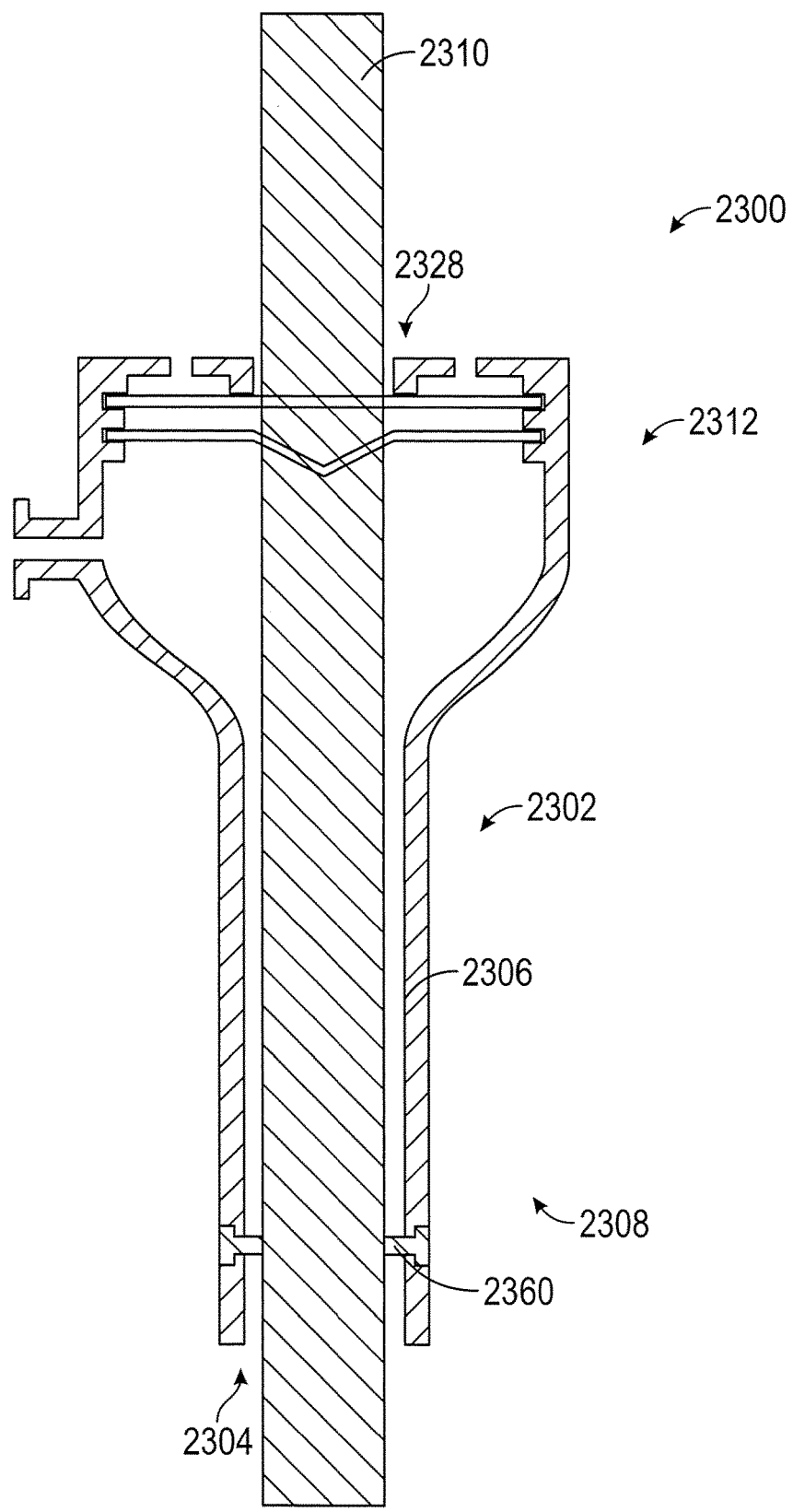
Figure 23P:
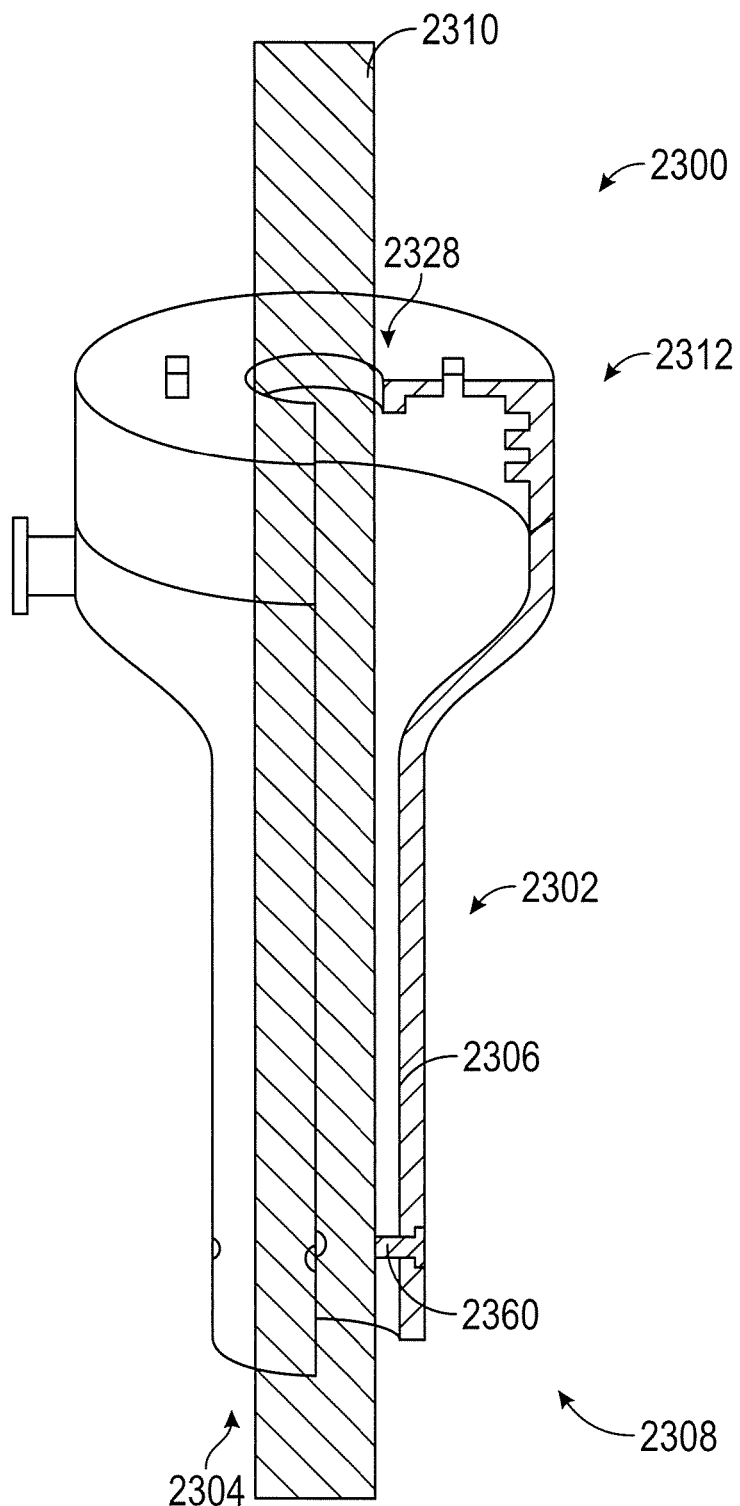
Figure 23Q:
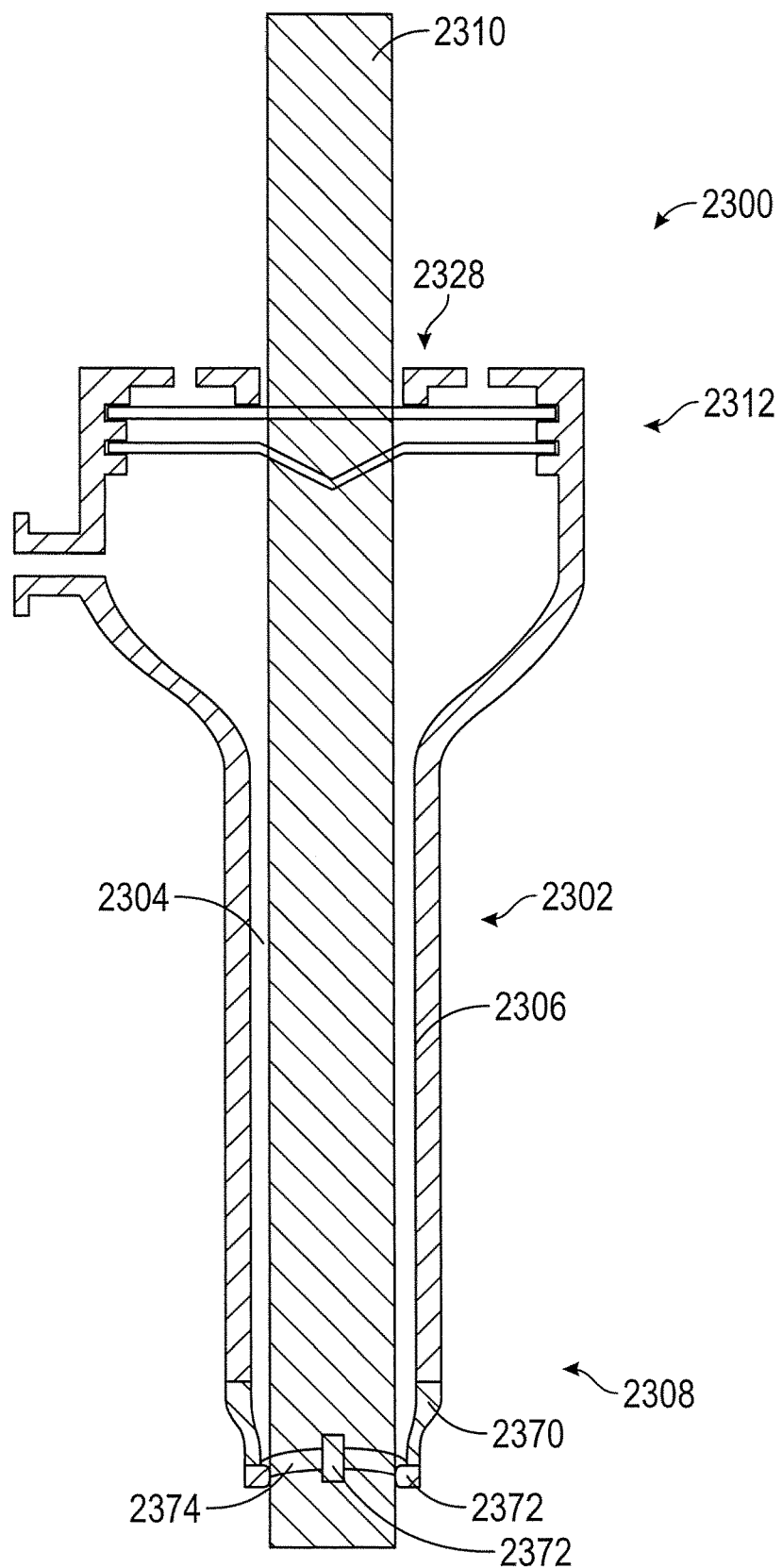
Figure 23R:
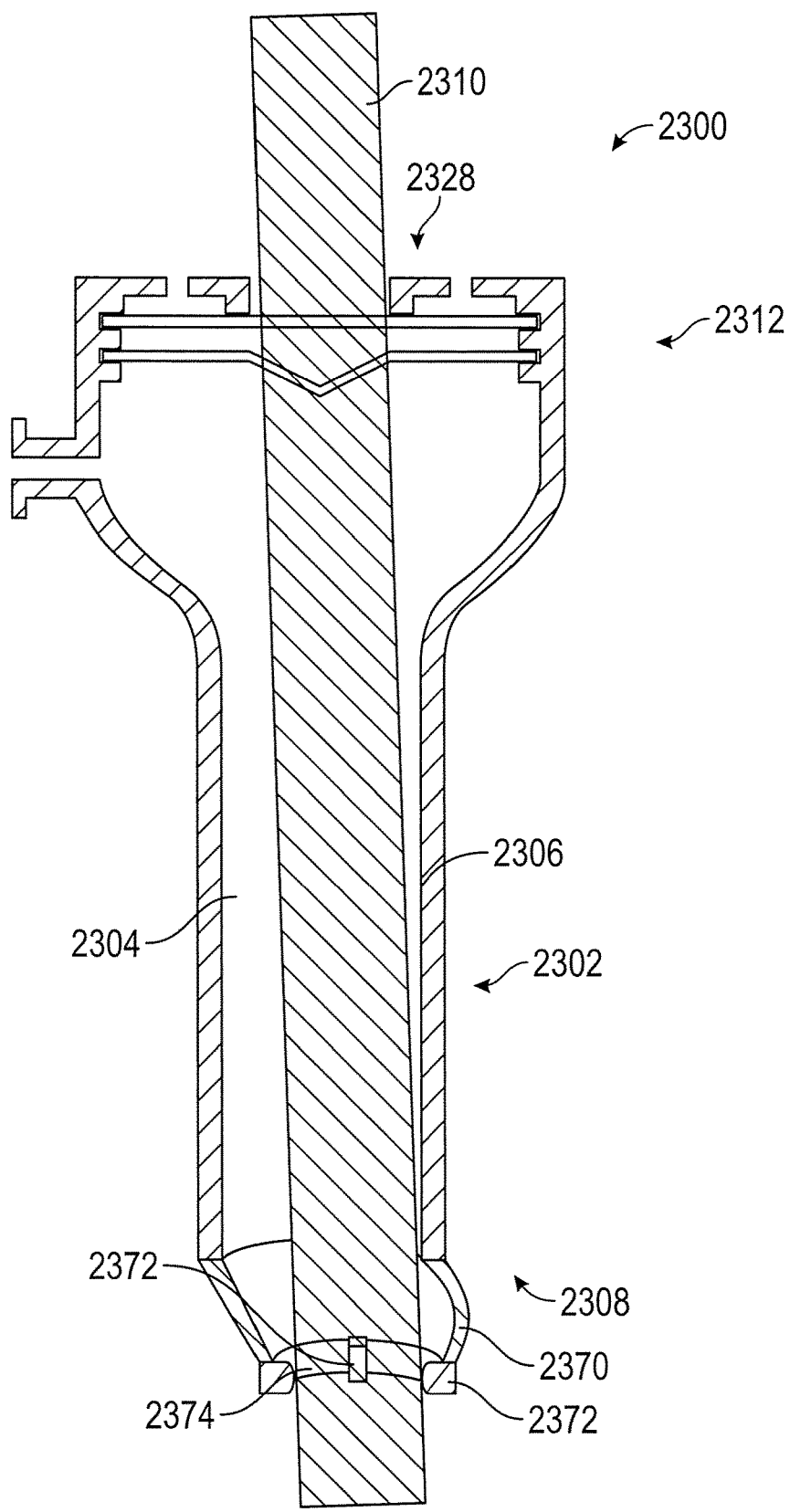
Figure 23S:
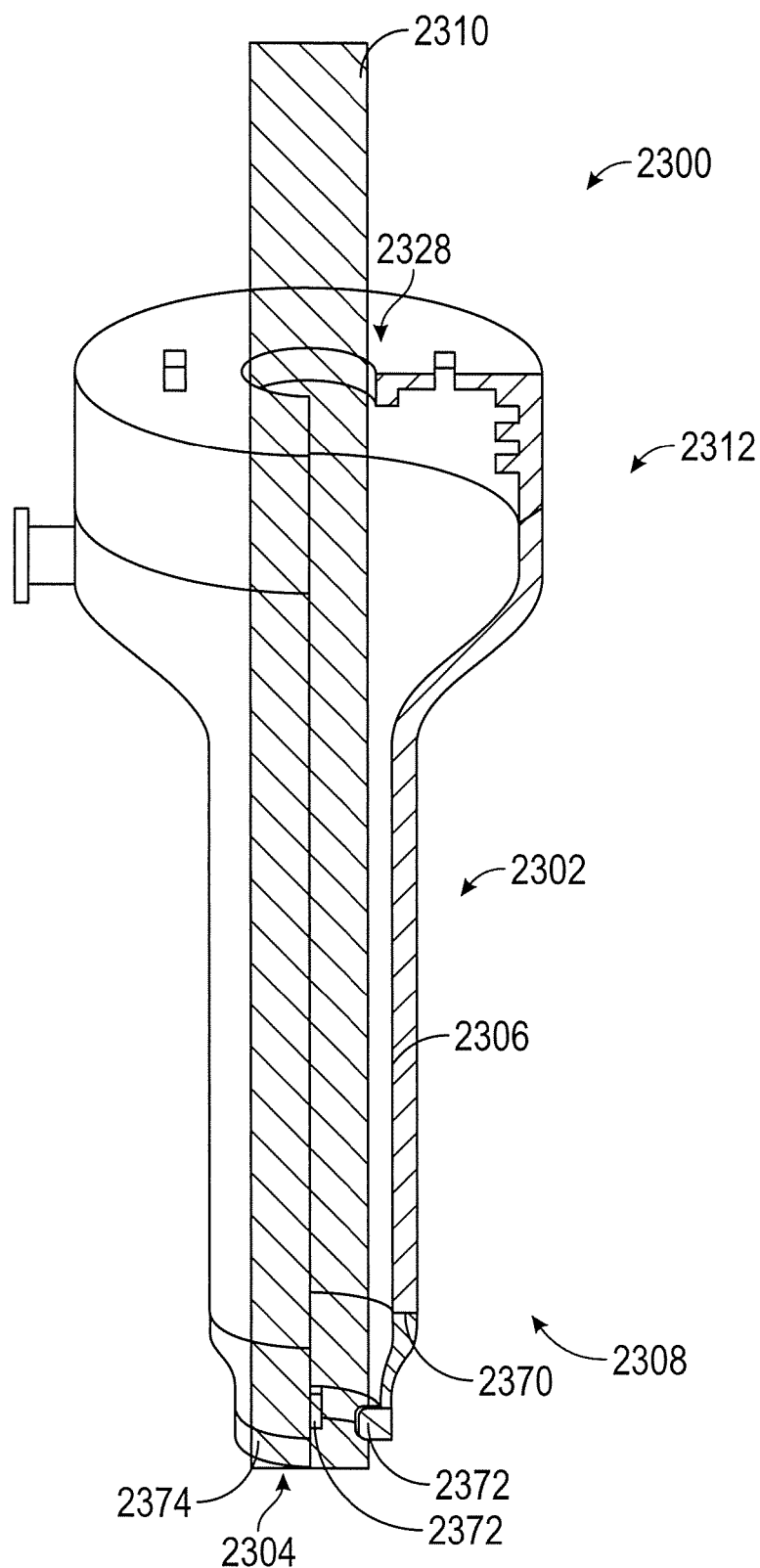
Figure 23T:
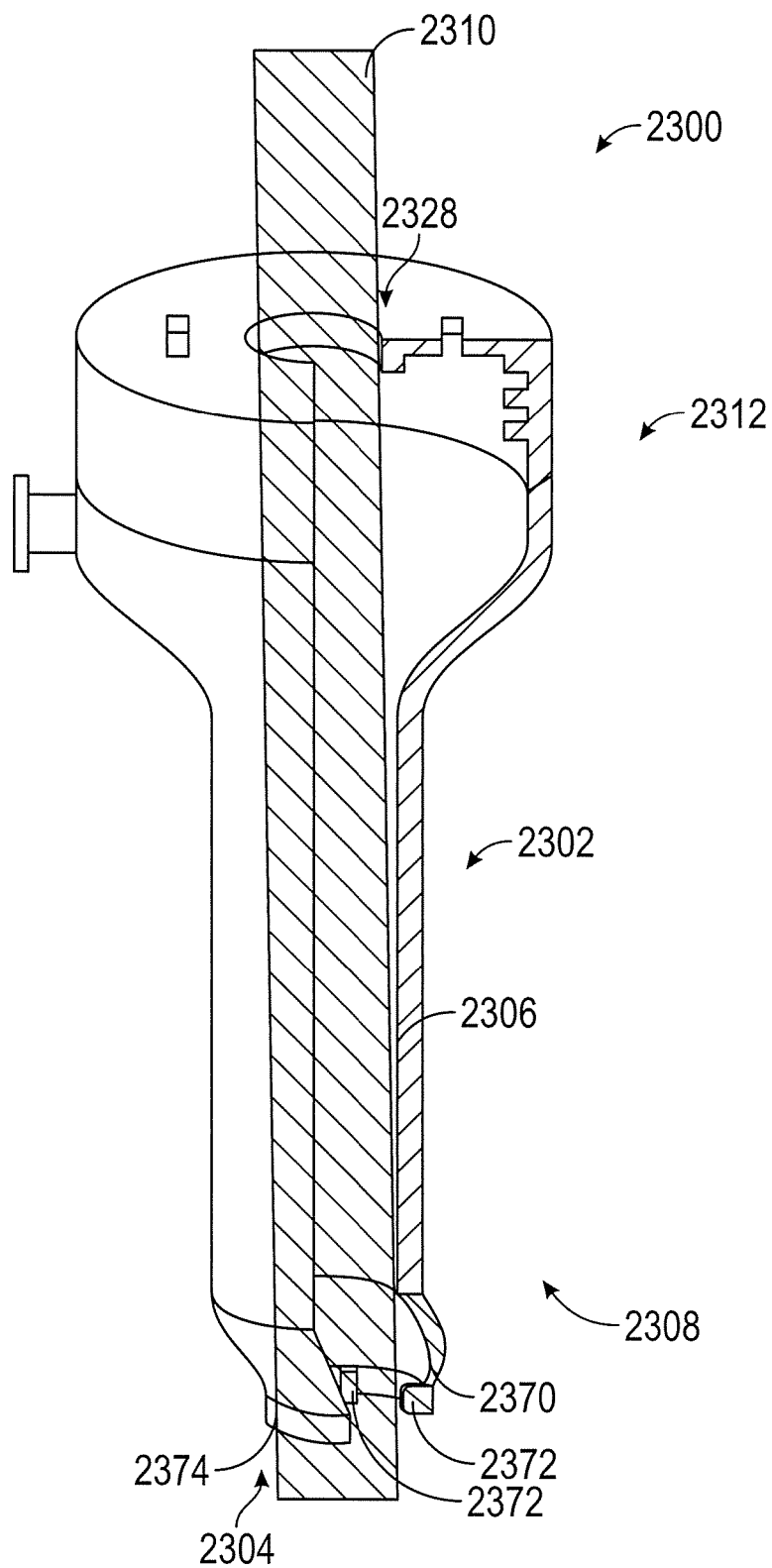

FIGS. 23A-23T illustrate embodiments of cannulas 2300 with guide elements that include flexible features at the distal end 2308 of the cannula 2300 to aid in concentricity of the medical instrument 2310 within the cannula 2300. The cannula 2300 can include a cannula body 2312 and elongate shaft 2302. The elongate shaft 2302 can include a cannula sidewall 2306 that forms the lumen 2304 of the cannula. The lumen 2304 can defined by the inner sidewall 2306 of the cannula 2300 as shown in FIGS. 23A-23T. As described herein, a medical instrument 2310 can be inserted through the cannula by being introduced through an inlet 2328 at the proximal end of the cannula body and extending through the lumen 2304 of the cannula 2300 toward the distal end 2308 of the elongate shaft 2302. As described herein the term inner, inner wall, inner circumference, inner cross-section, or inner portion with respect to a cannula, cannula wall, or an insert within the cannula can refer to the portion of the feature facing the interior of the cannula including the lumen of the cannula and the term outer, outer wall, outer circumference, outer cross-section, or outer portion with respect to a cannula, cannula wall, or insert within the cannula can refer to a portion of the feature that is opposite the inner portion.

As shown in FIG. 23A, the medical instrument can be supported by guide elements, such as flexible ribs 2320 at the distal end 2308 of the cannula to accomplish medical instrument 2310 concentricity. The flexible features ribs 2320 can be molded onto or attached to the distal end 2308 of the cannula elongate shaft 2302. The flexible features ribs 2320 can be over molded into the cannula sidewall 2306. The flexible features or flexible ribs can be flexible or semi-flexible. FIG. 23B is a cross-section through line 23A-23A of FIG. 23A, better illustrating ribs 2320.

FIG. 23C illustrates a partial cut-away schematic view of the cannula of FIGS. 23A-23B. Features in FIGS. 23C and 23D can be the same or substantially the same features as shown and described in FIGS. 23A and 23B and reference numerals of the same or substantially the same features may share the same reference numerals. FIG. 23D is a cross-section through line 23C-23C of FIG. 23C, better illustrating ribs 2320.

FIGS. 23E and 23F illustrate a cannula 2300 with guide elements, such as flexible pins 2330 at the distal end 2308 of the cannula 2300 to accomplish medical instrument 2310 concentricity. Features of FIGS. 23E and 23F are similar to the features described with reference to FIGS. 23A-23D. Accordingly, similar features of FIGS. 23E and 23F have the same reference numerals as in FIGS. 23A-23D. The flexible pins 2330 can protrude into the lumen 2304 of the cannula elongate shaft 2302. As shown in FIG. 23F, when the medical instrument 2310 is inserted within the lumen 2304 of the cannula elongate shaft 2302 the medical instrument 2310 can push the flexible pins 2330 out of the way or against the cannula sidewall 2306. The flexible pins 2330 therefore push back on the medical instrument 2310 and hold it concentrically within the cannula 2300.

FIGS. 23G and 23H illustrate partial cut-away schematic views of the cannula of FIGS. 23E-23F. Features in FIGS. 23G and 23H can be the same or substantially the same features as shown and described in FIGS. 23E and 23F and reference numerals of the same or substantially the same features may share the same reference numerals. FIGS. 23E and 23G illustrate the cannula 2300 without the medical instrument 2310 inserted within the cannula. In this configuration, the flexible pins 2330 protrude radially into the lumen 2304. FIGS. 23F and 23H illustrate the cannula 2300 with the medical instrument inserted within the cannula 2300. The flexible pins care pushed against the cannula sidewall 2306 as the medical instrument 2310 is inserted and maintained concentrically in the cannula 2300.

FIGS. 23I and 23J illustrate a cannula 2300 with guide elements including a flexible or semi-flexible flaring fin structure 2340 at the distal end 2308 of the cannula 2300 to accomplish medical instrument 2310 concentricity. Features of FIGS. 23I and 23J are similar to the features described with reference to FIGS. 23A-23D. Accordingly, similar features of FIGS. 23I and 23J have the same reference numerals as in FIGS. 23A-23D. FIG. 23I illustrates the cannula 2300 with a flaring fin structure 2340 shown without the medical instrument 2310. The flaring fin structure 2340 can be made of thin plastic or another semi-flexible material at the cannula distal end 2308. As illustrated in FIG. 23J, when the medical instrument 2310 is inserted within the lumen 2304, the medical instrument 2310 can be pushed past the flaring fin structure 2340 which deform and push back on the medical instrument 2310, holding medical instrument 2310 concentrically at the cannula elongate shaft 2302. The fin structure 2340 can flare outward when the medical instrument 2310 is pushed through the fin structure 2340 of the cannula 2300.

FIGS. 23K and 23L illustrate partial cut-away schematic views of the cannula of FIGS. 23I-23J. Features in FIGS. 23K and 23L can be the same or substantially the same features as shown and described in FIGS. 23I and 23J and reference numerals of the same or substantially the same features may share the same reference numerals. FIG. 23K illustrates the cannula 2300 with a flaring fin structure 2340 shown without the medical instrument 2310. As illustrated in FIG. 23L, when the medical instrument 2310 is inserted within the lumen 2304, the medical instrument 2310 can pushed past the flaring fin structure 2340 which deform and push back on the medical instrument 2310, holding medical instrument 2310 concentrically at the cannula elongate shaft 2302.

FIG. 23M illustrate a cannula 2300 with guide elements including a flexible distal end protrusion 2350 at the distal end 2308 of the cannula 2300 to accomplish medical instrument 2310 concentricity. Features of FIG. 23M are similar to the features described with reference to FIGS. 23A-23D. Accordingly, similar features of FIG. 23M have the same reference numerals as in FIGS. 23A-23D. FIG. 23M illustrates the cannula 2300 with a distal end protrusion 2350 shown with the medical instrument 2310 inserted within the cannula 2300. The flexible distal end protrusion 2350 can be molded onto the distal most end of the cannula elongate shaft 2302. One or more flexible distal end protrusions 2350 can be spaced around the circumference of the outlet of the elongate shaft of the cannula at the distal end 2308 as shown in FIG. 23M. The flexible distal end protrusion 2350 can be over-molded into the cannula. The flexible distal end protrusion 2350 can contains concentric features, such as pins, at the outlet of the elongate shaft 2302 of the cannula 2300, which hold the medical instrument 2310 concentrically in the flexible distal most end of the cannula as shown in FIG. 23M. As illustrated in FIG. 23M, when the medical instrument 2310 is inserted within the lumen 2304, the medical instrument 2310 abuts the one or more flexible distal end protrusions 2350 which holds the medical instrument 2310 concentrically in the cannula elongate shaft 2302.

FIG. 23N illustrates a partial cut-away schematic view of the cannula of FIG. 23M. Features in FIG. 23N can be the same or substantially the same features as shown and described in FIG. 23M and reference numerals of the same or substantially the same features may share the same reference numerals.

FIG. 23O illustrates a cannula 2300 with guide elements including a flexible protrusion 2360 inside the cannula shaft 2302 to accomplish medical instrument 2310 concentricity. Features of FIG. 23O are similar to the features described with reference to FIGS. 23A-23D. Accordingly, similar features of FIG. 23O have the same reference numerals as in FIGS. 23A-23D. FIG. 23O illustrates the cannula 2300 with a protrusion 2360 shown with the medical instrument 2310 inserted within the cannula 2300. The flexible protrusions 2360 can be formed in the cannula elongate shaft 2302. The flexible protrusions 2360 are similar to the distal end protrusions 2350 described with reference to FIGS. 23M and 23N, however, the flexible protrusions 2360 are located within the cannula elongate shaft 2302 while the distal end protrusions 2350 are located on the distal most end of the cannula elongate shaft 2302. One or more flexible protrusions 2360 can be spaced around the circumference of the cannula elongate shaft 2302 as shown in FIG. 23O. The flexible protrusion 2360 can be molded or over-molded into the cannula shaft 2302. The flexible protrusion 2350 can contains concentric features, such as pins within the elongate shaft 2302, which hold the medical instrument 2310 concentrically in the cannula as shown in FIG. 22O. As illustrated in FIG. 23O, when the medical instrument 2310 is inserted within the lumen 2304, the medical instrument 2310 abuts the one or more flexible protrusions 2360 which holds the medical instrument 2310 concentrically in the cannula elongate shaft 2302.

FIG. 23P illustrates a partial cut-away schematic view of the cannula of FIG. 23O. Features in FIG. 23P can be the same or substantially the same features as shown and described in FIG. 23O and reference numerals of the same or substantially the same features may share the same reference numerals. One or more flexible protrusions 2360 can be spaced around the circumference of the cannula elongate shaft 2302 as shown in FIG. 23P.

FIGS. 23Q and 23R illustrate a cannula 2300 with guide elements including flexible bellows 2370 at the distal end 2308 of the cannula elongate shaft 2302 to accomplish medical instrument 2310 concentricity. Features of 23Q and 23R are similar to the features described with reference to FIGS. 23A-23D. Accordingly, similar features of 23Q and 23R have the same reference numerals as in FIGS. 23A-23D. FIG. 23Q illustrates the cannula 2300 with the flexible bellows 2370 shown with the medical instrument 2310 inserted within the cannula 2300. The flexible bellows 2370 can include concentric features, such as pins 2372, attached to a rigid or semi-rigid ring 2374 at the distal most end of the cannula 2300. The ring 2374 is attached to the cannula elongate shaft 2302 via the flexible bellows 2370. The bellows 2370 can enable the ring 2374 to move with the medical instrument 2310 but retain the medical instrument 2310 concentricity at the distal most end of the cannula 2300. In such cases, the medical instrument 2310 can be held concentrically in the gas flow within the cannula 2300. One or more pins 2372 can be spaced around the circumference of the ring 2374 as shown in FIGS. 23Q and 23R.

FIGS. 23S and 23T illustrate a partial cut-away schematic view of the cannula of FIGS. 23Q and 23R. Features in FIGS. 23S and 23T can be the same or substantially the same features as shown and described in FIGS. 23Q and 23R and reference numerals of the same or substantially the same features may share the same reference numerals.

FIGS. 23Q and 23S illustrate the medical instrument 2310 inserted parallel to or substantially parallel to the cannula elongate shaft 2302. In such cases, the ring 2374 at the distal most end of the bellows 2370 is aligned with the elongate shaft 2302. FIGS. 23R and 23T illustrate the medical instrument 2310 inserted at an angle within the cannula elongate shaft 2302. In such cases, the ring 2374 at the distal most end of the bellows 2370 is offset from the elongate shaft 2302 by stretching or otherwise causing flexing of the flexible bellows 2370 as illustrated in FIGS. 23R and 23T. The medical instrument 2310 can move around at different angles to the cannula 2300 and the bellows 2370 and ring 2374 can keep the medical instrument 2310 concentric in the gases flow within the cannula 2300. The bellows 2370 can be soft bellows that allow the pins 2372 on the ring 2374 at the distal most end of the cannula to move with the medical instrument 2310.

Figures 24A, 24B:
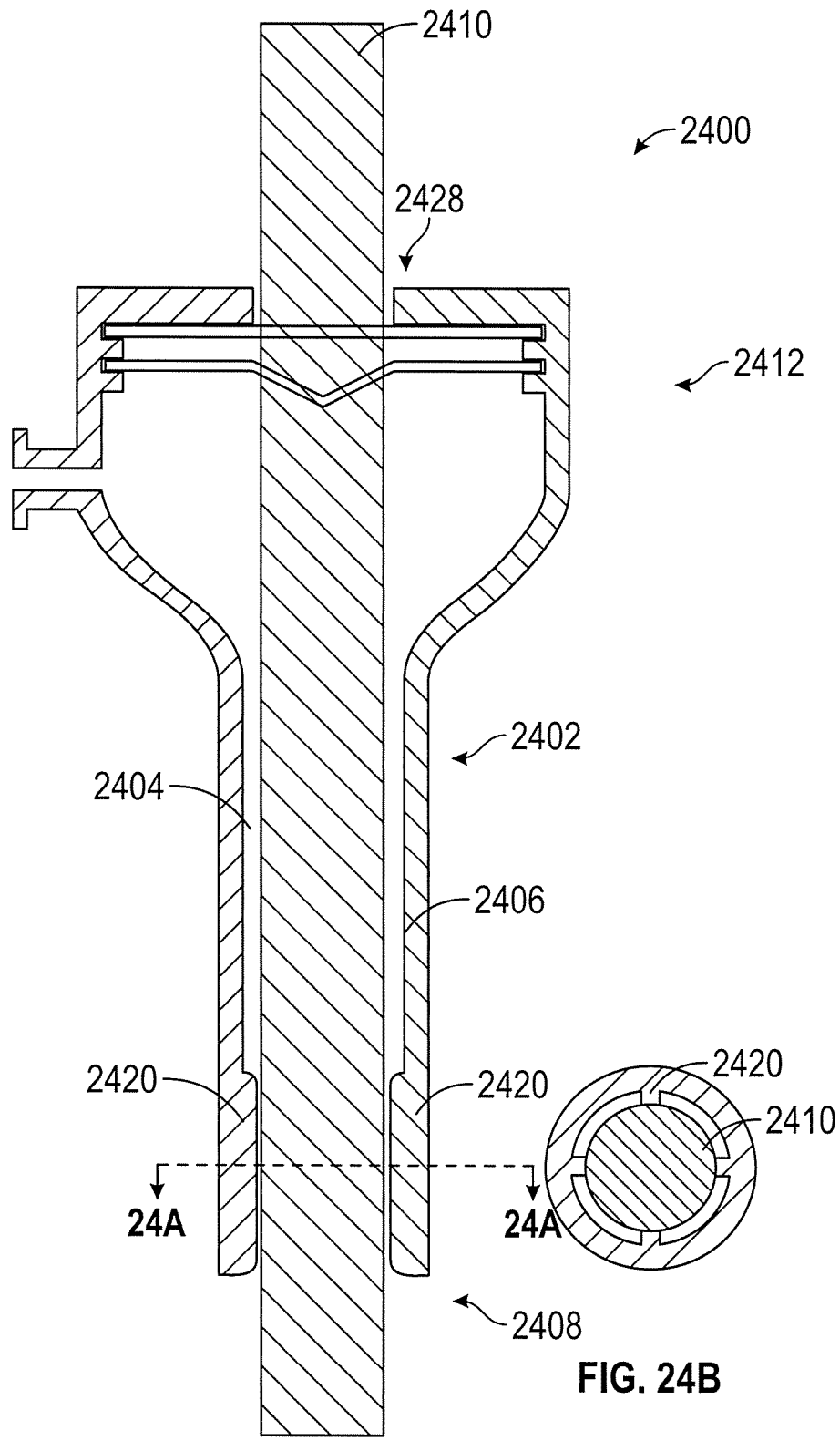
FIGS. 24A-24N illustrate views of embodiments of cannulas with rigid features within the cannula to aid in concentricity of the medical instrument within the cannula.
Figures 24E, 24F:
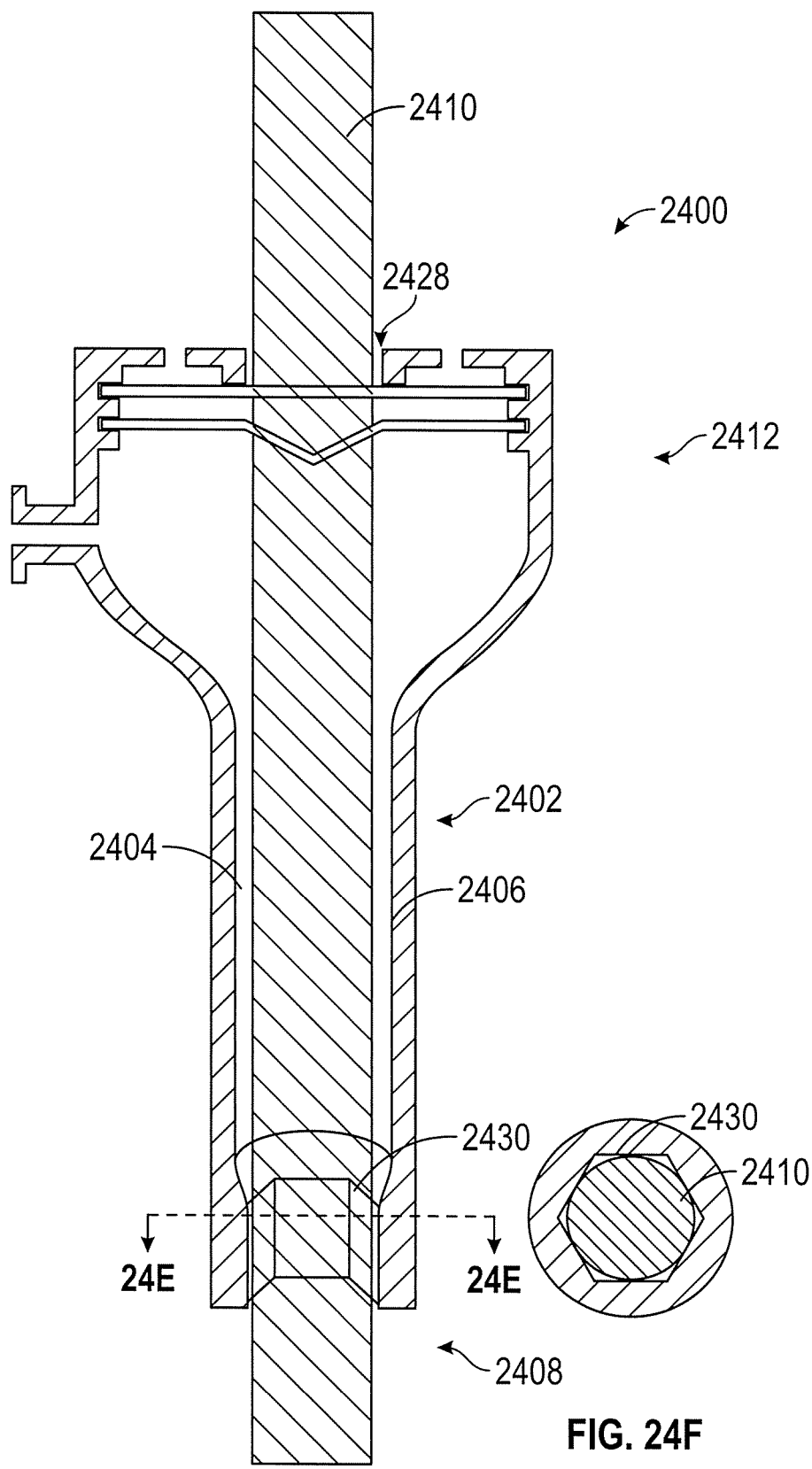
Figures 24G, 24H:
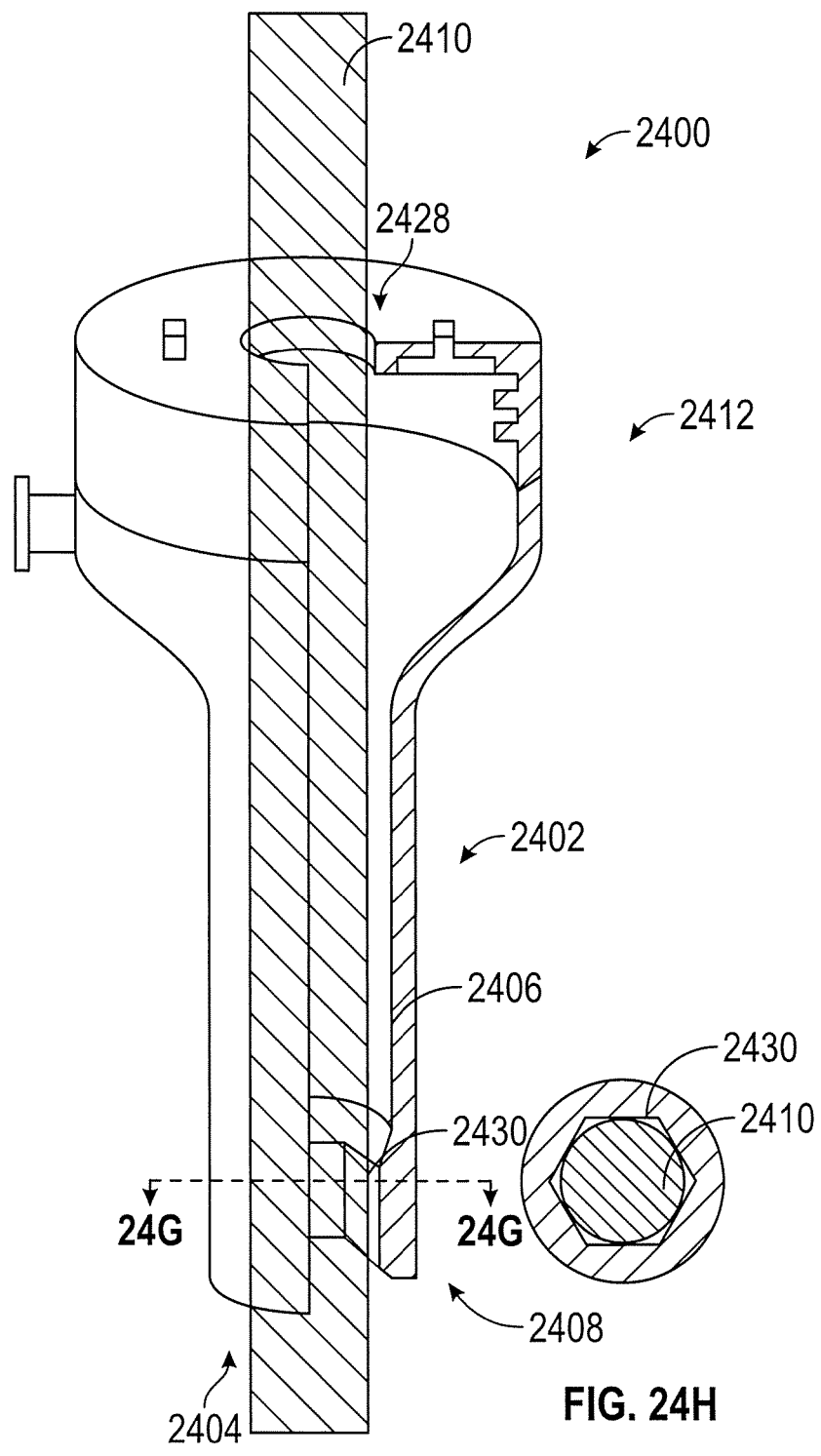
Figure 24I:
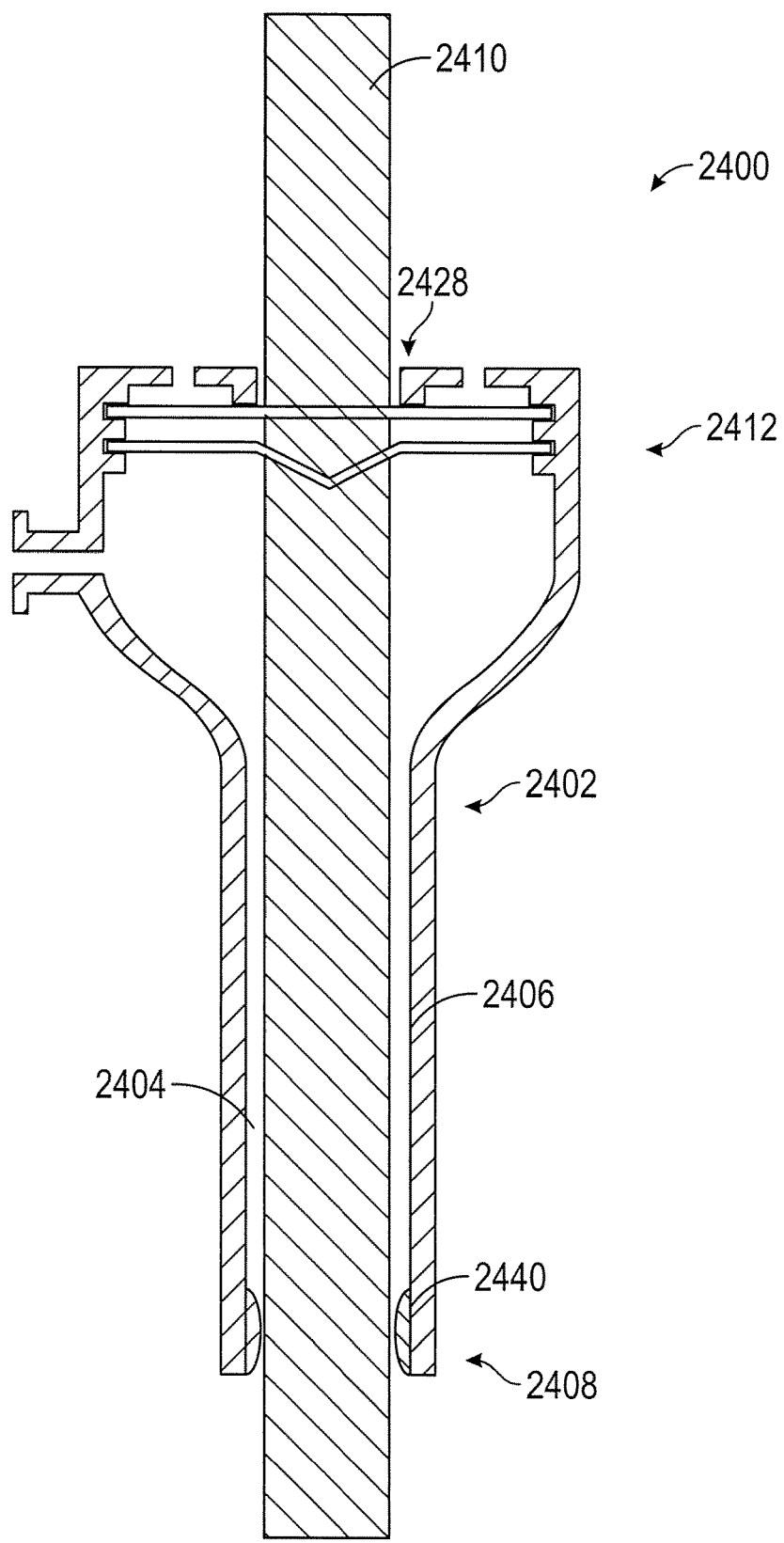
Figure 24J:
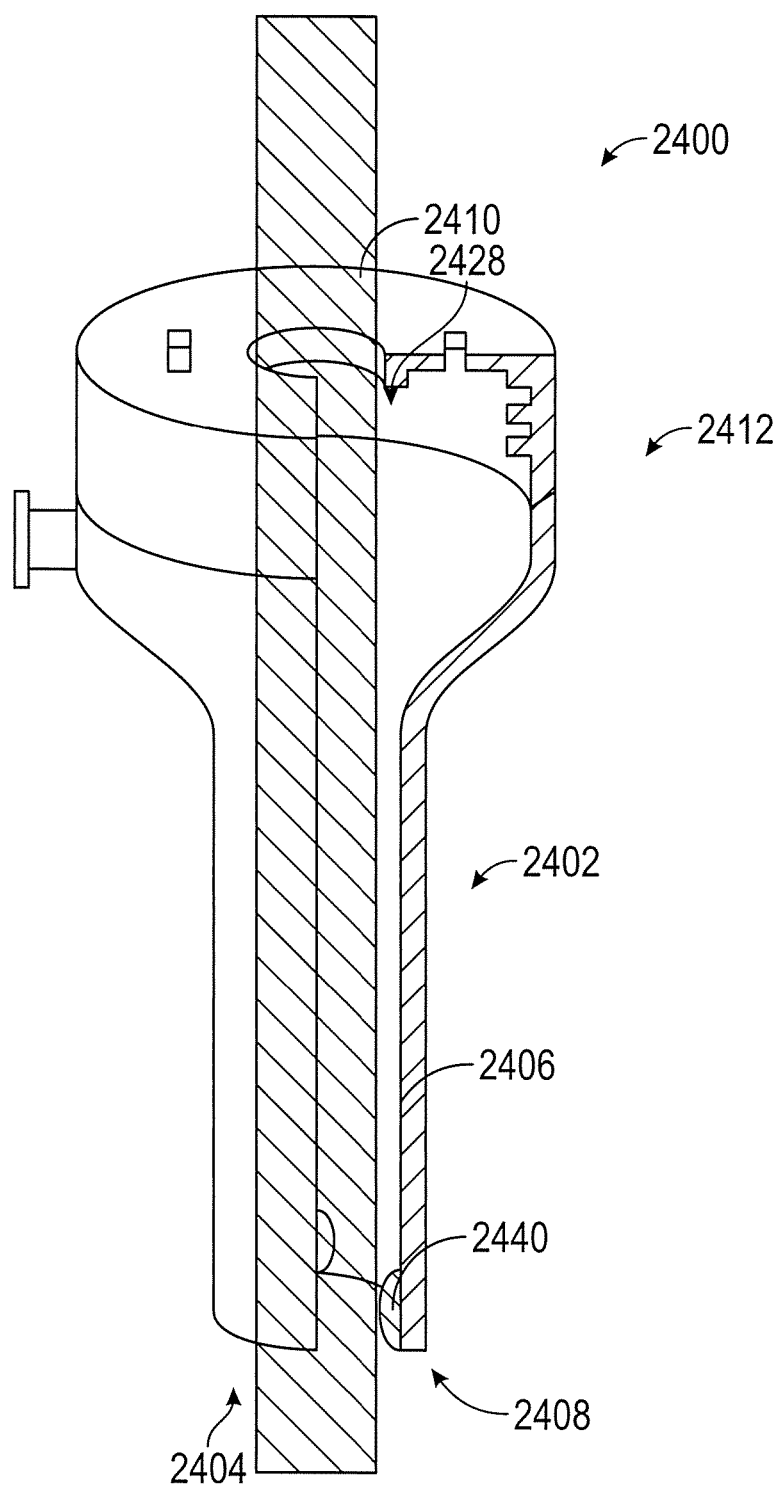
Figure 24K:
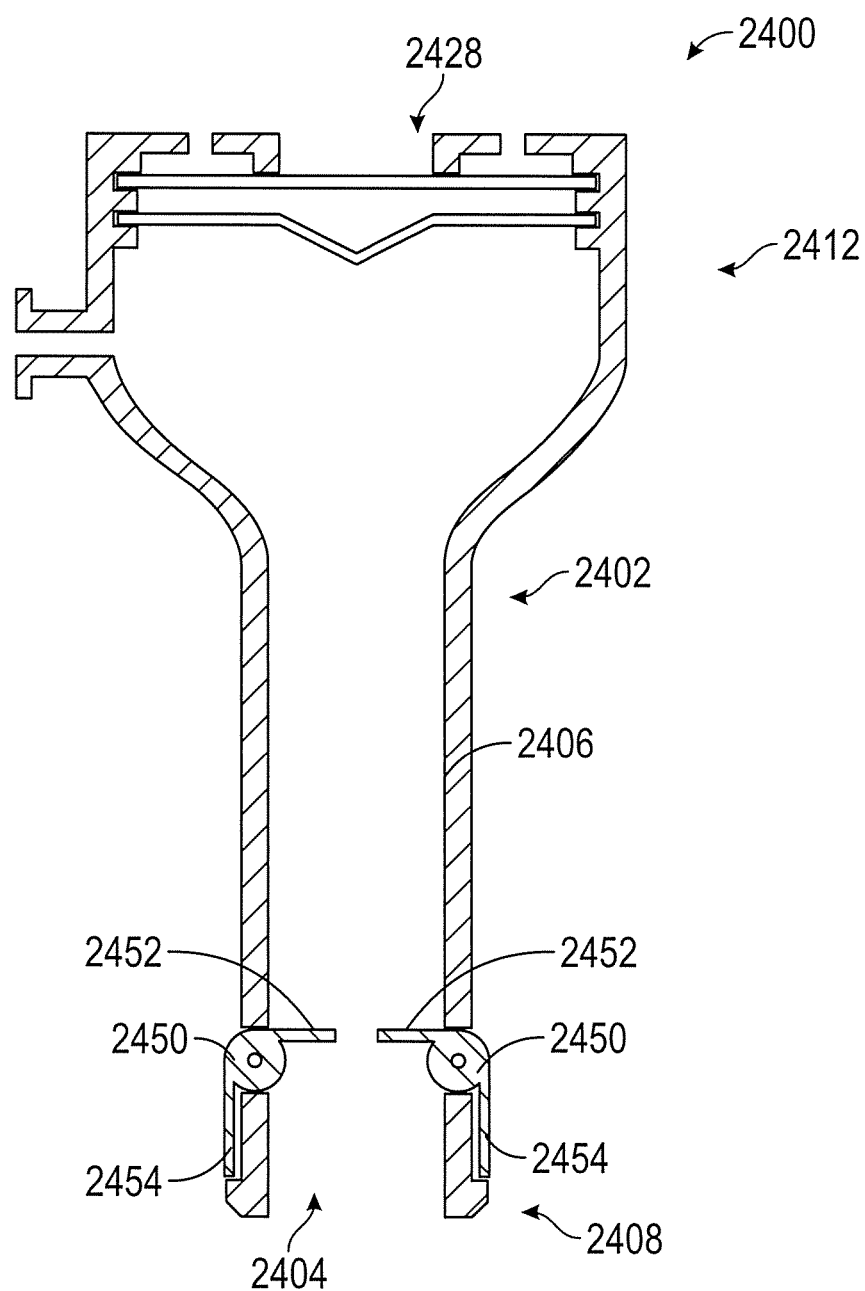
Figure 24L:
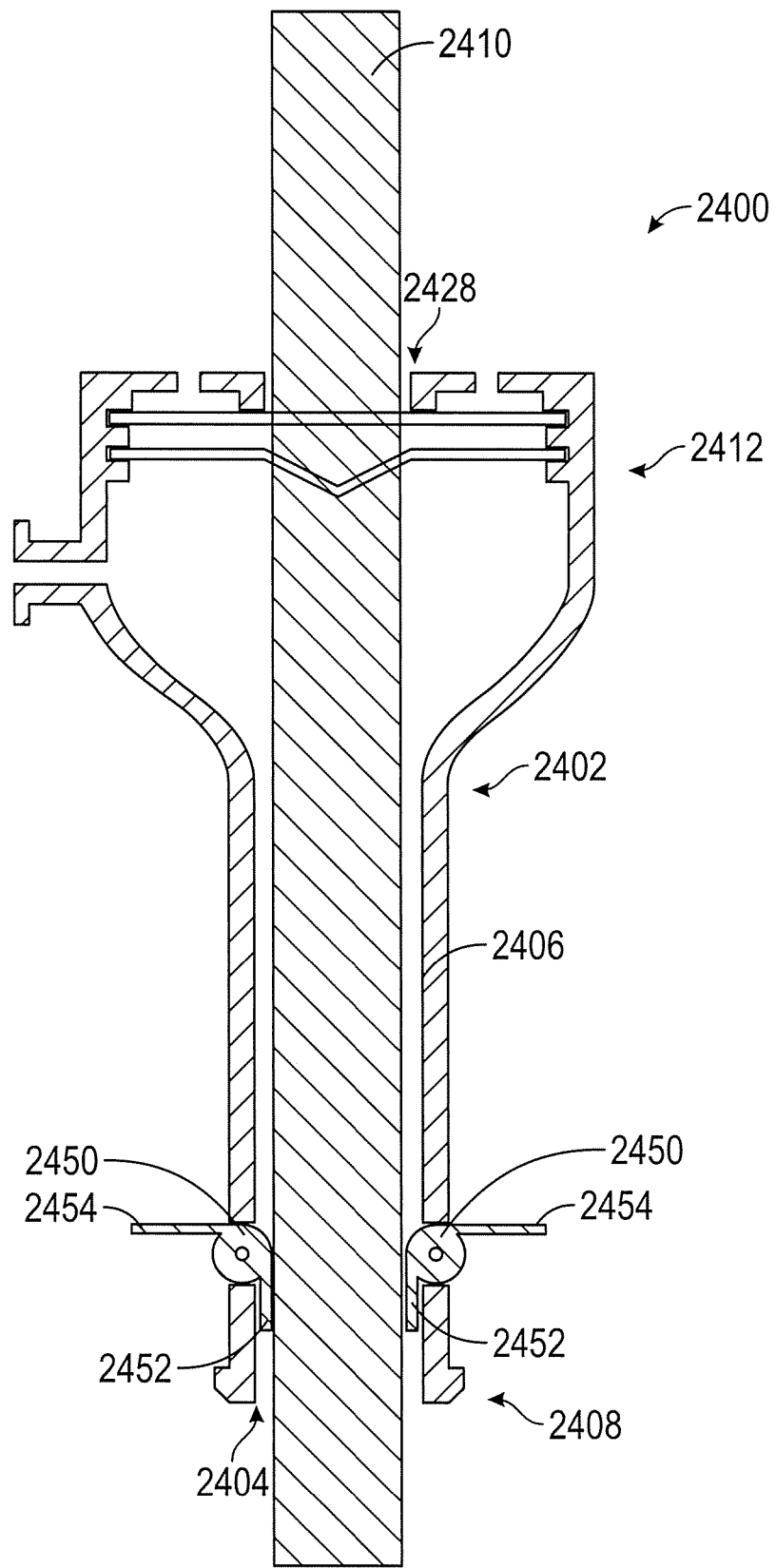
Figure 24M:
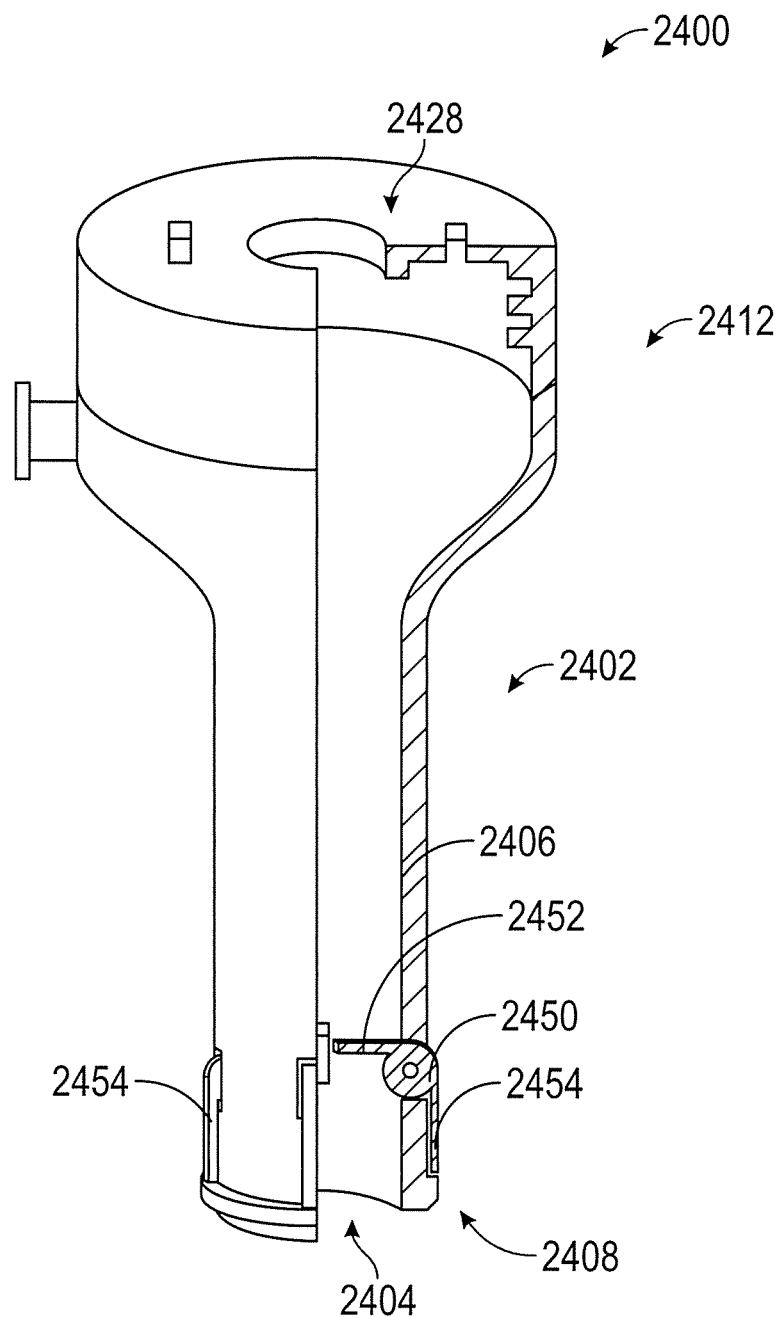
Figure 24N:
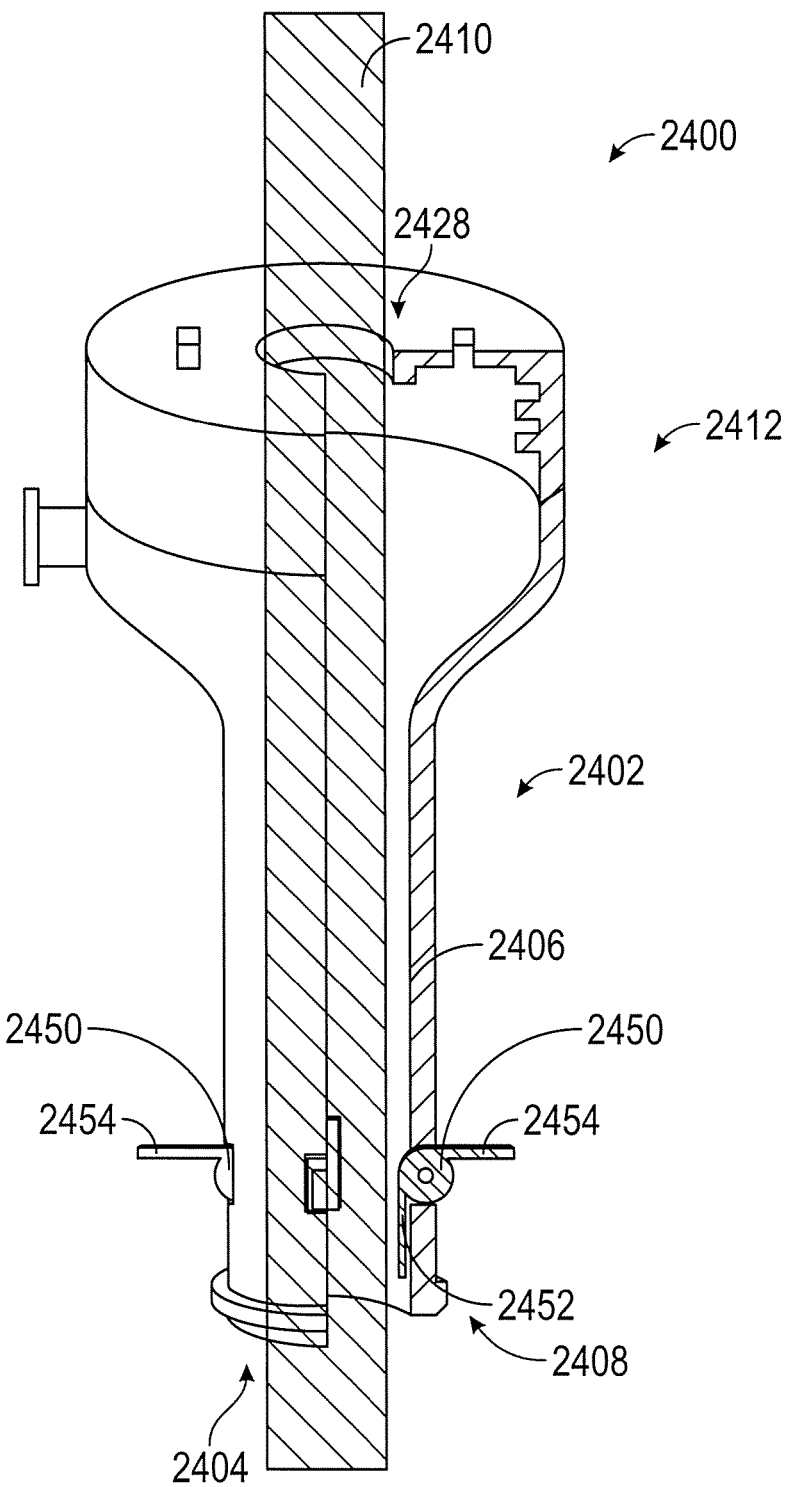

FIGS. 24A-24N illustrate embodiments of cannulas 2400 with guide elements including rigid features within the cannula 2400 to aid in concentricity of the medical instrument 2410 within the cannula 2400. The cannula 2400 can include a cannula body 2412 and elongate shaft 2402. The elongate shaft 2402 can include a cannula sidewall 2406 that forms the lumen 2404 of the cannula 2400. The lumen 2404 can defined by the inner sidewall 2406 of the cannula 2400 as shown in FIGS. 24A-24N. As described herein, a medical instrument 2410 can be inserted through the cannula 2400 by being introduced through the inlet 2428 of the cannula body 2412 and extending through the lumen 2404 of the cannula 2400 toward the distal end 2408 of the elongate shaft 2402.

As shown in FIG. 24A, the medical instrument 2410 can be supported by guide elements including rigid ribs 2420 at the distal end 2408 of the cannula to accomplish medical instrument 2410 concentricity. The rigid ribs 2420 can be molded or over-molded into the distal end 2408 of the cannula elongate shaft 2402. The rigid ribs 2420 hold the medical instrument 2410 concentrically in the cannula elongate shaft 2302 while allowing the insufflation gases to pass down the cannula lumen 2404. FIG. 24B is a cross-section through line 24A-24A of FIG. 24A, better illustrating ribs 2420.

FIG. 24C illustrates a partial cut-away schematic view of the cannula of FIGS. 24A-24B. FIG. 24D is a cross-section through line 24C-24C of FIG. 24C. Features in FIGS. 24C and 24D can be the same or substantially the same features as shown and described in FIGS. 24A and 24B and reference numerals of the same or substantially the same features may share the same reference numerals. The cross-section in FIG. 24D illustrates the ribs 2420 radially spaced apart within the cannula 2400.

As shown in FIG. 24E, the medical instrument 2410 can be supported by guide elements including a non-circular cannula shaft cross-section 2430 at the distal end 2408 of the cannula 2400 to accomplish medical instrument 2410 concentricity. Features of FIGS. 24E and 24F are similar to the features described with reference to FIGS. 24A-24D. Accordingly, similar features of FIGS. 24E and 24F have the same reference numerals as in FIGS. 24A-24D. The non-circular cannula shaft cross-section 2430 can include a non-circular cross-section at the distal end 2408 which holds the medical instrument 2410 concentrically in the cannula 2400 and allows the gases to pass down the lumen 2404 of the cannula elongate shaft 2402. FIG. 24F is a cross-section through line 24E-24E of FIG. 24E, better illustrating the configuration of the medical instrument 2410 within the non-circular cannula shaft cross-section 2430. As illustrated in FIG. 24F, the medical instrument 2410 is circular and the non-circular cannula shaft cross-section 2430 is non-circular, thereby, creating gaps for the insufflation gases to pass down the cannula lumen 2404.

FIG. 24G illustrates a partial cut-away schematic view of the cannula of FIGS. 24E-24F. Features in FIGS. 24G and 24H can be the same or substantially the same features as shown and described in FIGS. 24E and 24F and reference numerals of the same or substantially the same features may share the same reference numerals. FIG. 24H is a cross-section through line 24G-24G of FIG. 24H, better illustrating the gaps for the insufflation gases to pass down the cannula lumen 2404.

FIG. 24I illustrates a cannula 2400 with guide elements, such as rigid bumps 2440 at the distal end 2408 of the cannula 2400 to accomplish medical instrument 2410 concentricity. Features of FIGS. 24I and 24J are similar to the features described with reference to FIGS. 24A-24D. Accordingly, similar features of FIGS. 24I and 24J have the same reference numerals as in FIGS. 24A-24D. The bumps 2440 can protrude into the lumen 2404 of the cannula elongate shaft 2402. The bumps 2440 can be circumferentially spaced in the lumen 2404 of the elongate shaft 2402. As shown in FIG. 24I, when the medical instrument 2410 is inserted within the lumen 2404 of the cannula elongate shaft 2402, the rigid bumps 2440 can hold the medical instrument 2410 concentrically while allowing the insufflation gases to flow down the lumen 2404.

FIG. 24J illustrates a partial cut-away schematic view of the cannula of FIG. 24I. Features in FIG. 24J can be the same or substantially the same features as shown and described in FIG. 24I and reference numerals of the same or substantially the same features may share the same reference numerals.

FIGS. 24K-24N illustrates a cannula 2400 with guide elements including pivoting structures 2450 at the distal end 2408 of the cannula 2400 to accomplish medical instrument 2410 concentricity. Features of FIGS. 24K-24N are similar to the features described with reference to FIGS. 24A-24D. Accordingly, similar features of FIGS. 24K-24N have the same reference numerals as in FIGS. 24A-24D. The pivoting structures 2450 can rotate when the medical instrument 2410 is pushed past the pivoting structures 2450. The pivoting structures 2450 then form a rib 2452 between the medical instrument 2410 and the cannula shaft sidewall 2406. The ribs 2452 formed from the pivoting structures 2450 can hold the scope concentrically and allows the insufflation gas to pass down the lumen 2404. The outside of the pivoting structures 2450 can include a fin 2454 which extend when the medical instrument 2410 is inserted within the cannula 2400 and the rib 2452 is pushed against the inner cannula wall. The fin 2454 can hold the cannula 2400 in the patient which helps prevent the cannula 2400 from being displaced.

FIGS. 24M-24N illustrate a partial cut-away schematic view of the cannula of FIGS. 24K and 24L. Features in FIGS. 24M-24N can be the same or substantially the same features as shown and described in FIGS. 24K and 24L and reference numerals of the same or substantially the same features may share the same reference numerals.

FIGS. 24K and 24M illustrate the cannula 2400 without the medical instrument 2410 within the cannula. In this configuration, the pivoting structures 2450 include the ribs 2452 protruding radially inward from the cannula sidewall 2406, into the lumen 2404. As illustrated in FIGS. 24K-24N, the pivoting structures 2450 can be on a pivot that rotates the ribs 2452 of the pivoting structures 2450 out of the way, opening up the lumen 2404, when the medical instrument 2410 is pushed past them. As the pivoting structures 2450 pivot, the fins 2454 then splay radially outward from the cannula sidewall 2406 as shown in FIGS. 24L and 24N. FIGS. 24L and 24N illustrate the medical instrument 2410 inserted within the cannula 2400. The ribs 2452 can hold the medical instrument 2410 concentrically within the cannula elongate shaft 2402 while allowing the gases to pass through the lumen 2404. The fins 2454 can form a mechanism to stop the cannula from being pulled out of the patient. As the ribs 2452 of the pivoting structures 2450 is pushed against the inner wall of the cannula, the ribs 2452 can create a mechanism between the cannula elongate shaft sidewall 2406 and the medical instrument 2410 holding the medical instrument 2410 concentrically in the cannula elongate shaft 2402.

FIGS. 25A-25L illustrate embodiments of cannulas 2500 with guide elements including flexible continuous structures 2520 extending axially along the elongate shaft 2502 of the cannula 2500 to aid in concentricity of the medical instrument 2510 within the cannula 2500. The cannula 2500 can include a cannula body 2512 and elongate shaft 2502. The elongate shaft 2502 can include a cannula sidewall 2506 that forms the lumen 2504 of the cannula 2500. The lumen 2504 can defined by the inner sidewall 2506 of the cannula 2500 as shown in FIGS. 25A-25L. As described herein, a medical instrument 2510 can be inserted through the cannula 2500 by being introduced through the inlet 2528 at the proximal end of the cannula body 2512 and extending through the lumen 2504 of the cannula 2500 toward the distal end 2508 of the elongate shaft 2502.

Figures 25A, 25B:
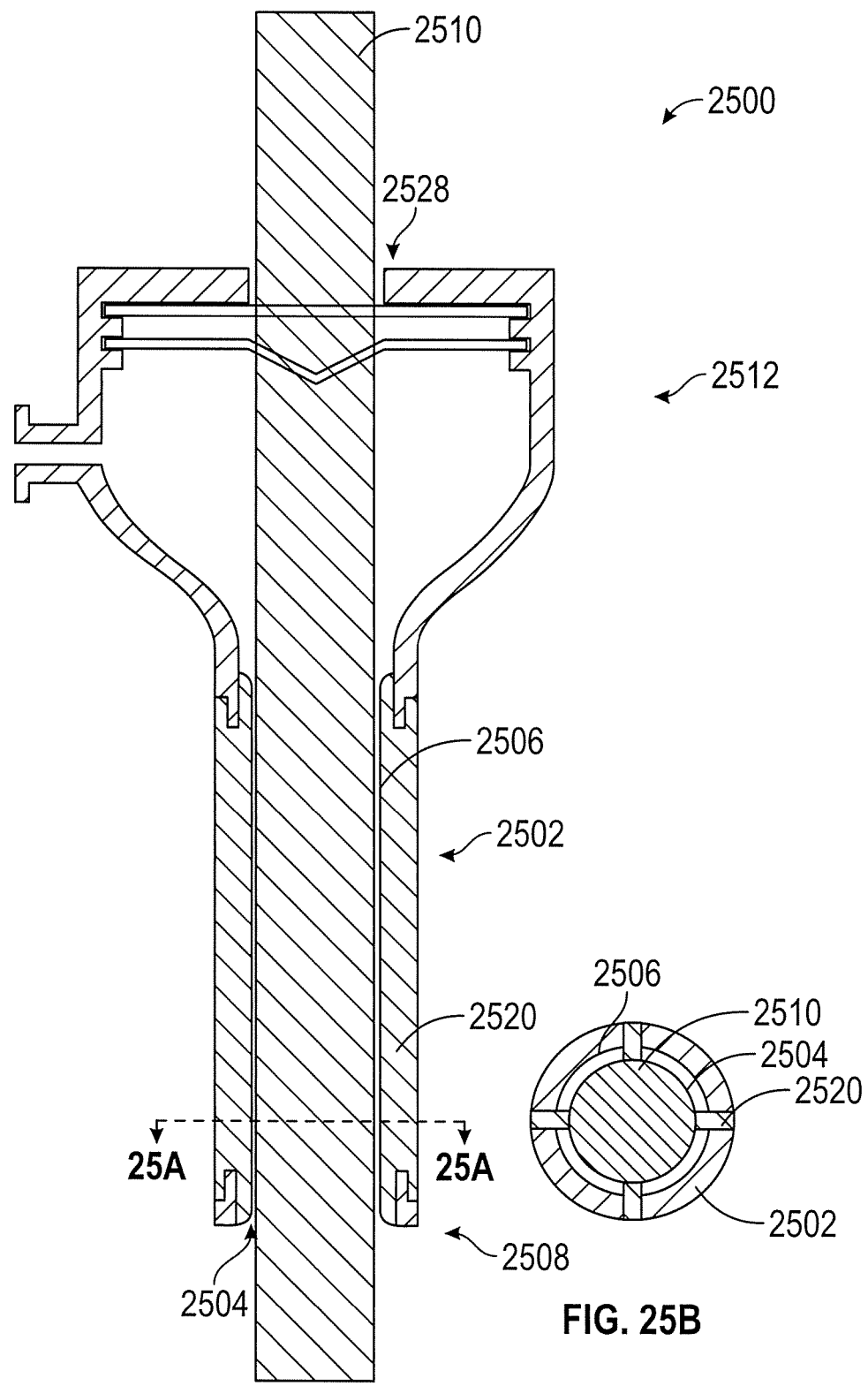
FIGS. 25A-25L illustrate views of embodiments of cannulas with flexible continuous structures along the elongate shaft of the cannula to aid in concentricity of the medical instrument within the cannula.

As shown in FIG. 25A, the medical instrument 2510 can be supported by guide elements including a flexible continuous rib 2520 in the elongate shaft 2502 of the cannula 2500 to accomplish medical instrument 2510 concentricity. The flexible continuous rib 2520 can be molded continuously along the cannula elongate shaft 2502. The flexible continuous rib 2520 can hold the medical instrument 2510 concentrically in the cannula elongate shaft 2502. The flexible continuous rib 2520 can be molded along the length of the elongate shaft 2502 as shown in FIG. 25A. FIG. 25B is a cross-section through line 25A-25A of FIG. 25A, better illustrating the flexible continuous rib 2520 spaced circumferentially around the elongate shaft 2502.

Figures 25C, 25D:
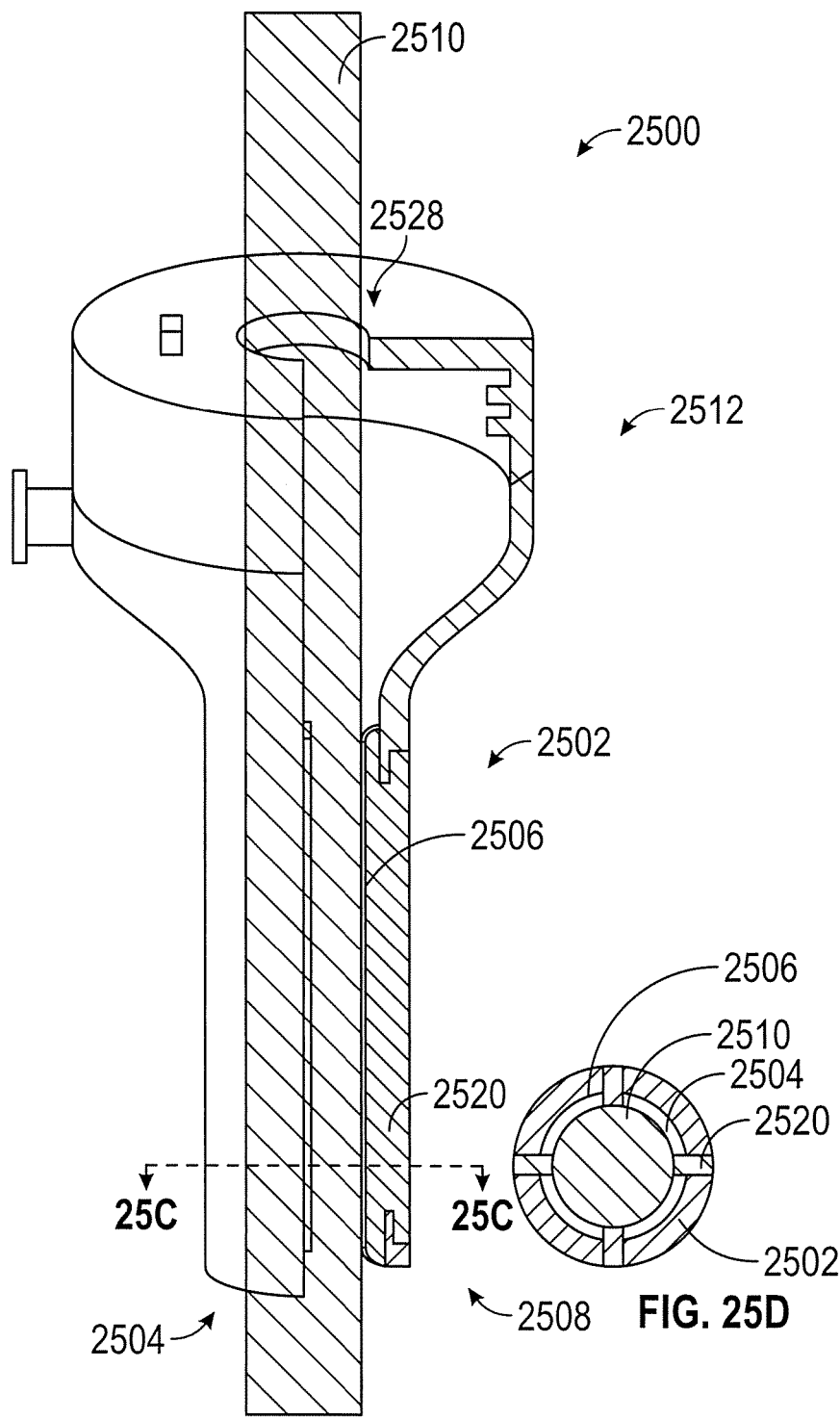

FIG. 25C illustrates a partial cut-away schematic view of the cannula of FIGS. 25A-25B. Features in FIGS. 25C and 25D can be the same or substantially the same features as shown and described in FIGS. 25A and 25B and reference numerals of the same or substantially the same features may share the same reference numerals. FIG. 25D is a cross-section through line 25C-25C of FIG. 25C, better illustrating the flexible continuous rib 2520 spaced circumferentially around the elongate shaft 2502. As shown in FIG. 25D, the flexible continuous rib 2520 can hold the medical instrument 2510 concentrically within the lumen 2504 allowing gases to pass through the lumen 2504.

Figure 25E:
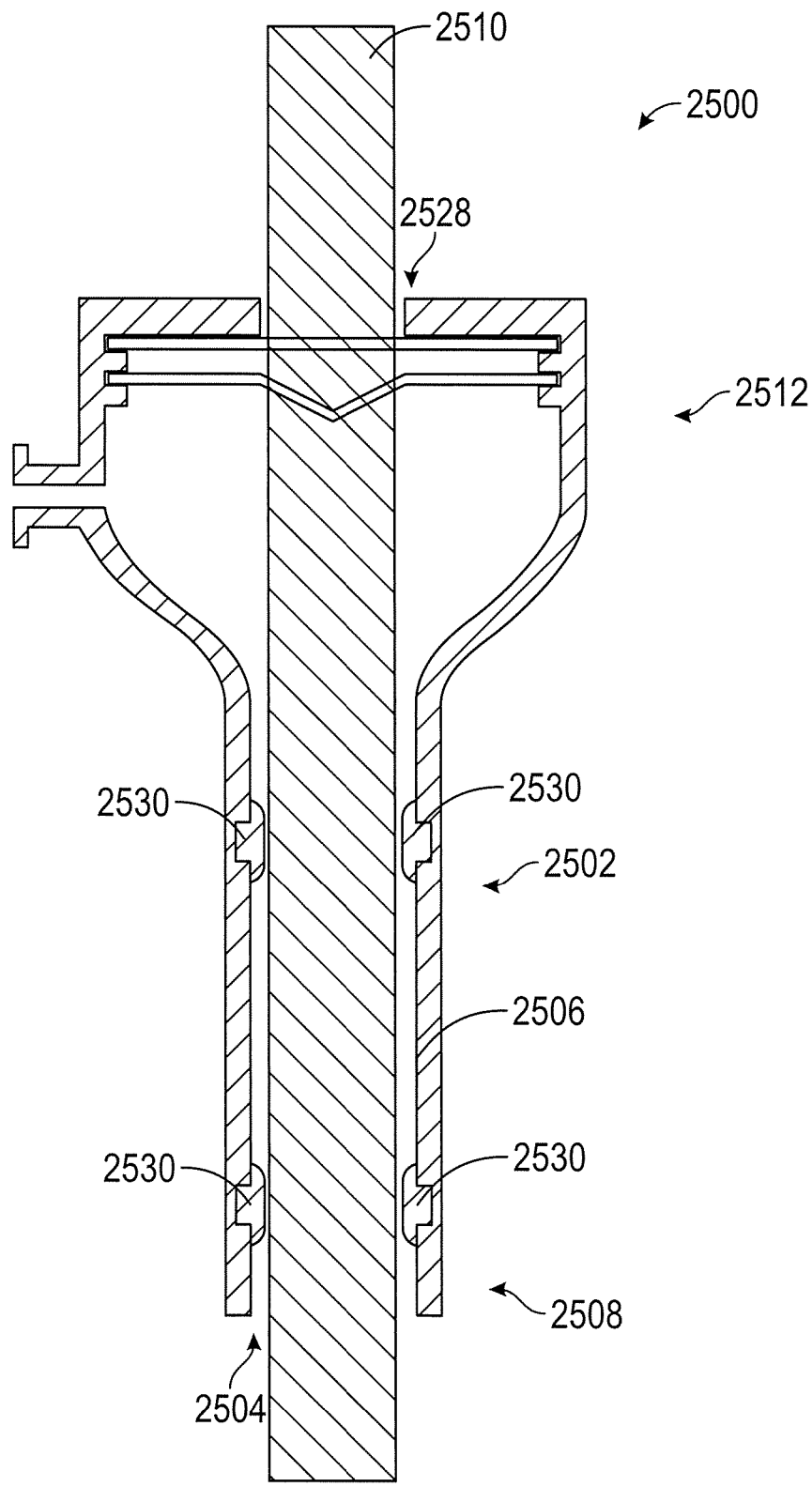

In some cases, the flexible continuous guide elements along the elongate shaft 2502 of the cannula 2500 can be discrete structures at one or more points along the elongate shaft 2502. FIG. 25E illustrates several sets of ribs 2530 along the elongate shaft 2502. The flexible continuous structures can be one or more ribs 2530 attached to flexible rings which can be molded or inserted into the elongate shaft 2502 as shown in FIG. 25E. The one or more ribs 2530 can be flexible. The one or more ribs 2530 at one or more points along the elongate shaft 2502 can hold the medical instrument 2510 concentrically within the cannula 2500.

Figure 25F:
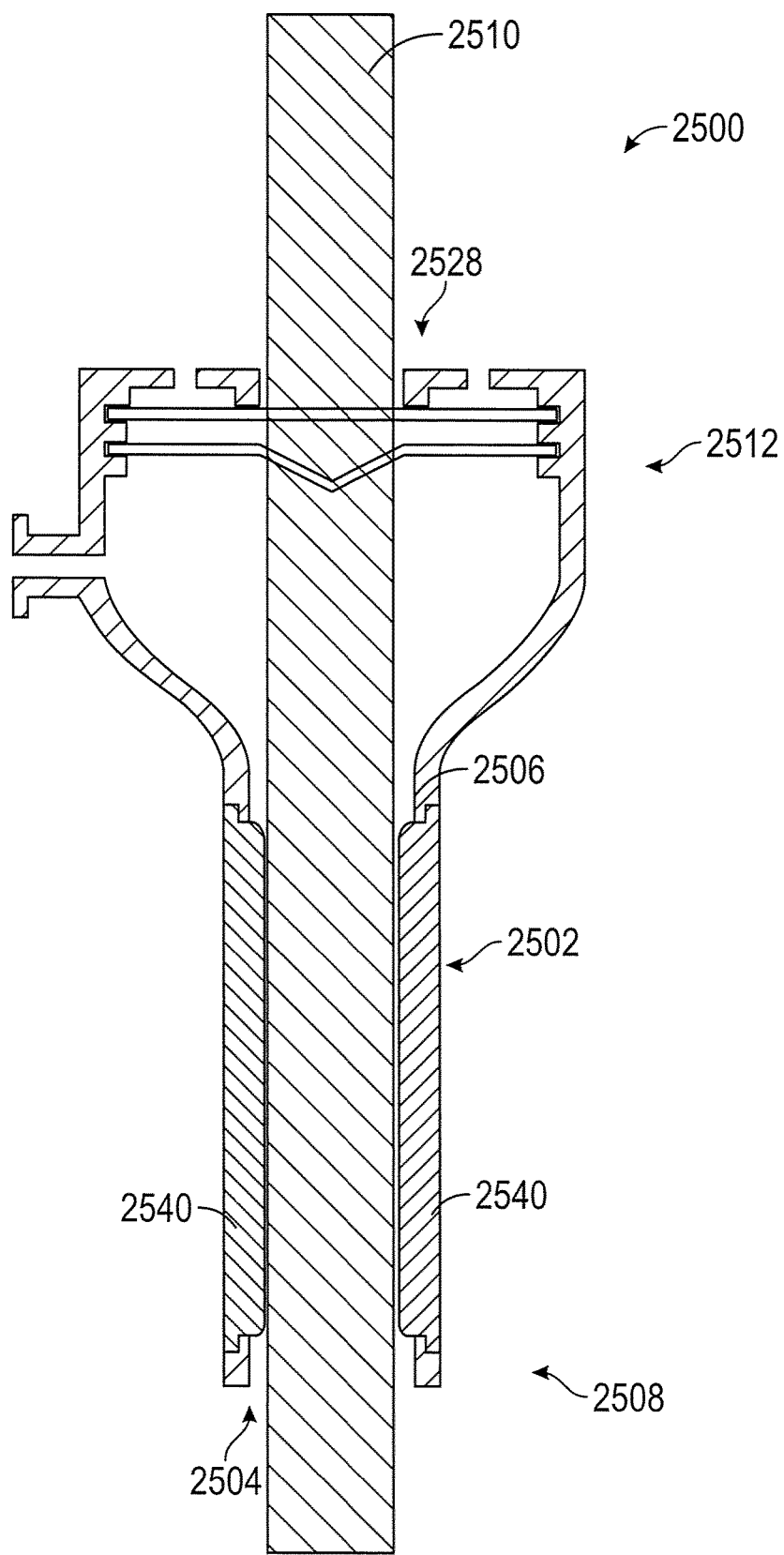

As shown in FIG. 25F, the medical instrument 2510 can be supported by guide elements including a flexible continuous rib 2540 in the elongate shaft 2502 of the cannula 2500 to accomplish medical instrument 2510 concentricity. The flexible continuous rib 2540 can be molded or overmolded directly into the cannula elongate shaft 2502. The flexible continuous rib 2540 can hold the medical instrument 2510 concentrically in the cannula elongate shaft 2502. The flexible continuous rib 2540 can be formed inside the cannula elongate shaft 2502. The flexible continuous rib 2540 can be over-molded into the cannula elongate shaft 2502.

Figure 25G:
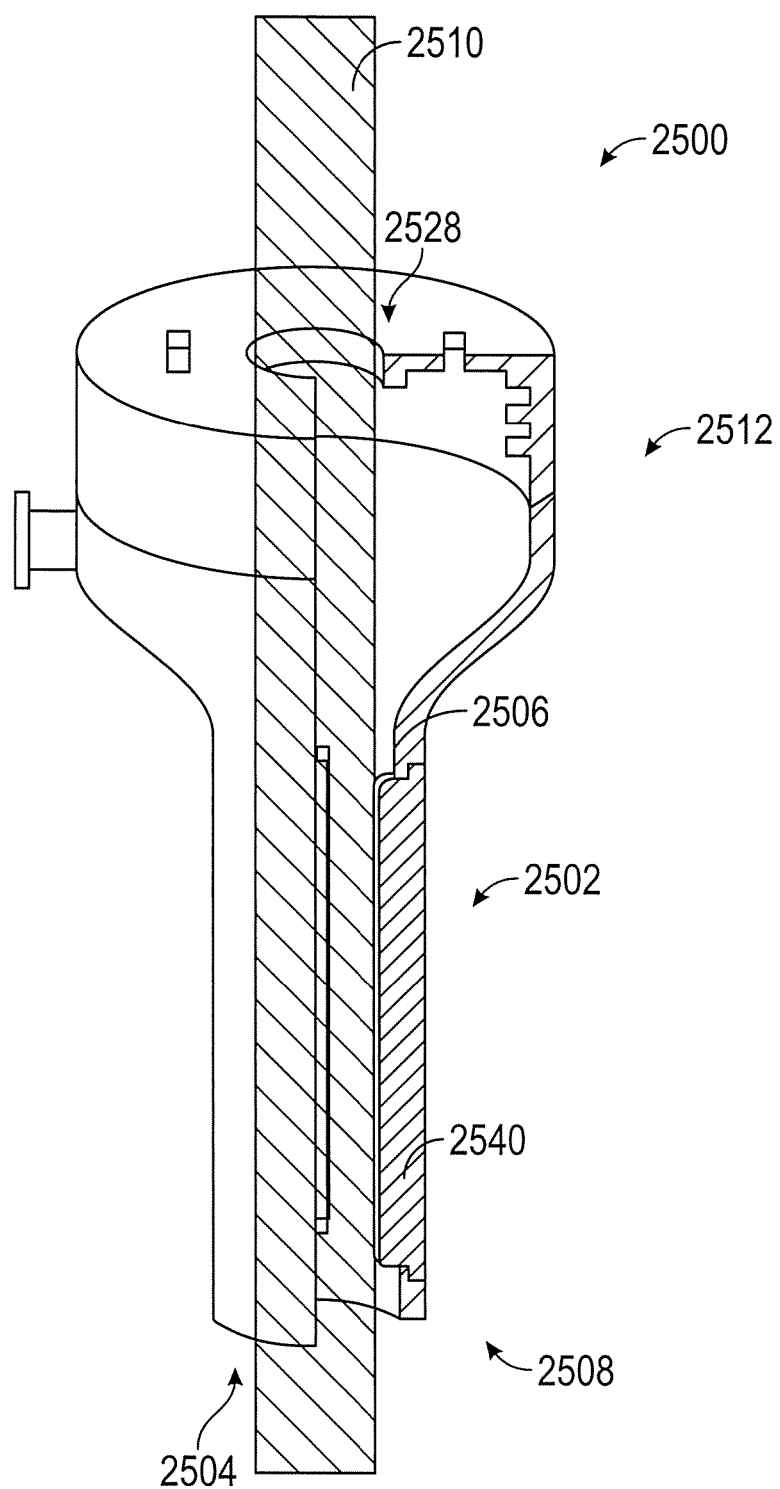

FIG. 25G illustrates a partial cut-away schematic view of the cannula of FIG. 25F. Features in FIG. 25G can be the same or substantially the same features as shown and described in FIG. 25F and reference numerals of the same or substantially the same features may share the same reference numerals. As shown in FIG. 25G, the flexible continuous rib 2540 can be spaced around the circumference of the elongate shaft 2502 to hold the medical instrument 2510 concentrically within the lumen 2504 allowing gases to pass through the lumen 2504.

Figure 25H:
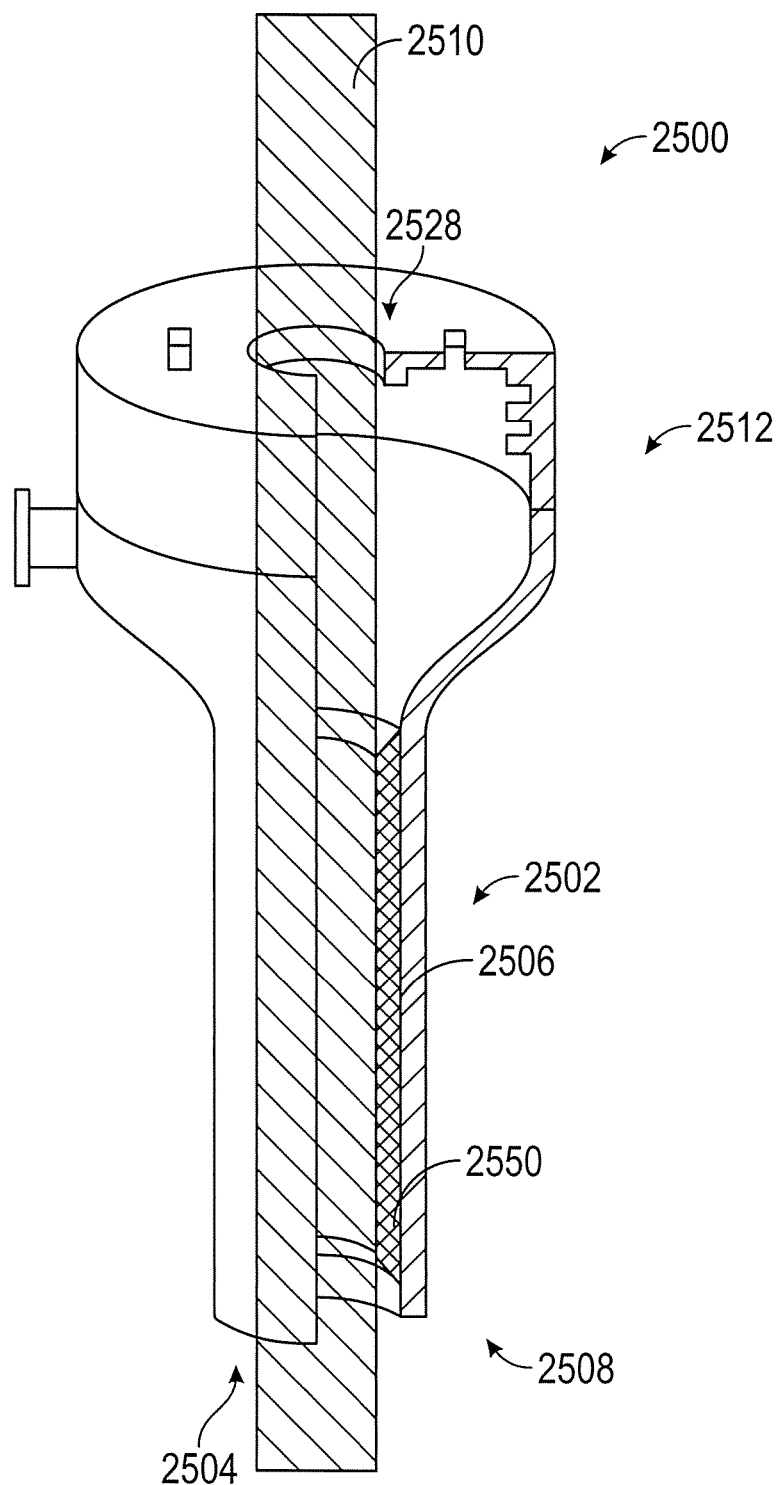

FIG. 25H illustrates an embodiment of the medical instrument 2510 supported by a guide element including a foam 2550 in the elongate shaft 2502 of the cannula 2500 to accomplish medical instrument 2510 concentricity. The foam 2550 can be a continuous foam structure extending substantially the entire length of the elongate shaft 2502. The foam 2550 can allow the gases to pass through the foam 2550 and through the lumen 2504. The foam 2550 can hold the medical instrument 2510 concentrically in the cannula elongate shaft 2502. The foam 2550 can deform as the medical instrument is pushed through the elongate shaft 2502 and the restoration force of the foam 2550 can hold the medical instrument concentric within the cannula 2500. In some cases, the foam 2550 can be a foam insert. In some cases, the foam can circumferentially surround the medical instrument 2510 when it is inserted within the cannula 2500 as shown in FIG. 25H. In other cases, one or more foam pieces can be positioned within the cannula lumen 2504 and can ask similarly to the ribs described herein to hold the medical instrument 2510 concentrically within the cannula 2500.

Figure 25I:
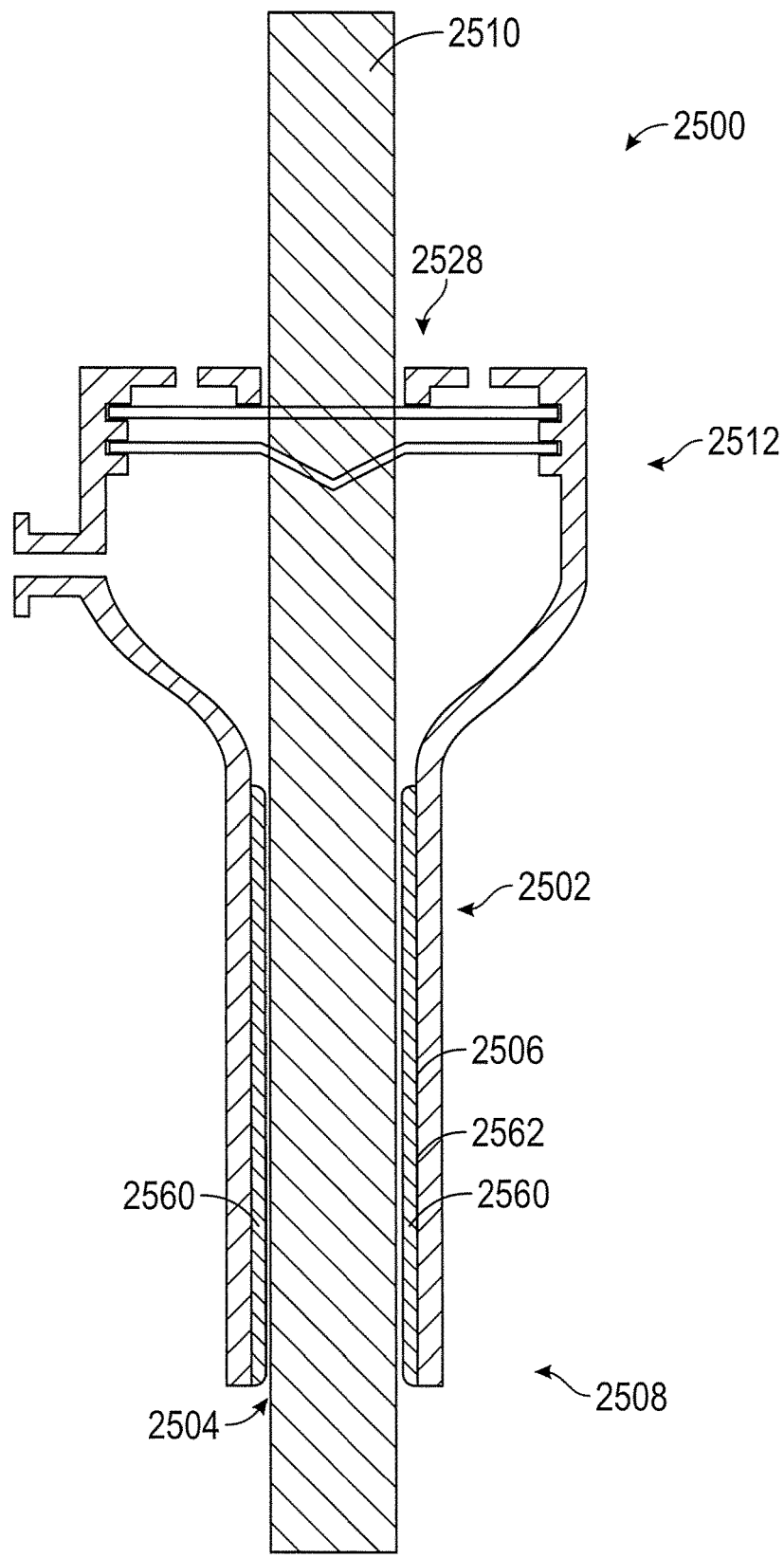

As shown in FIGS. 25I-25L, the medical instrument 2510 can be supported by a guide element including a flexible continuous rib 2560 on an insert 2562 in the elongate shaft 2502 of the cannula 2500 to accomplish medical instrument 2510 concentricity. As illustrated in FIG. 25I, the flexible continuous rib 2560 can be molded onto an insert 2562 which can be attached to the inside of the cannula elongate shaft 2502. The insert 2562 can be permanently or temporarily attached to the cannula elongate shaft 2502. The one or more flexible continuous ribs 2560 hold the medical instrument 2510 concentrically in the cannula elongate shaft 2502. In some cases, the insert 2562 can be attached to the cannula elongate shaft 2502 by a friction fit or other method. The insert 2562 can be assembled as part of the cannula 2500 or can be a separate attachment.

Figure 25J:
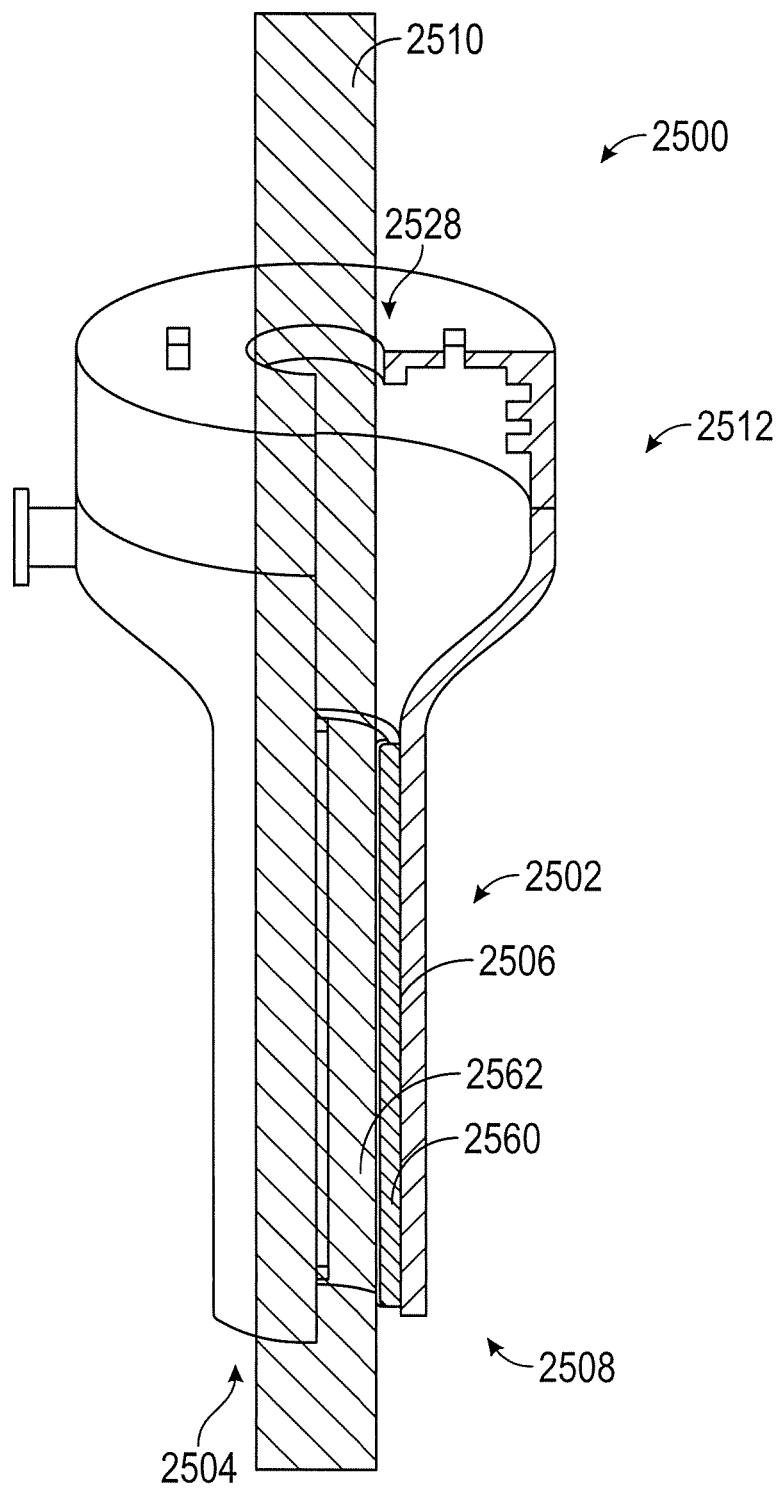

FIG. 25J illustrates a partial cut-away schematic view of the cannula of FIG. 25I. Features in FIG. 25J can be the same or substantially the same features as shown and described in FIG. 25I and reference numerals of the same or substantially the same features may share the same reference numerals. As shown in FIG. 25J, the flexible continuous rib 2560 on the insert 2562 can be spaced around the circumference of the insert 2562 to hold the medical instrument 2510 concentrically within the lumen 2504 allowing gases to pass through the lumen 2504.

Figures 25K, 25L:
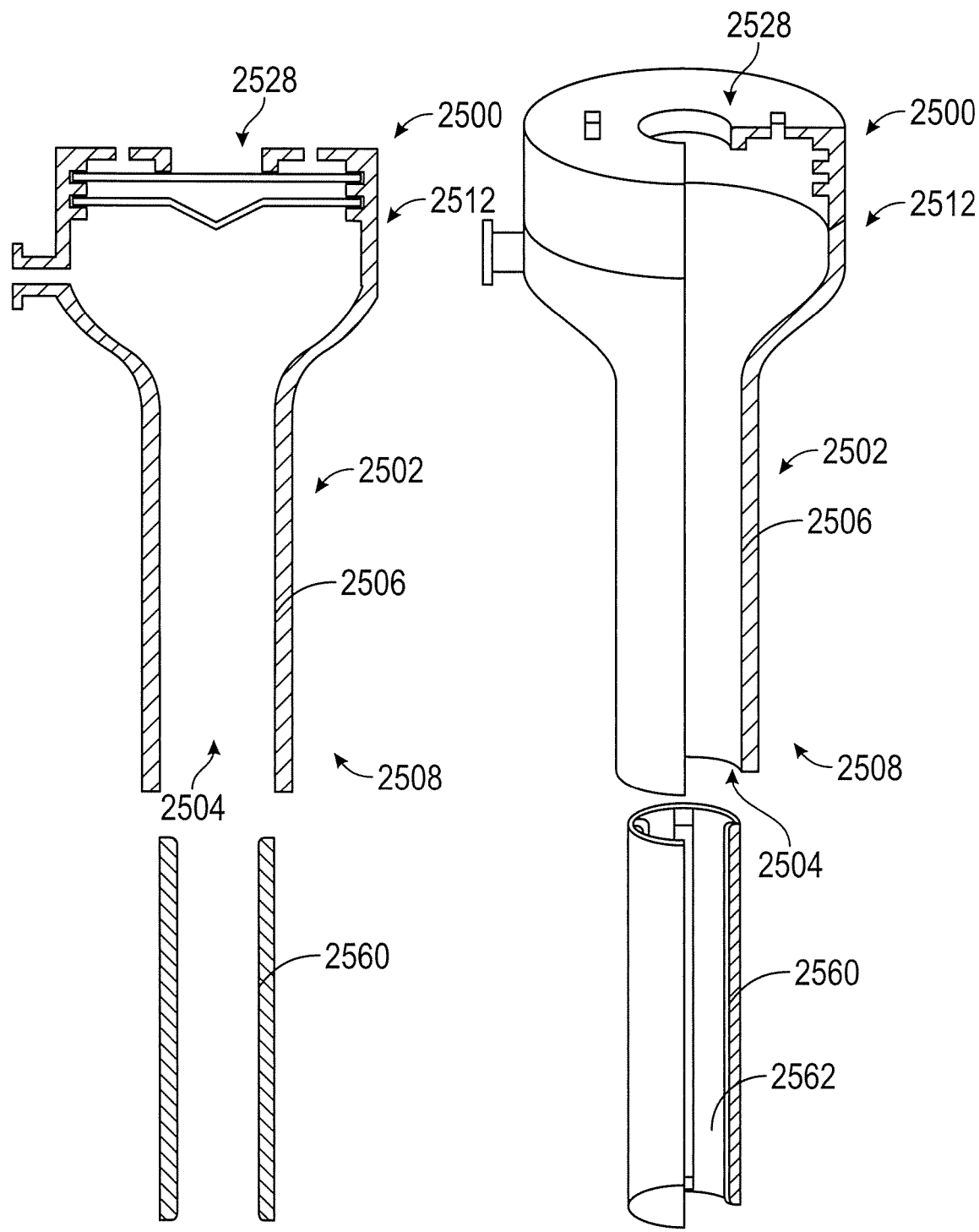

FIG. 25K illustrates a cannula 2500 with the flexible continuous rib 2560 and insert 2562 removed from the cannula 2500. Features in FIG. 25K can be the same or substantially the same features as shown and described in FIG. 25I and reference numerals of the same or substantially the same features may share the same reference numerals.

FIG. 25L illustrates a partial cut-away schematic view of the cannula of FIG. 25K with the flexible continuous rib 2560 and insert 2562 removed from the cannula 2500. Features in FIG. 25L can be the same or substantially the same features as shown and described in FIG. 25I and reference numerals of the same or substantially the same features may share the same reference numerals. As illustrated in FIG. 25L, the insert can be a hollow cylindrical shape. As shown in FIG. 25L, the flexible continuous rib 2560 on the insert 2562 can be spaced around the inner circumference of the insert 2562 to hold the medical instrument 2510 concentrically within the lumen 2504 allowing gases to pass through the lumen 2504.

Figures 26A, 26B:
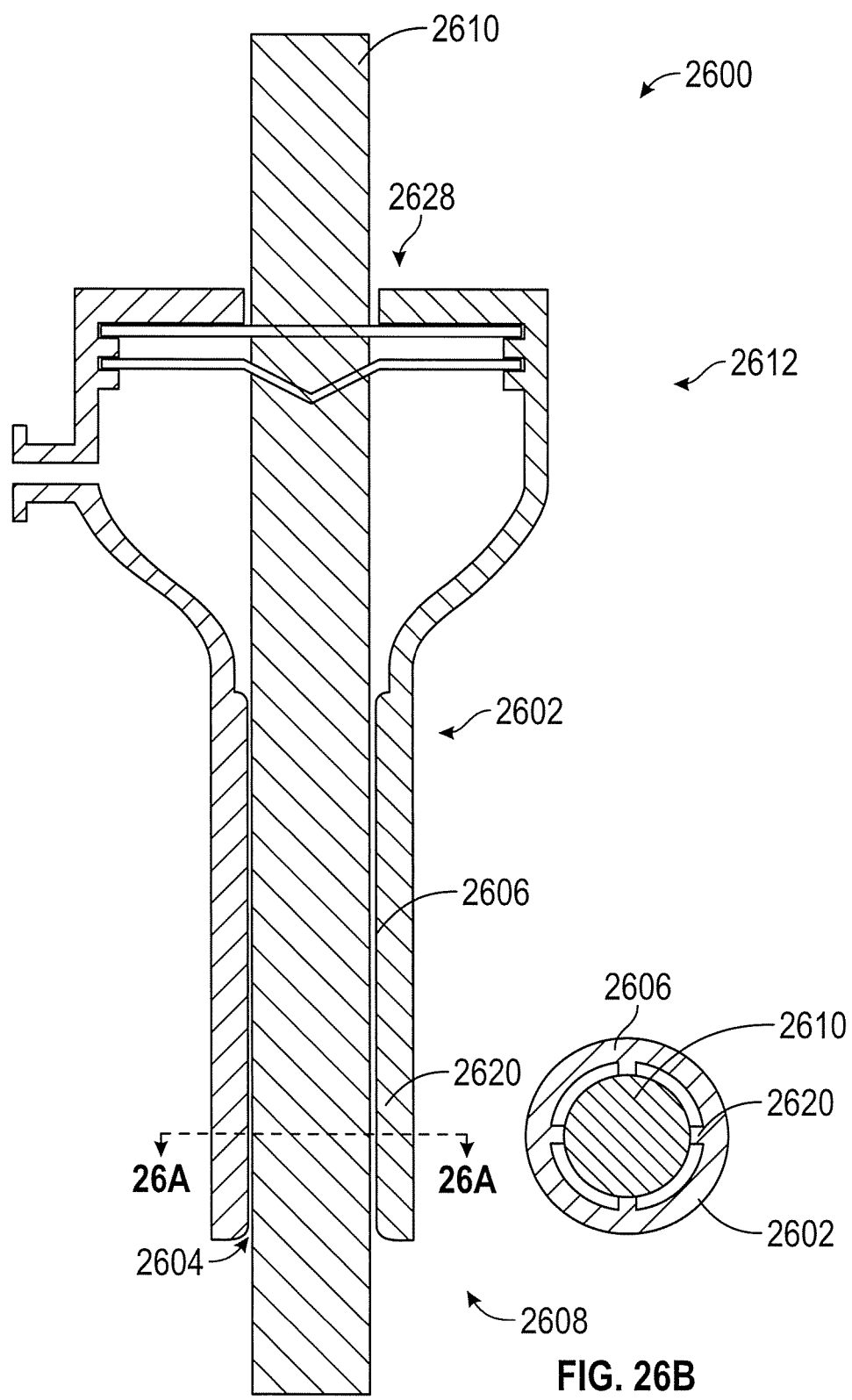
FIGS. 26A-26R illustrate views of embodiments of cannulas with rigid continuous structures along the elongate shaft of the cannula to aid in concentricity of the medical instrument within the cannula.
Figures 26C, 26D:
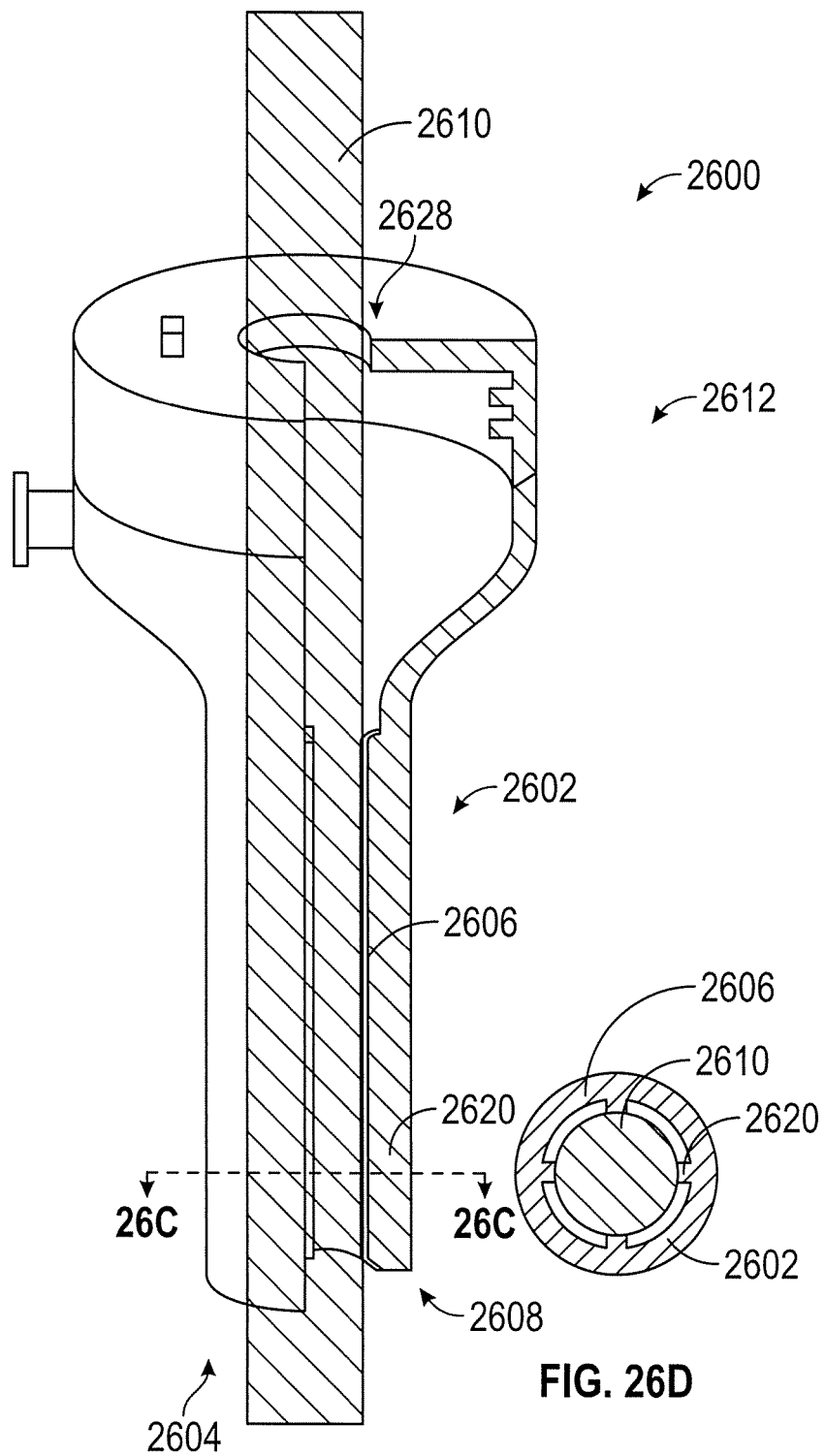
Figure 26E:
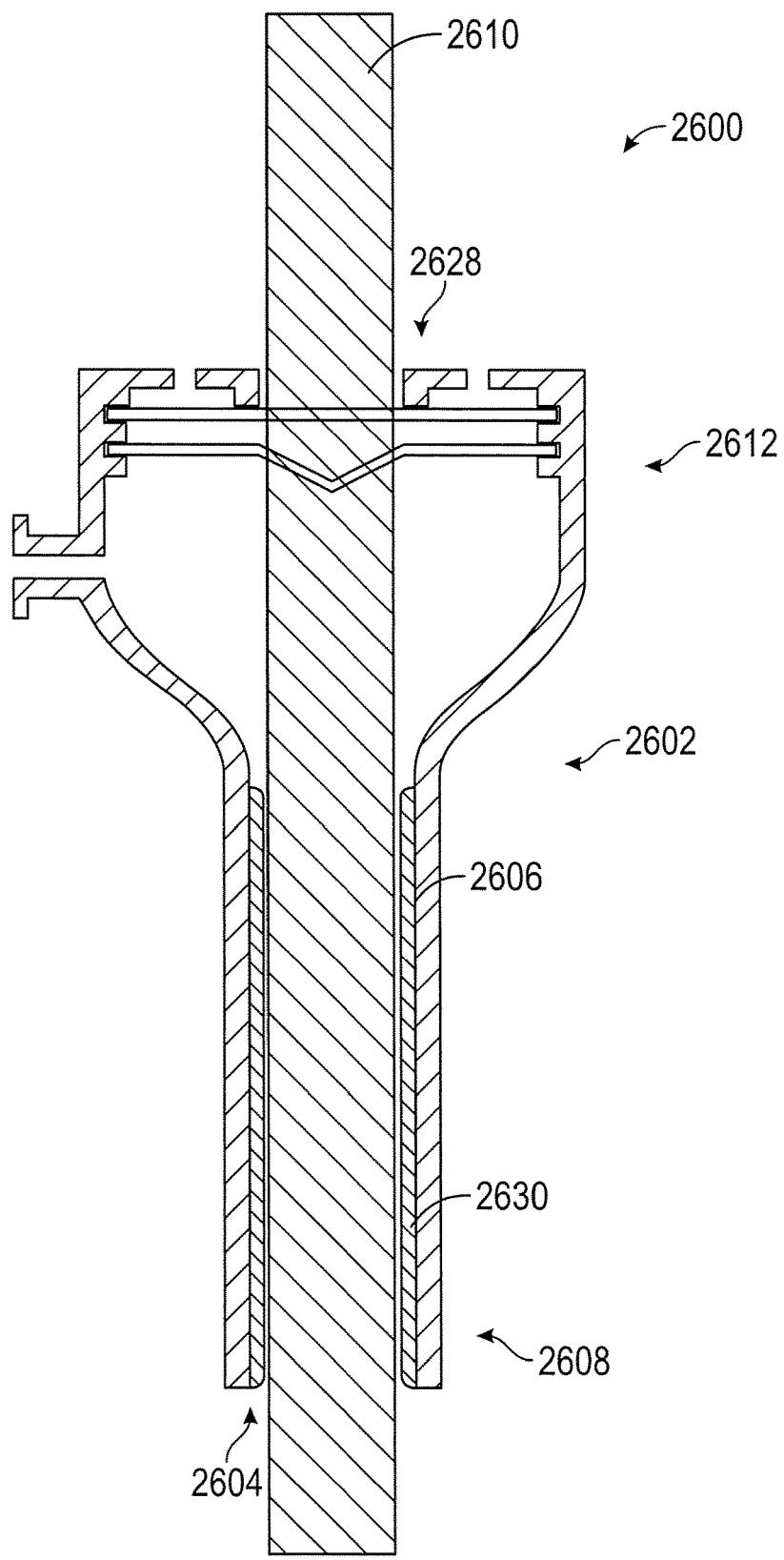
Figure 26F:
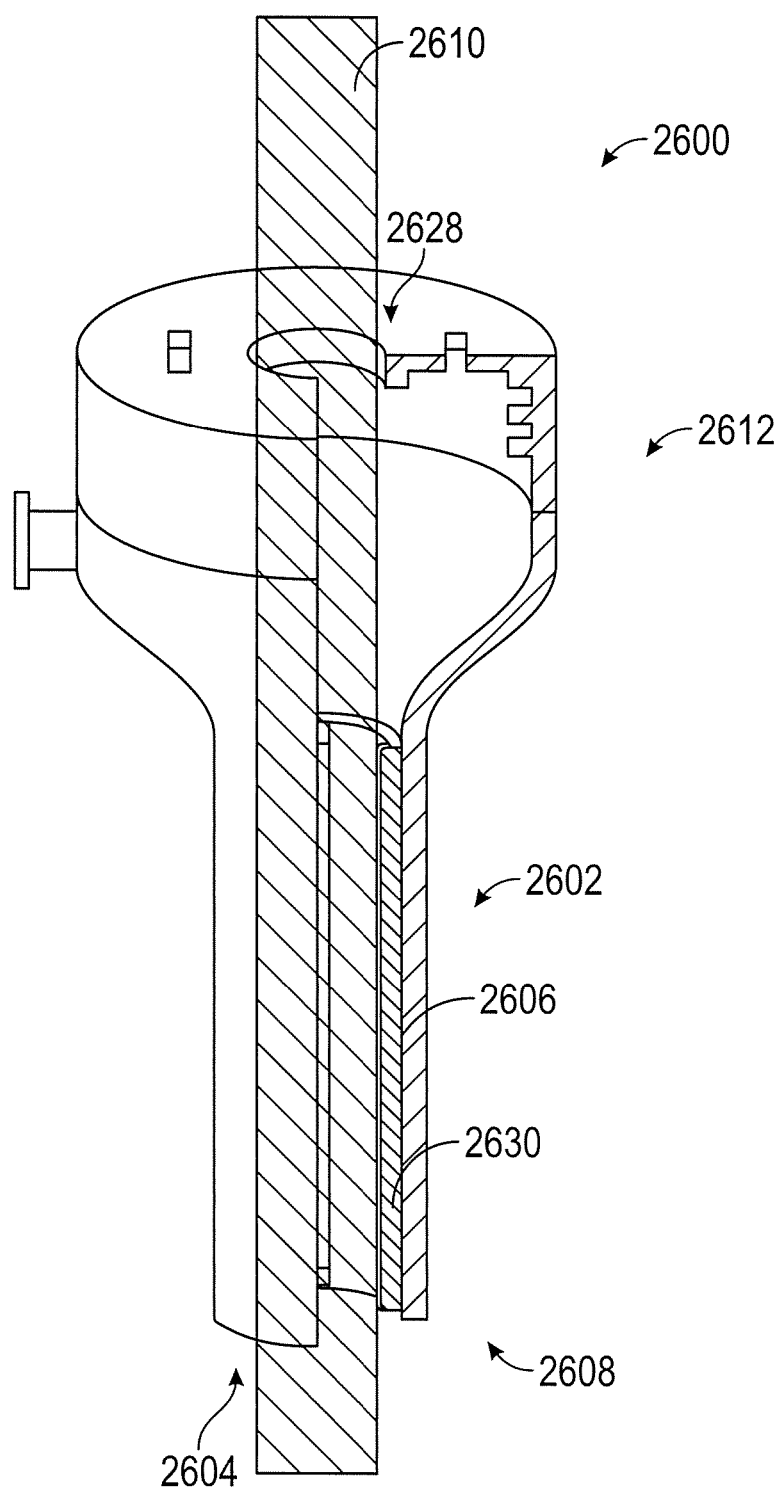
Figures 26G, 26H:
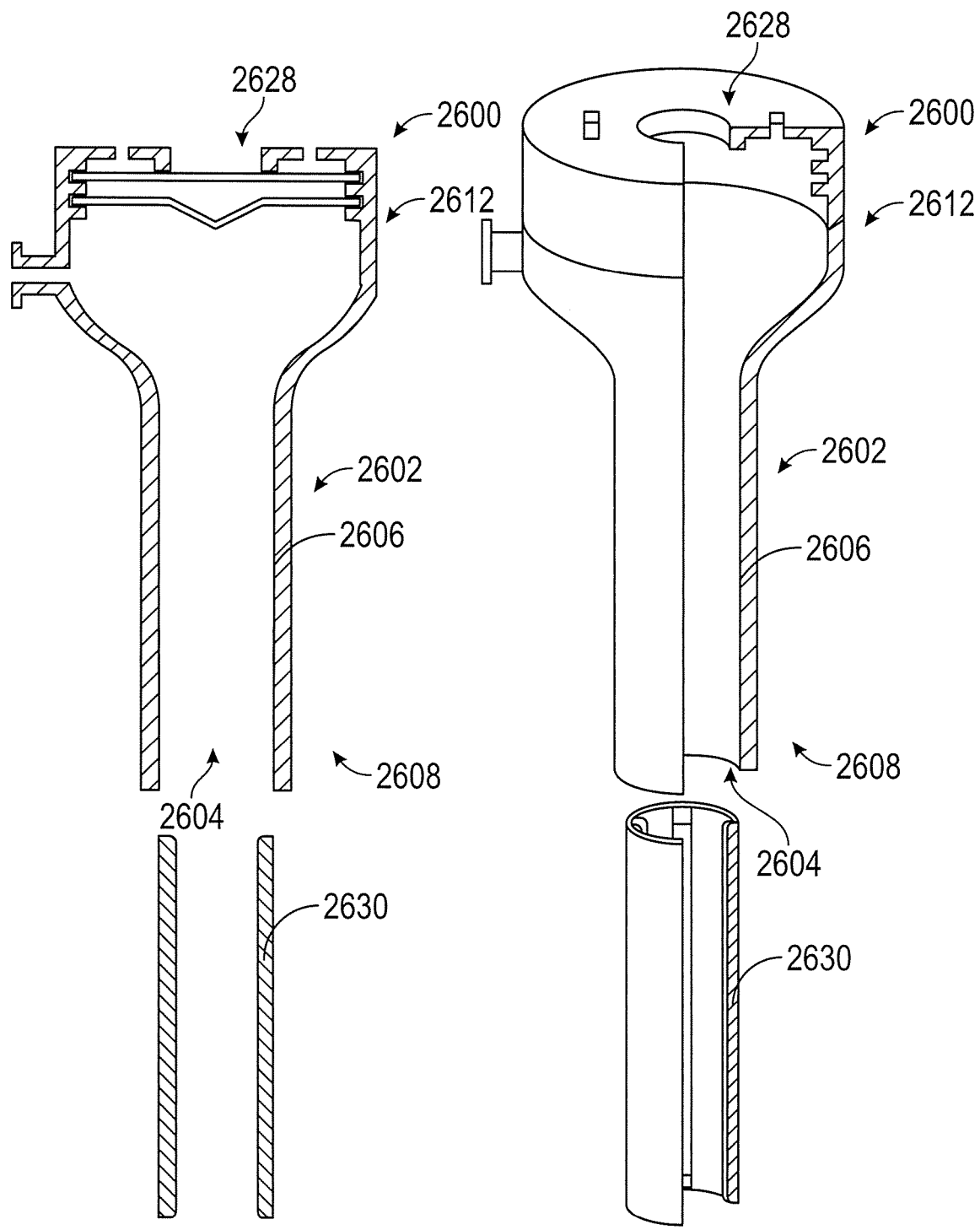
Figure 26I:
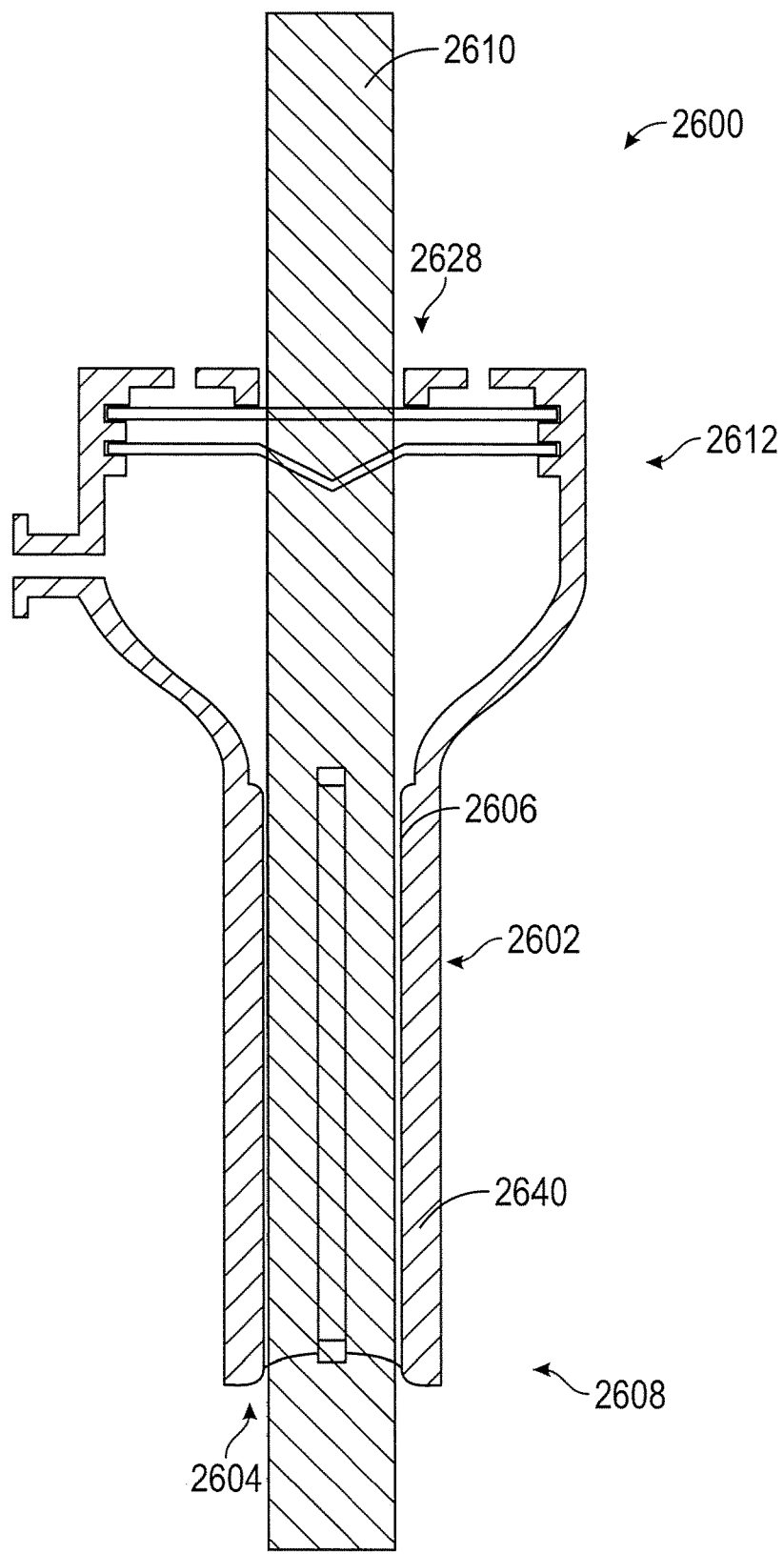
Figure 26J:
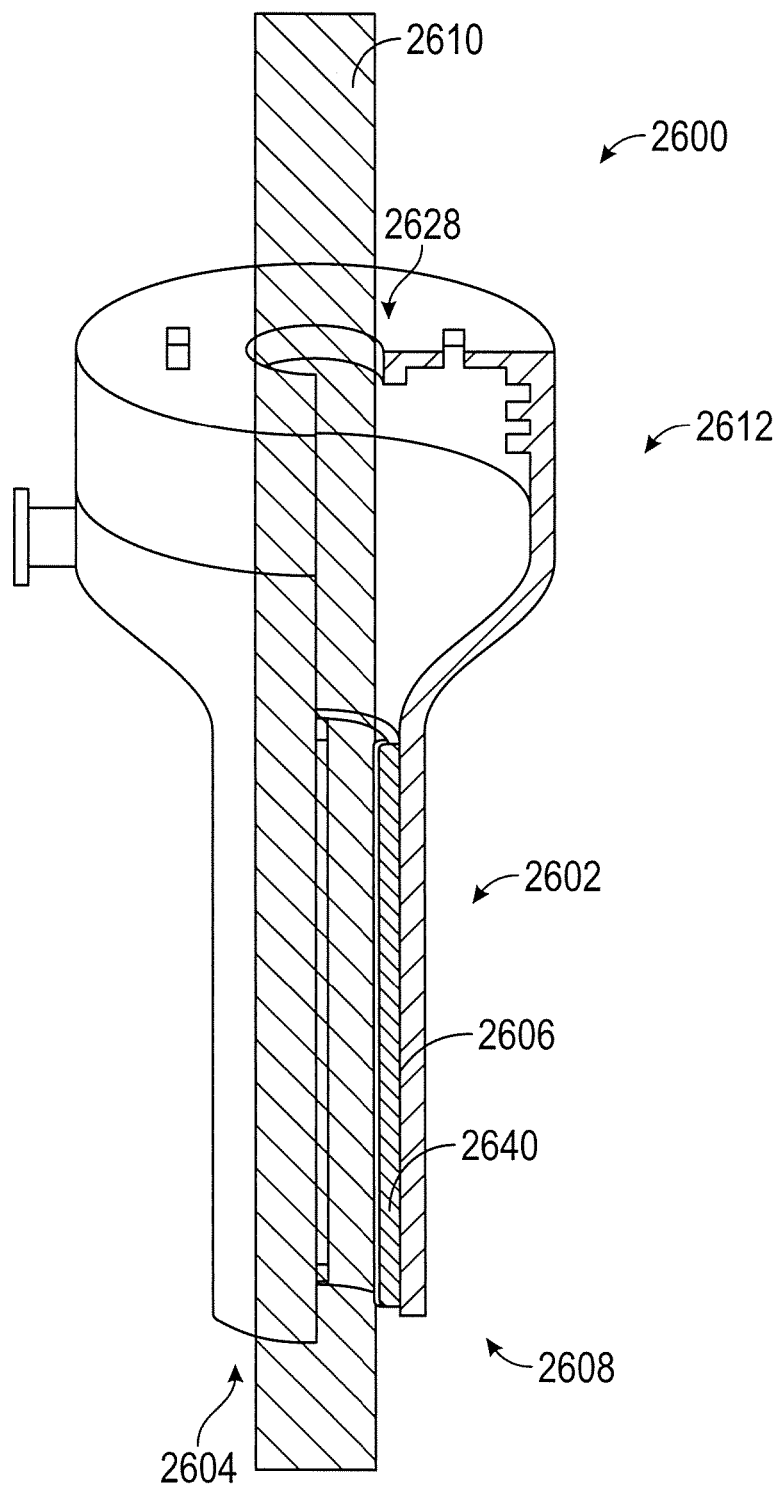
Figure 26K:
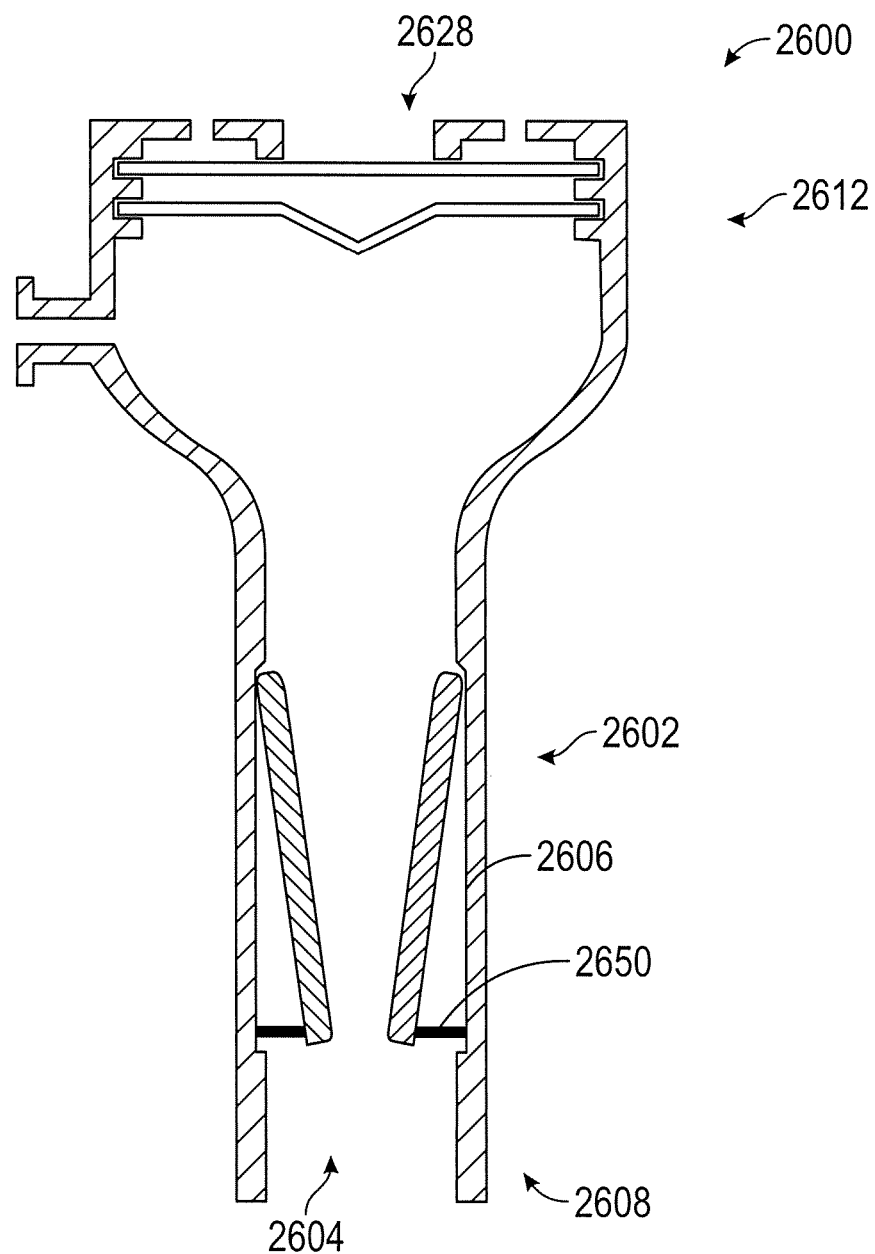
Figure 26L:
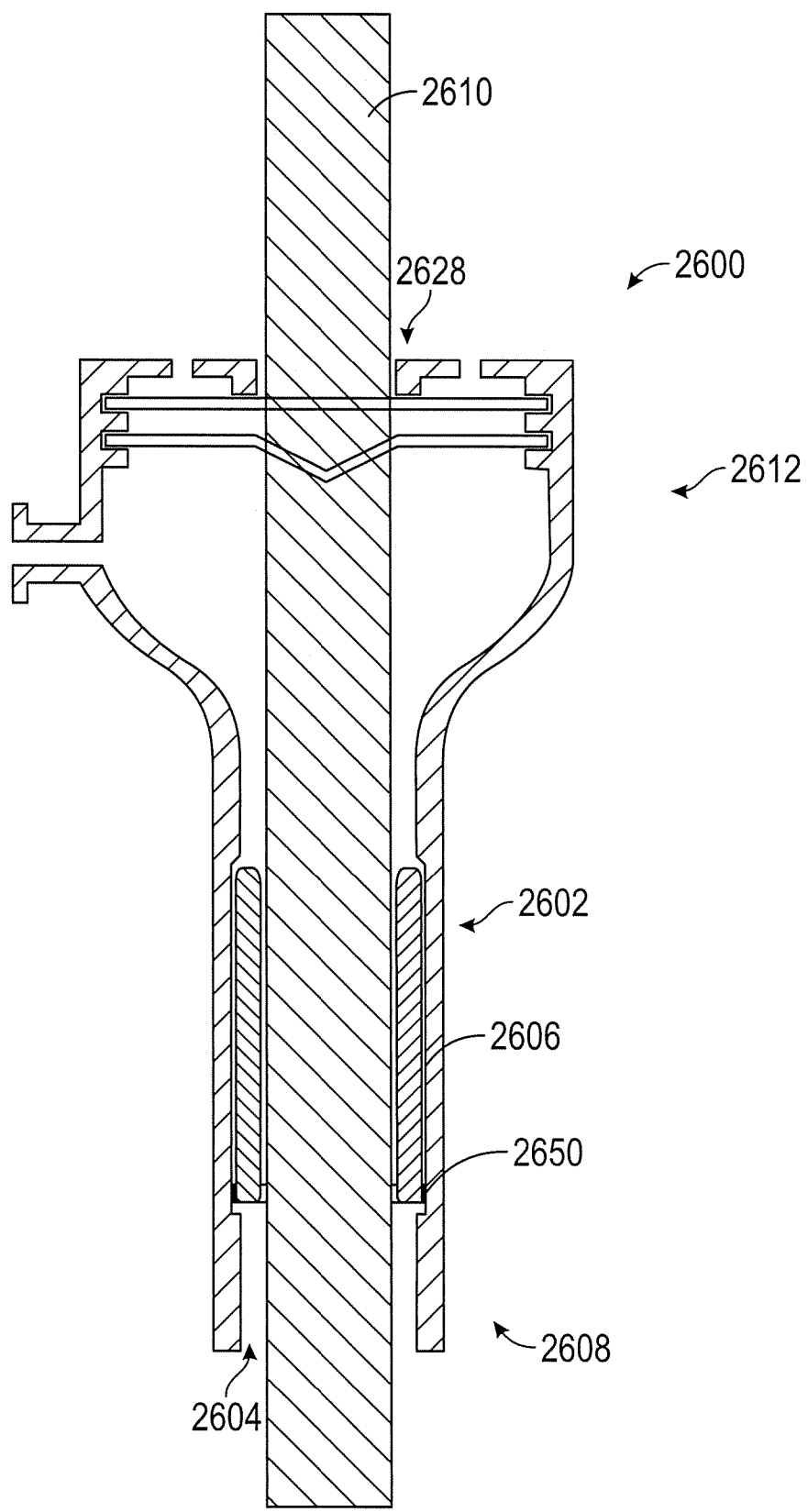
Figure 26M:
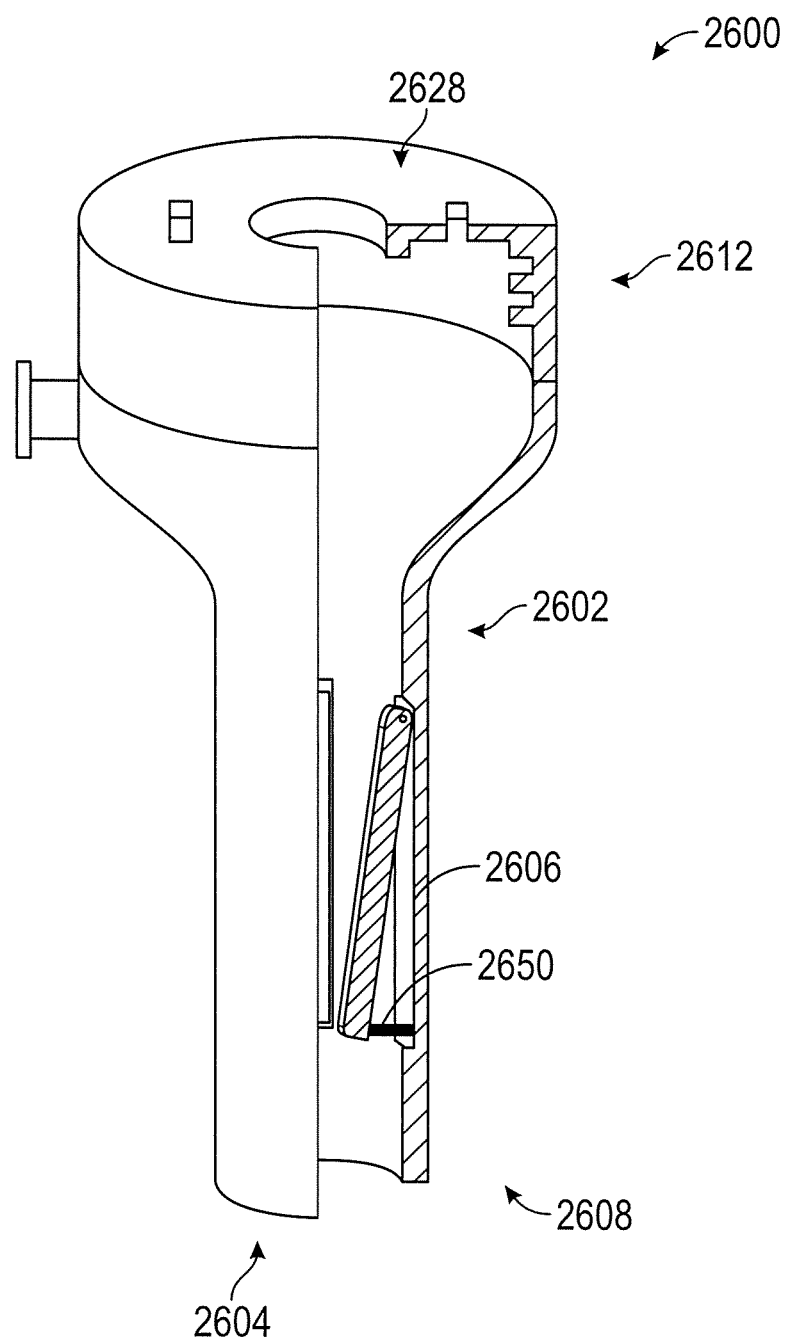
Figure 26N:
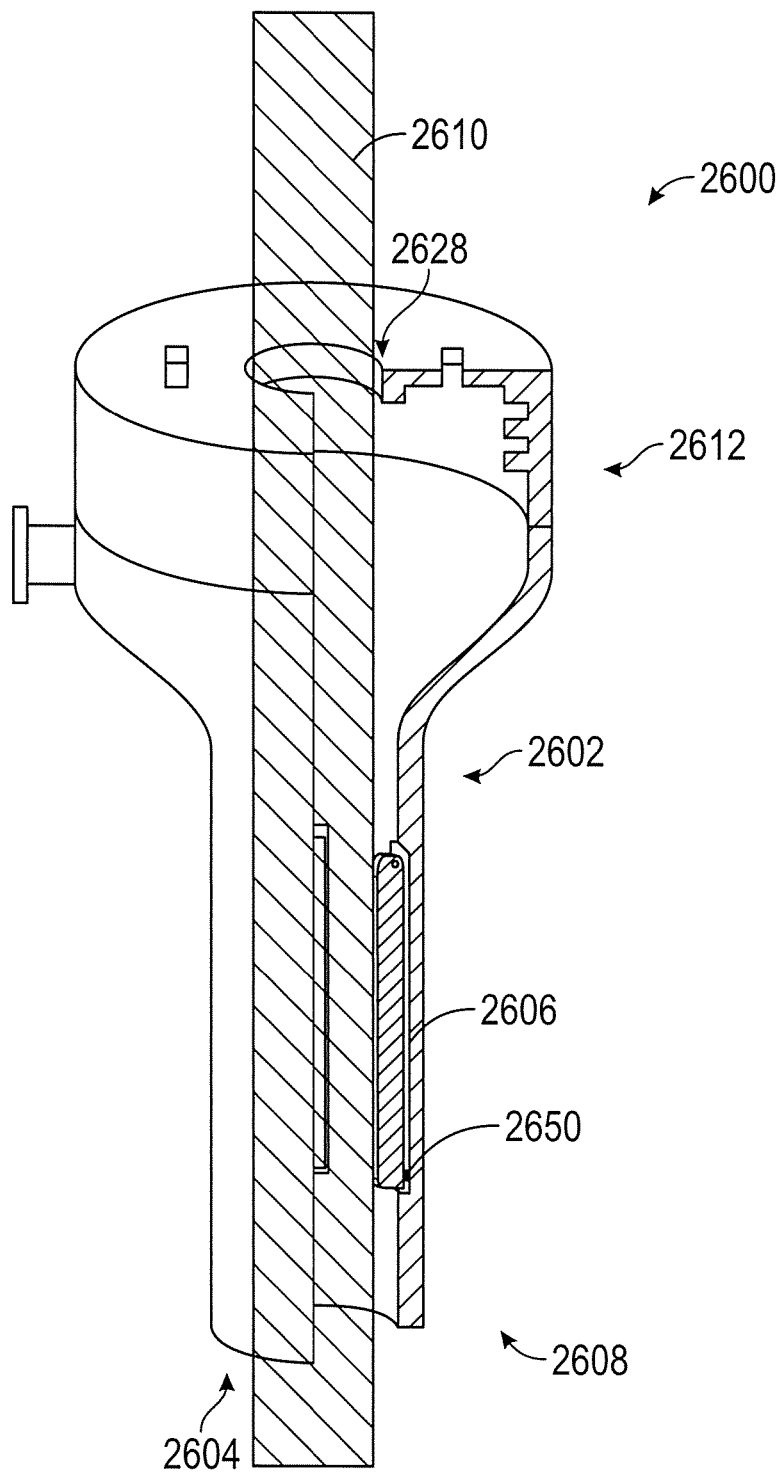
Figure 26O:
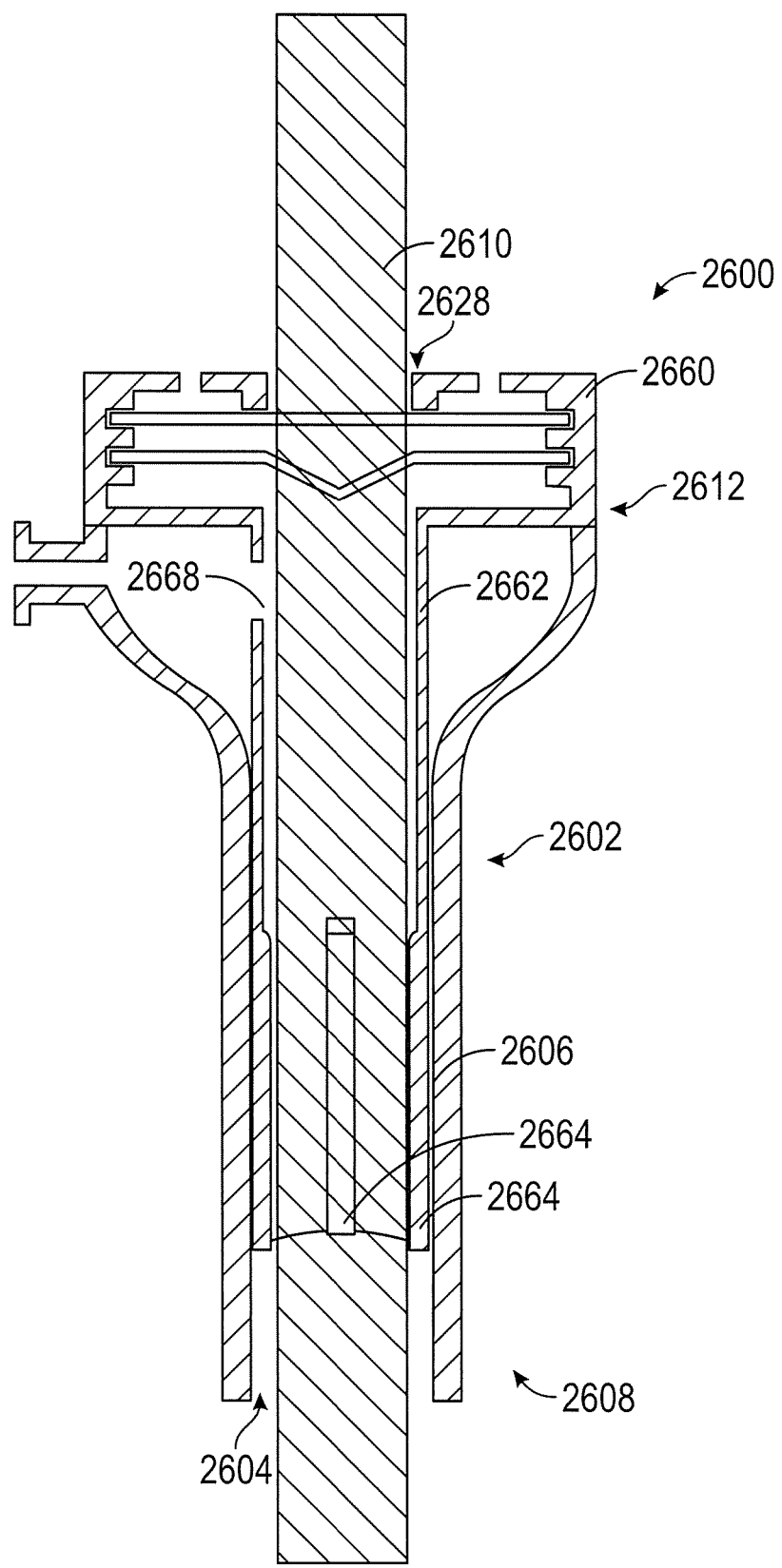
Figure 26P:
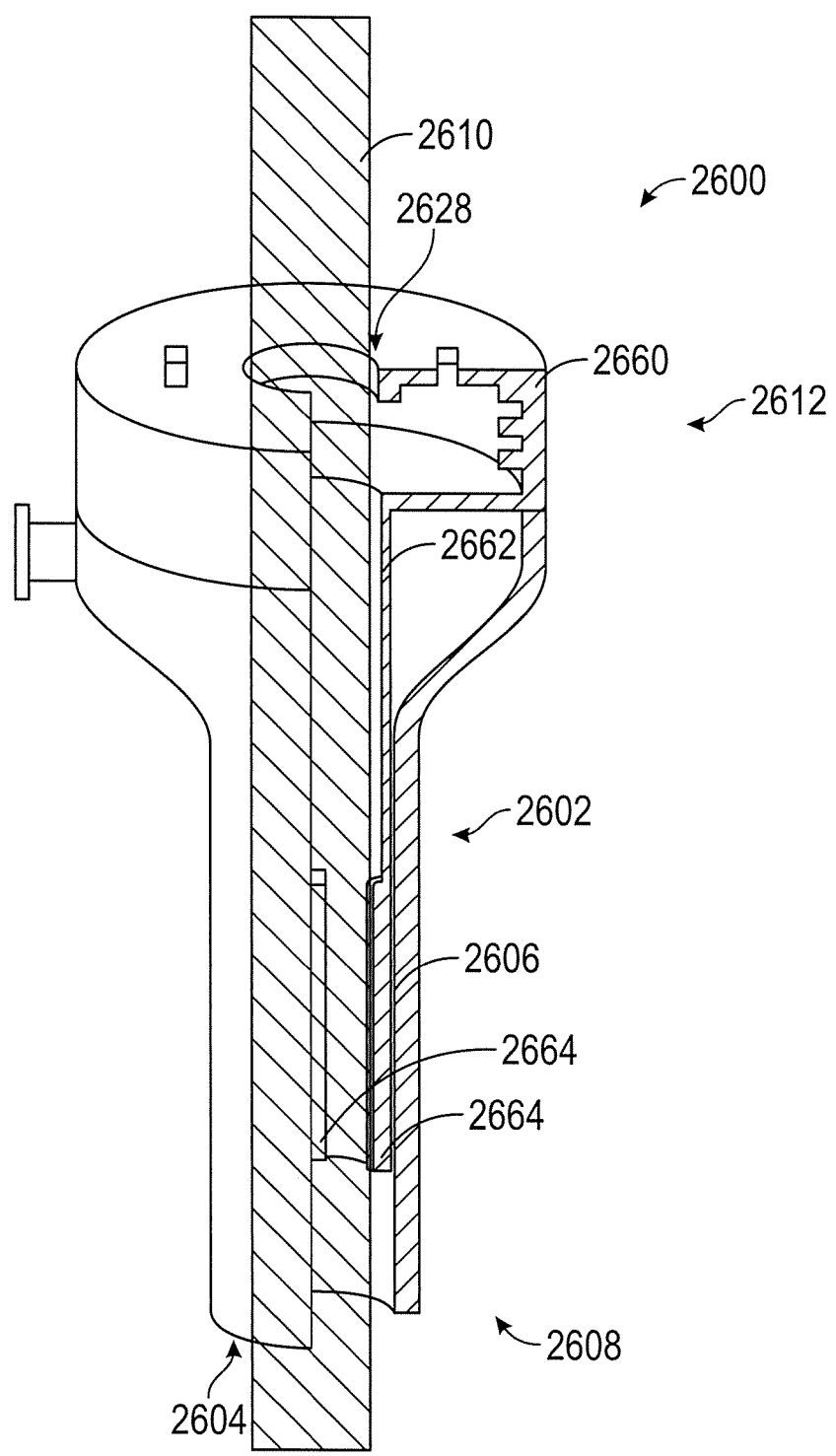
Figures 26Q, 26R:
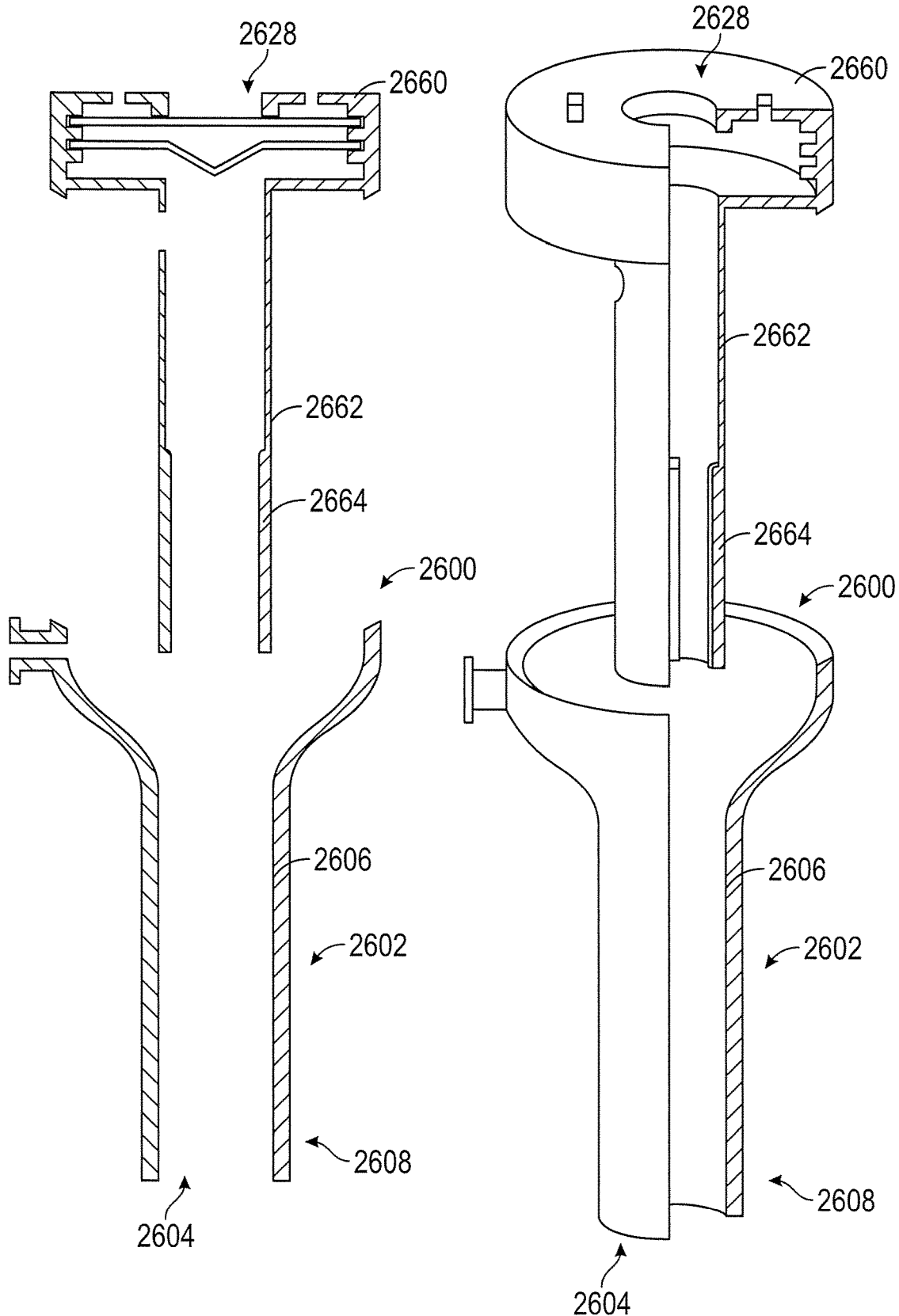

FIGS. 26A-26R illustrate embodiments of cannulas 2600 with a guide element including rigid continuous structures along the elongate shaft 2602 of the cannula 2600 to aid in concentricity of the medical instrument 2610 within the cannula 2600. The cannula 2600 can include a cannula body 2612 and elongate shaft 2602. The elongate shaft 2602 can include a cannula sidewall 2606 that forms the lumen 2604 of the cannula 2600. The lumen 2604 can defined by the inner sidewall 2606 of the cannula 2600 as shown in FIGS. 26A-26R. As described herein, a medical instrument 2610 can be inserted through the cannula 2600 by being introduced through the inlet 2628 at the proximal end of the cannula body 2612 and extending through the lumen 2604 of the cannula 2600 toward the distal end 2608 of the elongate shaft 2602.

As shown in FIG. 26A, the medical instrument 2610 can be supported by a guide element including a rigid continuous rib 2620 in the elongate shaft 2602 of the cannula 2600 to accomplish medical instrument 2610 concentricity. The rigid continuous rib 2620 can be molded continuously along the cannula elongate shaft 2602. The rigid continuous rib 2620 can be molded directly into the cannula elongate shaft 2602. The rigid continuous rib 2620 can hold the medical instrument 2610 concentrically in the cannula elongate shaft 2602. The rigid continuous rib 2620 can be molded along the length of the elongate shaft 2602 as shown in FIG. 26A. FIG. 26B is a cross-section through line 26A-26A of FIG. 26A, better illustrating the rigid continuous rib 2620 spaced circumferentially around the elongate shaft 2502.

FIG. 26C illustrates a partial cut-away schematic view of the cannula of FIGS. 26A-26B. Features in FIGS. 26C and 26D can be the same or substantially the same features as shown and described in FIGS. 26A and 26B and reference numerals of the same or substantially the same features may share the same reference numerals. FIG. 26D is a cross-section through line 26C-26C of FIG. 26C, better illustrating the rigid continuous rib 2620 spaced circumferentially around the elongate shaft 2602. As shown in FIG. 26D, the rigid continuous rib 2620 can hold the medical instrument 2610 concentrically within the lumen 2604 allowing gases to pass through the lumen 2604.

As shown in FIGS. 26E-26H, the medical instrument 2610 can be supported by a guide element including a rigid continuous rib 2630 on an insert 2632 in the elongate shaft 2602 of the cannula 2600 to accomplish medical instrument 2610 concentricity. As illustrated in FIG. 26E, the rigid continuous rib 2630 can be molded onto an insert 2632 which can be attached to the inside of the cannula elongate shaft 2602. The insert 2632 can be permanently or temporarily attached to the cannula sidewall 2606 of the elongate shaft 2602. The one or more rigid continuous rib 2630 can hold the medical instrument 2610 concentrically in the cannula elongate shaft 2602. In some cases, the insert 2632 can be attached to the cannula elongate shaft 2602 by a friction fit or other method. The insert 2632 can be assembled as part of the cannula 2600 or can be a separate attachment.

FIG. 26F illustrates a partial cut-away schematic view of the cannula of FIG. 26E. Features in FIG. 26F can be the same or substantially the same features as shown and described in FIG. 26E and reference numerals of the same or substantially the same features may share the same reference numerals. As shown in FIG. 26F, the rigid continuous rib 2630 on the insert 2632 can be spaced around the circumference of the insert 2632 to hold the medical instrument 2610 concentrically within the lumen 2604 allowing gases to pass through the lumen 2604.

FIG. 26G illustrates a cannula 2600 with the rigid continuous rib 2630 and insert 2632 removed from the cannula 2600. Features in FIG. 26G can be the same or substantially the same features as shown and described in FIG. 26F and reference numerals of the same or substantially the same features may share the same reference numerals.

FIG. 26H illustrates a partial cut-away schematic view of the cannula of FIG. 26G with the rigid continuous rib 2630 and insert 2632 removed from the cannula 2600. Features in FIG. 26H can be the same or substantially the same features as shown and described in FIG. 26F and reference numerals of the same or substantially the same features may share the same reference numerals. As illustrated in FIG. 26H, the insert can be a hollow cylindrical shape. As shown in FIG. 26H, the rigid continuous rib 2630 on the insert 2632 can be spaced around the inner circumference of the insert 2632 to hold the medical instrument 2610 concentrically within the lumen 2604 allowing gases to pass through the lumen 2604.

As shown in FIG. 26I, the medical instrument 2610 can be supported by a guide element including a rigid continuous rib 2640 molded directly into the elongate shaft 2602 of the cannula 2600 to accomplish medical instrument 2610 concentricity. The rigid continuous rib 2620 can be molded continuously along the length of the cannula elongate shaft 2602. The rigid continuous rib 2640 can be molded directly into or formed as part of the cannula elongate shaft 2602. The rigid continuous rib 2640 can hold the medical instrument 2610 concentrically in the cannula elongate shaft 2602. The rigid continuous rib 2640 can be molded directly into the cannula along substantially the entire length of the elongate shaft 2602 as shown in FIGS. 26I and 26J.

FIG. 26J illustrates a partial cut-away schematic view of the cannula of FIG. 26I. Features in FIG. 26J can be the same or substantially the same features as shown and described in FIG. 26I and reference numerals of the same or substantially the same features may share the same reference numerals. As shown in FIG. 26J, the rigid continuous rib 2640 can be spaced around the inner circumference of the cannula sidewall 2606 to hold the medical instrument 2610 concentrically within the lumen 2604 allowing gases to pass through the lumen 2604.

FIGS. 26K-26N illustrate a cannula 2600 with a guide element including adjustable structures 2650 along the length of the cannula 2600 to accomplish medical instrument 2610 concentricity. Features of FIGS. 26K-26N are similar to the features described with reference to FIGS. 26A-26D. Accordingly, similar features of FIGS. 26K-26N have the same reference numerals as in FIGS. 26A-26D. The adjustable structures 2650 can be spring loaded to allow the adjustable structures 2650 to support and accommodate medical instruments 2610 of different sizes. The spring loaded adjustable structures 2650 can be pushed outwards by the medical instrument 2610 when the medical instruments 2610 is inserted and the springs push back on the medical instruments 2610 which keeps the medical instruments 2610 concentric in the cannula elongate shaft 2602. The spring loaded adjustable structures 2650 allow them to be adjustable. The spring loaded adjustable structures 2650 can rotate inward and outward of the cannula sidewall 2606 to accommodate different medical instrument 2610 sizes.

FIGS. 26M-26N illustrate a partial cut-away schematic view of the cannula of FIGS. 26K and 26L. Features in FIGS. 26M-26N can be the same or substantially the same features as shown and described in FIGS. 26K and 26L and reference numerals of the same or substantially the same features may share the same reference numerals.

FIGS. 26K and 26M illustrate the cannula 2600 without the medical instrument 2610 within the cannula. In this configuration, the adjustable structures 2650 are bias outward into the lumen 2604 of the cannula elongate shaft 2602. As illustrated in FIGS. 26K-26N, the adjustable structures 2650 can be on a pivot that rotates the adjustable structures 2650 out of the way, opening up the lumen 2604, when the medical instrument 2610 is pushed past them. As the adjustable structures 2650 pivot, the adjustable structures 2650 then move inwardly toward the cannula sidewall 2406 as shown in FIGS. 26L and 26N. FIGS. 26L and 26N illustrate the medical instrument 2610 inserted within the cannula 2600. The adjustable structures 2650 can hold the medical instrument 2610 concentrically within the cannula elongate shaft 2602 while allowing the gases to pass through the lumen 2604. As shown in FIGS. 26M-26N, the adjustable structures 2650 can be spaced around the inner circumference of the cannula sidewall 2606 to hold the medical instrument 2610 concentrically within the lumen 2604 allowing gases to pass through the lumen 2604.

As shown in FIGS. 26O-26R, the medical instrument 2610 can be supported by a guide element including a rigid rib 2664 on an insert 2660 that extends from the top housing. The rigid rib 2664 can be on an inner surface of the insert that extends into the elongate shaft 2602 of the cannula 2600 to accomplish medical instrument 2610 concentricity. As illustrated in FIG. 26O, the rigid rib 2664 can be molded onto an elongate wall 2662 of the insert 2660. The insert 2660 can include at least a portion of the body 2612 of the cannula 2600. The rigid rib 2664 can be located on the insert 2660 which includes the top portion of the body 2612 of the cannula 2600 as shown in FIGS. 26O-26R. Therefore, the rigid rib 2664 on an insert 2660 can be changed by changing the insert 2660 including the top housing for the cannula 2600. The insert 2660 including the body 2612 of the cannula 2600 can be removed from the cannula elongate shaft 2602 and the elongate shaft 2602 can stay in the patient during a surgery. The rigid rib 2664 on an insert 2660 can be removed or changed to accommodate different medical instruments 2610, for example, scopes or surgical tools, by only changing the body portion 2610 of the cannula 2600. In some cases, as shown in FIG. 26O the insert 2660 can include an insert elongate shaft 2662 with rigid rib 2664 and an aperture 2668 for the gases to pass into the shaft 2602 of the cannula 2600. The rigid rib 2664 on the insert 2660 can be used to hold the medical instruments 2610 concentrically in the cannula elongate shaft 2602. In some cases, the rigid rib 2664 can be continuous or dis-continuous along the insert 2660.

In some cases, the insert 2660 can be permanently or temporarily attached to or integrally formed with the cannula elongate shaft 2602. In some cases, the insert 2660 can be attached to the cannula elongate shaft 2602 by a friction fit or other method. The insert 2660 can be assembled as part of the cannula 2600 or can be a separate attachment.

FIG. 26P illustrates a partial cut-away schematic view of the cannula and insert of FIG. 26O. Features in FIG. 26P can be the same or substantially the same features as shown and described in FIG. 26O and reference numerals of the same or substantially the same features may share the same reference numerals. As shown in FIG. 26P, the rigid rib 2664 on the insert 2660 can be spaced around the circumference of the elongate shaft 2662 of the insert 2660 to hold the medical instrument 2610 concentrically within the lumen 2604 allowing gases to pass through the lumen 2604.

FIG. 26Q illustrates a cannula 2600 with the insert 2660 with rigid rib 2664 removed from the cannula 2600. Features in FIG. 26Q can be the same or substantially the same features as shown and described in FIG. 26O and reference numerals of the same or substantially the same features may share the same reference numerals.

FIG. 26R illustrates a partial cut-away schematic view of the cannula of FIG. 26Q with the insert 2660 with rigid rib 2664 removed from the cannula 2600. Features in FIG. 26R can be the same or substantially the same features as shown and described in FIG. 26O and reference numerals of the same or substantially the same features may share the same reference numerals. As illustrated in FIG. 26R, the insert 2660 can include a top portion 2666 and an elongate shaft portion 2662 extending distally from the top portion 2666. The elongate shaft portion 2662 can be a hollow cylindrical shape with rigid rib 2664. As shown in FIG. 26R, the rigid rib 2664 on the insert 2660 can be spaced around the inner circumference of the elongate shaft 2662 of the insert 2660 to hold the medical instrument 2610 concentrically within the lumen 2604 allowing gases to pass through the lumen 2604.

Figures 27A, 27B:
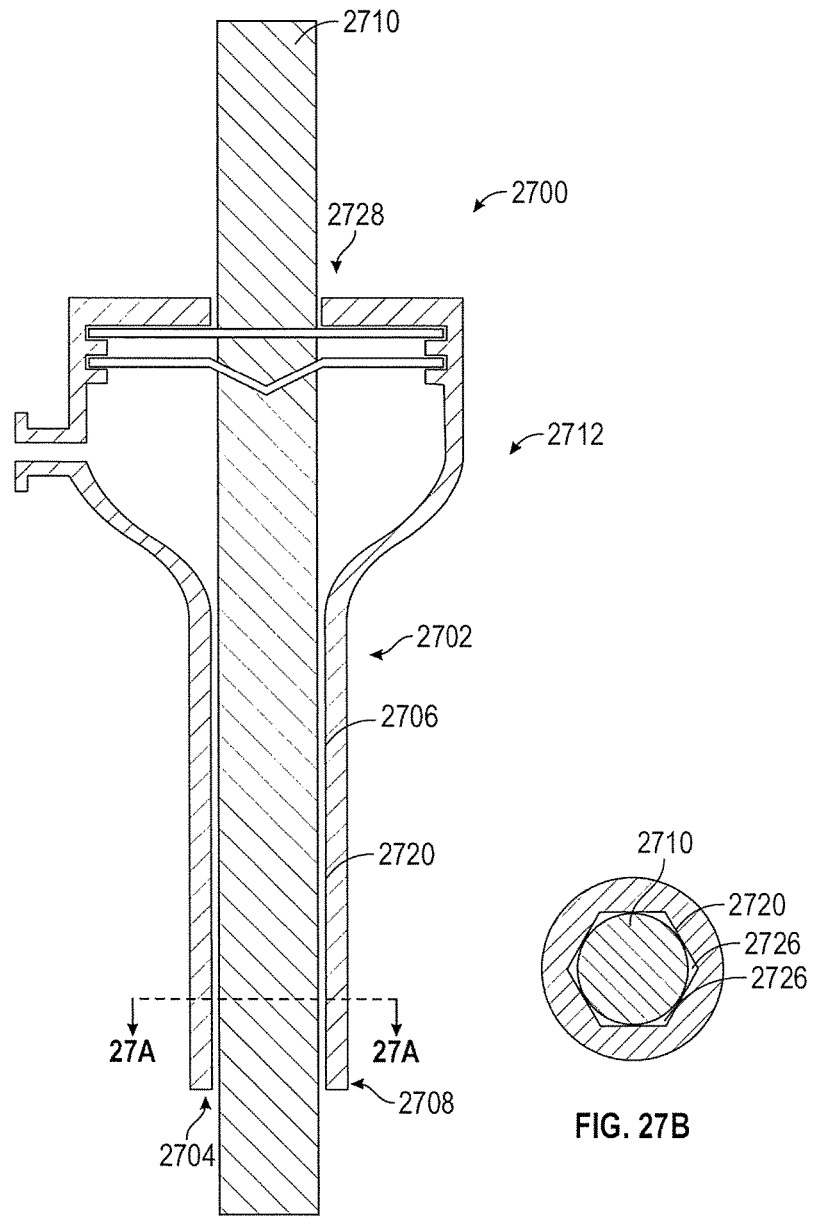
FIGS. 27A-27T illustrate views of embodiments of cannulas with non-circular inner cross-section for the cannula wall along the elongate shaft of the cannula to aid in concentricity of the medical instrument within the cannula.

FIGS. 27A-27T illustrate embodiments of cannulas 2700 with non-circular inner cross-sections for the cannula sidewall 2706 along the elongate shaft 2702 that act as guide element within the cannula 2700 to aid in concentricity of the medical instrument 2710 within the cannula 2700. The cannula 2700 can include a cannula body 2712 and elongate shaft 2702. The elongate shaft 2702 can include a cannula sidewall 2706 that forms the lumen 2704 of the cannula 2700. The lumen 2704 can defined by the inner sidewall 2706 of the cannula 2700 as shown in FIGS. 27A-27T. As described herein, a medical instrument 2710 can be inserted through the cannula 2700 by being introduced through the inlet 2728 on the proximal end of the cannula body 2712 and extending through the lumen 2704 of the cannula 2700 toward the distal end 2708 of the elongate shaft 2702.

As shown in FIG. 27A, the medical instrument 2710 can be supported by a non-circular inner cross-section 2720 for the cannula sidewall 2706 along the elongate shaft 2702 that act as guide element within of the cannula 2700 to accomplish medical instrument 2710 concentricity. As the medical instrument can be circular or substantially circular, the non-circular inner cross-section 2720 can be designed to have air gaps 2726 for the gases to pass down lumen 2704 while maintaining the medical instrument 2710 concentrically in the lumen 2704. The air gap 2726 can be the region formed between an outer surface of the medical instrument 2710 and the non-circular inner cross-section 2720 of the elongate shaft. FIG. 27B is a cross-section through line 27A-27A of FIG. 27A, better illustrating the non-circular inner cross-section 2720 with the medical instrument 2710 inserted within the elongate shaft 2702 and the air gaps 2726. For example, a hexagon cross-section shape can be used. As illustrated in FIG. 27B, the non-circular inner cross-section 2720 for the cannula sidewall 2706 can hold the medical instrument 2710 concentrically while allowing the gases to pass down the lumen 2704. The non-circular inner cross-section 2720 can be positioned on any portion of the cannula wall of the elongate shaft 2702 of the cannula 2700.

Figures 27C, 27D:
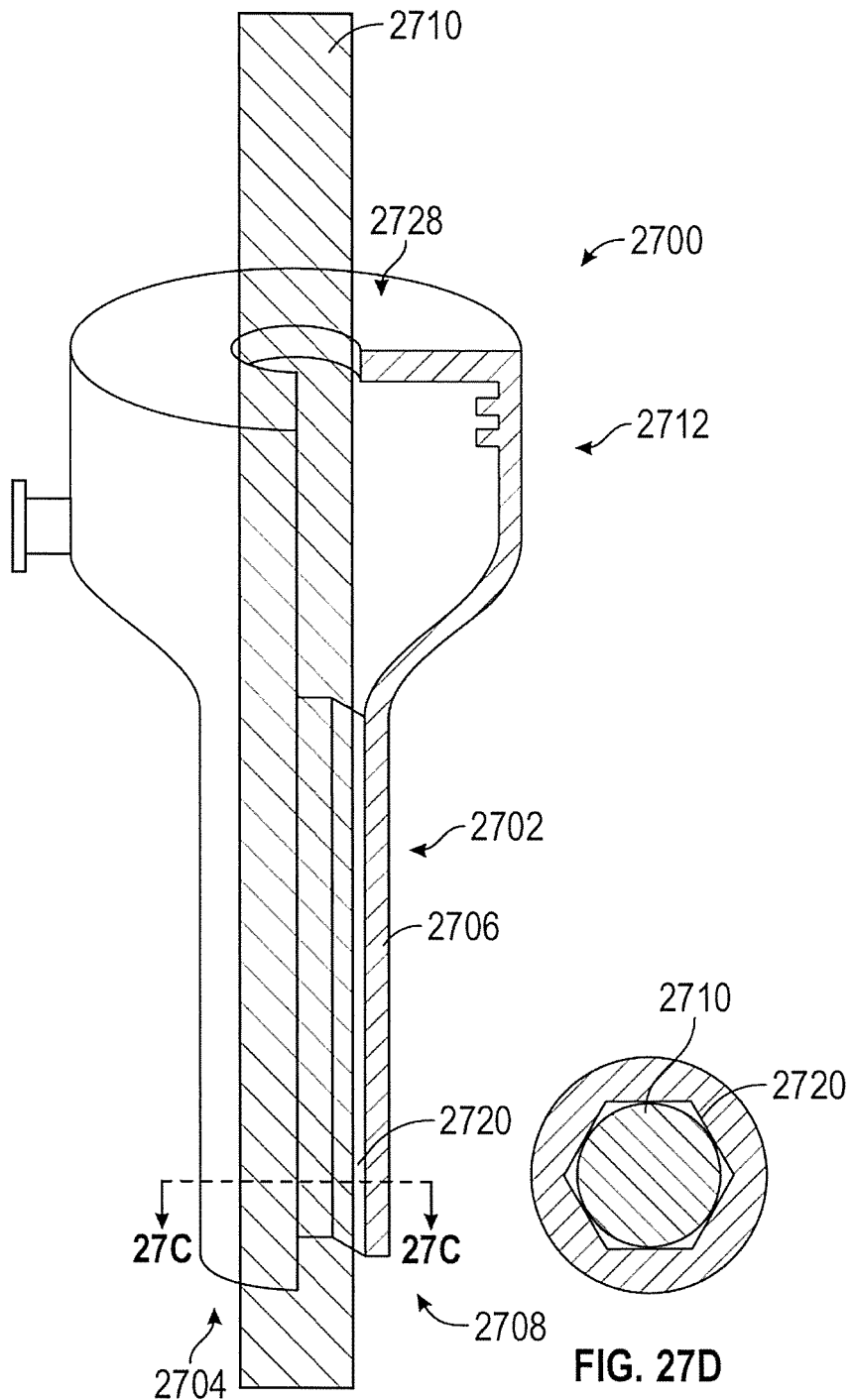

FIG. 27C illustrates a partial cut-away schematic view of the cannula of FIGS. 27A-27B. Features in FIGS. 27C and 27D can be the same or substantially the same features as shown and described in FIGS. 27A and 27B and reference numerals of the same or substantially the same features may share the same reference numerals. FIG. 27C illustrates the non-circular inner cross-section 2720 extending around the inner circumference of the elongate shaft 2702. FIG. 27D is a cross-section through line 27C-27C of FIG. 27C, better illustrating the non-circular inner cross-section 2720 with the medical instrument 2710 inserted within the elongate shaft 2702. As shown in FIG. 27D, the non-circular inner cross-section 2720 can hold the medical instrument 2710 concentrically within the lumen 2704 allowing gases to pass through the lumen 2704.

Figures 27E, 27F:
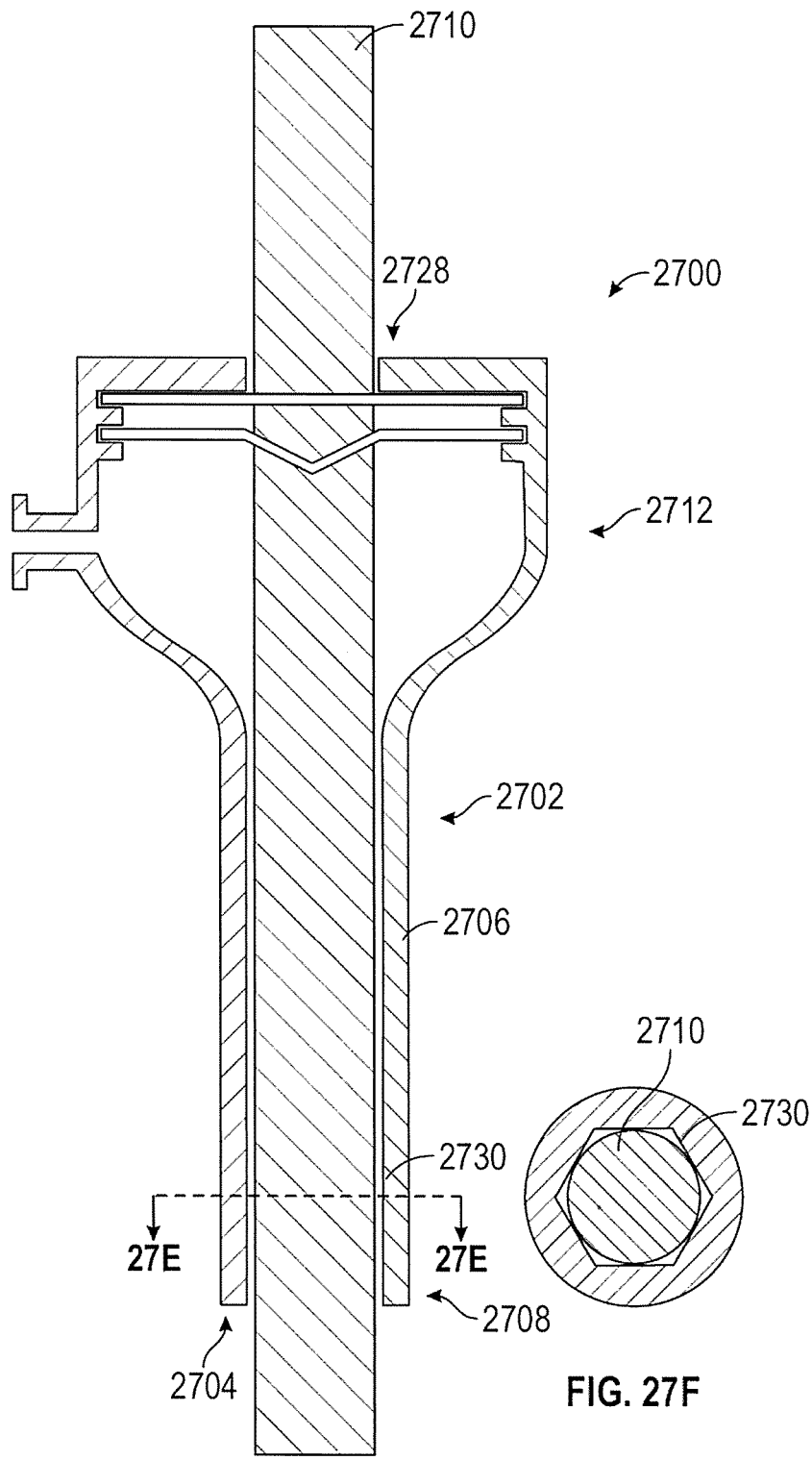

As shown in FIGS. 27E-27F, the medical instrument 2710 can be supported by a non-circular inner cross-section 2730 for the cannula sidewall 2706 along the elongate shaft 2702 of the cannula 2700 to accomplish medical instrument 2710 concentricity. The non-circular inner cross-section 2730 maintains the non-circular cross-sectional shape for the entirety or substantially the entirety of the cannula elongate shaft length as illustrated in FIG. 27E. As the medical instrument can be circular or substantially circular, the non-circular inner cross-section 2730 can be designed to have air gaps for the gases to pass down lumen 2704 while maintaining the medical instrument 2710 concentrically in the lumen 2704. FIG. 27F is a cross-section through line 27E-27E of FIG. 27E, better illustrating the non-circular inner cross-section 2720 with the medical instrument 2710 inserted within the elongate shaft 2702. As illustrated in FIG. 27F, the non-circular inner cross-section 2730 for the cannula sidewall 2706 can hold the medical instrument 2710 concentrically while allowing the gases to pass down the lumen 2704.

Figure 27G:
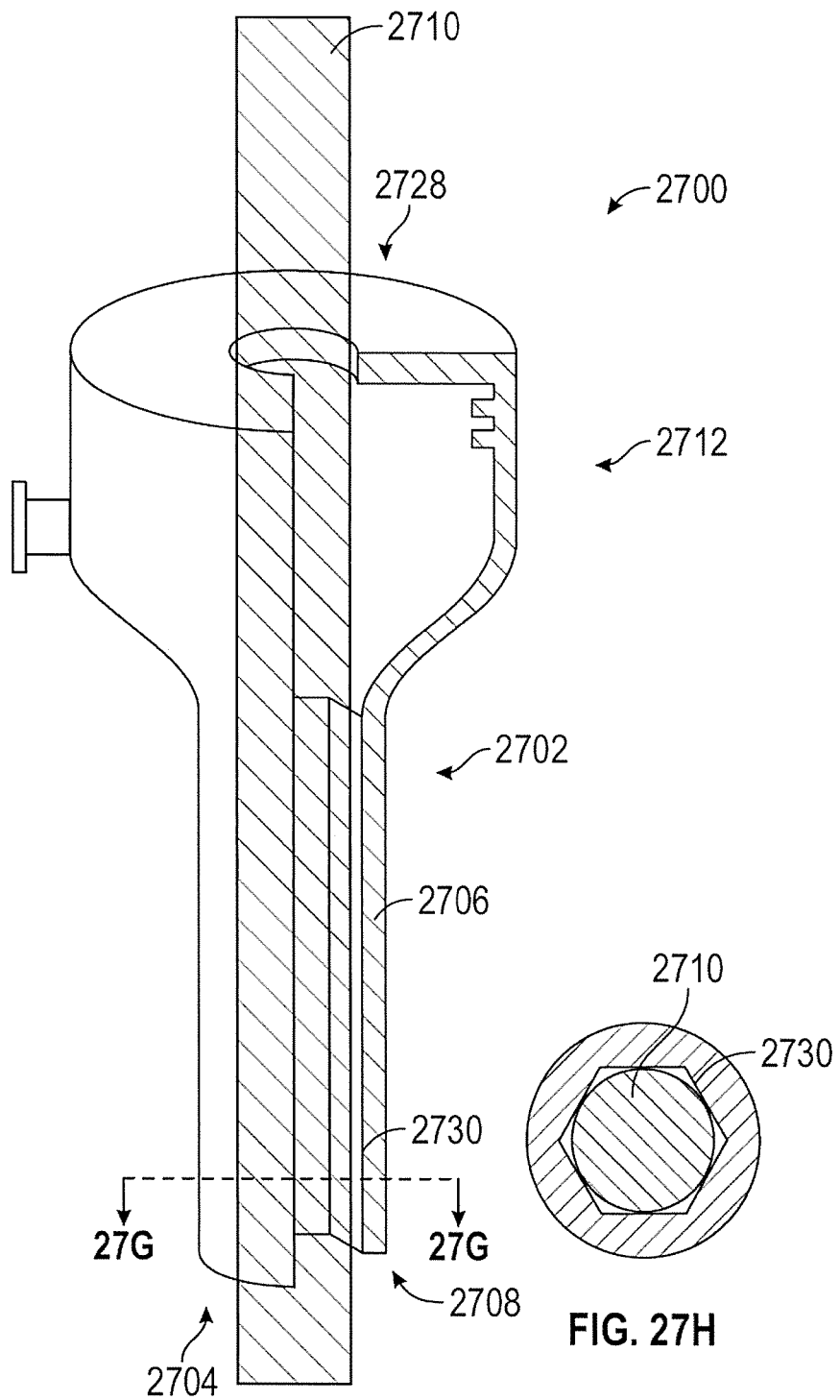

FIG. 27G illustrates a partial cut-away schematic view of the cannula of FIGS. 27E-27F. Features in FIGS. 27G and 27H can be the same or substantially the same features as shown and described in FIGS. 27E and 27F and reference numerals of the same or substantially the same features may share the same reference numerals. FIG. 27G illustrates the non-circular inner cross-section 2730 extending around the inner circumference of the elongate shaft 2702 and extending the entirety or substantially the entirety of the cannula elongate shaft length. FIG. 27H is a cross-section through line 27G-27G of FIG. 27G, better illustrating the non-circular inner cross-section 2730 with the medical instrument 2710 inserted within the elongate shaft 2702. As shown in FIG. 27H, the non-circular inner cross-section 2730 can hold the medical instrument 2710 concentrically within the lumen 2704 allowing gases to pass through the lumen 2704.

Figures 27I, 27J:
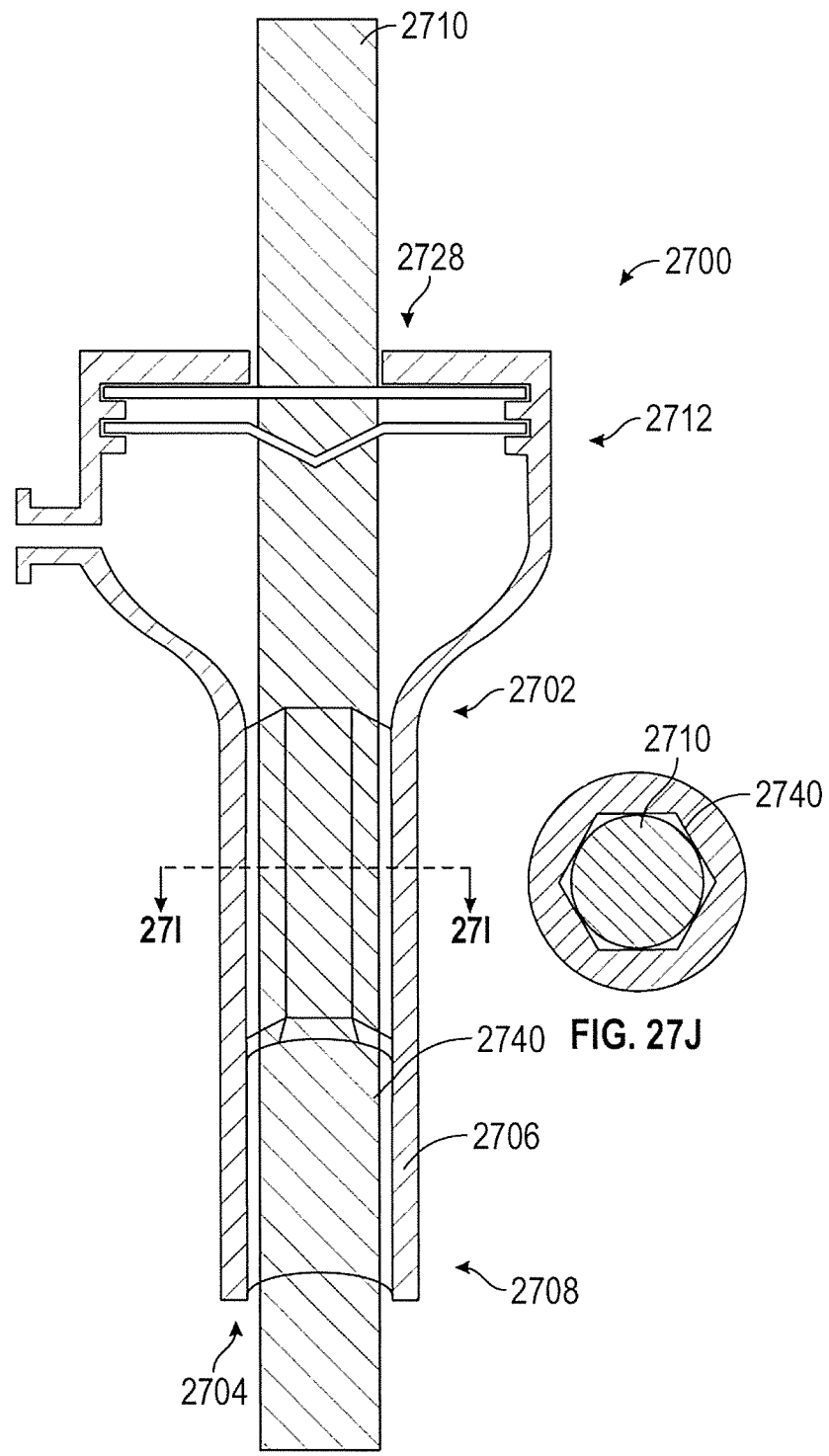

As shown in FIGS. 27I-27J, the medical instrument 2710 can be supported by a non-circular inner cross-section 2740 for the cannula sidewall 2706 along the elongate shaft 2702 that act as a guide element within the cannula 2700 to accomplish medical instrument 2710 concentricity. The non-circular inner cross-section 2740 maintains the non-circular cross-sectional shape for only part of the elongate shaft length. FIG. 27I illustrates the portion of the cannula shaft with the non-circular inner cross-section 2740 in the middle of the elongate shaft length. This positioning allows the medical instrument 2710 to be held concentrically in the cannula elongate shaft 2702 but the gases flow can join back up into a circular flow after the non-circular cross-section 2740 part of the cannula elongate shaft 2702. As shown in FIG. 27I, the circular part of the cross section at the distal end 2708 of the elongate shaft 2702 can allow for gas to combine into a single stream of flow after the non-circular cross-section 2740. As the medical instrument can be circular or substantially circular, the non-circular inner cross-section 2740 can be designed to have air gaps for the gases to pass down lumen 2704 while maintaining the medical instrument 2710 concentrically in the lumen 2704. FIG. 27J is a cross-section through line 27I-27I of FIG. 27I, better illustrating the non-circular inner cross-section 2740 with the medical instrument 2710 inserted within the elongate shaft 2702. As illustrated in FIG. 27J, the non-circular inner cross-section 2740 for the cannula sidewall 2706 can hold the medical instrument 2710 concentrically while allowing the gases to pass down the lumen 2704.

Figures 27K, 27L:
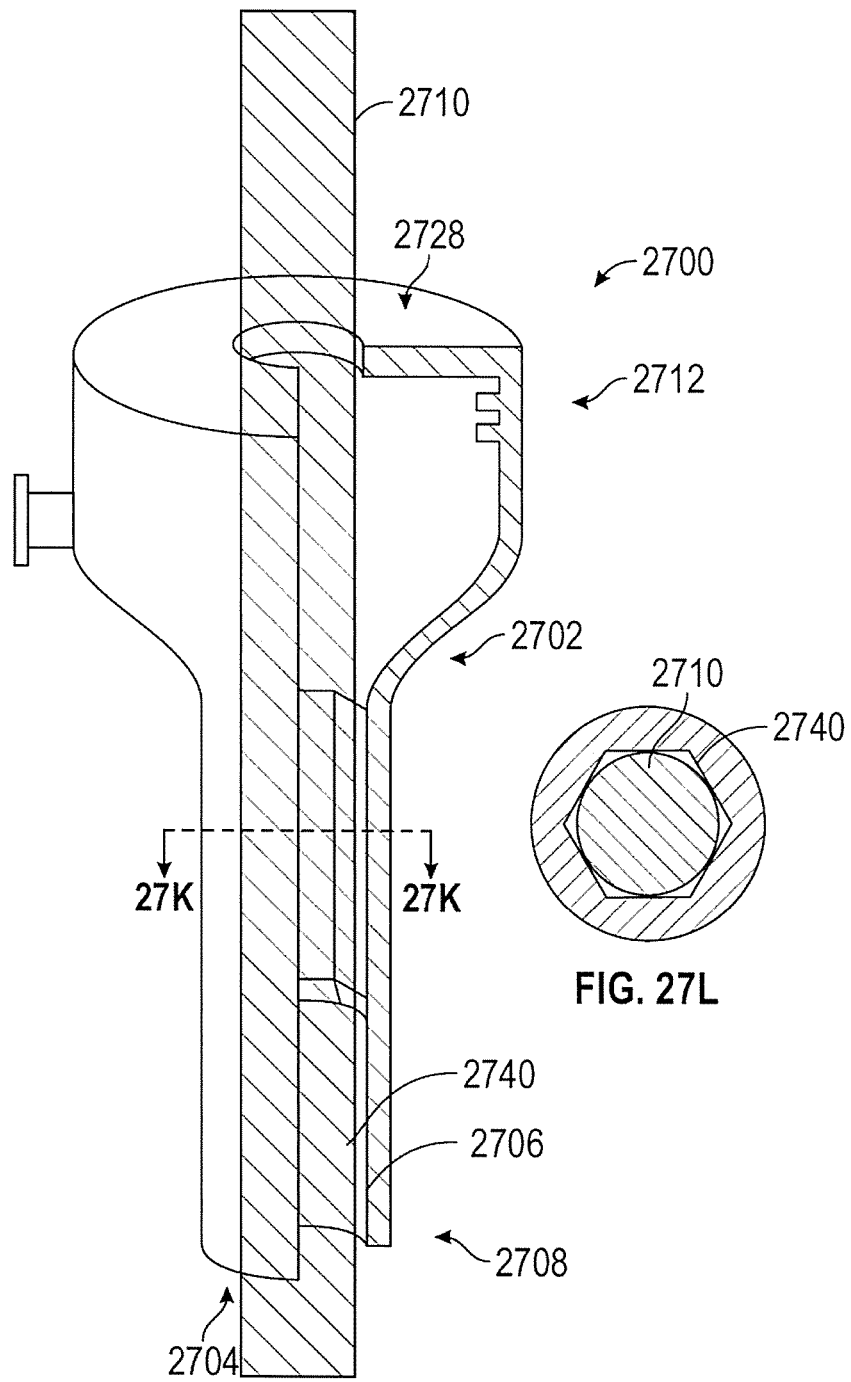

FIG. 27K illustrates a partial cut-away schematic view of the cannula of FIGS. 27I-27J. Features in FIGS. 27K and 27L can be the same or substantially the same features as shown and described in FIGS. 27I and 27J and reference numerals of the same or substantially the same features may share the same reference numerals. FIG. 27K illustrates the non-circular inner cross-section 2740 extending around the inner circumference of the elongate shaft 2702 and extending for only a portion of the cannula elongate shaft length. FIG. 27L is a cross-section through line 27K-27K of FIG. 27K, better illustrating the non-circular inner cross-section 2740 with the medical instrument 2710 inserted within the elongate shaft 2702. As shown in FIG. 27L, the non-circular inner cross-section 2740 can hold the medical instrument 2710 concentrically within the lumen 2704 allowing gases to pass through the lumen 2704.

Figures 27M, 27N:
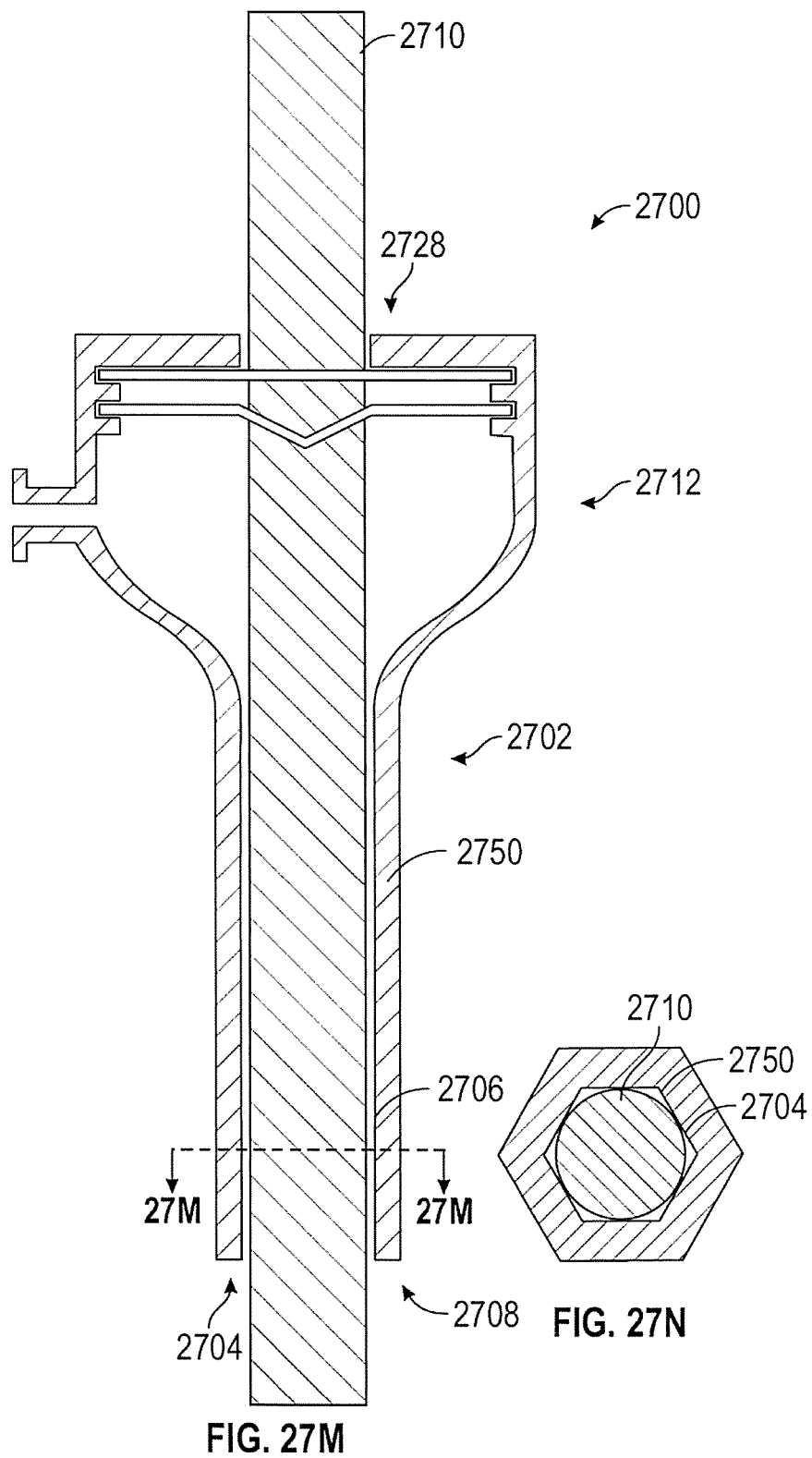

As shown in FIGS. 27M-27N, the medical instrument 2710 can be supported by a cannula elongate shaft 2702 with a non-circular inner and outer cross-section 2750 that act as a guide element to accomplish medical instrument 2710 concentricity. The non-circular inner and outer cross-section 2750 can maintain the non-circular cross-sectional shape for only part of the elongate shaft length or for the entirety or substantially the entirety of the elongate shaft length. As the medical instrument can be circular or substantially circular, the non-circular inner and outer cross-section 2750 can be designed to have air gaps for the gases to pass down lumen 2704 while maintaining the medical instrument 2710 concentrically in the lumen 2704. FIG. 27N is a cross-section through line 27M-27M of FIG. 27M, better illustrating the non-circular inner and outer cross-section 2750 with the medical instrument 2710 inserted within the elongate shaft 2702. As illustrated in FIG. 27N, the non-circular inner and outer cross-section 2750 for the cannula sidewall 2706 can hold the medical instrument 2710 concentrically while allowing the gases to pass down the lumen 2704. The outer non-circular cross-section can mirror the inner non-circular cross-section which gives the cannula shaft wall a constant wall thickness. In some cases, the constant wall thickness of the cannula elongate shaft can make molding easier during manufacture of the cannula.

Figures 27O, 27P:
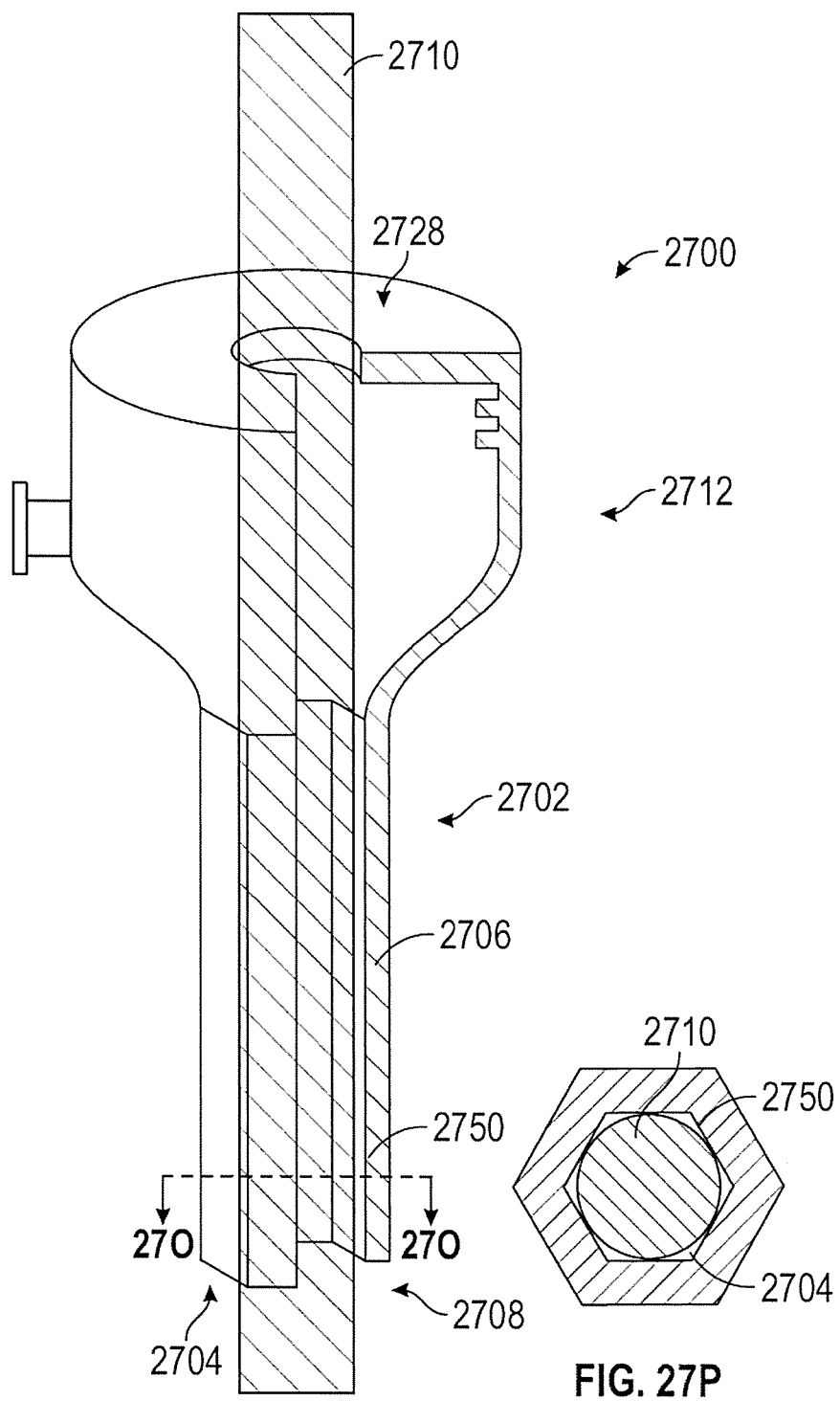

FIG. 27O illustrates a partial cut-away schematic view of the cannula of FIGS. 27M-27N. Features in FIGS. 27O and 27P can be the same or substantially the same features as shown and described in FIGS. 27M and 27N and reference numerals of the same or substantially the same features may share the same reference numerals. FIG. 27O illustrates the non-circular inner and outer cross-section 2750 extending around the circumference of the elongate shaft 2702 and extending along the cannula elongate shaft length. FIG. 27P is a cross-section through line 27O-27O of FIG. 27O, better illustrating the non-circular inner and outer cross-section 2750 with the medical instrument 2710 inserted within the elongate shaft 2702. As shown in FIG. 27P, the non-circular inner and outer cross-section 2750 can hold the medical instrument 2710 concentrically within the lumen 2704 allowing gases to pass through the lumen 2704.

Figures 27Q, 27R:
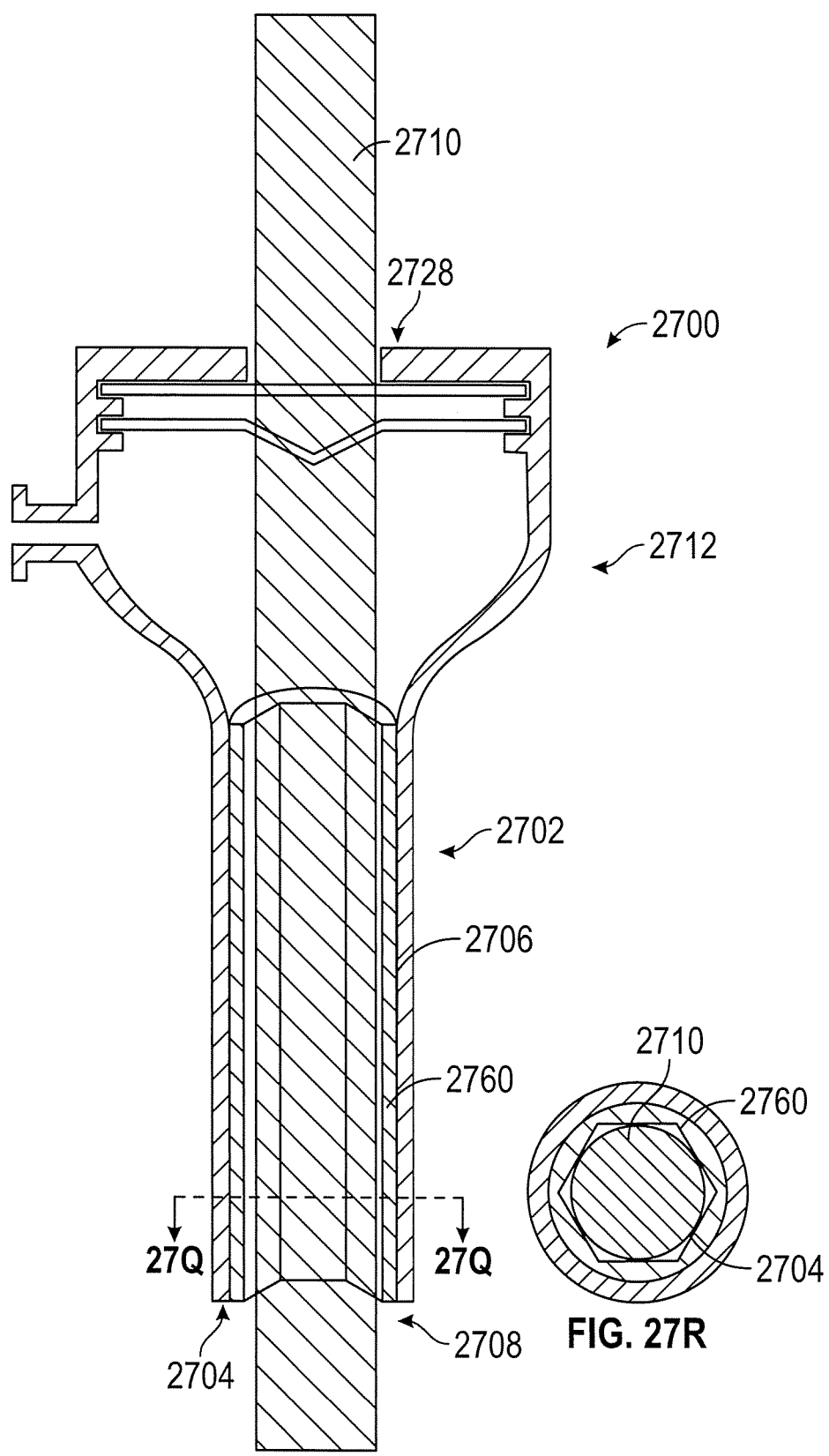

As shown in FIGS. 27Q-27R, the medical instrument 2710 can be supported by a cannula elongate shaft 2702 with a guide element, such as a non-circular inner cross-section insert 2760 to accomplish medical instrument 2710 concentricity. The non-circular inner cross-section insert 2760 can be a length that spans a portion of the elongate shaft length or can be a length equal to or substantially equal to the elongate shaft length. As the medical instrument can be circular or substantially circular, the non-circular inner cross-section insert 2760 can be designed to have air gaps for the gases to pass down lumen 2704 while maintaining the medical instrument 2710 concentrically in the lumen 2704. FIG. 27R is a cross-section through line 27Q-27Q of FIG. 27Q, better illustrating the non-circular inner cross-section insert 2760 with the medical instrument 2710 inserted within the elongate shaft 2702. As illustrated in FIG. 27R, the non-circular inner cross-section insert 2760 can hold the medical instrument 2710 concentrically while allowing the gases to pass down the lumen 2704. The non-circular inner cross-section insert 2760 can be attached to the cannula sidewall 2706 permanently or temporarily.

FIG. 27S illustrates a partial cut-away schematic view of the cannula of FIGS. 27Q-27R. Features in FIGS. 27S and 27T can be the same or substantially the same features as shown and described in FIGS. 27Q and 27R and reference numerals of the same or substantially the same features may share the same reference numerals. FIG. 27S illustrates the non-circular inner cross-section insert 2760 extending around the inner circumference of the elongate shaft 2702 and extending along the cannula elongate shaft length. FIG. 27T is a cross-section through line 27S-27S of FIG. 27S, better illustrating the various layers of the non-circular inner cross-section insert 2760 between the inner surface of the cannula sidewall 2706 and the medical instrument 2710 inserted within the elongate shaft 2702. As shown in FIG. 27T, the non-circular inner cross-section insert 2760 can hold the medical instrument 2710 concentrically within the lumen 2704 allowing gases to pass through the lumen 2704. The outer surface of the non-circular inner cross-section insert 2760 can abut the inner surface of the cannula sidewall 2706 as illustrated in FIGS. 27S and 27T.

Figures 28A, 28B:
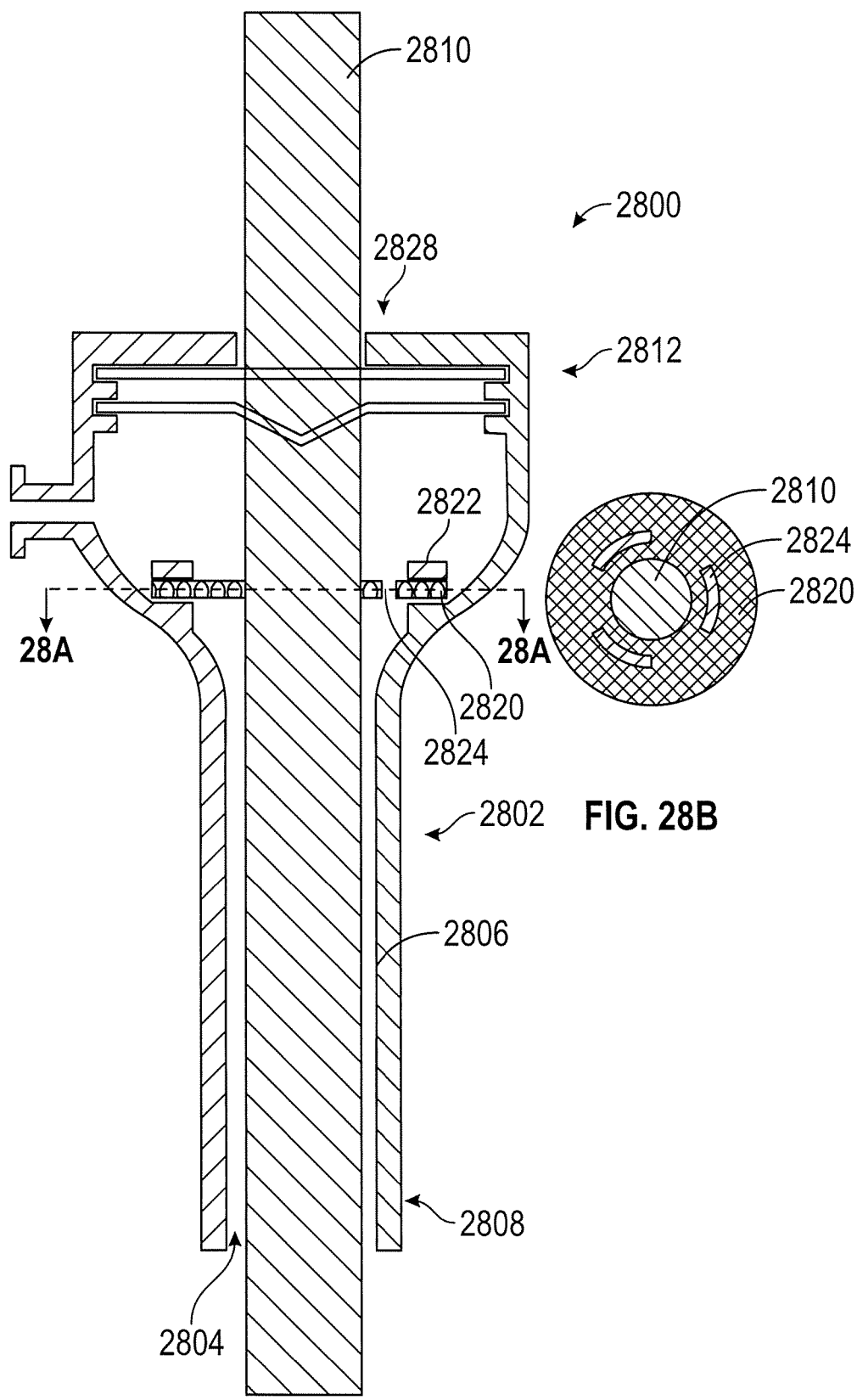
FIGS. 28A-28Q illustrate views of embodiments of cannulas with flexible structures in a body of the cannula to aid in concentricity of the medical instrument within the cannula.
Figures 28C, 28D:
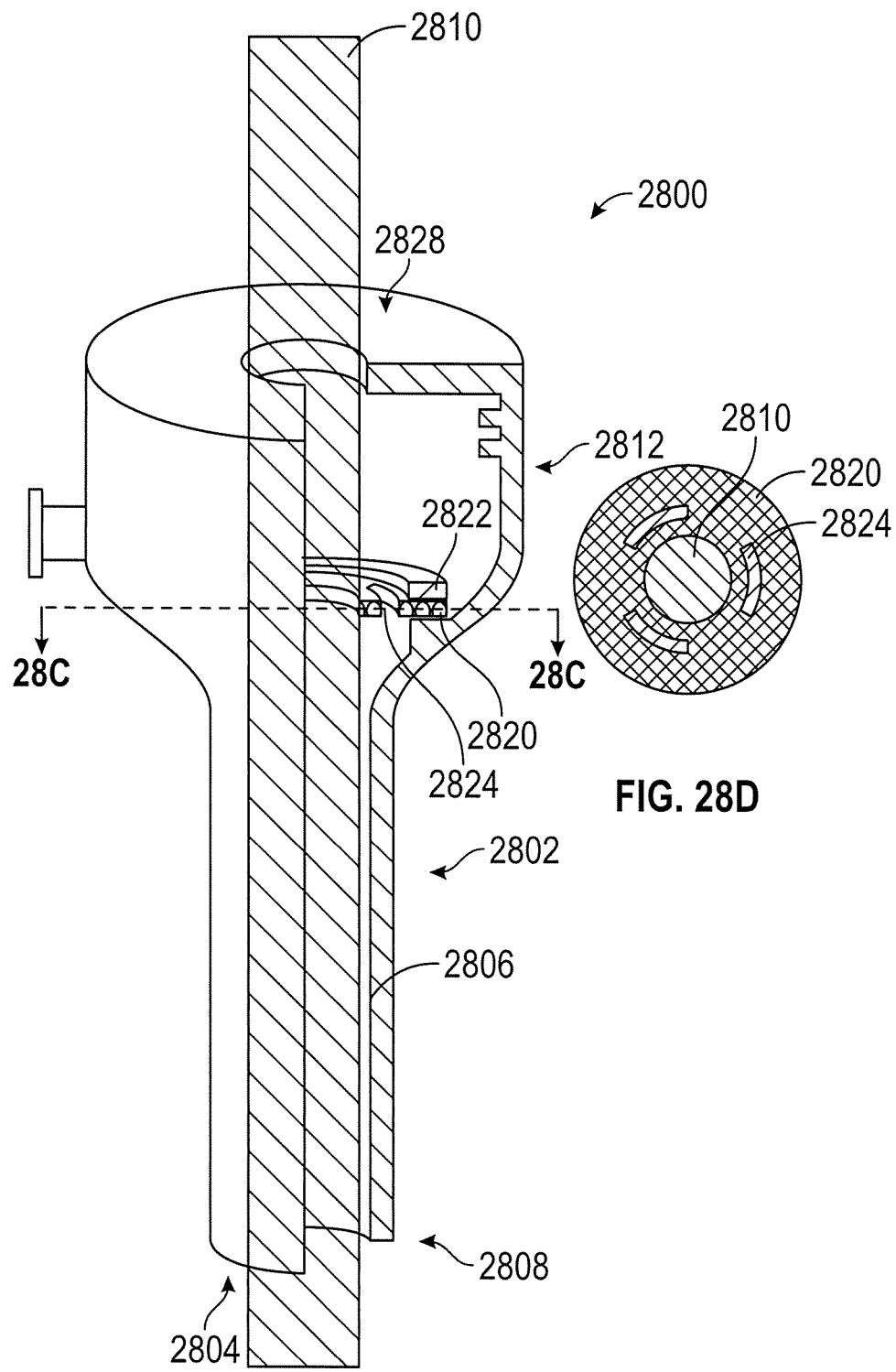
Figure 28E:
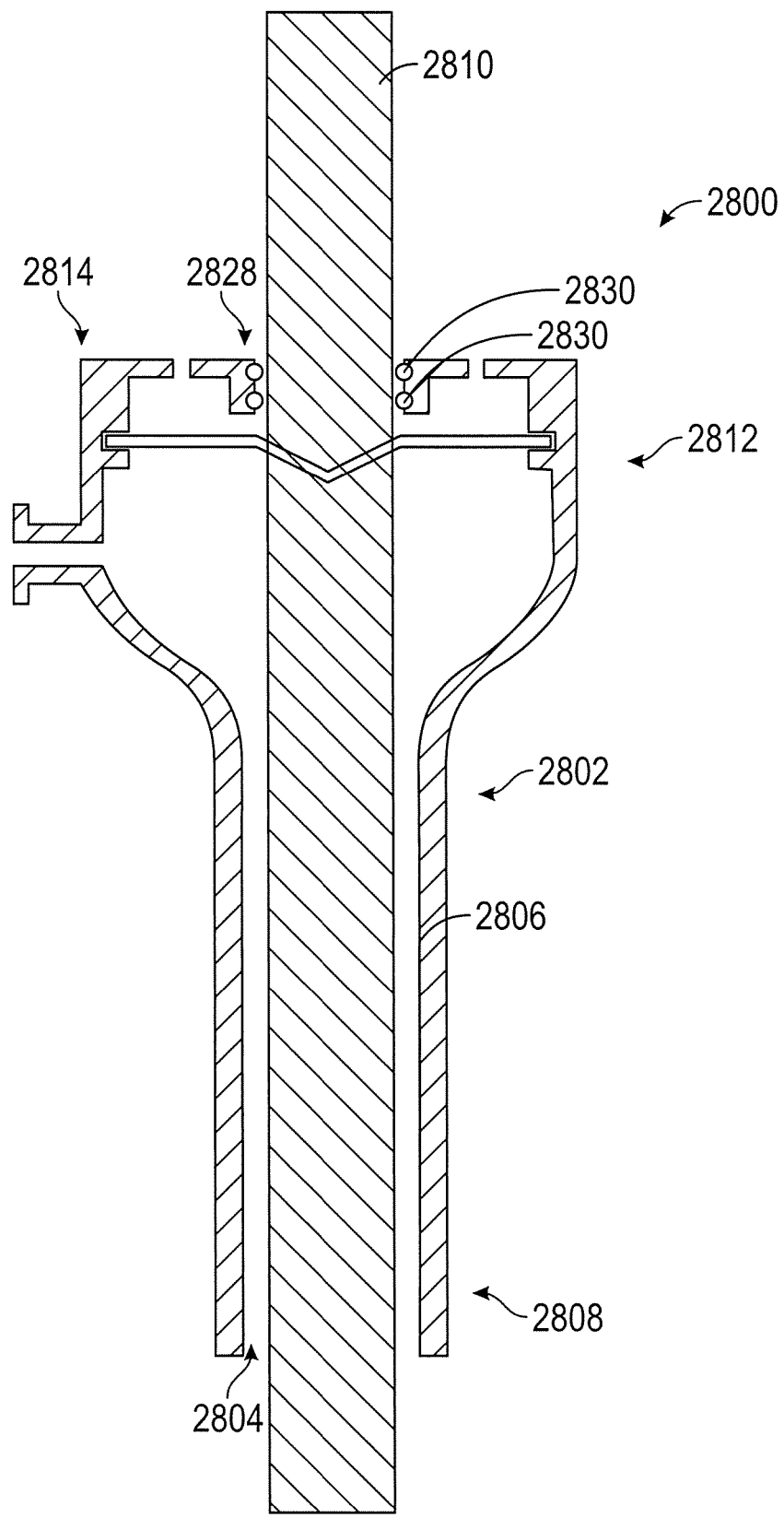
Figure 28F:
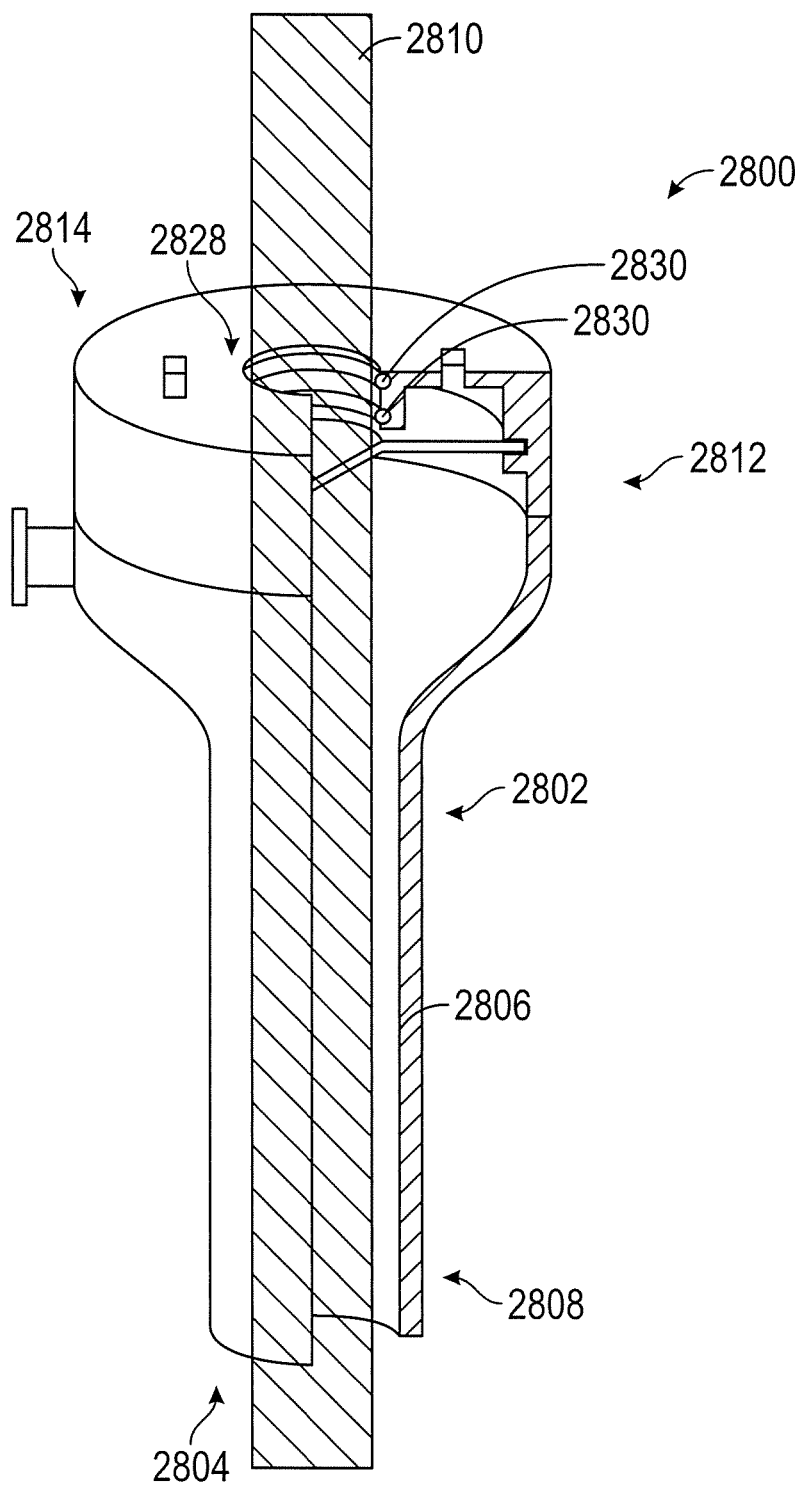
Figure 28G:
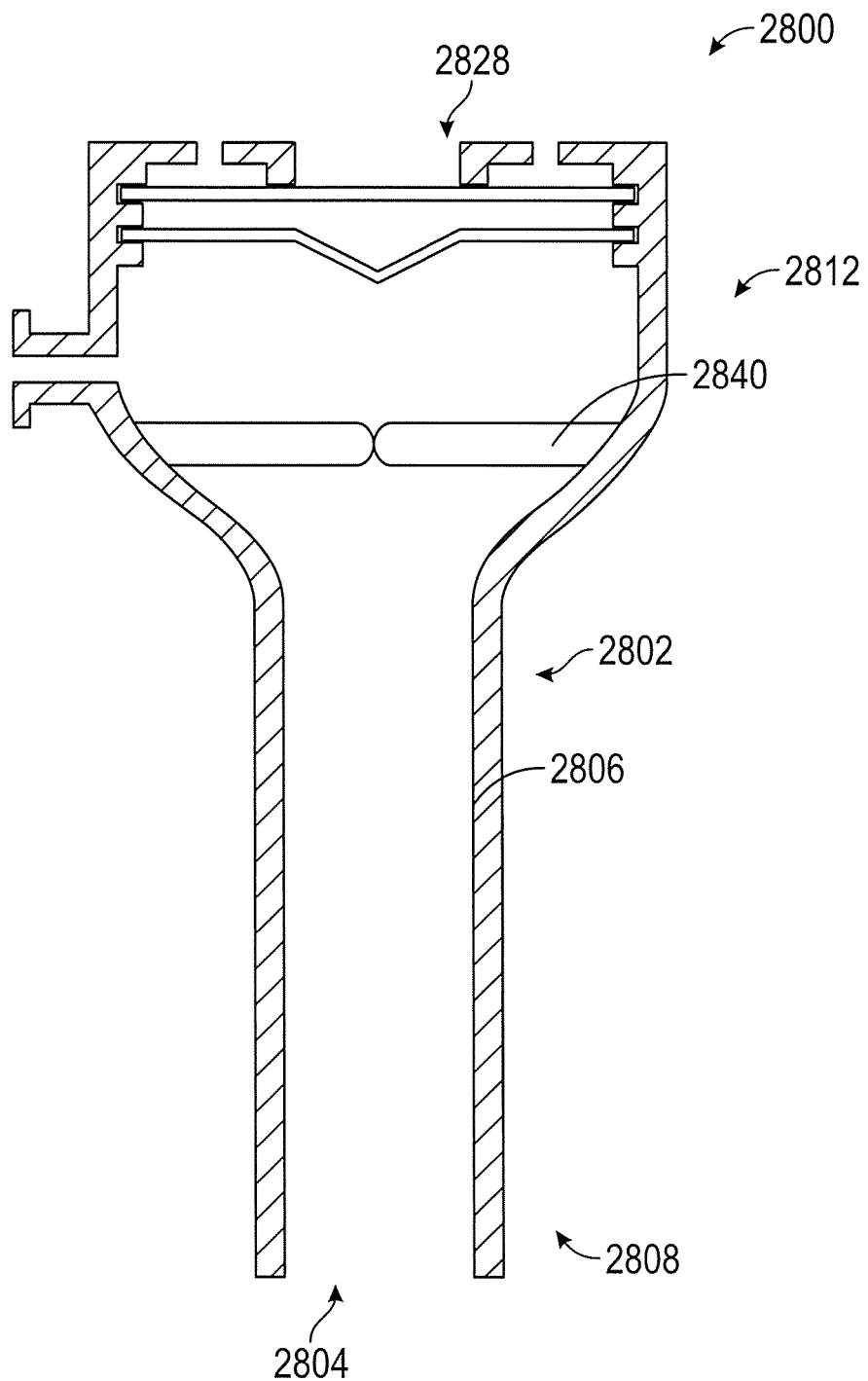
Figure 28H:
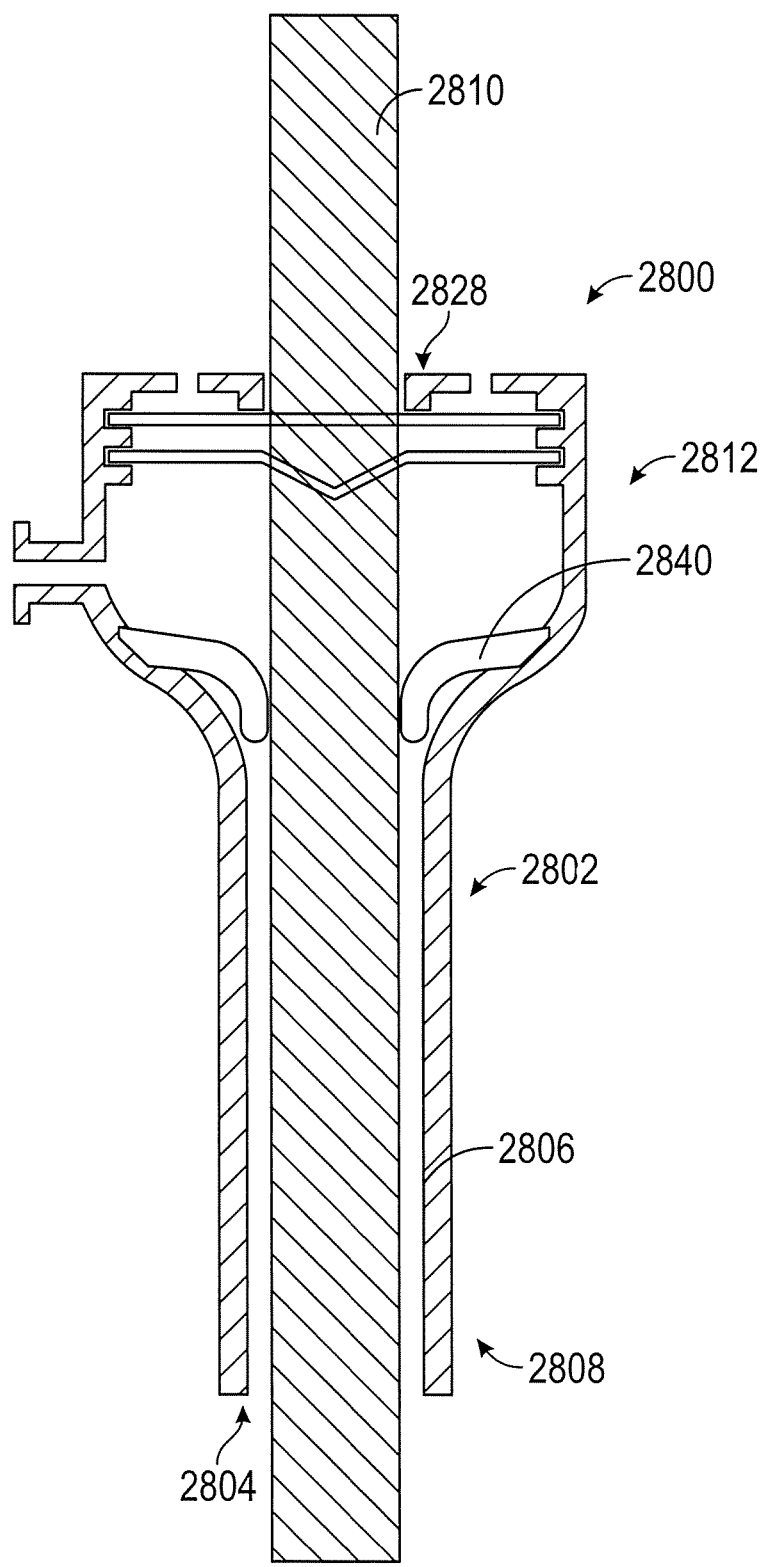
Figure 28I:
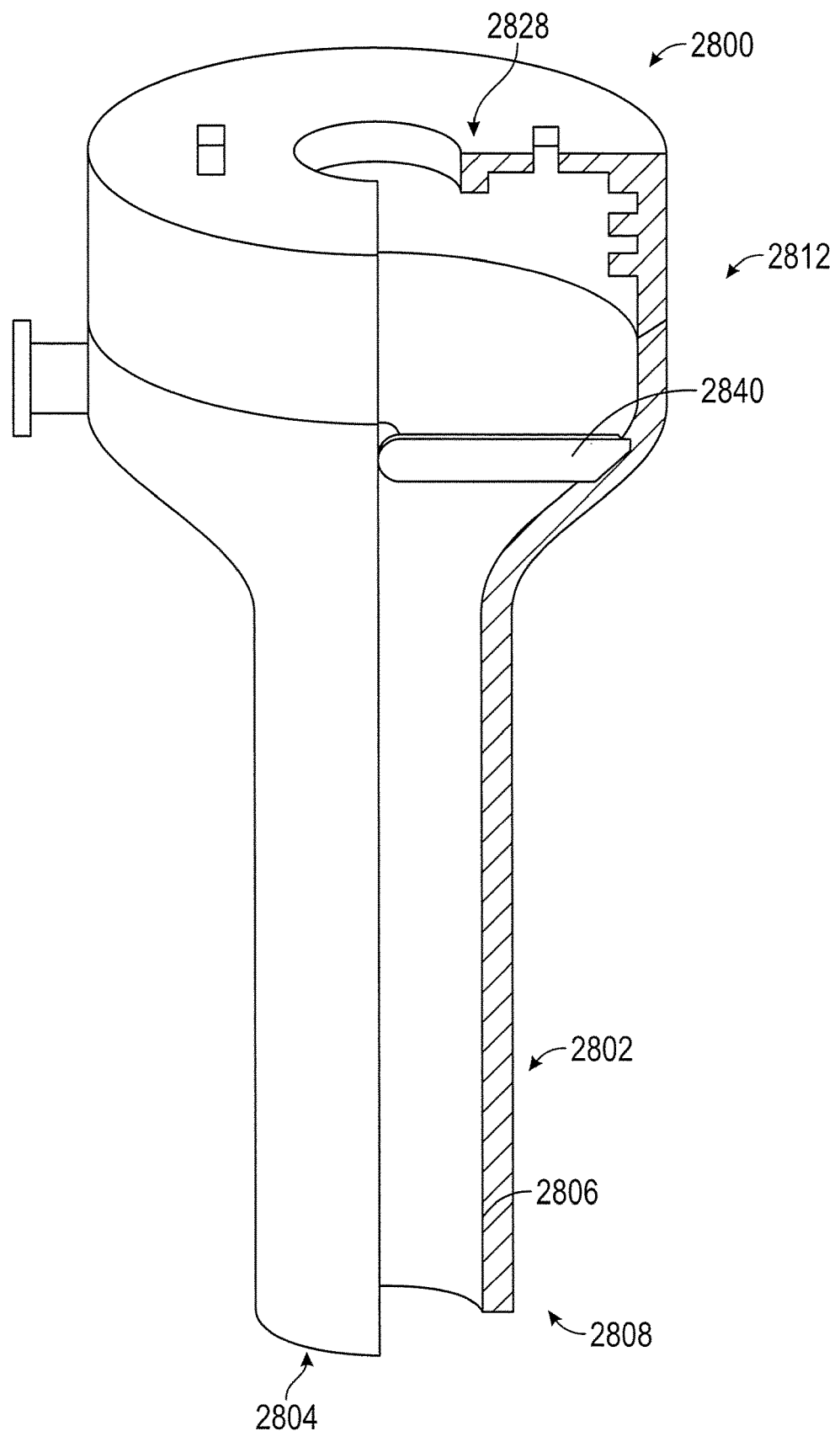
Figure 28J:
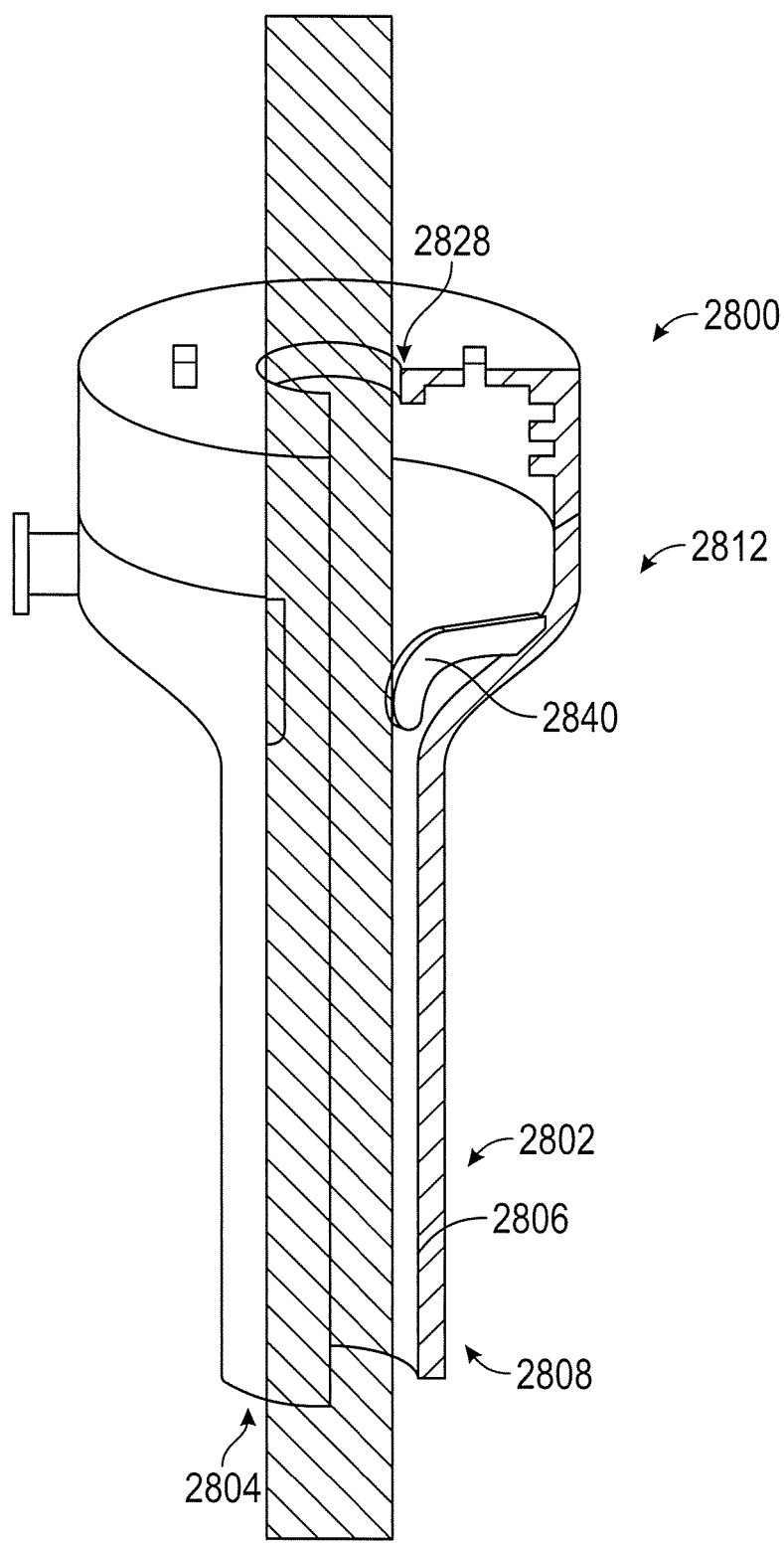
Figure 28K:
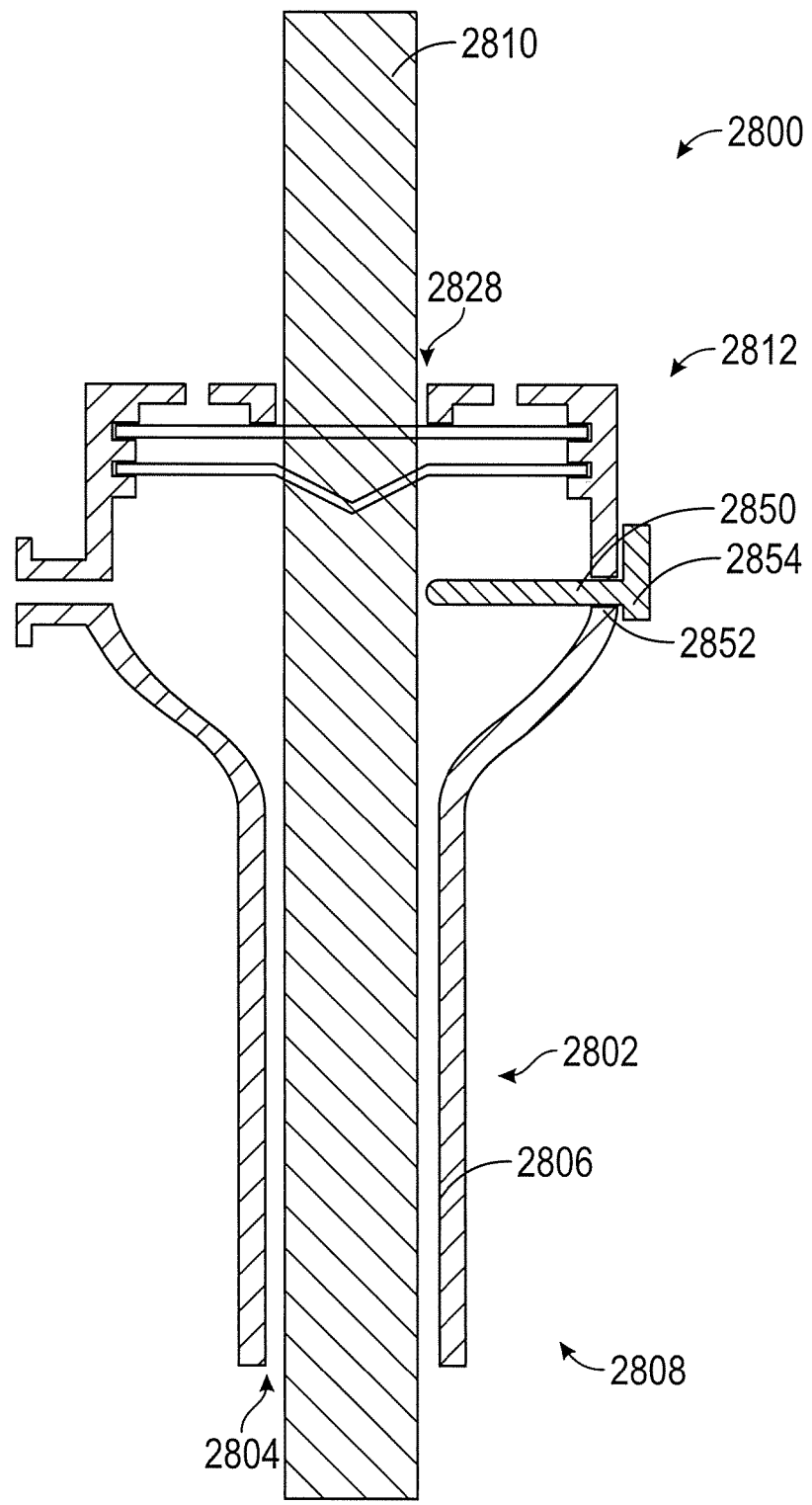
Figure 28L:
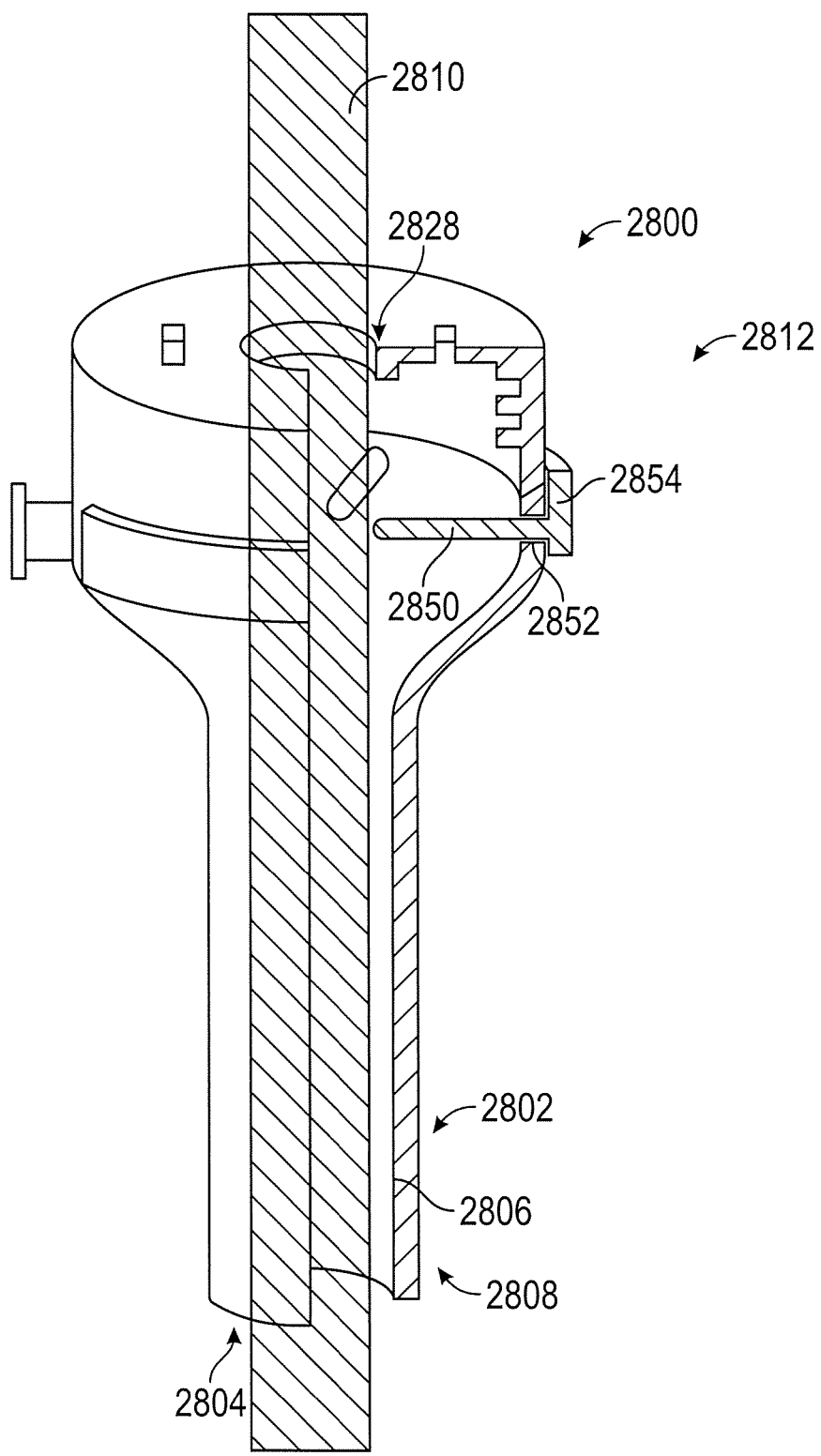
Figure 28M:
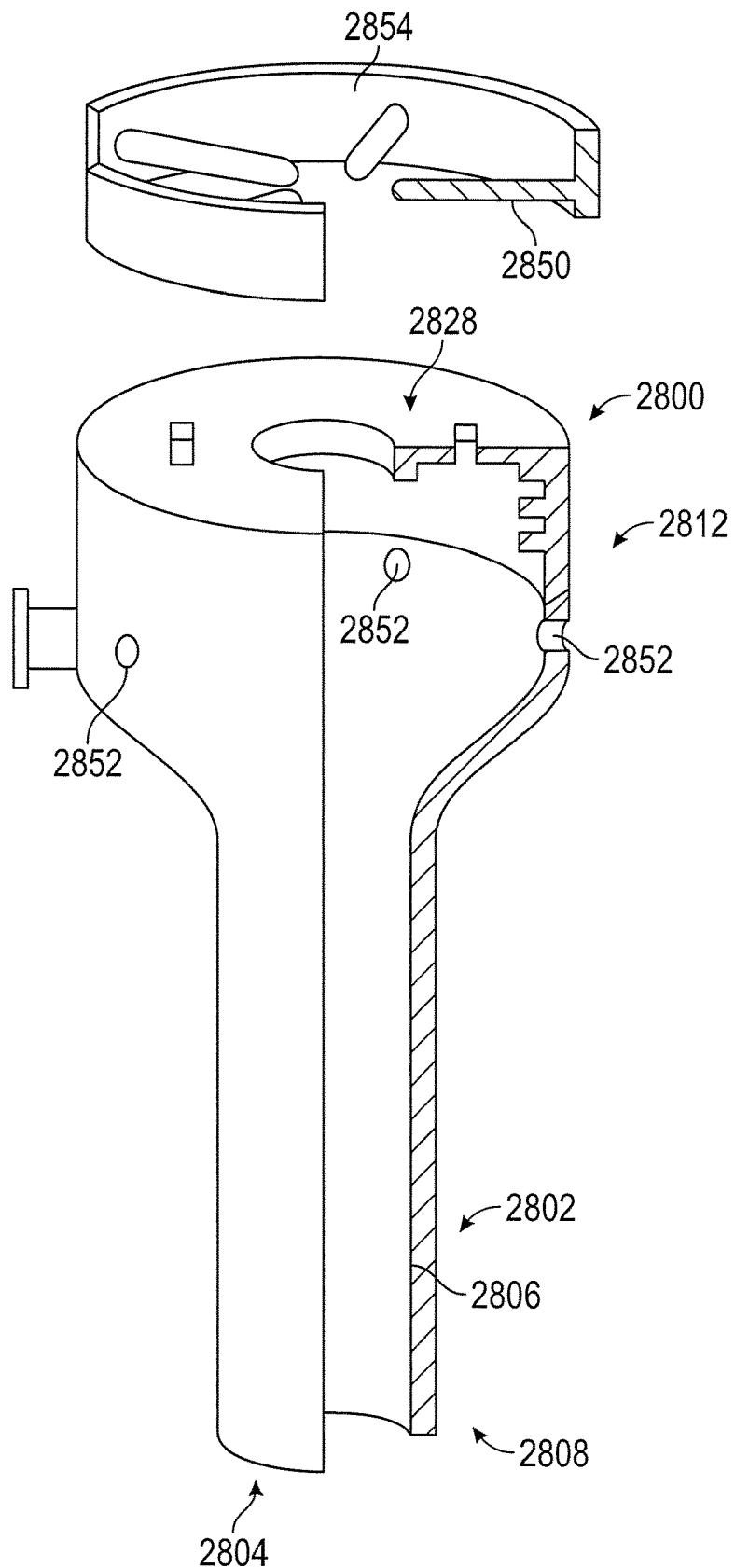
Figure 28N:
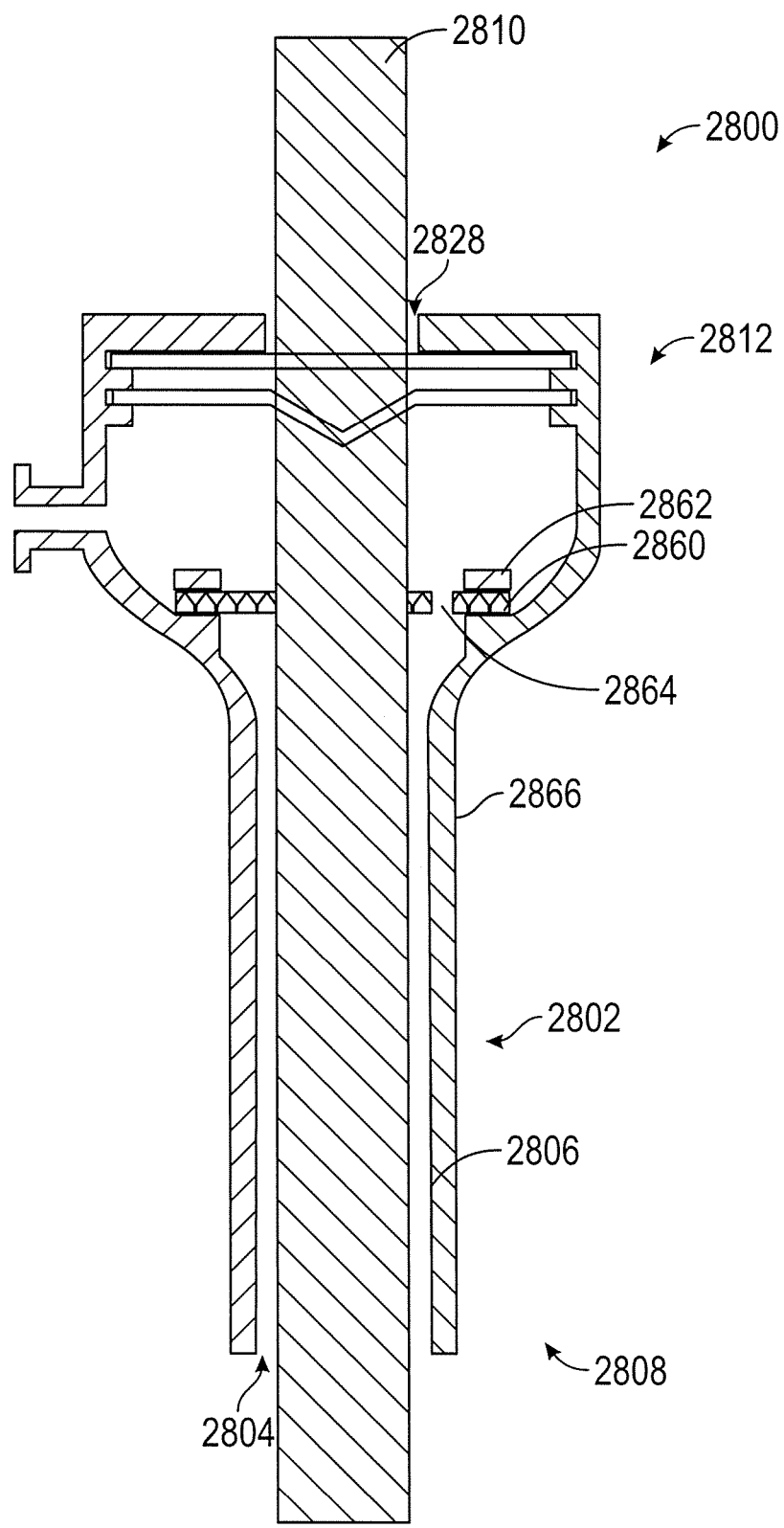
Figure 28O:
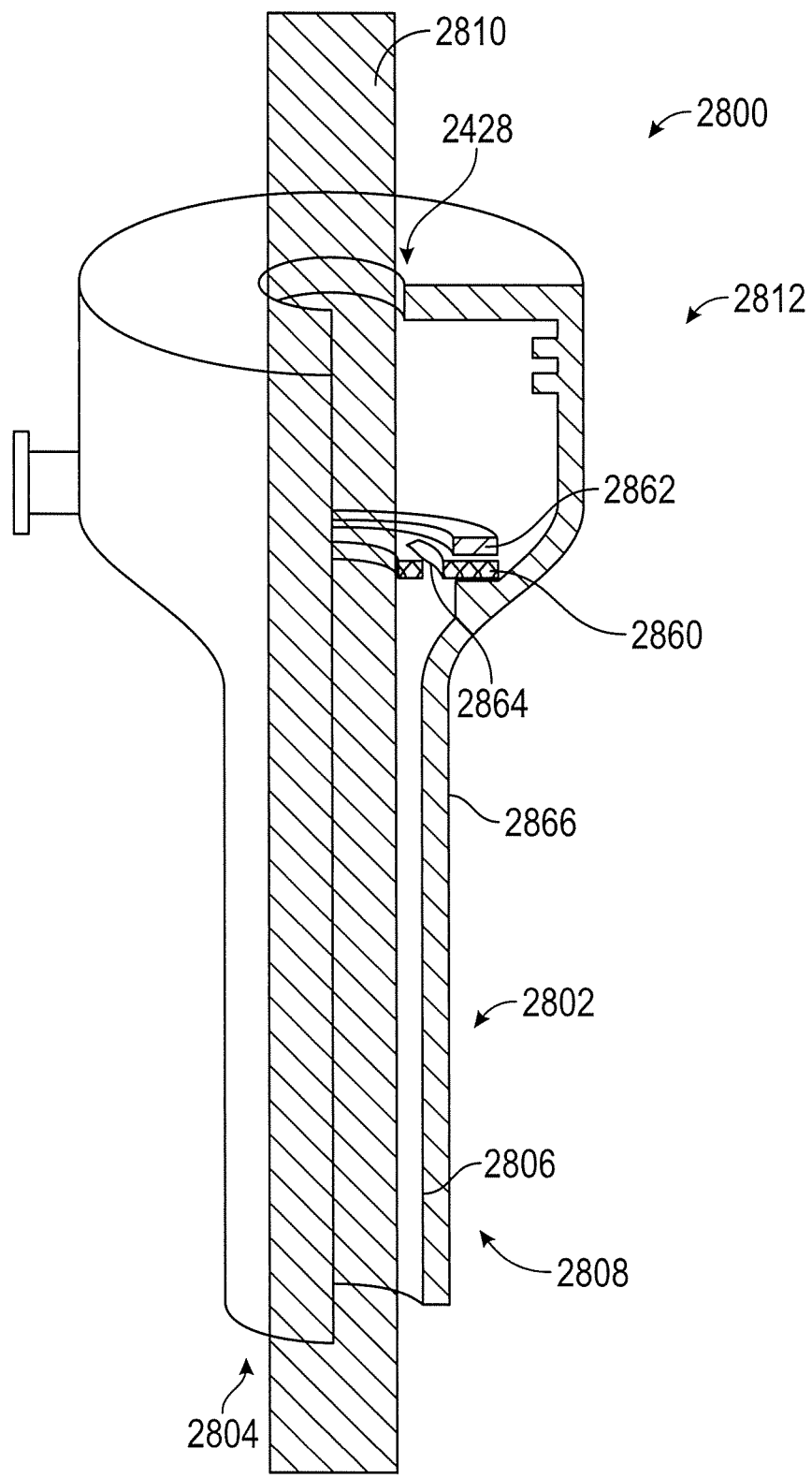
Figure 28P:
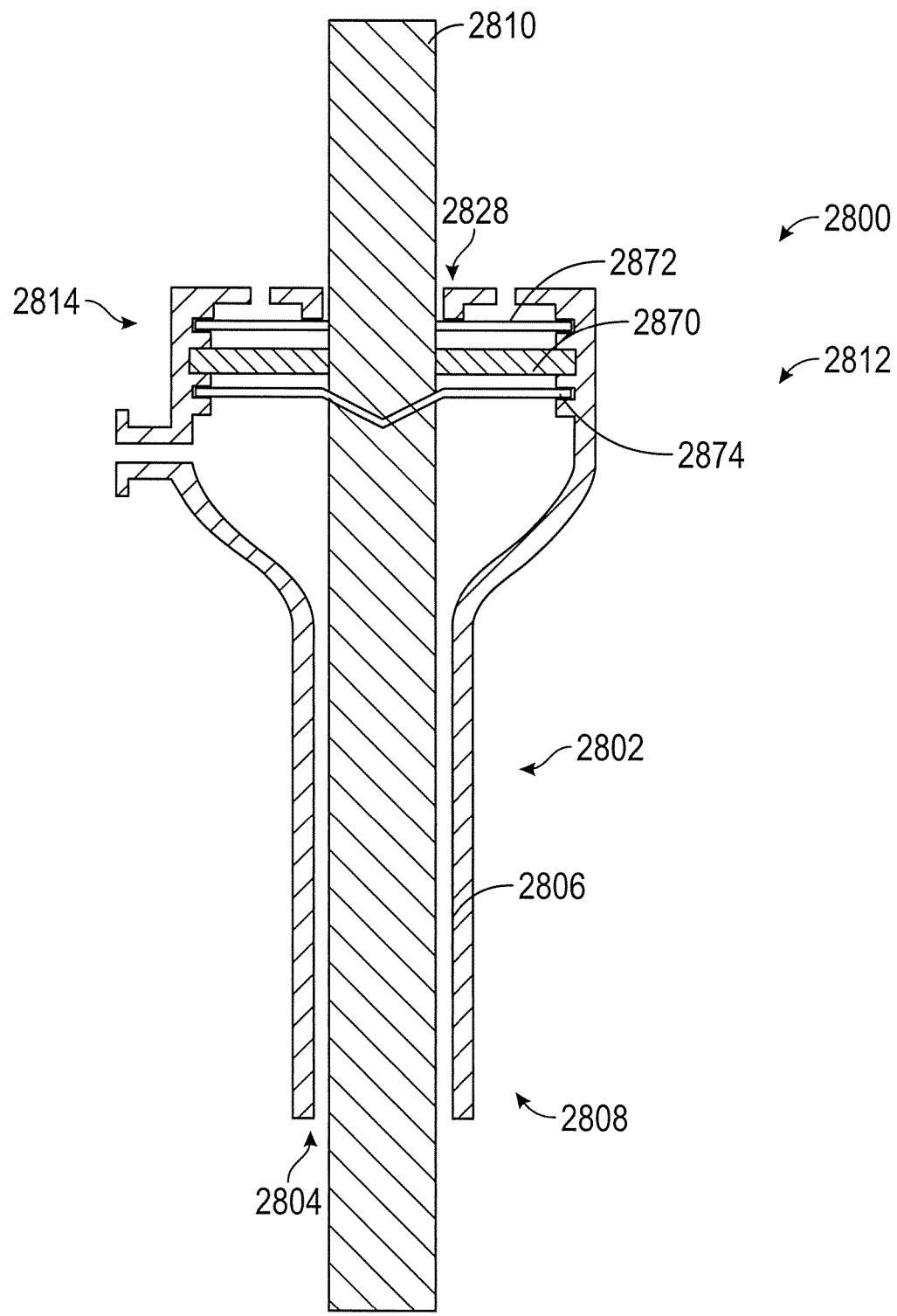
Figure 28Q:
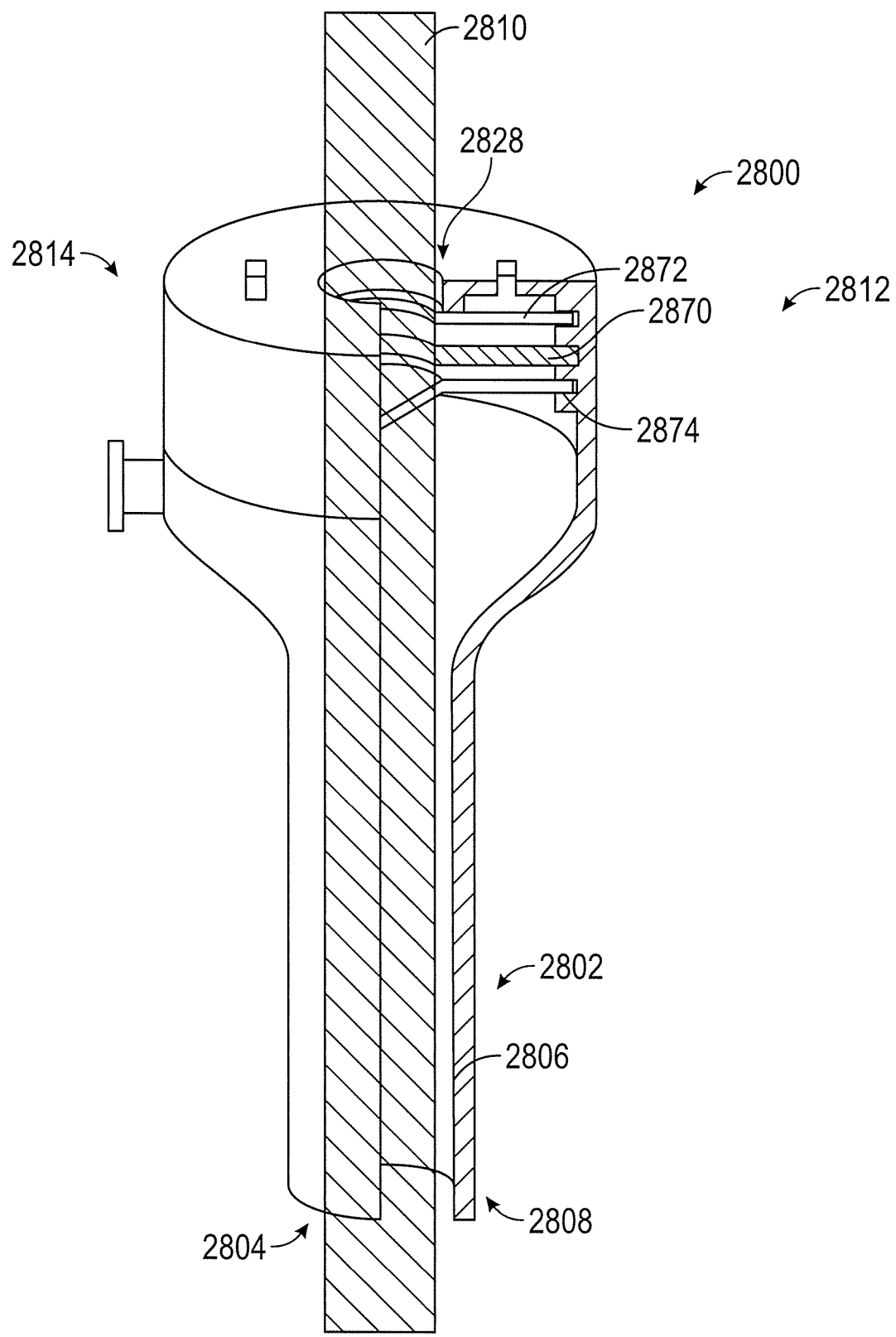

FIGS. 28A-28Q illustrate embodiments of cannulas 2800 with a guide element including flexible structures in a body 2812 of the cannula 2800 to aid in concentricity of the medical instrument 2810 within the cannula 2800. The cannula 2800 can include the cannula body 2812 and elongate shaft 2802. The elongate shaft 2802 can include a cannula sidewall 2806 that forms the lumen 2804 of the cannula 2800. The lumen 2804 can defined by the inner sidewall 2806 of the cannula 2800 as shown in FIGS. 28A-28Q. As described herein, a medical instrument 2810 can be inserted through the cannula 2800 by being introduced through the inlet 2828 on the proximal end of the cannula body 2812 and extending through the lumen 2804 of the cannula 2800 toward the distal end 2808 of the elongate shaft 2802.

The body of the cannula can include an opening formed therein. The shaft can be extending from the body and the shaft can include an outlet. The lumen terminates at the outlet and the lumen is positioned in fluid communication with the opening. The shaft and/or body may comprise a guide element projecting from an inner surface of the shaft and/or body. The guide element can be configured to retain the instrument received within the lumen, such that the medical instrument does not come into physical contact with the inner surface of the shaft and/or body.

In some cases, the body can have a seal configured to prevent insufflation gases from escaping when the medical instrument is inserted or configured to prevent insufflation gases from escaping prior to inserting the instrument. In some cases, one or more seals can be used. In some cases, a first seal and a second seal can be used. In some cases, the guide element in the body of the cannula can be proximal to the first seal. In some cases, the guide element in the body can be distal to the second seal. In some cases, the guide element in the body is between the first and second seal. In some cases, the guide element is integrated with the first and/or second seal.

In some cases, the body can comprise a first sealing structure arranged to limit gas escape, and a second sealing structure to provide an instrument seal when a medical instrument is inserted into the lumen. The first sealing structure can be a seal configured to form a seal over the cannula when no medical instrument is present in the cannula. The second sealing structure can be an instrument seal configured to form a seal around the medical instrument inserted through the cannula. In some cases, the guide element in the body can be proximal to the first sealing structure. In some cases, the guide element in the body can be distal to the second sealing structure. In some cases, the guide element in the body can be between the first and second sealing structure. In some cases, the guide element can be integrated with the first and/or second sealing structure.

As shown in FIG. 28A, the medical instrument 2810 can be supported by a guide element, such as a flexible disk, 2820 in the body 2812 of the cannula 2800 to aid in medical instrument 2810 concentricity. The flexible structure 2820 in the body 2812 can hold the medical instrument 2810 concentrically in the cannula 2800 and allow the gases to pass down the cannula lumen 2804. The flexible structure 2820 can have a plate or other securing structure 2822 to clamp the flexible structure 2820 inside the body 2812 of the cannula 2800. The flexible structure 2820 can include apertures 2824 to allow gases to pass down the lumen 2804. FIG. 28B is a cross-section through line 28A-28A of FIG. 28A, illustrating flexible structure 2820 with the medical instrument 2810 inserted within the cannula 2800.

FIG. 28C illustrates a partial cut-away schematic view of the cannula of FIGS. 28A-28B. Features in FIGS. 28C and 28D can be the same or substantially the same features as shown and described in FIGS. 28A and 28B and reference numerals of the same or substantially the same features may share the same reference numerals. FIG. 28C illustrates the flexible structure 2820 extending around the inner circumference of the cannula body 2812. FIG. 28D is a cross-section through line 28C-28C of FIG. 28C, illustrating flexible structure 2820 with the medical instrument 2810 inserted within the elongate shaft 2802. As shown in FIG. 28D, the flexible structure 2820 can hold the medical instrument 2810 concentrically within the cannula 2800 allowing gases to pass through the lumen 2804.

FIG. 28E illustrates a cannula 2800 with a medical instrument 2810 supported by a guide element including a seal 2830 in the body 2812 of the cannula 2800 to aid in medical instrument 2810 concentricity. The body 2812 of the cannula 2800 can include the proximal end 2814 with inlet 2828. The seal 2830 can be positioned at the inlet 2828 on the proximal end 2814 of the body 2812. In some cases, the seal 2830 can make the inlet 2828 more rigid and aid in holding the medical instrument 2810 concentrically in the cannula 2800. In some cases, this can be achieved by using O-rings as the seal 2830 at the inlet 2828. The seal 2830 can be located proximal to the gases inlet 2829 and can thereby allow the gases to pass through the lumen 2804. In some cases, the seal 2830 can act as a sealing structure to prevent gases from escaping.

FIG. 28F illustrates a partial cut-away schematic view of the cannula of FIG. 28E. Features in FIG. 28F can be the same or substantially the same features as shown and described in FIG. 28E and reference numerals of the same or substantially the same features may share the same reference numerals. FIG. 28F illustrates seal 2830 extending around the inner circumference of the inlet 2828. The seal 2830 can be made of a rigid material which can hold the medical instrument 2810 tighter within the inlet 2828 than if the seal 2830 was not present in the inlet.

FIGS. 28G and 28H illustrate a cannula 2800 with a guide element including flexible fins 2840 in the body 2812 of the cannula 2800 to support a medical instrument 2810 and aid in medical instrument 2810 concentricity. The flexible fins 2840 can be positioned within the body 2812 and extend radially inward into the body 2812 of the cannula 2800 to hold the medical instrument 2810 concentrically in the cannula 2800. The fins 2840 can be deformed when the medical instrument 2810 is pushed past them. The fins can push back on the medical instrument 2810 which can hold the medical instrument 2810 concentrically in the cannula body 2812 and elongate shaft 2802. FIGS. 28I and 28J illustrate a partial cut-away schematic view of the cannula of FIGS. 28G and 28H. Features in FIGS. 28I and 28J can be the same or substantially the same features as shown and described in FIGS. 28G and 28H and reference numerals of the same or substantially the same features may share the same reference numerals. FIGS. 28I and 28J illustrate the flexible fins 2840 spaced apart circumferentially around the cannula body 2812. One or more flexible fins 2840 can be positioned within the cannula body 2812.

FIGS. 28G and 28I illustrate a first configuration of the fins 2840 without the medical instrument 2810 inserted within the cannula 2800. In this configuration the fins 2840 are positioned within the cannula body 2812 and extend radially inward within the cannula body 2812 as shown in FIGS. 28G and 28I. FIGS. 28H and 28J illustrate a second configuration of the fins 2840 when the medical instrument 2810 is inserted through the cannula 2800. The fins 2840 are pushed out of the way by the medical instrument 2810 as it is inserted passed the fins 2840. As illustrated in FIGS. 28H and 28J, the fins can push back on the medical instrument 2810 and can hold the medical instrument 2810 concentrically within the cannula 2800.

FIG. 28K illustrates a cannula 2800 with a medical instrument 2810 supported by a guide element including flexible pins 2850 inserted into the body 2812 of the cannula 2800 to aid in medical instrument 2810 concentricity. The flexible pins 2850 can be inserted within an opening 2852 in the body 2812 to hold the medical instrument 2810 concentrically in the cannula 2800. The flexible pins 2850 can be mounted on a ring 2854 which holds them together and helps keep them inserted into the cannula 2800. The flexible pins 2850 can keep the medical instrument 2810 concentric in the cannula 2800. FIG. 28L illustrates a partial cut-away schematic view of the cannula of FIG. 28K. Features in FIG. 28L can be the same or substantially the same features as shown and described in FIG. 28K and reference numerals of the same or substantially the same features may share the same reference numerals. FIG. 28L illustrates the ring 2854 positioned circumferentially around the outer surface of the cannula body 2812 and the flexible pins 2850 extending through the opening 2852 and radially inward within the cannula body 2812. One or more flexible pins 2850 can be positioned within the cannula body 2812. In some cases, the ring 2854 can cover only a portion or a circumferential portion of the outer surface of the cannula body or can completely circumferentially surround an outer surface of the cannula body.

FIG. 28M illustrates the ring 2854 removed from the cannula 2800. Features in FIG. 28M can be the same or substantially the same features as shown and described in FIG. 28K and reference numerals of the same or substantially the same features may share the same reference numerals. The ring 2854 can support the flexible pins 2850 as shown in FIG. 28M. In some cases, the ring 2854 can be flush against the outer surface of the cannula body 2812.

FIG. 28N illustrates a cannula 2800 with a medical instrument 2810 supported by a guide element including a flexible disk 2860 inserted into the body 2812 of the cannula 2800 to aid in medical instrument 2810 concentricity. The flexible disk 2860 can be mounted below seals 2872, 2874 in the cannula body. The flexible disk 2860 can hold the medical instrument 2810 concentrically in the cannula 2800. The flexible disk 2860 can be made to deform when the medical instrument 2810 is pushed through the flexible disk 2860 and thus the flexible disk 2860 can push or pull back on the medical instrument 2810 to hold it concentrically in the cannula 2800. The flexible disk 2860 can have apertures 2864 to allow the gases to pass down the cannula lumen 2804. The flexible disk 2860 can have a plate or other securing structure 2862 to clamp the flexible disk 2860 inside the body 2812 of the cannula 2800. The flexible disk 2860 can be positioned inside the body 2812 of the cannula 2800. The flexible disk 2860 can be clamped between the plate 2862 and a proximal portion of the cannula elongate shaft 2866 as illustrated in FIG. 28N.

FIG. 28O illustrates a partial cut-away schematic view of the cannula of FIG. 28N. Features in FIG. 28O can be the same or substantially the same features as shown and described in FIG. 28N and reference numerals of the same or substantially the same features may share the same reference numerals. FIG. 28O illustrates the flexible disk 2860 with apertures 2864 positioned within the cannula body 2812 and secured within the cannula body 2812 by the plate 2862 and the proximal portion of the cannula elongate shaft 2866.

FIG. 28P illustrates a cannula 2800 with a medical instrument 2810 supported by a guide element including a supportive seal 2870 at a proximal end 2814 of the body 2812 of the cannula 2800 to aid in medical instrument 2810 concentricity. The proximal end 2814 of the cannula 2800 can include seals or sealing structures 2872, 2874 that are used to seal around the medical instrument and cover the cannula interior. The sealing structures can be a first sealing structure arranged to limit gas escape and a second sealing structure to provide an instrument seal when a medical instrument is inserted into the lumen. The first sealing structure can be a seal configured to form a seal over the cannula when no medical instrument is present in the cannula. The second sealing structure can be an instrument seal configured to form a seal around the medical instrument inserted through the cannula. In some cases, the seal or sealing structure 2872 can be the first seal and the seal or sealing structure 2874 can be the second seal. In other cases, seal or sealing structure 2872 can be the second seal and the seal or sealing structure 2874 can be the first seal. In some cases, both seals or sealing structures 2872 and 2874 can be a seal configured to form a seal over the cannula when no medical instrument is present in the cannula. In some cases, both seals or sealing structures 2872 and 2874 can be an instrument seal. The cannula body 2812 can incorporate a semi-rigid seal, such as the supportive seal 2870, that is used to hold the medical instrument 2810 concentrically in the cannula 2800. The supportive seal 2870 can be included in series with the other seals 2872, 2874 in the cannula body 2812.

FIG. 28Q illustrates a partial cut-away schematic view of the cannula of FIG. 28P. Features in FIG. 28Q can be the same or substantially the same features as shown and described in FIG. 28P and reference numerals of the same or substantially the same features may share the same reference numerals. FIG. 28Q illustrates the supportive seal 2870 positioned within the cannula body 2812 between seal 2872 and 2874.

FIGS. 29A-29M illustrate embodiments of cannulas 2900 with a guide element including rigid features in the body 2912 of the cannula 2900 to aid in concentricity of the medical instrument 2910 within the cannula 2900. The cannula 2900 can include the cannula body 2912 and elongate shaft 2902. The elongate shaft 2902 can include a cannula sidewall 2906 that forms the lumen 2904 of the cannula 2900. The lumen 2904 can defined by the inner sidewall 2906 of the cannula 2900 as shown in FIGS. 29A-29M. As described herein, a medical instrument 2910 can be inserted through the cannula 2900 by being introduced through an inlet 2928 at the proximal end of the cannula body 2912 and extending through the lumen 2904 of the cannula 2900 toward the distal end 2908 of the elongate shaft 2902.

The body of the cannula can include an opening formed therein. The shaft can be extending from the body and the shaft can include an outlet. The lumen terminates at the outlet and the lumen is positioned in fluid communication with the opening. The shaft and/or body comprising a guide element projecting from an inner surface of the shaft and/or body. The guide element can be configured to retain the instrument received within the lumen, such that the medical instrument does not come into physical contact with the inner surface of the shaft and/or body.

In some cases, the body can have a seal configured to prevent insufflation gases from escaping when the medical instrument is inserted or configured to prevent insufflation gases from escaping prior to inserting the instrument. In some cases, one or more seals can be used. In some cases, a first seal and a second seal can be used. In some cases, the guide element in the body of the cannula can be proximal to the first seal. In some cases, the guide element in the body can be distal to the second seal. In some cases, the guide element in the body is between the first and second seal. In some cases, the guide element is integrated with the first and/or second seal.

In some cases, the body can comprise a first sealing structure arranged to limit gas escape, and a second sealing structure to provide an instrument seal when a medical instrument is inserted into the lumen. The first sealing structure can be a seal configured to form a seal over the cannula when no medical instrument is present in the cannula. The second sealing structure can be an instrument seal configured to form a seal around the medical instrument inserted through the cannula. In some cases, the guide element in the body can be proximal to the first sealing structure. In some cases, the guide element in the body can be distal to the second sealing structure. In some cases, the guide element in the body can be between the first and second sealing structure. In some cases, the guide element can be integrated with the first and/or second sealing structure.

Figures 29A, 29B:
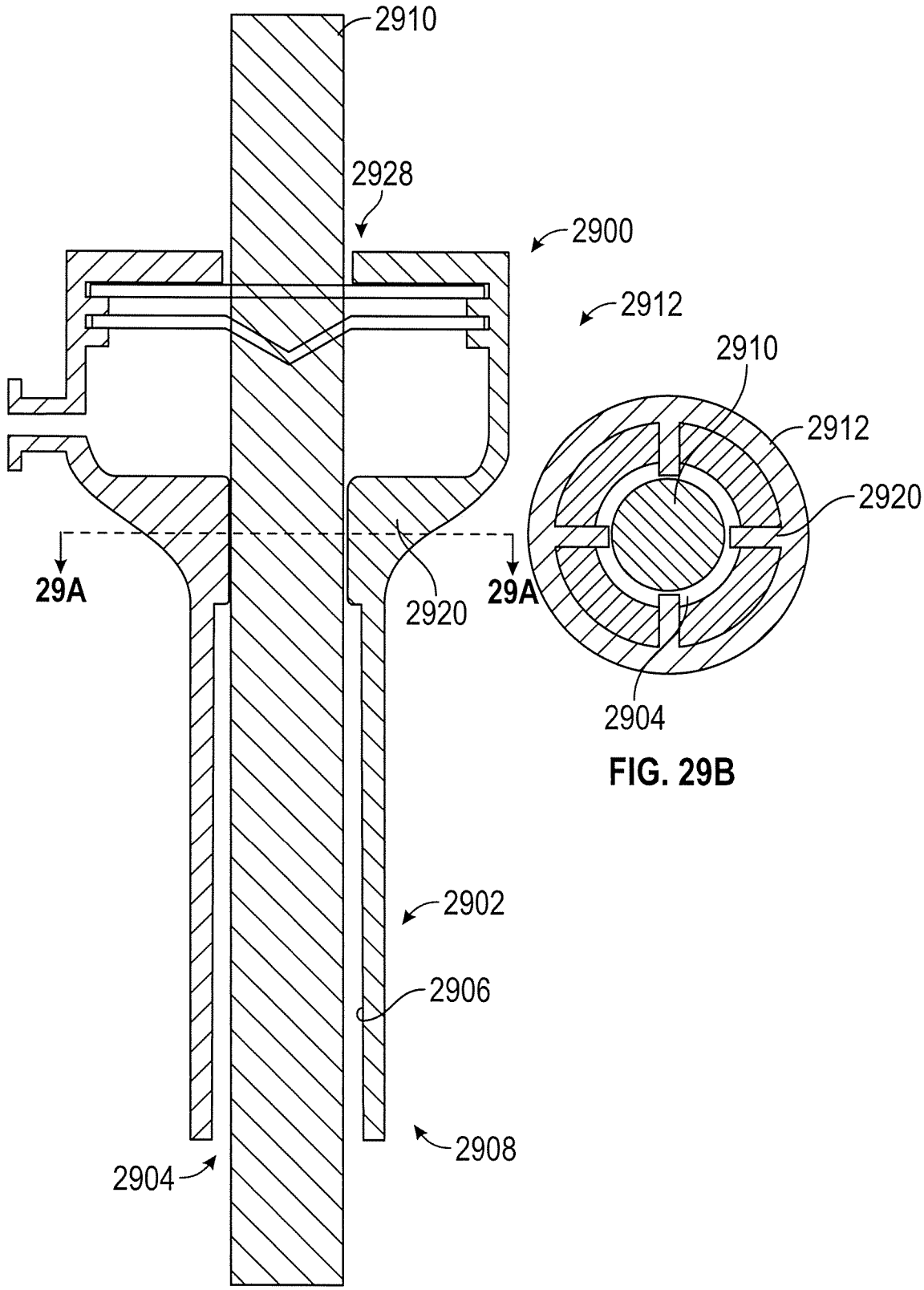
FIGS. 29A-29M illustrate views of embodiments of cannulas with rigid features in the body of the cannula to aid in concentricity of the medical instrument within the cannula.

As shown in FIG. 29A, the medical instrument 2910 can be supported by a guide element including rigid features, such as ribs 2920, in the body 2912 of the cannula 2900 to aid in medical instrument 2910 concentricity. The ribs 2920 in the body 2912 can hold the medical instrument 2910 concentrically in the cannula 2900 and allow the gases to pass down the cannula lumen 2904. The ribs 2920 in the body 2912 can be molded into the body 2912 of the cannula 2900 as shown in FIG. 29A. FIG. 29B is a cross-section through line 29A-29A of FIG. 29A, illustrating ribs 2920 in the body 2912 with the medical instrument 2910 inserted within the cannula 2900. The ribs 2920 in the body 2912 of the cannula can be radially spaced apart around the inner circumference of the body 2912. The ribs 2920 in the body 2912 can hold the medical instrument 2910 concentrically in the cannula 2900 while allowing the gases to pass down the lumen 2904.

Figures 29C, 29D:
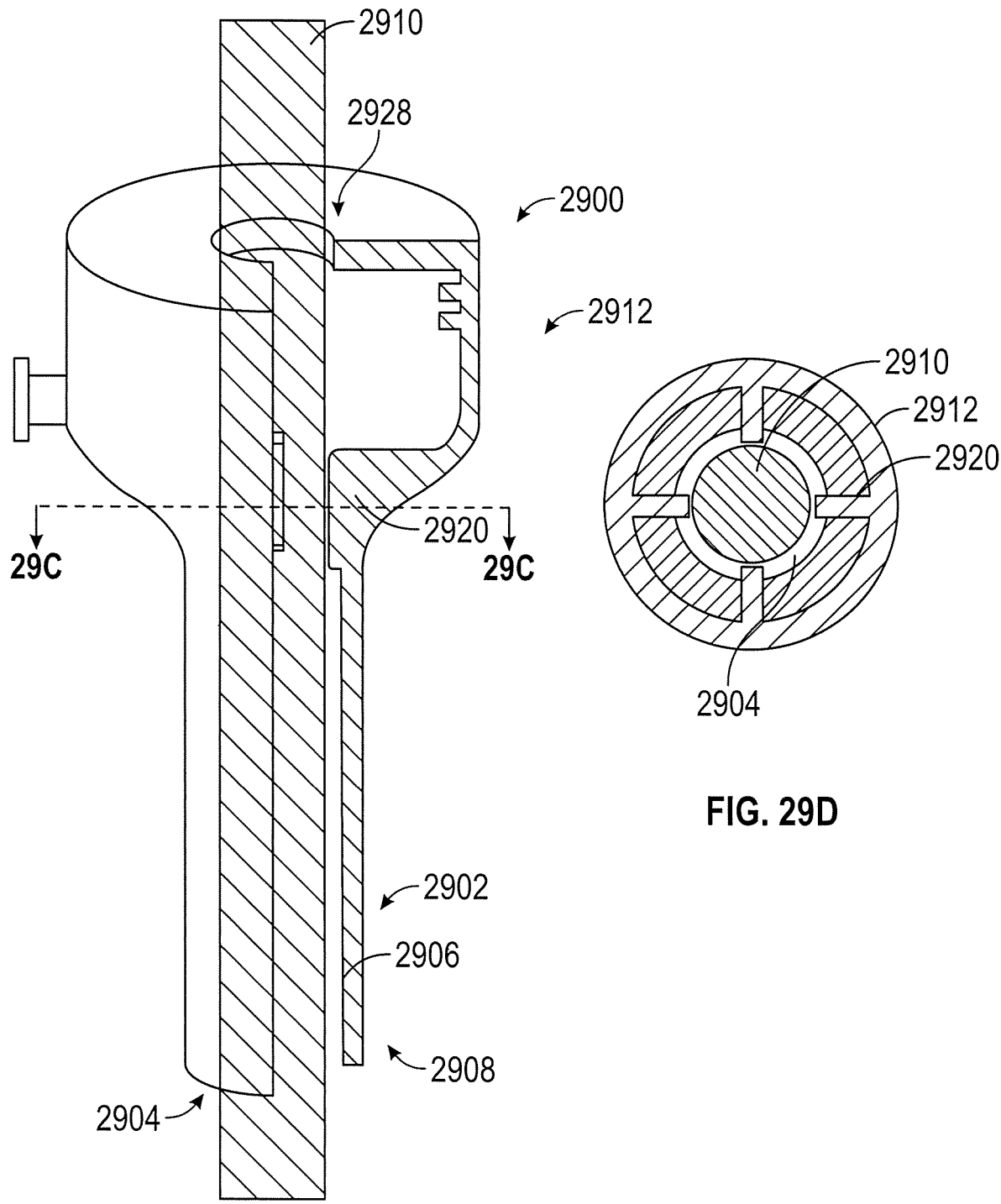

FIG. 29C illustrates a partial cut-away schematic view of the cannula of FIGS. 29A-29B. Features in FIGS. 29C and 29D can be the same or substantially the same features as shown and described in FIGS. 29A and 29B and reference numerals of the same or substantially the same features may share the same reference numerals. FIGS. 29C and 29D illustrate the ribs 2920 in the body 2912 radially spaced apart around the inner circumference of the cannula body 2912. FIG. 29D is a cross-section through line 29C-29C of FIG. 29C, illustrating ribs 2920 in the body 2912 with the medical instrument 2910 inserted within the cannula 2900. As shown in FIG. 29D, the ribs 2920 in the body 2912 can hold the medical instrument 2910 concentrically within the cannula 2900 allowing gases to pass through the lumen 2904.

Figure 29E:
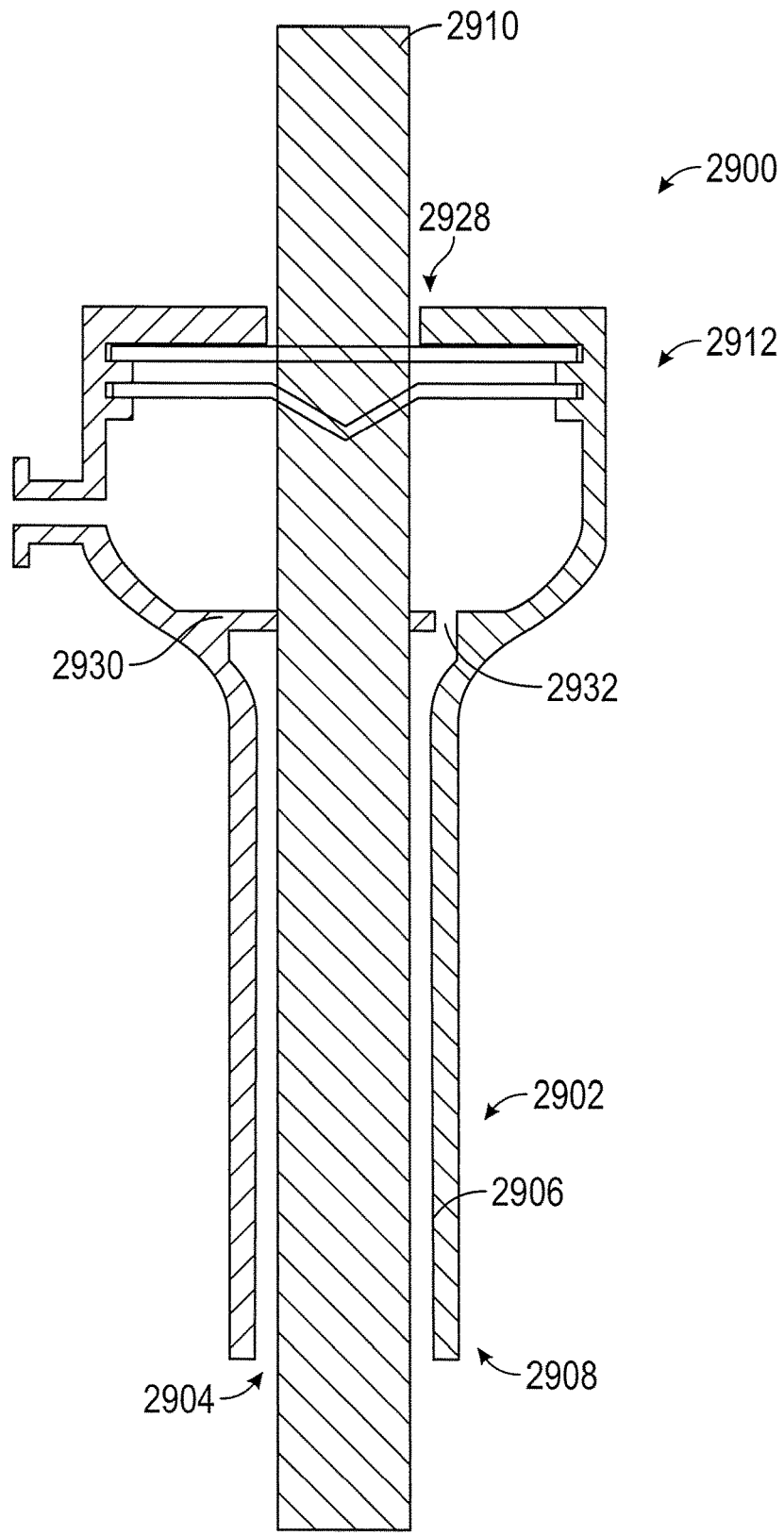

As shown in FIG. 29E, the medical instrument 2910 can be supported by a guide element including rigid features such as a rigid disk 2930 molded into the body 2912 of the cannula 2900 to aid in medical instrument 2910 concentricity. The rigid disk 2930 in the body 2912 can hold the medical instrument 2910 concentrically in the cannula 2900. The rigid disk 2930 can include apertures 2932 to allow the gases to pass down the cannula lumen 2904. The body 2912 can be formed with the rigid disk 2930 molded into it.

Figure 29F:
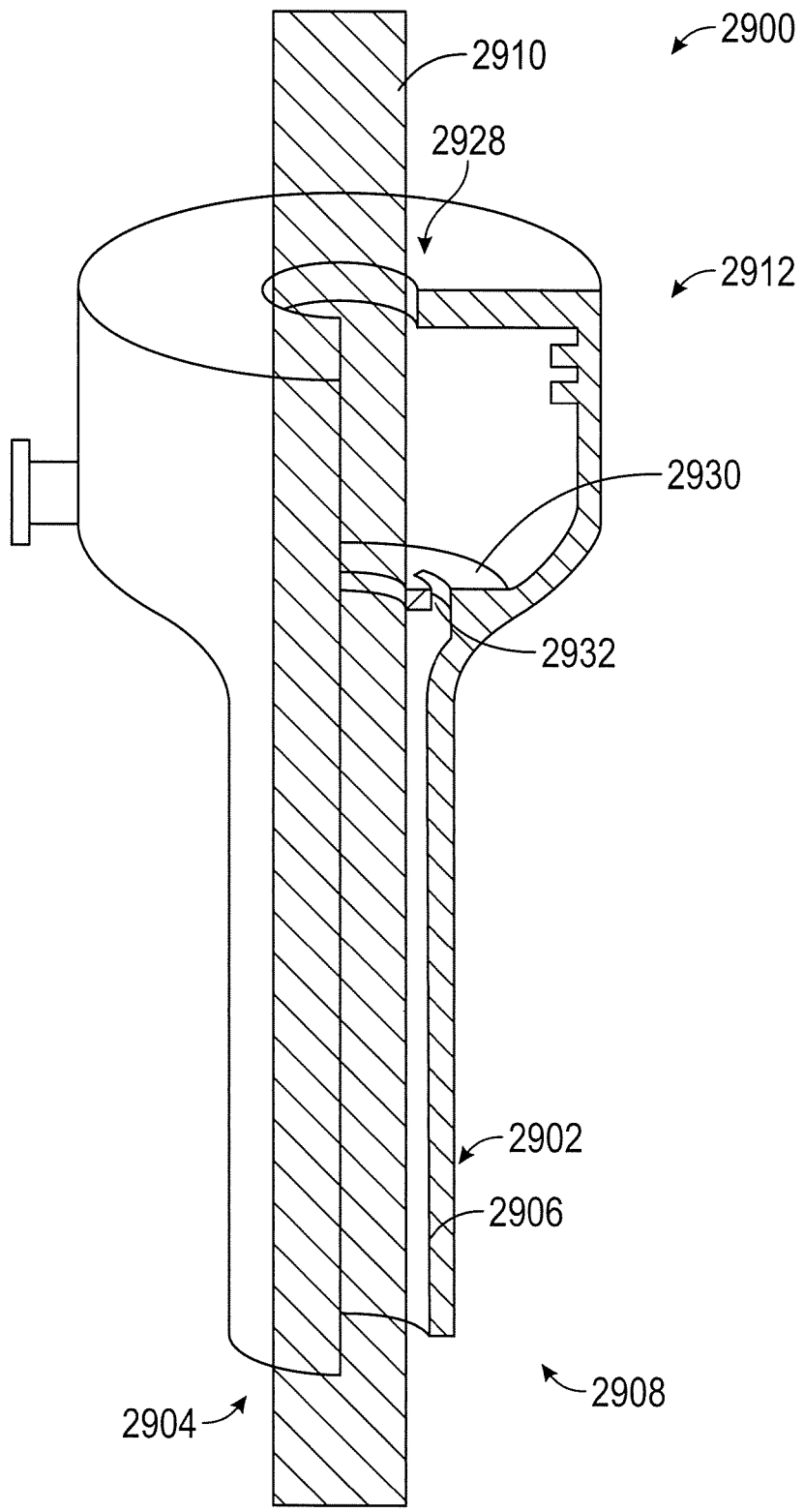

FIG. 29F illustrates a partial cut-away schematic view of the cannula of FIG. 29E. Features in FIG. 29F can be the same or substantially the same features as shown and described in FIG. 29E and reference numerals of the same or substantially the same features may share the same reference numerals. FIG. 29F illustrates the rigid disk 2930 in the body 2912 extending around the inner circumference of the cannula body 2912.

Figure 29G:
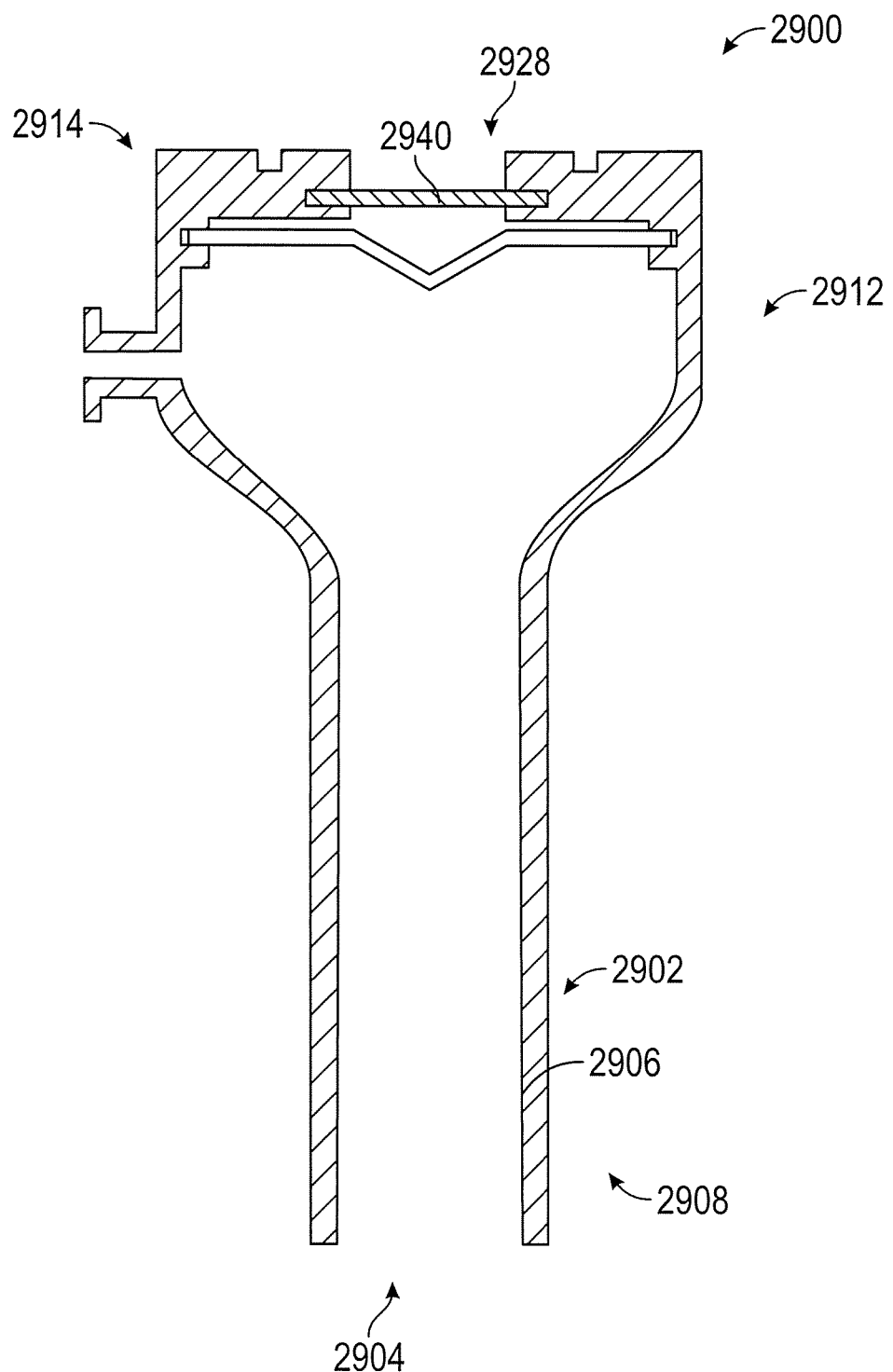
Figure 29H:
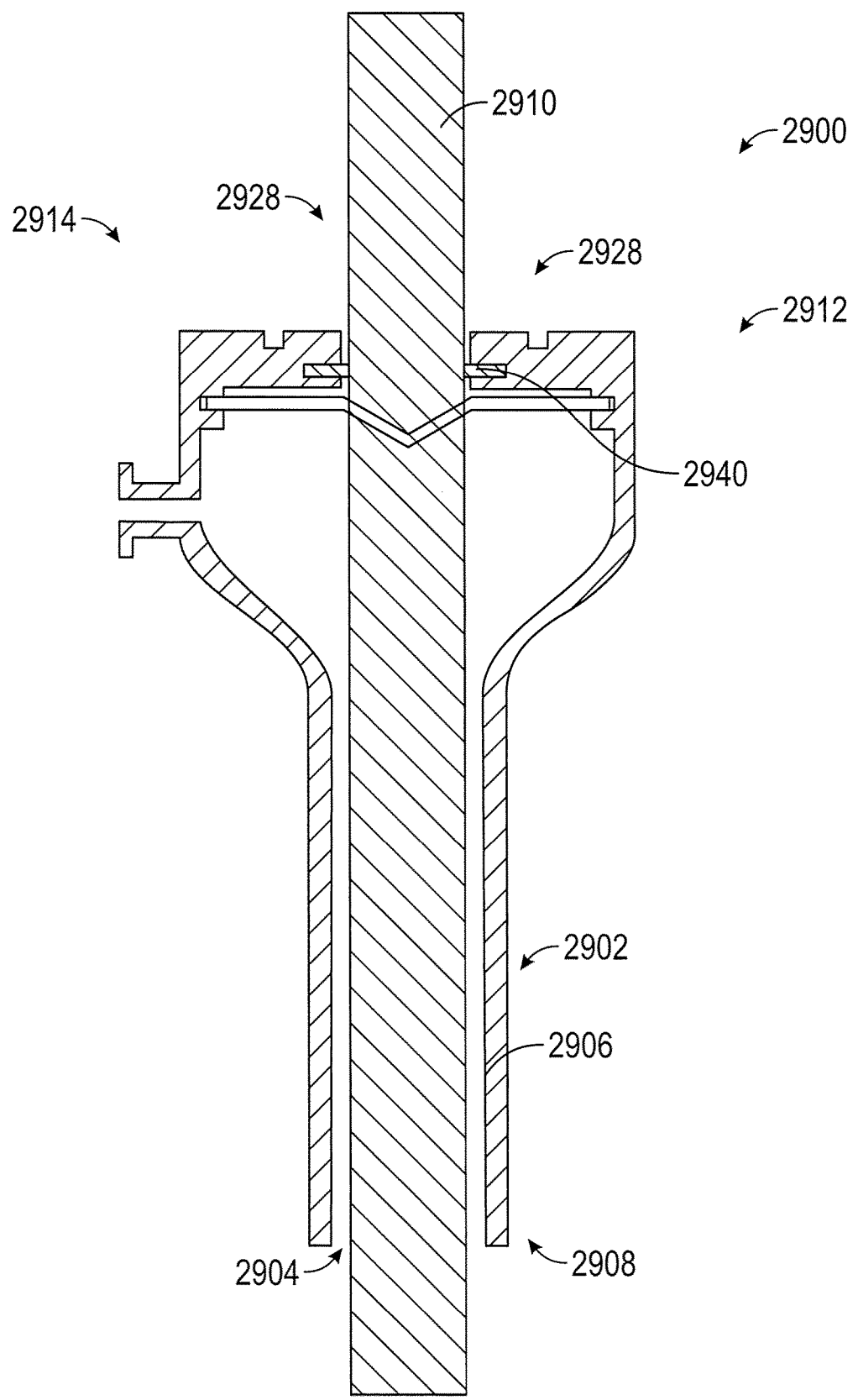

As shown in FIGS. 29G and 29H, the cannula 2900 can include guide elements such as a seal 2940 on the proximal end 2914 of the body 2912 of the cannula 2900 to aid in medical instrument 2910 concentricity. The seal 2940 on the proximal end 2914 of the body 2912 can hold the medical instrument 2910 concentrically in the cannula 2900. The seal 2940 on the proximal end 2914 of the body 2912 can be stiffened by clamping the seal 2940 down closer to the inlet 2928 on the proximal end 2914 of the cannula body 2900. The medical instrument 2910 can be inserted through the inlet 2928. Clamping the seal 2940 closer to the opening can limit the lateral movement of the medical instrument 2910 in the seal 2940 as the seal 2940 is less mobile. This can help hold the medical instrument 2910 concentrically in the cannula 2900. FIG. 29G illustrates the cannula without the medical instrument inserted and the seal 2940 is shown extending across the entire inlet 2928. FIG. 29H illustrates the cannula 2900 with the medical instrument 2910 inserted through the inlet 2928 on the proximal end 2914 of the cannula body 2912. The seal 2940 can be clamped at a portion adjacent to or substantially adjacent to or next to the medical instrument thereby limiting the movement of the medical instrument 2910 and holding the medical instrument concentrically in the cannula 2900. In some cases, other seals can be used, including, but not limited to, one or more of the seals or sealing structures similar to the first and second seal or sealing structures 2872 and 2874 described with reference to FIGS. 28P and Q.

Figure 29I:
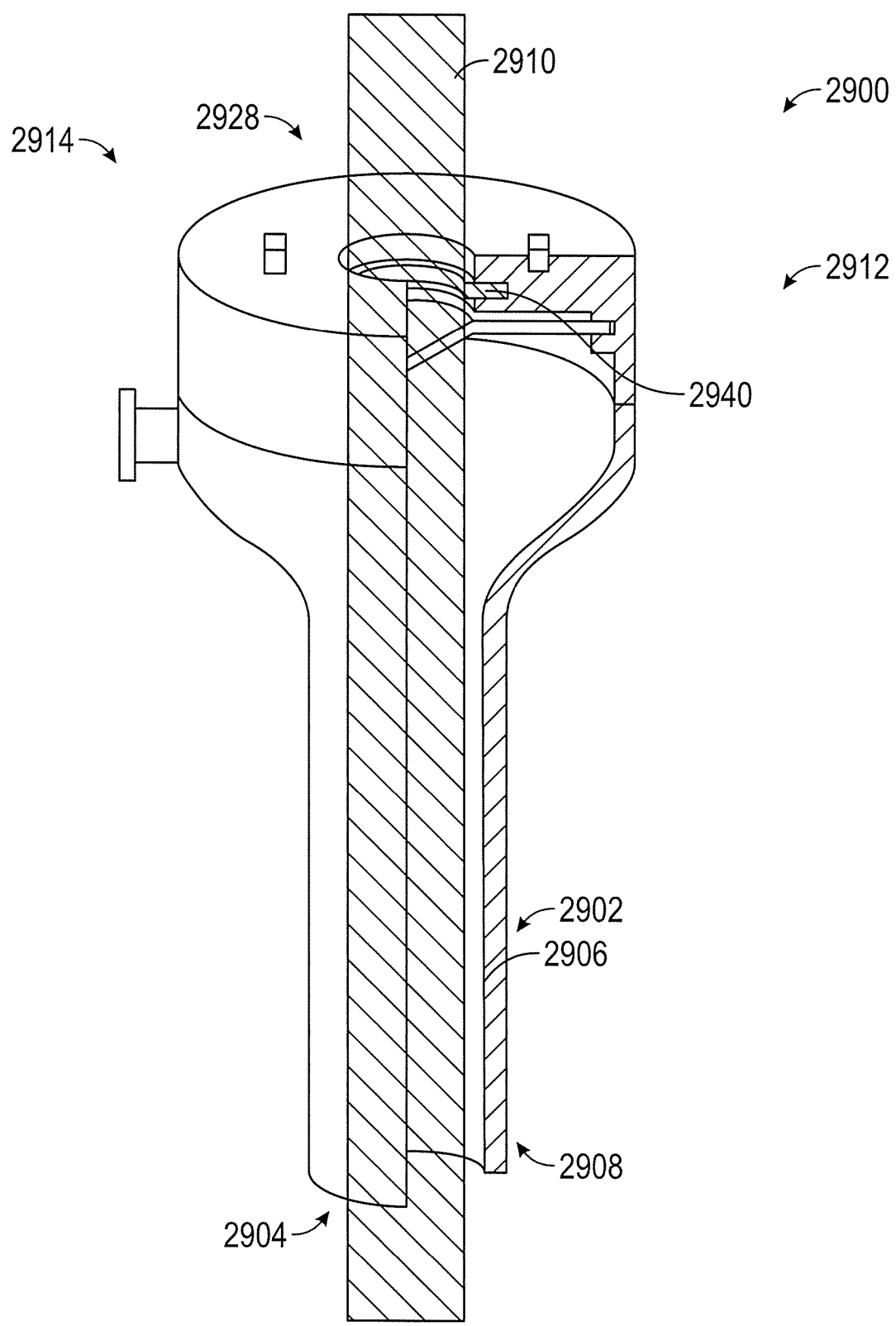

FIG. 29I illustrates a partial cut-away schematic view of the cannula of FIGS. 29G and 29H. Features in FIG. 29I can be the same or substantially the same features as shown and described in FIGS. 29G and 29H and reference numerals of the same or substantially the same features may share the same reference numerals. FIG. 29I illustrates the seal 2940 in the body 2912 extending around the inlet 2928 opening surrounding the medical instrument 2910 within the cannula 2902.

Figure 29J:
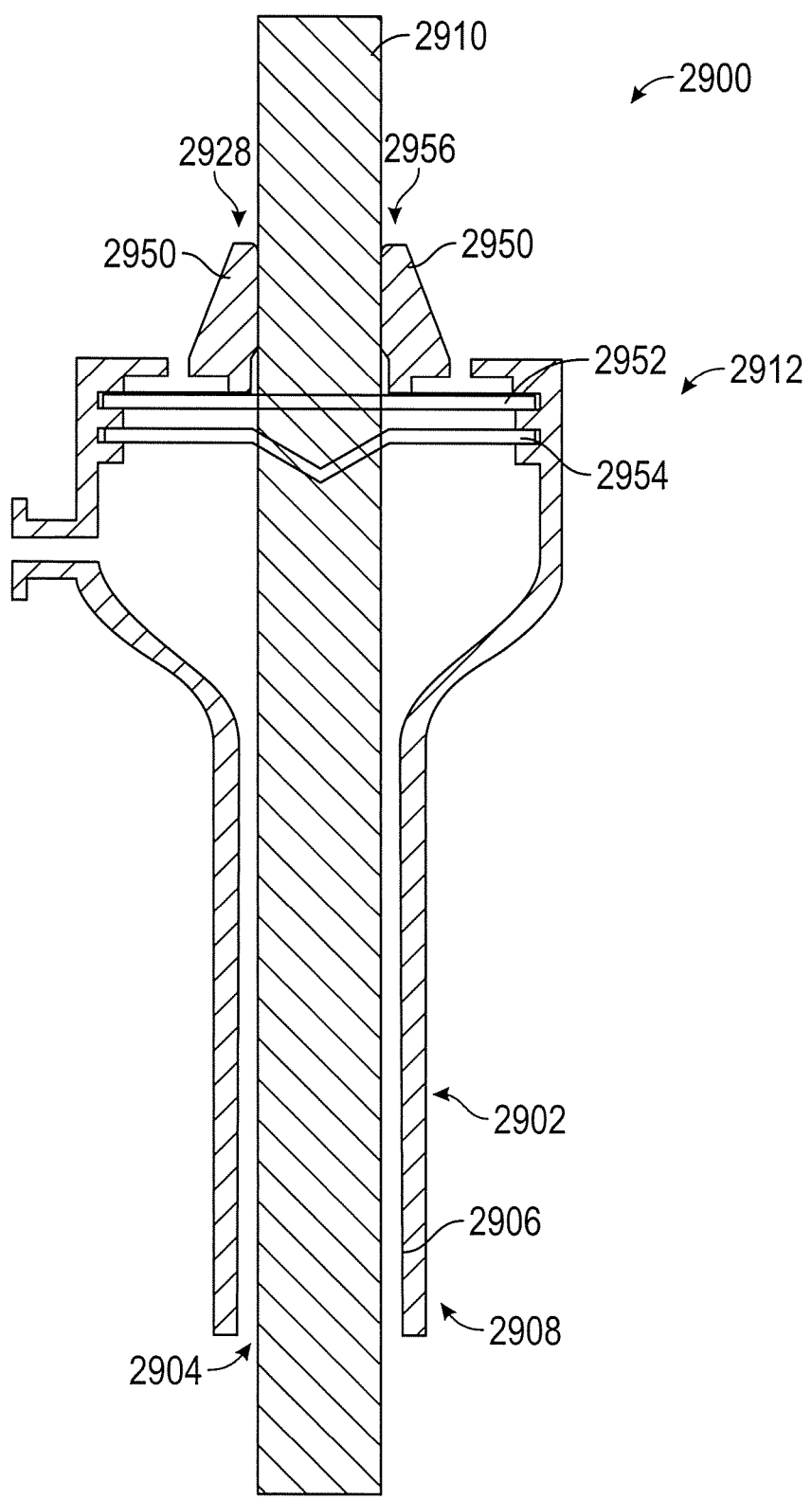

As shown in FIG. 29J, the cannula 2900 can include guide elements such as a rigid feature 2950 above or proximal to seals or sealing structures 2952, 2954 at a proximal end 2914 of the body 2912 of the cannula 2900 to aid in medical instrument 2910 concentricity. The sealing structures can be a first sealing structure arranged to limit gas escape and a second sealing structure to provide an instrument seal when a medical instrument is inserted into the lumen. The first sealing structure can be a seal configured to form a seal over the cannula when no medical instrument is present in the cannula. The second sealing structure can be an instrument seal configured to form a seal around the medical instrument inserted through the cannula. In some cases, the seal or sealing structure 2952 can be the first seal and the seal or sealing structure 2954 can be the second seal. In other cases, seal or sealing structure 2952 can be the second seal and the seal or sealing structure 2954 can be the first seal. In some cases, both seals or sealing structures 2952 and 2954 can be a seal configured to form a seal over the cannula when no medical instrument is present in the cannula. In some cases, both seals or sealing structures 2952 and 2954 can be an instrument seal.

The rigid feature 2950 at the proximal most end of the body 2912 can hold the medical instrument 2910 concentrically in the cannula 2900. The rigid feature 2950 can form a tight fitting channel 2956 that aligns with the cannula inlet 2928 and the medical instrument 2910 is inserted through the tight fitting channel. The tight fitting channel 2956 of the rigid feature 2950 can hold the medical instrument 2910 concentrically within the cannula 2900. In some cases, the rigid feature 2950 can seal against the medical instrument 2910 when the medical instrument 2910 is inserted within the cannula 2900.

Figure 29K:
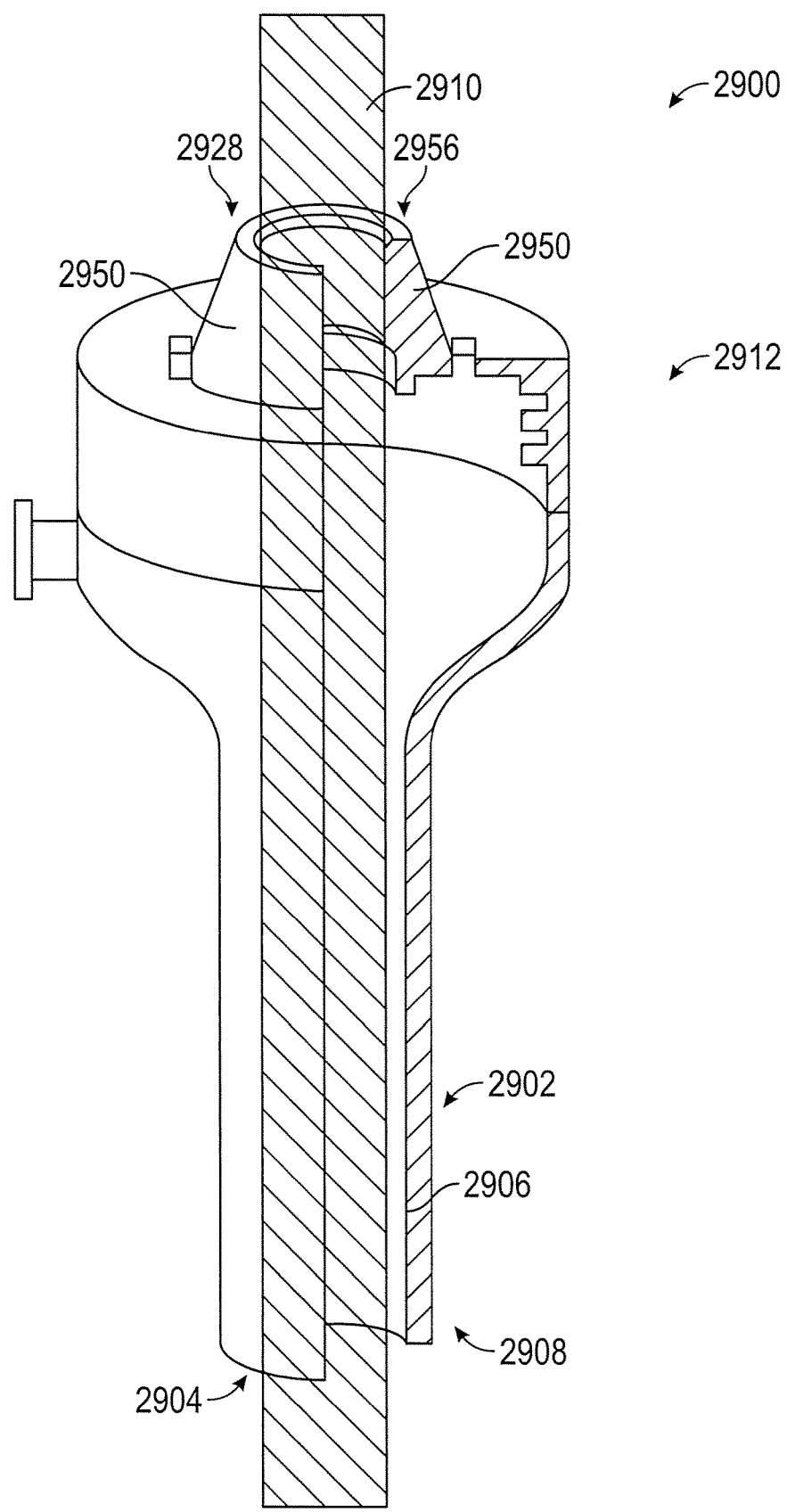

FIG. 29K illustrates a partial cut-away schematic view of the cannula of FIG. 29J. Features in FIG. 29K can be the same or substantially the same features as shown and described in FIG. 29J and reference numerals of the same or substantially the same features may share the same reference numerals. FIG. 29K illustrates the rigid feature 2950 on the proximal end 2914 of the cannula 2900. The rigid feature 2950 can extend proximally from the proximal surface 2914 of the cannula 2900 as illustrated in FIG. 29K. The rigid feature 2950 can be a hollow cone shaped feature with a tight fitting channel as shown in FIG. 29K. In some cases, the rigid feature 2950 can be a tube, hollow cylindrical, hollow cone, or any other shaped feature with a channel. In some cases, the rigid feature 2950 is removable or interchangeable. For example, the rigid feature 2950 can be interchanged with a different rigid feature to accommodate a different shaft size of the medical instrument 2910. In some cases, the rigid feature 2950 is permanent or semi-permanent.

Figure 29L:
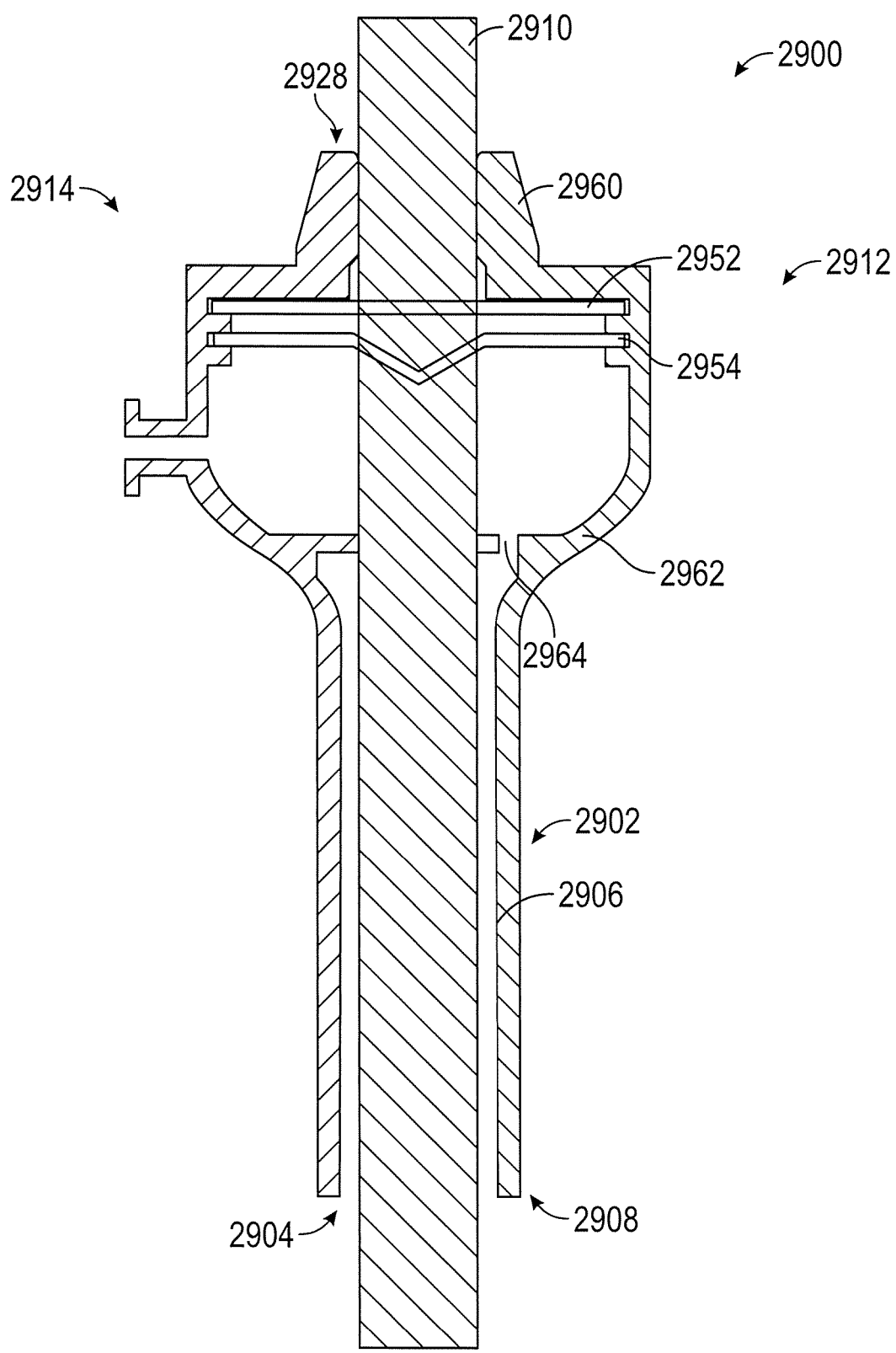

FIG. 29L illustrates a medical instrument 2910 inserted within a cannula 2900 and the medical instrument 2910 can be held within the cannula 2900 with two or more guide elements creating two or more points of contact within the cannula body 2912. In some cases, a rigid feature can be used above or proximal to the one or more seals in the cannula body and a rigid feature can be used below or distal to the seals in the cannula body. In such cases, the cannula 2900 can have two points of contact with the medical instrument 2910 and can provide support for the medical instrument 2910 at two points along the length of the cannula 2900. All of the combinations of the previous flexible and rigid features can be included in this design and can be used in any combination to hold the medical instrument 2910 concentrically in the cannula 2900. As illustrated in FIG. 29L, the cannula body 2912 can have a first point of contact above the seals of the cannula. The first point of contact can be a tight fitting channel as described with reference to FIGS. 29J and 29K. The second point of contact on the medical instrument 2910 can be a rigid disk 2962 below the seals in the cannula body. As described with reference to FIGS. 29E and 29F, the rigid disk 2962 can have openings 2964 to allow gases to pass down the cannula lumen 2904. As an example, FIG. 29L illustrates the use of a rigid feature 2960 above or proximal to seals 2952, 2954 at a proximal end 2914 of the body 2912 of the cannula 2900 in combination with a rigid disk 2962 in the cannula body 2912 to hold the medical instrument 2910 concentrically within the cannula 2900. As illustrated in FIG. 29L, both points of contact can occur in the cannula body 2912.

Figure 29M:
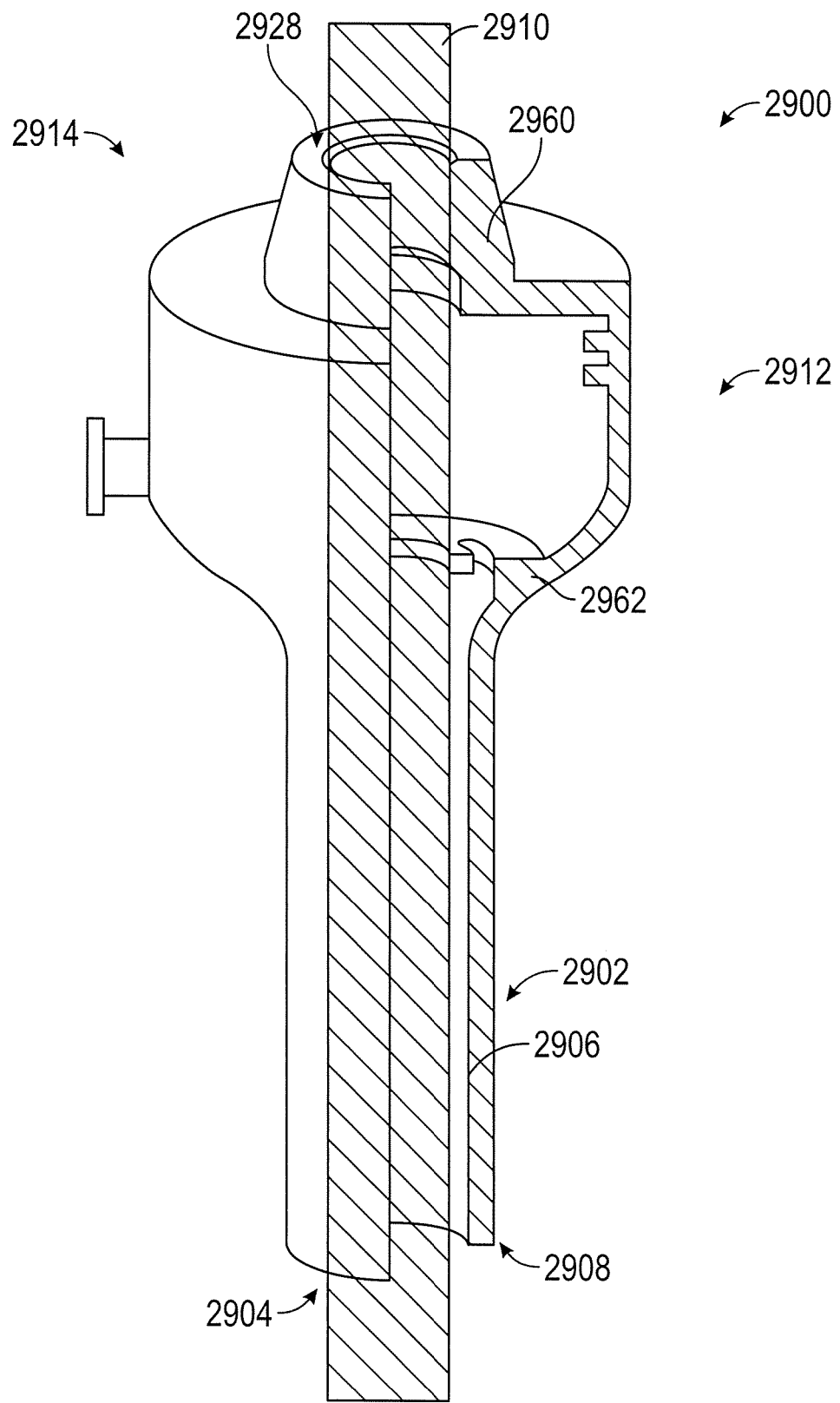

FIG. 29M illustrates a partial cut-away schematic view of the cannula of FIG. 29L. Features in FIG. 29M can be the same or substantially the same features as shown and described in FIG. 29L and reference numerals of the same or substantially the same features may share the same reference numerals. FIG. 29K illustrates the rigid feature 2960 on the proximal end 2914 of the cannula 2900 and the rigid disk 2962 within the cannula body 2912. The rigid feature 2960 can be similar to the rigid feature 2950 described with reference to FIGS. 29J and 29K and the rigid disk 2962 can be similar to the rigid disk 2930 described with reference to FIGS. 29E and 29F, FIGS. 30A-30H illustrate embodiments of cannulas 3000 with two or more guide elements including flexible features at a proximal end 3014 and a distal end 3008 of the cannula 3000 to aid in concentricity of the medical instrument 3010 within the cannula 3000. The cannula 3000 can include the cannula body 3012 and elongate shaft 3002. The elongate shaft 3002 can include a cannula sidewall 3006 that forms the lumen 3004 of the cannula 3000. The lumen 3004 can defined by the inner sidewall 3006 of the cannula 3000 as shown in FIGS. 30A-30H. As described herein, a medical instrument 3010 can be inserted through the cannula 3000 by being introduced through the inlet 3028 on the proximal end 3014 of the cannula body 3012 and extending through the lumen 3004 of the cannula 3000 toward the distal end 3008 of the elongate shaft 3002.

As shown in FIG. 30A, the medical instrument 3010 can be supported by a combination of any of the guide elements with flexible features described in previous embodiments. This combination of flexible features can hold the medical instrument 3010 concentrically in the cannula 3000. In some cases, two points of contact within the cannula 3000 can maintain the concentricity better than only one point of concentricity. As illustrated in FIG. 30A, a first point of contact can be achieved by a flexible feature, such as a flexible disk 3020, can be attached or molded to the body 3012 of the cannula 3000. The flexible disk 3020 can include openings 3022 to allow gases to pass through the lumen 3004. The flexible disk 3020 can include a plate 3024 to secure the flexible disk 3020 within the body 3012 of the cannula 3000. Additionally, a second point of contact can be achieved at the distal end 3008 of the elongate shaft 3002 with flexible concentric ribs 3030 molded into the cannula elongate shaft 3002. The flexible ribs 3026 can be similar to and include any of the features of the flexible ribs described herein in other embodiments. The flexible disk 3020 and flexible concentric ribs 3026 can hold the medical instrument 3010 concentrically in the cannula 3000 while allowing the gases to pass down the lumen 3004.

FIG. 30B is a cross-section through line 30A-30A of FIG. 30A, illustrating the flexible disk 3020 in the body 3012 with the medical instrument 3010 inserted within the cannula 3000. The flexible disk 3020 in the body 3012 can hold the medical instrument 3010 concentrically in the cannula 3000 while allowing the gases to pass through the openings 3022 and down through the lumen 3004. As illustrated in FIG. 30B, the flexible disk 3020 can circumferentially surround the medical instrument 3010.

FIG. 30C is a cross-section through line 30A'-30A' of FIG. 30A, illustrating ribs 3026 in the elongate shaft with the medical instrument 3010 inserted within the cannula 3000. The ribs 3026 in the elongate shaft 3002 can hold the medical instrument 3010 concentrically in the cannula 3000 while allowing the gases to pass down the lumen 3004. As shown in FIG. 30C, the ribs can be radially spaced apart around the inner circumference of the cannula sidewall 3006 at the proximal end of the elongate shaft 3002.

Figures 30D, 30E, 30F:
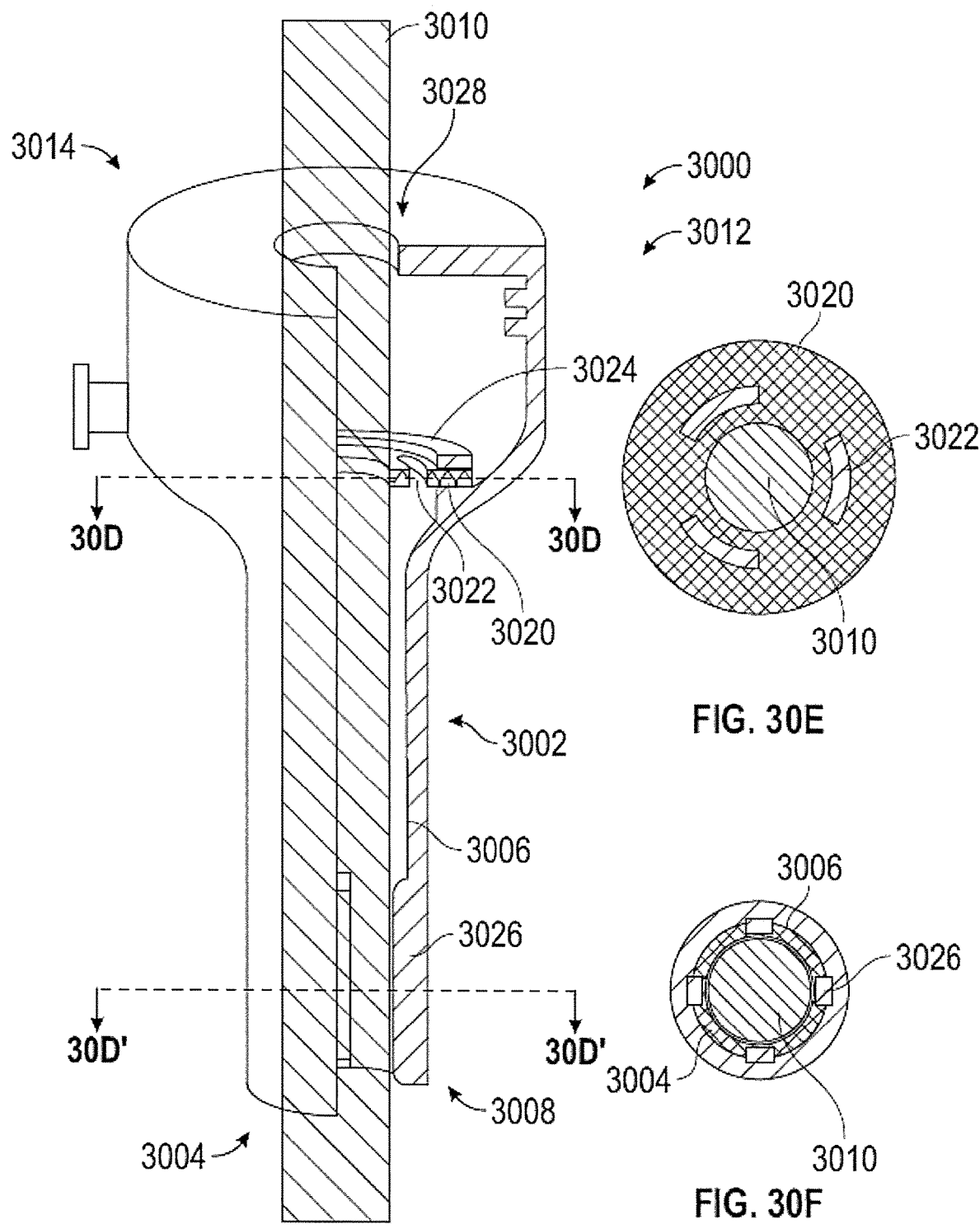

FIG. 30D illustrates a partial cut-away schematic view of the cannula of FIG. 30A. Features in FIGS. 30D, 30E, and 30F can be the same or substantially the same features as shown and described in FIGS. 30A, 30B, and 30C and reference numerals of the same or substantially the same features may share the same reference numerals. FIG. 30E is a cross-section through line 30D-30D of FIG. 30D, illustrating the flexible disk 3020 in the body 3012 with the medical instrument 3010 inserted within the cannula 3000. FIG. 30F is a cross-section through line 30D'-30D' of FIG. 30D, illustrating ribs 3026 on the cannula sidewall 3006 in the elongate shaft 3002 with the medical instrument 3010 inserted within the cannula 3000.

Figure 30G:
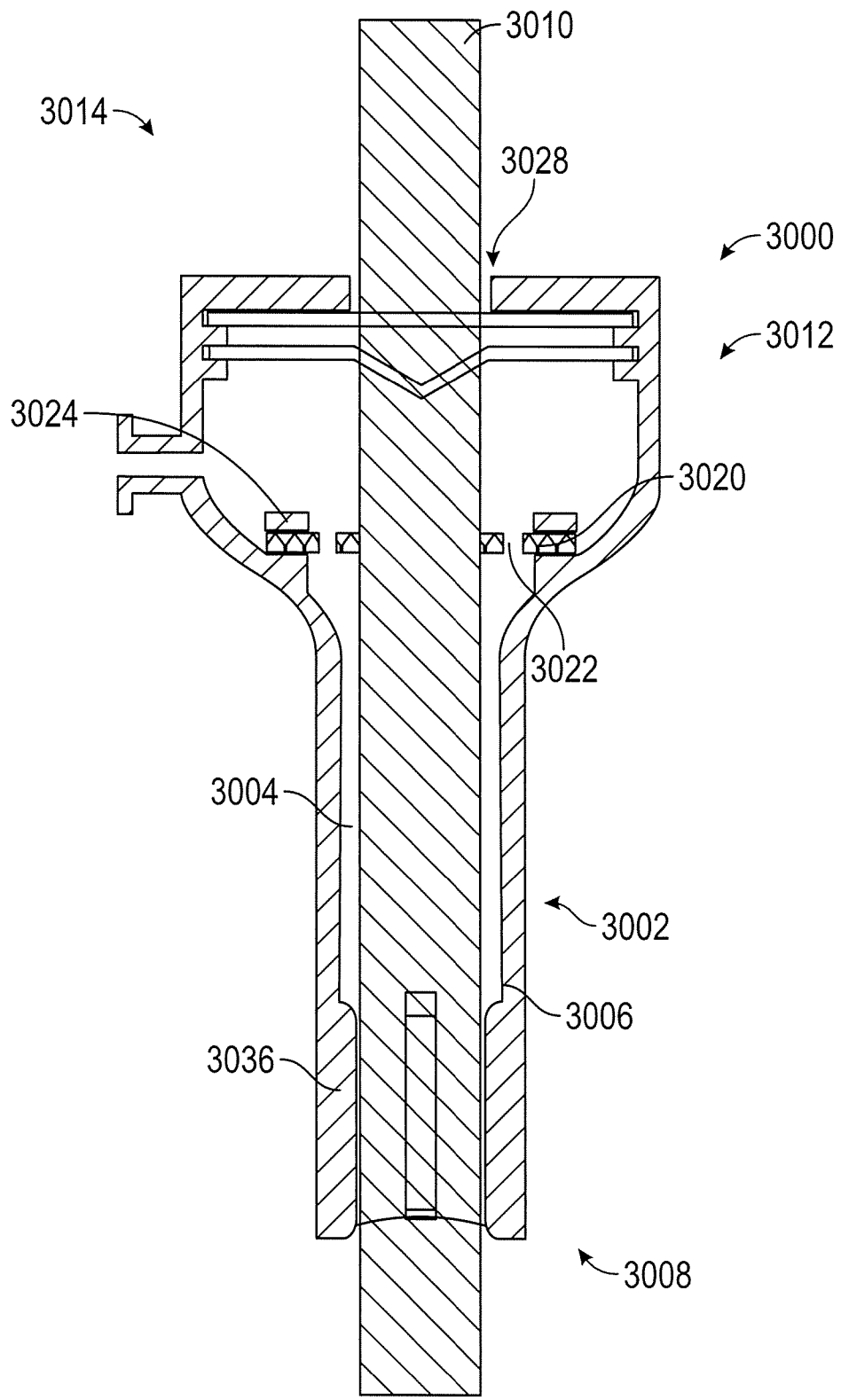
Figure 30H:
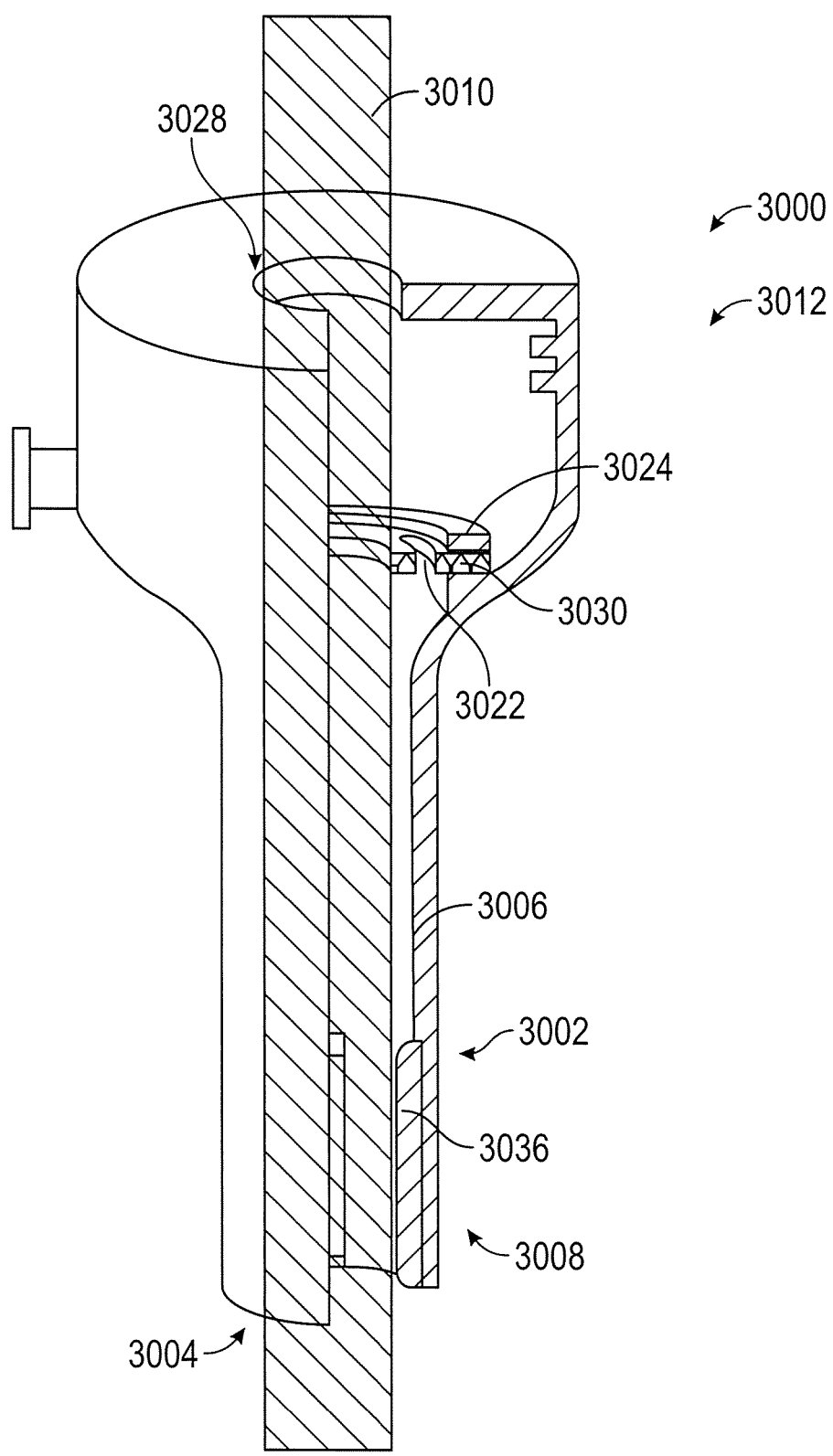

As shown in FIG. 30G, the medical instrument 3010 can be supported by a combination of any of the guide elements with flexible or rigid features described in previous embodiments. This combination of flexible and/or rigid features can hold the medical instrument 3010 concentrically in the cannula 3000 with at least two points of contact in the cannula. In some cases, the two points of contact within the cannula 3000 can maintain the concentricity better than only one point of concentricity. The two points of contact can be a disk 3030 and ribs 3036 similar to the disk 3020 and ribs 3026 described with reference to FIGS. 30A-30F but the disk 3030 and ribs 3036 can be either flexible or rigid. In some cases, both the disk 3030 and ribs 3036 can be flexible, both the disk 3030 and ribs 3036 can be rigid, or one of the disk 3030 and ribs 3036 can be flexible and the other of the disk 3030 and ribs 3036 can be rigid. FIG. 30H illustrates a partial cut-away schematic view of the cannula of FIG. 30G. Features in FIG. 30H can be the same or substantially the same features as shown and described in FIG. 30G and reference numerals of the same or substantially the same features may share the same reference numerals.

FIGS. 31A-31H illustrate embodiments of cannulas 3100 with two or more guide elements including rigid features at a proximal end 3114 and a distal end 3108 of the cannula 3100 to aid in concentricity of the medical instrument 3110 within the cannula 3100. The cannula 3100 can include the cannula body 3112 and elongate shaft 3102. The elongate shaft 3102 can include a cannula sidewall 3106 that forms the lumen 3104 of the cannula 3100. The lumen 3104 can defined by the inner sidewall 3106 of the cannula 3100 as shown in FIGS. 31A-31H. As described herein, a medical instrument 3110 can be inserted through the cannula 3100 by being introduced through the inlet 3128 at the proximal end 3114 of the cannula body 3112 and extending through the lumen 3104 of the cannula 3100 toward the distal end 3108 of the elongate shaft 3102.

Figure 31A:
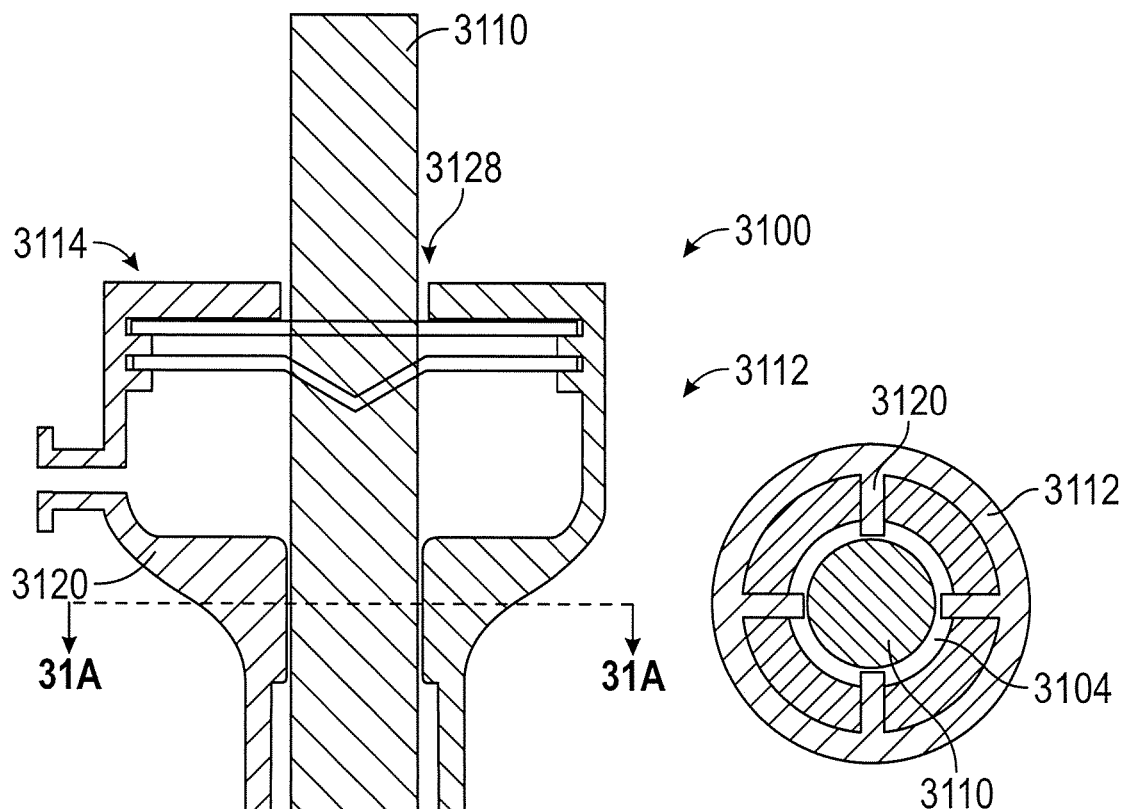
Figure 31A:
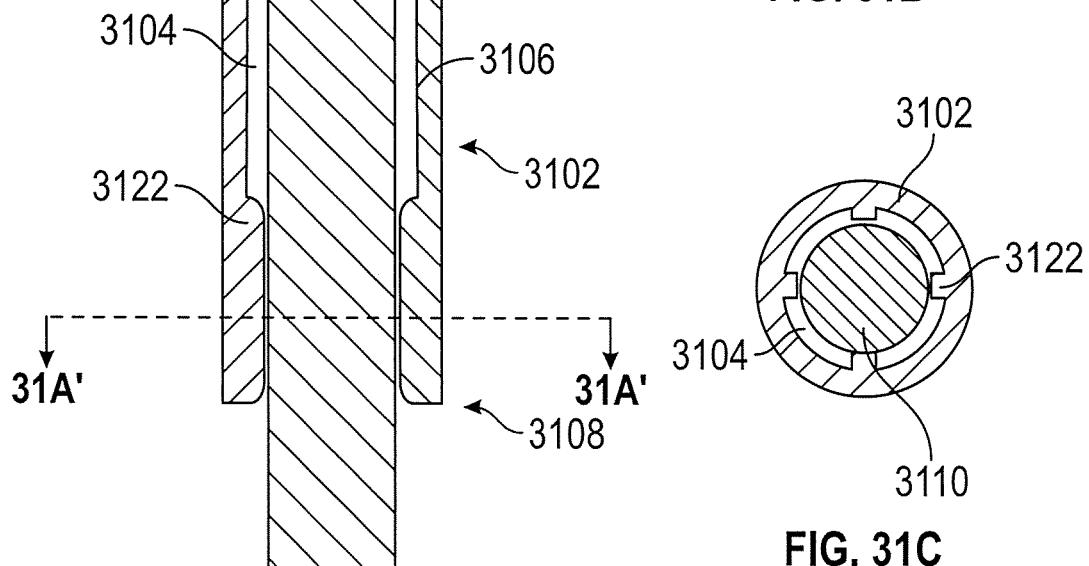

As shown in FIG. 31A, the medical instrument 3110 can be supported by a combination of any of the guide elements with rigid features described in previous embodiments. This combination of rigid features can hold the medical instrument 3110 concentrically in the cannula 3100. In some cases, two points of contact within the cannula 3100 can maintain the concentricity better than only one point of concentricity. FIG. 31A illustrates a cannula with two points of connect with the medical instrument with one point of contact in the cannula body 3112 and one point of contact in the elongate shaft 3102. As illustrated in FIG. 31A, a rigid feature, such as rigid ribs 3120, can be attached or molded to the body 3112 of the cannula 3100 forming the first point of contact with the medical instrument 3110. The distal end 3008 can include rigid ribs 3122 attached or molded into the cannula elongate shaft 3102 forming the second point of contact with the medical instrument 3130. The rigid ribs 3122 can be similar to and include any of the features of the rigid ribs described herein in other embodiments. The rigid ribs 3120 and rigid ribs 3122 can hold the medical instrument 3110 concentrically in the cannula 3100 while allowing the gases to pass down the lumen 3104.

FIG. 31B is a cross-section through line 31A-31A of FIG. 31A, illustrating the rigid ribs 3120 in the body 3112 with the medical instrument 3110 inserted within the cannula 3100. The rigid ribs 3120 in the body 3112 can hold the medical instrument 3110 concentrically in the cannula 3100 while allowing the gases to pass down through the lumen 3104. The rigid ribs 3120 can be spaced circumferentially around the inner wall of the body 3112 of the cannula 3100.

FIG. 31C is a cross-section through line 31A'-31A' of FIG. 31A, illustrating rigid ribs 3122 in the elongate shaft 3102 with the medical instrument 3110 inserted within the cannula 3100. The rigid ribs 3122 in the elongate shaft 3102 can hold the medical instrument 3110 concentrically in the cannula 3100 while allowing the gases to pass down the lumen 3104. As shown in FIG. 30C, the rigid ribs 3122 can be spaced circumferentially around the inner wall of the proximal end of the elongate shaft 3102.

FIG. 31D illustrates a partial cut-away schematic view of the cannula of FIG. 31A. Features in FIGS. 31D, 31E, and 31F can be the same or substantially the same features as shown and described in FIGS. 31A, 31B, and 31C and reference numerals of the same or substantially the same features may share the same reference numerals. FIG. 31E is a cross-section through line 31D-31D of FIG. 31D, illustrating the rigid ribs 3120 in the body 3112 with the medical instrument 3110 inserted within the cannula 3100. FIG. 31F is a cross-section through line 31D'-31D' of FIG. 31D, illustrating rigid ribs 3122 in the elongate shaft 3102 with the medical instrument 3110 inserted within the cannula 3100. As illustrated in FIGS. 31D, 31E, and 31F, the rigid ribs 3120 are radially spaced around the inner circumference of the cannula body and the rigid ribs 3126 are radially spaced around the inner circumference of the cannula shaft 3102.

Figure 31G:
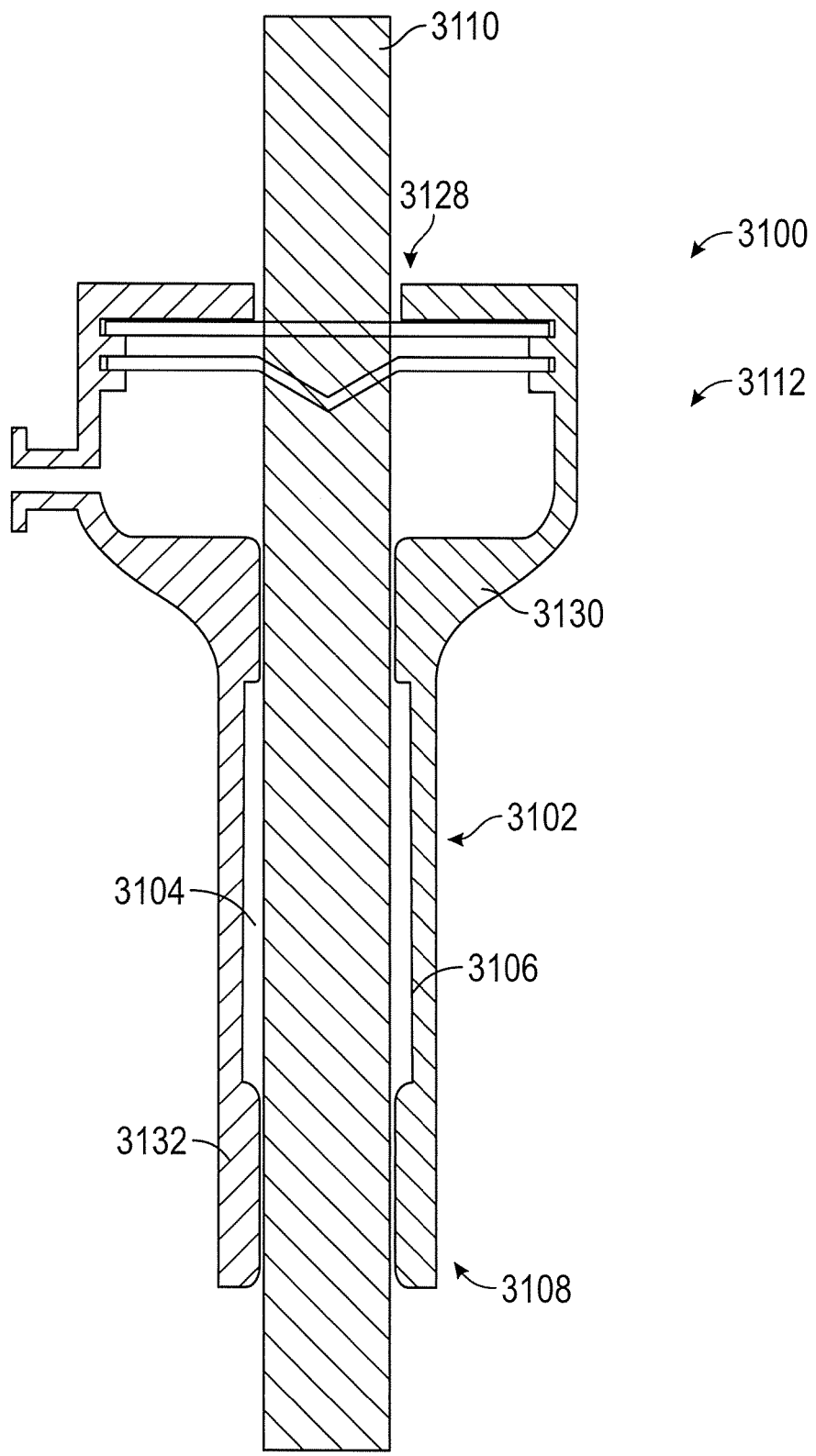
Figure 31H:
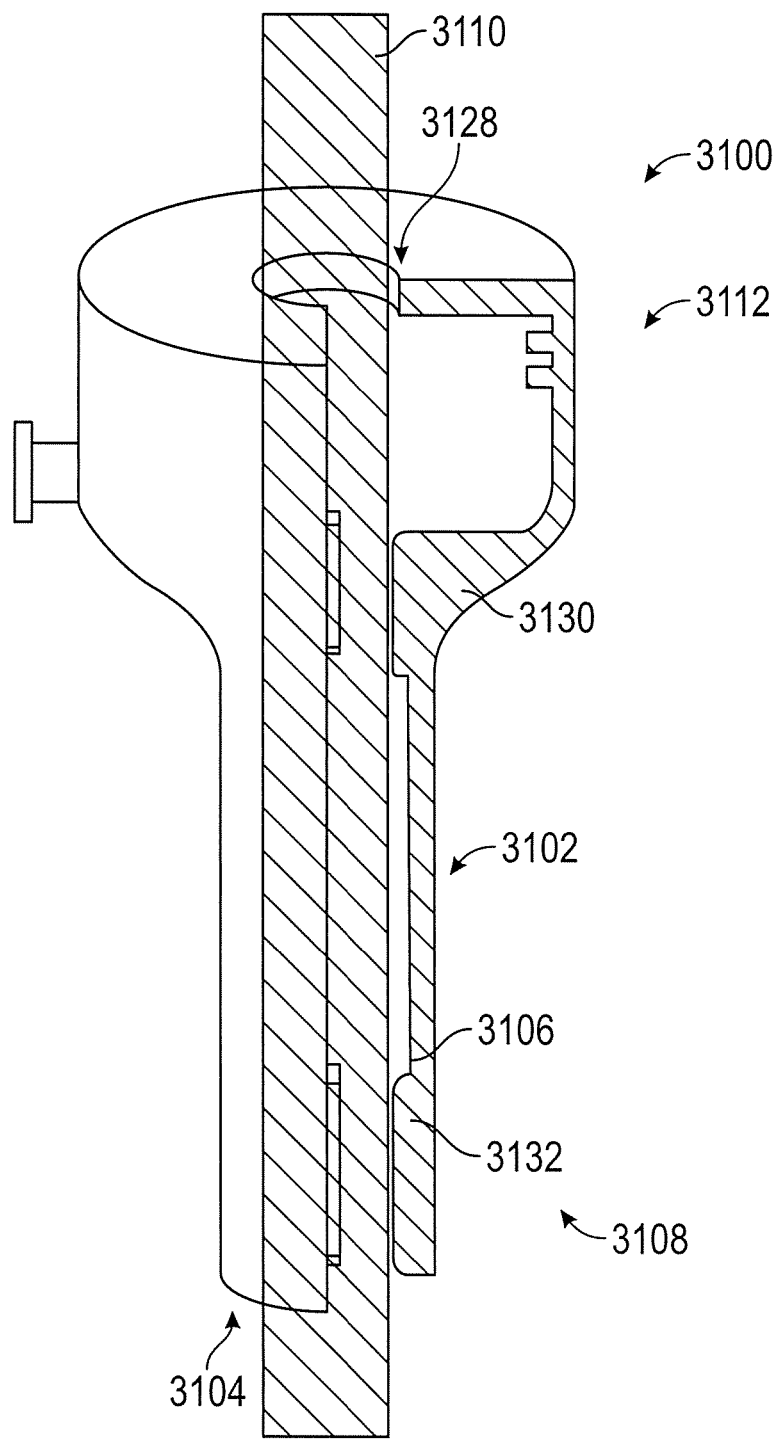

As shown in FIG. 31G, the medical instrument 3110 can be supported by a combination of any of the guide elements with flexible or rigid features described in previous embodiments. This combination of flexible and/or rigid features can hold the medical instrument 3110 concentrically in the cannula 3100 with at least two points of contact in the cannula. In some cases, the two points of contact within the cannula 3100 can maintain the concentricity better than only one point of concentricity. The two points of contact can be ribs 3130 and ribs 3132 similar to the ribs 3120 and ribs 3122 described with reference to FIGS. 31A-31F but the ribs 3130 and ribs 3132 can be either flexible or rigid. In some cases, both the ribs 3130 and ribs 3132 can be flexible, both the ribs 3130 and ribs 3132 can be rigid, or one of the ribs 3130 and ribs 3132 can be flexible and the other of the ribs 3130 and ribs 3132 can be rigid. FIG. 31H illustrates a partial cut-away schematic view of the cannula of FIG. 31G. Features in FIG. 31H can be the same or substantially the same features as shown and described in FIG. 31G and reference numerals of the same or substantially the same features may share the same reference numerals.

Any of the foregoing embodiments can also be modified to include additional features, including but not limited to one or more venting passageways defined within the cannula. For example, any of the cannulas described herein may include one, two, or more additional passageway/lumens that defines a venting passage to vent gases/smoke out of the surgical cavity. The venting lumen could be, for example, concentric, offset, or sharing a common lumen with respect to a gas supply lumen and/or an instrument retaining lumen. The cannula may optionally include a filter integrated into the cannula to filter gases delivered into the cannula. The filter may also be arranged in fluid communication with the venting passage (if it is present) such that the vented gases/smoke is filtered. A heating element may be located within the cannula to heat the cannula lumen thereby increasing the dew point of the gases within the cannula. A portion of the heating element or a second heating element may be positioned within the venting passage to prevent or at least reduce condensation in the venting passage. Furthermore, the heating element or another heating element may be arranged in contact with the filter to prevent or at least reduce condensation in the filter.

Terminology

Examples of medical gases delivery systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate the principles and details regarding divisions of modules or systems have been provided for ease of description rather than attempting to delineate separate physical embodiments. The examples and figures are intended to illustrate and not to limit the scope of the inventions described herein. For example, the principles herein may be applied to a surgical humidifier as well as other types of humidification systems, including respiratory humidifiers.

Examples described herein illustrate a concentric cannula used in combination with and supporting a scope concentrically. However, in some cases, the cannula can be used to hold other medical instruments concentrically such as surgical tools. Additionally, as referred to herein the terms "concentric", "concentrically", and/or "substantially concentric" or any variations of these terms can also refer to minor axis offsets between the cannula and medical instrument. In some case, for example, the axis offsets can include 0-30 degrees offset.

Examples described herein refer to reducing fogging or condensation on the medical instrument. However, other obstructions to visualization or complications can be prevented or reduced. When reference is made herein to reducing fogging or condensation with the methods, procedures, and devices described herein, it can be understood that these methods, procedures, and devices can also reduce or prevent fogging, condensation, unwanted debris, and/or other field of view obstructions.

As used herein, the term "processor" refers broadly to any suitable device, logical block, module, circuit, or combination of elements for executing instructions. For example, the controller 8 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module can be a software-implemented function block which does not utilize any additional and/or specialized hardware elements. The controller can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A surgical cannula for providing insufflation gases to a surgical cavity and providing a passage for insertion of one or more medical instruments, the cannula comprising:
   a cannula body including an inlet;
   an elongate shaft extending from the cannula body, the shaft defining a lumen defined by a sidewall, the lumen configured to provide the insufflation gases to the surgical cavity between a gases inlet and an outlet proximate a distal end of the elongate shaft, the lumen in fluid communication with the inlet and the outlet, the lumen also configured to receive a medical instrument therethrough; and
   a guide element disposed on, within, or around at least a portion of the lumen, the guide element configured to limit radial movement of the medical instrument within the lumen and prevent the medical instrument from contacting the sidewall of the lumen such that as the gases flow along the lumen from the inlet to the outlet of the lumen the gases flow around the medical instrument and create an envelope of insufflation gases that extends along and distally beyond a distal end of the instrument, wherein the medical instrument is configured to extend beyond the outlet of the elongate shaft; and
   wherein the gases flow along the lumen of the elongate shaft between an outer surface of the medical instrument and an inner sidewall of the lumen.

2. The surgical cannula of claim 1, wherein the guide element is further configured to maintain the medical instrument substantially co-axially and/or concentrically within the lumen.

3. The surgical cannula of claim 1, wherein the guide element comprises a plurality of ribs extending inward from the inner sidewall of the lumen toward a center of the lumen.

4. The surgical cannula of claim 3, wherein the plurality of ribs are configured to contact the medical instrument to grasp the instrument concentrically within the lumen.

5. A surgical cannula for providing gases to a surgical cavity and providing a passage for insertion of one or more medical instruments, the cannula comprising:
   a cannula body including an inlet;
   an elongate shaft extending from the cannula body, the shaft comprising an inner wall that defines a lumen, the lumen configured to provide the gases to the surgical cavity between a gases inlet and an outlet proximate a distal end of the elongate shaft, the lumen in fluid communication with the inlet and the outlet, the lumen also configured to receive a medical instrument therethrough; and
   a guide element extending inward from the inner wall, the guide element configured to limit radial movement of the medical instrument within the lumen such that as the gases flow along the lumen from the inlet to the outlet of the lumen the gases flow around the medical instrument and create an envelope of gases that extends along and distally beyond a distal end of the instrument, wherein the medical instrument is configured to extend beyond the outlet of the elongate shaft; and
   wherein the gases flow along the lumen of the elongate shaft between an outer surface of the medical instrument and the inner wall.

6. The surgical cannula of claim 5, wherein the guide element is further configured to maintain the medical instrument substantially co-axially and/or concentrically within the lumen.

7. The surgical cannula of claim 5, wherein the envelope extends distally beyond the outlet of the elongate shaft and the medical instrument.

8. The surgical cannula of claim 5, wherein the guide element is configured such that the envelope concentrically surrounds the medical instrument within the lumen and beyond the outlet of the elongate shaft.

9. The surgical cannula of claim 5, wherein the guide element is configured such that the envelope maintains a temperature controlled environment about the elongate shaft and outlet of the elongate shaft, wherein the envelope maintains the temperature above the dew point.

10. The surgical cannula of claim 5, wherein the guide element comprises a plurality of ribs extending inward from the inner wall of the lumen toward a center of the lumen.

11. The surgical cannula of claim 10, wherein the plurality of ribs are configured to contact the medical instrument to grasp the instrument concentrically within the lumen.

12. The surgical cannula of claim 10, wherein the plurality of ribs are configured to limit radial movement of the medical instrument to prevent the medical instrument from contacting the inner wall of the lumen.

13. The surgical cannula of claim 10, wherein the guide element comprises at least four radially or axially spaced-apart ribs.

14. The surgical cannula of claim 10, wherein the plurality of ribs are positioned at the distal end of the elongate shaft.

15. The surgical cannula of claim 10, wherein the plurality of ribs comprise a first set of ribs and a second set of ribs spaced axially apart by a gap between the first set of ribs and the second set of ribs.

16. The surgical cannula of claim 15, wherein the gap between the first set of ribs and the second set of ribs is sized and configured to reduce flow velocity and/or reduce flow turbulence of the gases.

17. The surgical cannula of claim 15, wherein the first set of ribs and the second set of ribs comprise the same number of ribs.

18. The surgical cannula of claim 15, wherein the first set of ribs comprises more ribs than the second set of ribs.

19. The surgical cannula of claim 15, wherein the first set of ribs comprises less ribs than the second set of ribs.

20. The surgical cannula of claim 5, wherein the guide element comprises radially spaced-apart protrusions.

21. The surgical cannula of claim 5, wherein the guide element comprises a plurality of fins extending inward and distally from the distal end of the elongate shaft.

22. The surgical cannula of claim 5, wherein the guide element comprises a plurality of flexible fins extending radially inward into the cannula.

* * * * *